United States Patent [19]

Osslund

[11] Patent Number: 5,581,476
[45] Date of Patent: Dec. 3, 1996

[54] COMPUTER-BASED METHODS AND ARTICLES OF MANUFACTURE FOR PREPARING G-CSF ANALOGS

[75] Inventor: Timothy D. Osslund, Camarillo, Calif.

[73] Assignee: Amgen Inc., Thousand Oaks, Calif.

[21] Appl. No.: 10,099

[22] Filed: Jan. 28, 1993

[51] Int. Cl.$^6$ ............ C12N 15/00; G06F 17/00; G06F 19/00
[52] U.S. Cl. ............ 364/496; 435/69.5; 435/172.3; 435/240.2; 435/252.3
[58] Field of Search ............ 364/496; 435/69.5, 435/172.3, 240.2, 252.34; 530/351, 412

[56] References Cited

U.S. PATENT DOCUMENTS

| | | | |
|---|---|---|---|
| 4,810,643 | 3/1989 | Souza | 435/69.5 |
| 4,853,871 | 8/1989 | Pantoliano et al. | 364/496 |
| 4,904,584 | 2/1990 | Shaw | 435/69.4 |
| 4,908,773 | 8/1990 | Pantoliano et al. | 364/413 |
| 5,265,030 | 11/1993 | Skolnick et al. | 364/496 |
| 5,307,287 | 4/1994 | Cramer et al. | 364/496 |
| 5,386,507 | 1/1995 | Teig et al. | 395/161 |

FOREIGN PATENT DOCUMENTS

| | | |
|---|---|---|
| 76380 | 11/1991 | Australia. |
| 10948 | 8/1992 | Australia. |
| 0243153 | 10/1987 | European Pat. Off.. |
| 0256843 | 2/1988 | European Pat. Off.. |
| 0272703 | 6/1988 | European Pat. Off.. |
| 0335423 | 10/1989 | European Pat. Off.. |
| 0344796 | 12/1989 | European Pat. Off.. |
| 0456200 | 11/1991 | European Pat. Off.. |
| 0459630 | 12/1991 | European Pat. Off.. |
| 2213821 | 8/1989 | United Kingdom. |
| WO85/00817 | 2/1985 | WIPO. |
| WO87/01132 | 2/1987 | WIPO. |
| WO88/01775 | 3/1988 | WIPO. |
| WO89/05824 | 6/1989 | WIPO. |
| WO90/12874 | 11/1990 | WIPO. |
| WO93/25687 | 12/1993 | WIPO. |

OTHER PUBLICATIONS

Abdel-Meguid et al., PNAS-USA 84: 6434 (1987).
Abrahmsen et al., Biochem. 30: 4151–4159 (1991).
Weber et al., Physical principles of protein crystallization. In: Eisenberg (ed.), Advances in Protein Chemistry 41:1–36 (1991).
Bazan, Immunology Today 11: 350–354 (1990).
Carter and Carter, J. Biol. Chem. 254:12219–12223 (1979).
Carter et al., J. Cryst. Growth 90: 60–73 (1988).
Cox and Weber, J. Appl. Crystallogr. 20: 366–373 (1987).
Cox and Weber, J. Cryst. Growth 90: 318–324 (1988).
Cunningham and Wells, Science 244: 1081–1084 (1989).
Diederichs et al., Science 254: 1779–1782 (1991).
Francis, Focus on Growth Factors 3: 4–10 (May 1992) (published by Mediscript, Mountview Court, Friern Barnet Lane, London N20 OLD, UK).
Gabrilove, J. Seminars in Hematology 26: (2) 1–14 (1989).
Hill et al., Proceedings of the National Acad. of Sciences of USA, 90: 5167–5171 (1993).
Huse et al., Science 246:1275 (1989).
Ishikawa et al., Cell Structure and Function, 17: 61–65 (1992).
Jancarik and Kim' J. App. Crystallogr. 24: 409 (1991).
Jones et al., Bailliere's Clinical Hematology 2 (1): 83–111 (1989).
Karplus, Protein Engineering, pp. 35–44 (1987).
Kuga et al., Biochem. Biophy. Res. Comm 159: 103–111 (1989).
Layton et al., JBC 266: 23815–23823 (1991).
Layton et al., J. of Cell Biochem. Suppl. 17B: 78 (1993).
Lieshke and Burgess, N. Engl. J. Med. 327: 28–34 and 99–106 (1992).
Lu et al., Arch. Biochem. Biophys. 268: 81–92 (1989).
McKay Science 257: 1673–1677 (1992).
Moore et al., PNAS-USA 84: 7134–7138 (1987).
Nagata et al., EMBO J 5: 575–581 (1986).
Nicola, Annu. Rev. Biochem. 58: 45–77 (1989).
Nicola, et al., Blood 54: 614–27 (1979).
Olson et al., Pour La Science, 183: 76–82 (1993).
Osslund et al., Dissertation Abstracts International B., 54: 1239 (1993).
Pandit et al., Science, 258: 1358–1362 (1992).
Parry et al., J. Molecular Recognition 8: 107–110 (1988).
Powers et al., Science 256: 1673–1677 (1992).
Remington's Pharmaceutical Sciences, 18th Ed. (1990, Mack Publishing Co., Easton, Pennsylvania 18042) pp. 1435–1712.
Senda et al., EMBO J. 11: 3193–3201 (1992).
Smith et al., J. Mol. Biol. 224: 899–904 (1992).
Souza et al., Science 232: 61–65 (1986).
Stryer, Biochemistry, 3d Ed., W. H. Freeman and Company, N.Y. 1988, inside back cover).
Vos et al., Science 255: 305–312 (1992).
Weber, J. Appl. Crystallogr. 20: 366–373 (1987).
Welte et al., PNAS-USA 82: 1526–1530 (1985).
Rastetter, *Trends in Biotechnology*, 1(3): 80–84, 1983.
Hill et al, *PNAS* 90, 1993 pp. 5167–5171.
Layton et al *JBC* 266(35) 1991, pp. 23815–23823.
Najahara et al, *J. Mol Biol* 214, 1990, pp. 25–26.
Lonejay et al *J. Mol Biol* 234, 1993, pp. 640–653.
Li et al, *JBC* 268(30) 1993, pp. 22377–22384.

*Primary Examiner*—Marianne P. Allen
*Attorney, Agent, or Firm*—Karol Pessin

[57] ABSTRACT

Provided are computer-based methods for preparing G-CSF analogs involving (a) providing computer expression of the three dimensional structure of a G-CSF molecule wherein the chemical moieties, such as each amino acid residue or each atom of each amino acid residue of the G-CSF molecule are correlated with said structure: (b) selecting from said computer expression a site on a G-CSF molecule for alteration; and (c) preparing a G-CSF molecule having such alteration. Also provided are articles of manufacture associated with such methods.

3 Claims, 55 Drawing Sheets

FIG. 1

```
                                          Met Thr Pro Leu Gly Pro Ala
TCTAGAAAAAACCAAGGAGGTAATAAATA ATG ACT CCA TTA GGT CCT GCT

Ser Ser Leu Pro Gln Ser Phe Leu Leu Lys Cys Leu Glu Gln
TCT TCT CTG CCG CAA AGC TTT CTG CTG AAA TGT CTG GAA CAG

Val Arg Lys Ile Gln Gly Asp Gly Ala Ala Leu Gln Glu Lys Leu
GTT CGT AAA ATC CAG GGT GAC GGT GCT GCA CTG CAA GAA AAA CTG

Cys Ala Thr Tyr Lys Leu Cys His Pro Glu Glu Leu Val Leu Leu
TGC GCT ACT TAC AAA CTG TGC CAT CCG GAA GAG CTG GTA CTG CTG

Gly His Ser Leu Gly Ile Pro Trp Ala Pro Leu Ser Ser Cys Pro
GGT CAT TCT CTT GGG ATC CCG TGG GCT CCG CTG TCT TCT TGT CCA

Ser Gln Ala Leu Gln Leu Ala Gly Cys Leu Ser Gln Leu His Ser
TCT CAA GCT CTT CAG CTG GCT GGT TGT CTG TCT CAA CTG CAT TCT

Gly Leu Phe Leu Tyr Gln Gly Leu Leu Gln Ala Leu Glu Gly Ile
GGT CTG TTC CTG TAT CAG GGT CTT CTG CAA GCT CTG GAA GGT ATC

Ser Pro Glu Leu Gly Pro Thr Leu Asp Thr Leu Gln Leu Asp Val
TCT CCG GAA CTG GGT CCG ACT CTG GAC ACT CTG CAG CTA GAT GTA

Ala Asp Phe Ala Thr Thr Ile Trp Gln Gln Met Glu Glu Leu Gly
GCT GAC TTT GCT ACT ACT ATT TGG CAA CAG ATG GAA GAG CTC GGT

Met Ala Pro Ala Leu Gln Pro Thr Gln Gly Ala Met Pro Ala Phe
ATG GCA CCA GCT CTG CAA CCG ACT CAA GGT GCT ATG CCG GCA TTC

Ala Ser Ala Phe Gln Arg Arg Ala Gly Gly Val Leu Val Ala Ser
GCT TCT GCA TTC CAG CGT CGT GCA GGA GGT GTA CTG GTT GCT TCT

His Leu Gln Ser Phe Leu Glu Val Ser Tyr Arg Val Leu Arg His
CAT CTG CAA TCT TTC CTG GAA GTA TCT TAC CGT GTT CTG CGT CAT

Leu Ala Gln Pro OC  AM
CTG GCT CAG CCG TAA TAG AATTC
``` rhG-CSF hGH pGH

GM-CSF

INF-B

IL-2

IL-4

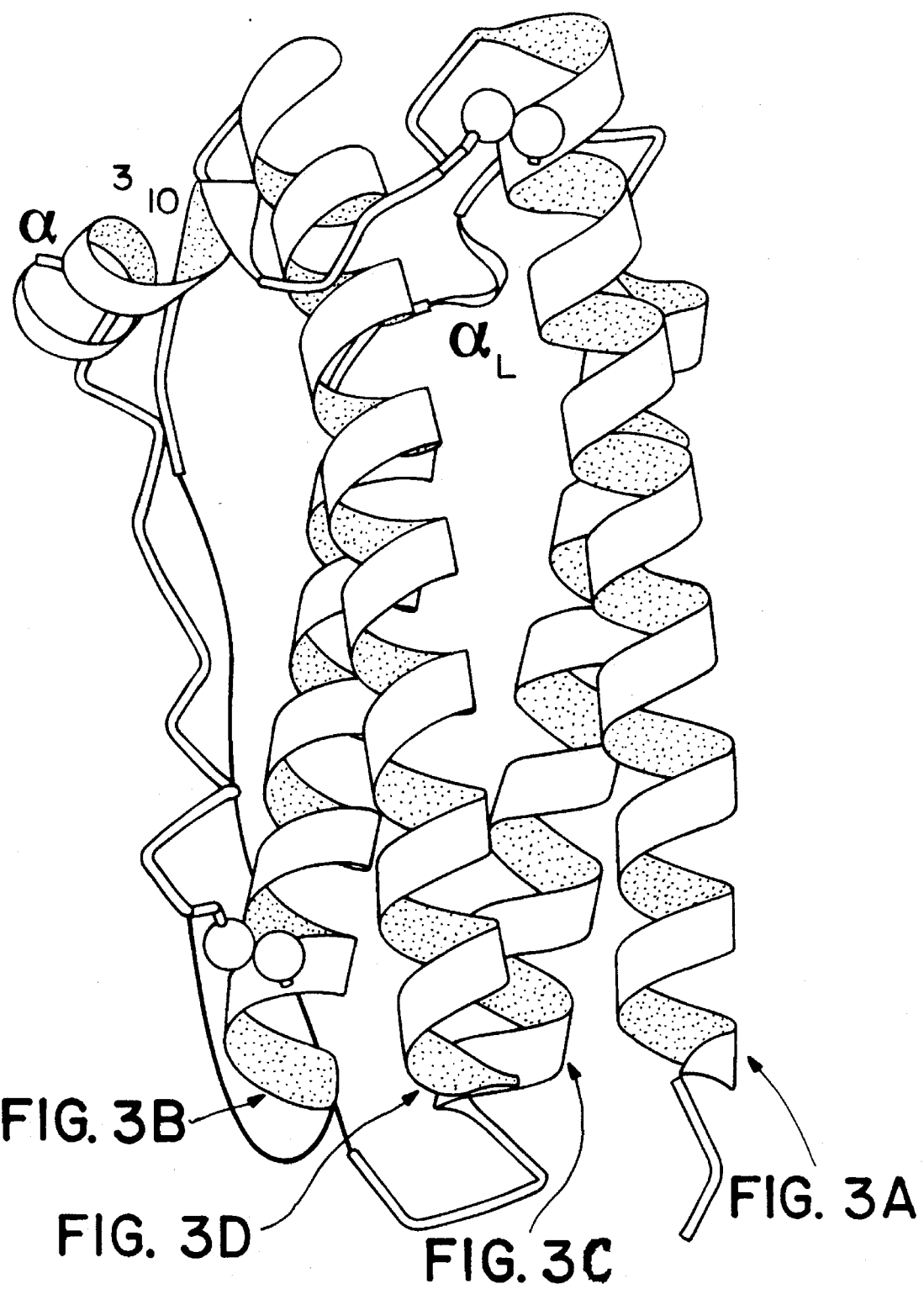

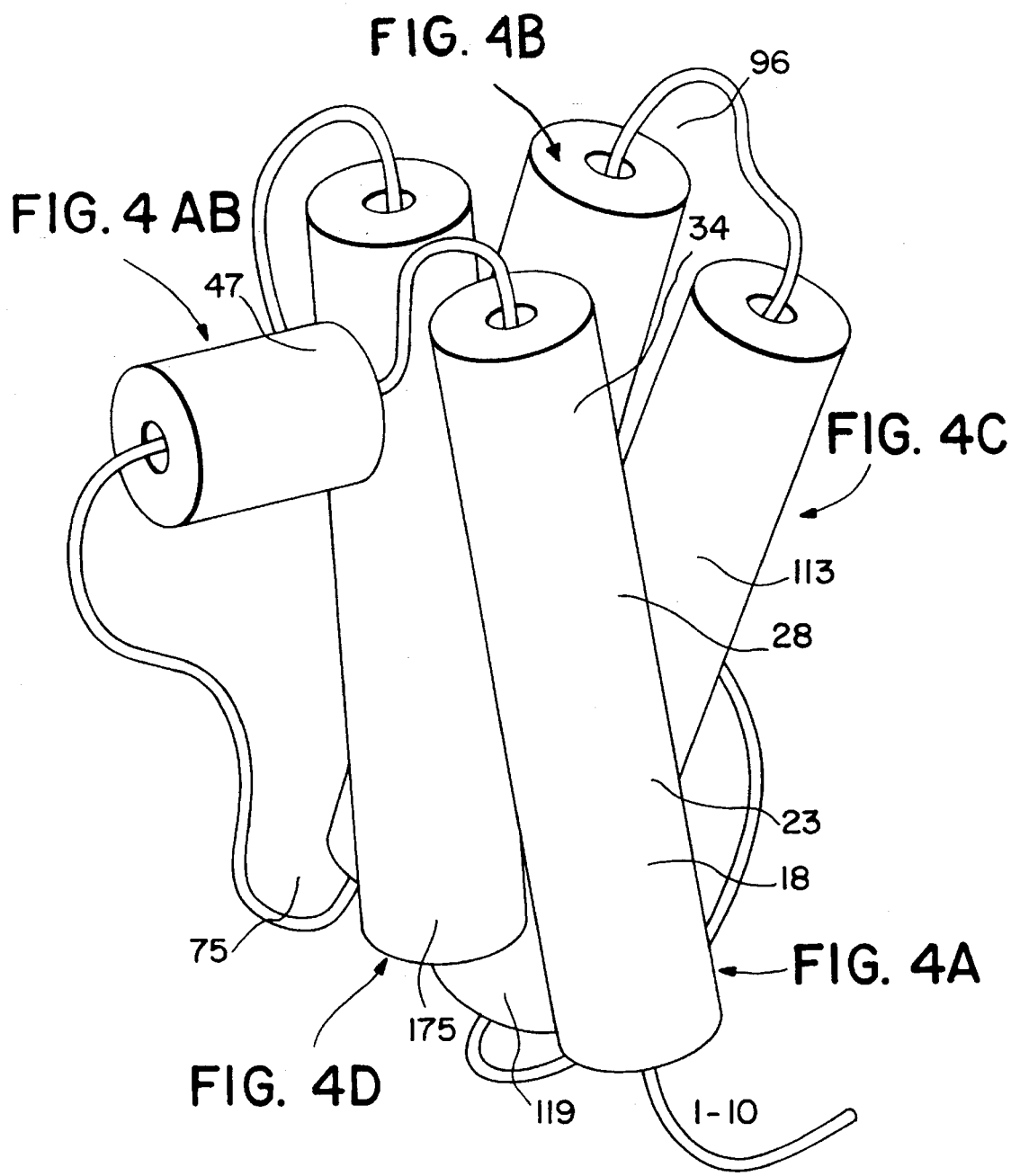

FIG.5-1

| ATOM | 1 | CB | LEU | 10 | 58.751 | 58.191 | -14.868 | 1.00 | 61.22 | A1 |
|------|---|----|----|-----|--------|--------|---------|------|-------|----|
| ATOM | 2 | CG | LEU | 10 | 58.360 | 59.271 | -13.939 | 1.00 | 60.19 | A1 |
| ATOM | 3 | CD1 | LEU | 10 | 59.307 | 60.461 | -14.022 | 1.00 | 60.14 | A1 |
| ATOM | 4 | CD2 | LEU | 10 | 56.954 | 59.658 | -14.335 | 1.00 | 60.68 | A1 |
| ATOM | 5 | C | LEU | 10 | 60.544 | 56.734 | -13.849 | 1.00 | 62.85 | A1 |
| ATOM | 6 | O | LEU | 10 | 60.079 | 55.595 | -14.041 | 1.00 | 63.08 | A1 |
| ATOM | 7 | HT1 | LEU | 10 | 59.876 | 56.135 | -15.998 | 1.00 | 0.00 | A1 |
| ATOM | 8 | HT2 | LEU | 10 | 61.323 | 56.887 | -16.434 | 1.00 | 0.00 | A1 |
| ATOM | 9 | N | LEU | 10 | 60.328 | 57.059 | -16.204 | 1.00 | 62.24 | A1 |
| ATOM | 10 | HT3 | LEU | 10 | 59.817 | 57.535 | -16.971 | 1.00 | 0.00 | A1 |
| ATOM | 11 | CA | LEU | 10 | 60.183 | 57.758 | -14.941 | 1.00 | 62.58 | A1 |
| ATOM | 12 | N | PRO | 11 | 61.357 | 56.962 | -12.780 | 1.00 | 61.96 | A1 |
| ATOM | 13 | CD | PRO | 11 | 61.960 | 58.238 | -12.383 | 1.00 | 61.21 | A1 |
| ATOM | 14 | CA | PRO | 11 | 61.832 | 55.889 | -11.906 | 1.00 | 61.34 | A1 |
| ATOM | 15 | CB | PRO | 11 | 62.915 | 56.547 | -11.043 | 1.00 | 59.77 | A1 |
| ATOM | 16 | CG | PRO | 11 | 62.511 | 57.983 | -10.975 | 1.00 | 59.16 | A1 |
| ATOM | 17 | C | PRO | 11 | 60.712 | 55.225 | -11.109 | 1.00 | 60.68 | A1 |
| ATOM | 18 | O | PRO | 11 | 60.075 | 55.843 | -10.250 | 1.00 | 61.73 | A1 |
| ATOM | 19 | N | GLN | 12 | 60.466 | 53.946 | -11.407 | 1.00 | 59.31 | A1 |
| ATOM | 20 | H | GLN | 12 | 60.944 | 53.573 | -12.175 | 1.00 | 0.00 | A1 |
| ATOM | 21 | CA | GLN | 12 | 59.468 | 53.121 | -10.743 | 1.00 | 57.22 | A1 |
| ATOM | 22 | CB | GLN | 12 | 59.779 | 51.646 | -10.970 | 1.00 | 59.27 | A1 |
| ATOM | 23 | CG | GLN | 12 | 58.620 | 50.714 | -10.591 | 1.00 | 59.70 | A1 |
| ATOM | 24 | CD | GLN | 12 | 57.604 | 50.575 | -11.702 | 1.00 | 61.71 | A1 |
| ATOM | 25 | OE1 | GLN | 12 | 57.170 | 49.465 | -11.970 | 1.00 | 65.82 | A1 |
| ATOM | 26 | NE2 | GLN | 12 | 57.227 | 51.534 | -12.541 | 1.00 | 63.02 | A1 |
| ATOM | 27 | HE21 | GLN | 12 | 57.639 | 52.419 | -12.489 | 1.00 | 0.00 | A1 |
| ATOM | 28 | HE22 | GLN | 12 | 56.500 | 51.308 | -13.156 | 1.00 | 0.00 | A1 |
| ATOM | 29 | C | GLN | 12 | 59.336 | 53.347 | -9.245 | 1.00 | 55.34 | A1 |
| ATOM | 30 | O | GLN | 12 | 58.242 | 53.196 | -8.708 | 1.00 | 54.56 | A1 |
| ATOM | 31 | N | SER | 13 | 60.423 | 53.732 | -8.576 | 1.00 | 53.44 | A1 |
| ATOM | 32 | H | SER | 13 | 61.276 | 53.839 | -9.033 | 1.00 | 0.00 | A1 |
| ATOM | 33 | CA | SER | 13 | 60.335 | 53.974 | -7.168 | 1.00 | 52.86 | A1 |
| ATOM | 34 | CB | SER | 13 | 61.704 | 54.144 | -6.626 | 1.00 | 52.24 | A1 |
| ATOM | 35 | OG | SER | 13 | 61.702 | 53.493 | -5.362 | 1.00 | 56.64 | A1 |
| ATOM | 36 | HG | SER | 13 | 61.534 | 52.551 | -5.477 | 1.00 | 0.00 | A1 |
| ATOM | 37 | C | SER | 13 | 59.497 | 55.214 | -6.900 | 1.00 | 52.58 | A1 |
| ATOM | 38 | O | SER | 13 | 58.509 | 55.144 | -6.160 | 1.00 | 53.55 | A1 |
| ATOM | 39 | N | PHE | 14 | 59.791 | 56.333 | -7.577 | 1.00 | 50.84 | A1 |
| ATOM | 40 | H | PHE | 14 | 60.469 | 56.292 | -8.279 | 1.00 | 0.00 | A1 |
| ATOM | 41 | CA | PHE | 14 | 59.067 | 57.590 | -7.423 | 1.00 | 47.21 | A1 |
| ATOM | 42 | CB | PHE | 14 | 59.611 | 58.590 | -8.454 | 1.00 | 44.68 | A1 |
| ATOM | 43 | CG | PHE | 14 | 58.618 | 59.669 | -8.866 | 1.00 | 42.88 | A1 |
| ATOM | 44 | CD1 | PHE | 14 | 58.052 | 59.594 | -10.123 | 1.00 | 40.40 | A1 |
| ATOM | 45 | CD2 | PHE | 14 | 58.264 | 60.673 | -7.978 | 1.00 | 40.30 | A1 |
| ATOM | 46 | CE1 | PHE | 14 | 57.114 | 60.518 | -10.507 | 1.00 | 39.59 | A1 |
| ATOM | 47 | CE2 | PHE | 14 | 57.329 | 61.587 | -8.380 | 1.00 | 41.82 | A1 |
| ATOM | 48 | CZ | PHE | 14 | 56.751 | 61.515 | -9.635 | 1.00 | 41.56 | A1 |
| ATOM | 49 | C | PHE | 14 | 57.605 | 57.263 | -7.661 | 1.00 | 45.83 | A1 |
| ATOM | 50 | O | PHE | 14 | 56.789 | 57.588 | -6.805 | 1.00 | 46.07 | A1 |
| ATOM | 51 | N | LEU | 15 | 57.298 | 56.509 | -8.718 | 1.00 | 44.64 | A1 |
| ATOM | 52 | H | LEU | 15 | 58.024 | 56.183 | -9.287 | 1.00 | 0.00 | A1 |
| ATOM | 53 | CA | LEU | 15 | 55.940 | 56.181 | -9.038 | 1.00 | 44.53 | A1 |
| ATOM | 54 | CB | LEU | 15 | 55.858 | 55.402 | -10.300 | 1.00 | 48.74 | A1 |
| ATOM | 55 | CG | LEU | 15 | 54.853 | 56.013 | -11.289 | 1.00 | 51.65 | A1 |
| ATOM | 56 | CD1 | LEU | 15 | 55.525 | 57.121 | -12.105 | 1.00 | 50.33 | A1 |
| ATOM | 57 | CD2 | LEU | 15 | 54.320 | 54.906 | -12.204 | 1.00 | 53.77 | A1 |
| ATOM | 58 | C | LEU | 15 | 55.169 | 55.410 | -8.014 | 1.00 | 44.07 | A1 |
| ATOM | 59 | O | LEU | 15 | 53.945 | 55.567 | -7.959 | 1.00 | 45.46 | A1 |
| ATOM | 60 | N | LEU | 16 | 55.809 | 54.620 | -7.166 | 1.00 | 43.18 | A1 |
| ATOM | 61 | H | LEU | 16 | 56.781 | 54.503 | -7.251 | 1.00 | 0.00 | A1 |
| ATOM | 62 | CA | LEU | 16 | 55.110 | 53.913 | -6.095 | 1.00 | 42.96 | A1 |
| ATOM | 63 | CB | LEU | 16 | 55.866 | 52.623 | -5.751 | 1.00 | 43.34 | A1 |
| ATOM | 64 | CG | LEU | 16 | 55.840 | 51.608 | -6.868 | 1.00 | 42.25 | A1 |
| ATOM | 65 | CD1 | LEU | 16 | 56.889 | 50.567 | -6.596 | 1.00 | 43.68 | A1 |
| ATOM | 66 | CD2 | LEU | 16 | 54.413 | 51.068 | -7.030 | 1.00 | 42.75 | A1 |
| ATOM | 67 | C | LEU | 16 | 54.963 | 54.778 | -4.852 | 1.00 | 42.35 | A1 |
| ATOM | 68 | O | LEU | 16 | 54.077 | 54.579 | -4.018 | 1.00 | 42.65 | A1 |
| ATOM | 69 | N | LYS | 17 | 55.823 | 55.779 | -4.703 | 1.00 | 42.47 | A1 |
| ATOM | 70 | H | LYS | 17 | 56.587 | 55.840 | -5.320 | 1.00 | 0.00 | A1 |
| ATOM | 71 | CA | LYS | 17 | 55.681 | 56.767 | -3.650 | 1.00 | 42.07 | A1 |
| ATOM | 72 | CB | LYS | 17 | 56.995 | 57.554 | -3.573 | 1.00 | 44.14 | A1 |
| ATOM | 73 | CG | LYS | 17 | 57.214 | 58.197 | -2.223 | 1.00 | 49.61 | A1 |
| ATOM | 74 | CD | LYS | 17 | 57.114 | 57.164 | -1.086 | 1.00 | 55.15 | A1 |
| ATOM | 75 | CE | LYS | 17 | 56.747 | 57.804 | 0.293 | 1.00 | 62.05 | A1 |
| ATOM | 76 | NZ | LYS | 17 | 55.462 | 58.533 | 0.331 | 1.00 | 65.43 | A1 |
| ATOM | 77 | HZ1 | LYS | 17 | 54.684 | 57.884 | 0.098 | 1.00 | 0.00 | A1 |
| ATOM | 78 | HZ2 | LYS | 17 | 55.482 | 59.308 | -0.362 | 1.00 | 0.00 | A1 |
| ATOM | 79 | HZ3 | LYS | 17 | 55.312 | 58.926 | 1.282 | 1.00 | 0.00 | A1 |
| ATOM | 80 | C | LYS | 17 | 54.463 | 57.640 | -4.051 | 1.00 | 41.20 | A1 |
| ATOM | 81 | O | LYS | 17 | 53.648 | 57.999 | -3.186 | 1.00 | 40.66 | A1 |
| ATOM | 82 | N | CYS | 18 | 54.272 | 57.992 | -5.346 | 1.00 | 39.13 | A1 |
| ATOM | 83 | H | CYS | 18 | 54.998 | 57.809 | -5.981 | 1.00 | 0.00 | A1 |
| ATOM | 84 | CA | CYS | 18 | 53.080 | 58.656 | -5.802 | 1.00 | 37.42 | A1 |
| ATOM | 85 | CB | CYS | 18 | 53.092 | 58.891 | -7.261 | 1.00 | 35.02 | A1 |

FIG. 5-2

| | | | | | | | | | | |
|---|---|---|---|---|---|---|---|---|---|---|
| ATOM | 86 | SG | CYS | 18 | 54.421 | 60.026 | -7.681 | 1.00 | 40.40 | A1 |
| ATOM | 87 | C | CYS | 18 | 51.859 | 57.789 | -5.502 | 1.00 | 39.33 | A1 |
| ATOM | 88 | O | CYS | 18 | 50.959 | 58.346 | -4.847 | 1.00 | 40.83 | A1 |
| ATOM | 89 | N | LEU | 19 | 51.738 | 56.475 | -5.842 | 1.00 | 37.15 | A1 |
| ATOM | 90 | H | LEU | 19 | 52.462 | 56.038 | -6.341 | 1.00 | 0.00 | A1 |
| ATOM | 91 | CA | LEU | 19 | 50.521 | 55.702 | -5.534 | 1.00 | 36.00 | A1 |
| ATOM | 92 | CB | LEU | 19 | 50.644 | 54.204 | -5.947 | 1.00 | 38.31 | A1 |
| ATOM | 93 | CG | LEU | 19 | 49.410 | 53.271 | -5.657 | 1.00 | 40.86 | A1 |
| ATOM | 94 | CD1 | LEU | 19 | 48.208 | 53.684 | -6.467 | 1.00 | 39.71 | A1 |
| ATOM | 95 | CD2 | LEU | 19 | 49.692 | 51.833 | -6.113 | 1.00 | 45.71 | A1 |
| ATOM | 96 | C | LEU | 19 | 50.102 | 55.736 | -4.076 | 1.00 | 33.52 | A1 |
| ATOM | 97 | O | LEU | 19 | 48.930 | 55.949 | -3.766 | 1.00 | 32.75 | A1 |
| ATOM | 98 | N | GLU | 20 | 51.030 | 55.576 | -3.166 | 1.00 | 31.88 | A1 |
| ATOM | 99 | H | GLU | 20 | 51.940 | 55.338 | -3.455 | 1.00 | 0.00 | A1 |
| ATOM | 100 | CA | GLU | 20 | 50.750 | 55.710 | -1.748 | 1.00 | 33.40 | A1 |
| ATOM | 101 | CB | GLU | 20 | 52.053 | 55.334 | -1.167 | 1.00 | 35.25 | A1 |
| ATOM | 102 | CG | GLU | 20 | 52.508 | 55.504 | 0.260 | 1.00 | 43.21 | A1 |
| ATOM | 103 | CD | GLU | 20 | 53.948 | 54.947 | 0.407 | 1.00 | 51.06 | A1 |
| ATOM | 104 | OE1 | GLU | 20 | 54.320 | 54.660 | 1.546 | 1.00 | 56.78 | A1 |
| ATOM | 105 | OE2 | GLU | 20 | 54.708 | 54.766 | -0.570 | 1.00 | 51.57 | A1 |
| ATOM | 106 | C | GLU | 20 | 50.230 | 57.117 | -1.326 | 1.00 | 33.25 | A1 |
| ATOM | 107 | O | GLU | 20 | 49.432 | 57.291 | -0.380 | 1.00 | 33.30 | A1 |
| ATOM | 108 | N | GLN | 21 | 50.660 | 58.167 | -2.044 | 1.00 | 32.33 | A1 |
| ATOM | 109 | H | GLN | 21 | 51.270 | 58.004 | -2.794 | 1.00 | 0.00 | A1 |
| ATOM | 110 | CA | GLN | 21 | 50.275 | 59.538 | -1.742 | 1.00 | 31.00 | A1 |
| ATOM | 111 | CB | GLN | 21 | 51.326 | 60.489 | -2.340 | 1.00 | 32.37 | A1 |
| ATOM | 112 | CG | GLN | 21 | 52.436 | 60.530 | -1.272 | 1.00 | 38.01 | A1 |
| ATOM | 113 | CD | GLN | 21 | 53.622 | 61.460 | -1.504 | 1.00 | 42.67 | A1 |
| ATOM | 114 | OE1 | GLN | 21 | 54.008 | 62.236 | -0.615 | 1.00 | 43.63 | A1 |
| ATOM | 115 | NE2 | GLN | 21 | 54.256 | 61.448 | -2.678 | 1.00 | 42.31 | A1 |
| ATOM | 116 | HE21 | GLN | 21 | 53.965 | 60.840 | -3.384 | 1.00 | 0.00 | A1 |
| ATOM | 117 | HE22 | GLN | 21 | 55.026 | 62.052 | -2.730 | 1.00 | 0.00 | A1 |
| ATOM | 118 | C | GLN | 21 | 48.894 | 59.765 | -2.288 | 1.00 | 28.51 | A1 |
| ATOM | 119 | O | GLN | 21 | 48.027 | 60.242 | -1.563 | 1.00 | 28.65 | A1 |
| ATOM | 120 | N | VAL | 22 | 48.682 | 59.319 | -3.521 | 1.00 | 25.85 | A1 |
| ATOM | 121 | H | VAL | 22 | 49.448 | 58.980 | -4.013 | 1.00 | 0.00 | A1 |
| ATOM | 122 | CA | VAL | 22 | 47.382 | 59.303 | -4.161 | 1.00 | 24.94 | A1 |
| ATOM | 123 | CB | VAL | 22 | 47.508 | 58.614 | -5.526 | 1.00 | 24.09 | A1 |
| ATOM | 124 | CG1 | VAL | 22 | 46.154 | 58.378 | -6.096 | 1.00 | 19.97 | A1 |
| ATOM | 125 | CG2 | VAL | 22 | 48.252 | 59.479 | -6.498 | 1.00 | 25.82 | A1 |
| ATOM | 126 | C | VAL | 22 | 46.418 | 58.549 | -3.226 | 1.00 | 25.65 | A1 |
| ATOM | 127 | O | VAL | 22 | 45.428 | 59.190 | -2.800 | 1.00 | 29.31 | A1 |
| ATOM | 128 | N | ARG | 23 | 46.643 | 57.291 | -2.759 | 1.00 | 23.93 | A1 |
| ATOM | 129 | H | ARG | 23 | 47.440 | 56.819 | -3.056 | 1.00 | 0.00 | A1 |
| ATOM | 130 | CA | ARG | 23 | 45.667 | 56.593 | -1.892 | 1.00 | 20.67 | A1 |
| ATOM | 131 | CB | ARG | 23 | 46.104 | 55.135 | -1.635 | 1.00 | 20.45 | A1 |
| ATOM | 132 | CG | ARG | 23 | 46.325 | 54.321 | -2.904 | 1.00 | 17.51 | A1 |
| ATOM | 133 | CD | ARG | 23 | 45.095 | 54.446 | -3.769 | 1.00 | 21.54 | A1 |
| ATOM | 134 | NE | ARG | 23 | 45.076 | 53.437 | -4.809 | 1.00 | 24.82 | A1 |
| ATOM | 135 | HE | ARG | 23 | 45.642 | 52.647 | -4.701 | 1.00 | 0.00 | A1 |
| ATOM | 136 | CZ | ARG | 23 | 44.323 | 53.556 | -5.904 | 1.00 | 27.69 | A1 |
| ATOM | 137 | NH1 | ARG | 23 | 43.567 | 54.669 | -6.006 | 1.00 | 29.51 | A1 |
| ATOM | 138 | HH11 | ARG | 23 | 43.562 | 55.377 | -5.303 | 1.00 | 0.00 | A1 |
| ATOM | 139 | HH12 | ARG | 23 | 42.956 | 54.730 | -6.789 | 1.00 | 0.00 | A1 |
| ATOM | 140 | NH2 | ARG | 23 | 44.345 | 52.604 | -6.891 | 1.00 | 24.22 | A1 |
| ATOM | 141 | HH21 | ARG | 23 | 43.780 | 52.713 | -7.709 | 1.00 | 0.00 | A1 |
| ATOM | 142 | HH22 | ARG | 23 | 44.936 | 51.802 | -6.793 | 1.00 | 0.00 | A1 |
| ATOM | 143 | C | ARG | 23 | 45.458 | 57.285 | -0.560 | 1.00 | 20.56 | A1 |
| ATOM | 144 | O | ARG | 23 | 44.374 | 57.254 | 0.042 | 1.00 | 20.04 | A1 |
| ATOM | 145 | N | LYS | 24 | 46.485 | 58.015 | -0.118 | 1.00 | 22.67 | A1 |
| ATOM | 146 | H | LYS | 24 | 47.291 | 58.105 | -0.668 | 1.00 | 0.00 | A1 |
| ATOM | 147 | CA | LYS | 24 | 46.431 | 58.729 | 1.166 | 1.00 | 22.85 | A1 |
| ATOM | 148 | CB | LYS | 24 | 47.811 | 59.255 | 1.506 | 1.00 | 26.86 | A1 |
| ATOM | 149 | CG | LYS | 24 | 47.821 | 59.661 | 2.971 | 1.00 | 33.79 | A1 |
| ATOM | 150 | CD | LYS | 24 | 49.121 | 60.265 | 3.404 | 1.00 | 40.73 | A1 |
| ATOM | 151 | CE | LYS | 24 | 50.258 | 59.258 | 3.335 | 1.00 | 46.19 | A1 |
| ATOM | 152 | NZ | LYS | 24 | 51.532 | 59.975 | 3.333 | 1.00 | 51.19 | A1 |
| ATOM | 153 | HZ1 | LYS | 24 | 51.637 | 60.498 | 4.225 | 1.00 | 0.00 | A1 |
| ATOM | 154 | HZ2 | LYS | 24 | 51.539 | 60.651 | 2.539 | 1.00 | 0.00 | A1 |
| ATOM | 155 | HZ3 | LYS | 24 | 52.317 | 59.303 | 3.216 | 1.00 | 0.00 | A1 |
| ATOM | 156 | C | LYS | 24 | 45.455 | 59.893 | 1.101 | 1.00 | 21.66 | A1 |
| ATOM | 157 | O | LYS | 24 | 44.588 | 60.068 | 1.962 | 1.00 | 20.90 | A1 |
| ATOM | 158 | N | ILE | 25 | 45.549 | 60.696 | 0.044 | 1.00 | 21.66 | A1 |
| ATOM | 159 | H | ILE | 25 | 46.242 | 60.509 | -0.629 | 1.00 | 0.00 | A1 |
| ATOM | 160 | CA | ILE | 25 | 44.667 | 61.841 | -0.115 | 1.00 | 22.53 | A1 |
| ATOM | 161 | CB | ILE | 25 | 45.075 | 62.694 | -1.307 | 1.00 | 22.15 | A1 |
| ATOM | 162 | CG2 | ILE | 25 | 44.097 | 63.834 | -1.439 | 1.00 | 20.44 | A1 |
| ATOM | 163 | CG1 | ILE | 25 | 46.475 | 63.230 | -1.136 | 1.00 | 21.03 | A1 |
| ATOM | 164 | CD | ILE | 25 | 47.188 | 63.281 | -2.497 | 1.00 | 20.03 | A1 |
| ATOM | 165 | C | ILE | 25 | 43.263 | 61.308 | -0.352 | 1.00 | 24.75 | A1 |
| ATOM | 166 | O | ILE | 25 | 42.339 | 61.839 | 0.301 | 1.00 | 26.13 | A1 |
| ATOM | 167 | N | GLN | 26 | 43.065 | 60.289 | -1.244 | 1.00 | 22.79 | A1 |
| ATOM | 168 | H | GLN | 26 | 43.842 | 59.926 | -1.726 | 1.00 | 0.00 | A1 |
| ATOM | 169 | CA | GLN | 26 | 41.737 | 59.713 | -1.437 | 1.00 | 20.12 | A1 |
| ATOM | 170 | CB | GLN | 26 | 41.729 | 58.539 | -2.341 | 1.00 | 18.89 | A1 |
| ATOM | 171 | CG | GLN | 26 | 42.203 | 59.042 | -3.627 | 1.00 | 19.77 | A1 |

FIG.5-3

| | | | | | | | | | |
|---|---|---|---|---|---|---|---|---|---|
| ATOM | 172 | CD | GLN | 26 | 42.163 | 57.996 | -4.684 | 1.00 24.26 | A1 |
| ATOM | 173 | OE1 | GLN | 26 | 42.550 | 56.853 | -4.465 | 1.00 26.82 | A1 |
| ATOM | 174 | NE2 | GLN | 26 | 41.732 | 58.351 | -5.890 | 1.00 27.68 | A1 |
| ATOM | 175 | HE21 | GLN | 26 | 41.421 | 59.265 | -6.042 | 1.00 0.00 | A1 |
| ATOM | 176 | HE22 | GLN | 26 | 41.743 | 57.649 | -6.552 | 1.00 0.00 | A1 |
| ATOM | 177 | C | GLN | 26 | 41.207 | 59.239 | -0.111 | 1.00 21.88 | A1 |
| ATOM | 178 | O | GLN | 26 | 40.067 | 59.550 | 0.220 | 1.00 27.02 | A1 |
| ATOM | 179 | N | GLY | 27 | 41.952 | 58.622 | 0.773 | 1.00 22.54 | A1 |
| ATOM | 180 | H | GLY | 27 | 42.891 | 58.420 | 0.576 | 1.00 0.00 | A1 |
| ATOM | 181 | CA | GLY | 27 | 41.386 | 58.191 | 2.037 | 1.00 25.55 | A1 |
| ATOM | 182 | C | GLY | 27 | 40.936 | 59.352 | 2.890 | 1.00 27.80 | A1 |
| ATOM | 183 | O | GLY | 27 | 39.889 | 59.251 | 3.526 | 1.00 29.95 | A1 |
| ATOM | 184 | N | ASP | 28 | 41.683 | 60.460 | 2.915 | 1.00 29.39 | A1 |
| ATOM | 185 | H | ASP | 28 | 42.547 | 60.454 | 2.448 | 1.00 0.00 | A1 |
| ATOM | 186 | CA | ASP | 28 | 41.257 | 61.680 | 3.624 | 1.00 28.45 | A1 |
| ATOM | 187 | CB | ASP | 28 | 42.266 | 62.789 | 3.552 | 1.00 30.13 | A1 |
| ATOM | 188 | CG | ASP | 28 | 43.737 | 62.502 | 3.777 | 1.00 31.72 | A1 |
| ATOM | 189 | OD1 | ASP | 28 | 44.539 | 63.024 | 2.995 | 1.00 31.95 | A1 |
| ATOM | 190 | OD2 | ASP | 28 | 44.063 | 61.811 | 4.741 | 1.00 32.00 | A1 |
| ATOM | 191 | C | ASP | 28 | 39.994 | 62.264 | 2.960 | 1.00 25.81 | A1 |
| ATOM | 192 | O | ASP | 28 | 39.101 | 62.699 | 3.655 | 1.00 26.21 | A1 |
| ATOM | 193 | N | GLY | 29 | 39.882 | 62.270 | 1.631 | 1.00 23.93 | A1 |
| ATOM | 194 | H | GLY | 29 | 40.660 | 61.950 | 1.135 | 1.00 0.00 | A1 |
| ATOM | 195 | CA | GLY | 29 | 38.729 | 62.694 | 0.886 | 1.00 25.69 | A1 |
| ATOM | 196 | C | GLY | 29 | 37.528 | 61.961 | 1.418 | 1.00 27.36 | A1 |
| ATOM | 197 | O | GLY | 29 | 36.648 | 62.558 | 2.061 | 1.00 28.14 | A1 |
| ATOM | 198 | N | ALA | 30 | 37.646 | 60.628 | 1.295 | 1.00 27.85 | A1 |
| ATOM | 199 | H | ALA | 30 | 38.442 | 60.288 | 0.843 | 1.00 0.00 | A1 |
| ATOM | 200 | CA | ALA | 30 | 36.683 | 59.655 | 1.814 | 1.00 25.94 | A1 |
| ATOM | 201 | CB | ALA | 30 | 37.269 | 58.303 | 1.556 | 1.00 22.15 | A1 |
| ATOM | 202 | C | ALA | 30 | 36.356 | 59.842 | 3.308 | 1.00 27.18 | A1 |
| ATOM | 203 | O | ALA | 30 | 35.194 | 59.772 | 3.754 | 1.00 28.82 | A1 |
| ATOM | 204 | N | ALA | 31 | 37.340 | 60.105 | 4.150 | 1.00 27.16 | A1 |
| ATOM | 205 | H | ALA | 31 | 38.253 | 60.114 | 3.809 | 1.00 0.00 | A1 |
| ATOM | 206 | CA | ALA | 31 | 37.113 | 60.470 | 5.531 | 1.00 27.70 | A1 |
| ATOM | 207 | CB | ALA | 31 | 38.383 | 60.881 | 6.177 | 1.00 27.65 | A1 |
| ATOM | 208 | C | ALA | 31 | 36.178 | 61.675 | 5.660 | 1.00 30.01 | A1 |
| ATOM | 209 | O | ALA | 31 | 35.195 | 61.624 | 6.413 | 1.00 32.91 | A1 |
| ATOM | 210 | N | LEU | 32 | 36.397 | 62.744 | 4.895 | 1.00 27.63 | A1 |
| ATOM | 211 | H | LEU | 32 | 37.133 | 62.734 | 4.242 | 1.00 0.00 | A1 |
| ATOM | 212 | CA | LEU | 32 | 35.560 | 63.898 | 4.997 | 1.00 28.52 | A1 |
| ATOM | 213 | CB | LEU | 32 | 36.226 | 65.019 | 4.167 | 1.00 32.94 | A1 |
| ATOM | 214 | CG | LEU | 32 | 35.658 | 66.472 | 4.091 | 1.00 32.54 | A1 |
| ATOM | 215 | CD1 | LEU | 32 | 35.516 | 67.082 | 5.499 | 1.00 32.87 | A1 |
| ATOM | 216 | CD2 | LEU | 32 | 36.555 | 67.267 | 3.181 | 1.00 30.97 | A1 |
| ATOM | 217 | C | LEU | 32 | 34.133 | 63.597 | 4.518 | 1.00 27.87 | A1 |
| ATOM | 218 | O | LEU | 32 | 33.169 | 63.889 | 5.250 | 1.00 25.93 | A1 |
| ATOM | 219 | N | GLN | 33 | 33.977 | 63.028 | 3.315 | 1.00 27.51 | A1 |
| ATOM | 220 | H | GLN | 33 | 34.787 | 62.826 | 2.802 | 1.00 0.00 | A1 |
| ATOM | 221 | CA | GLN | 33 | 32.687 | 62.671 | 2.775 | 1.00 30.40 | A1 |
| ATOM | 222 | CB | GLN | 33 | 32.737 | 61.721 | 1.614 | 1.00 29.47 | A1 |
| ATOM | 223 | CG | GLN | 33 | 32.888 | 62.584 | 0.436 | 1.00 29.26 | A1 |
| ATOM | 224 | CD | GLN | 33 | 33.015 | 61.869 | -0.887 | 1.00 30.21 | A1 |
| ATOM | 225 | OE1 | GLN | 33 | 34.064 | 61.495 | -1.452 | 1.00 29.61 | A1 |
| ATOM | 226 | NE2 | GLN | 33 | 31.823 | 61.759 | -1.426 | 1.00 33.19 | A1 |
| ATOM | 227 | HE21 | GLN | 33 | 31.781 | 61.328 | -2.302 | 1.00 0.00 | A1 |
| ATOM | 228 | HE22 | GLN | 33 | 31.042 | 62.060 | -0.914 | 1.00 0.00 | A1 |
| ATOM | 229 | C | GLN | 33 | 31.839 | 61.963 | 3.788 | 1.00 35.60 | A1 |
| ATOM | 230 | O | GLN | 33 | 30.715 | 62.416 | 4.073 | 1.00 36.49 | A1 |
| ATOM | 231 | N | GLU | 34 | 32.386 | 60.925 | 4.438 | 1.00 39.81 | A1 |
| ATOM | 232 | H | GLU | 34 | 33.340 | 60.707 | 4.328 | 1.00 0.00 | A1 |
| ATOM | 233 | CA | GLU | 34 | 31.541 | 60.131 | 5.304 | 1.00 43.24 | A1 |
| ATOM | 234 | CB | GLU | 34 | 32.228 | 58.792 | 5.571 | 1.00 46.46 | A1 |
| ATOM | 235 | CG | GLU | 34 | 33.274 | 58.721 | 6.624 | 1.00 55.01 | A1 |
| ATOM | 236 | CD | GLU | 34 | 32.777 | 58.092 | 7.930 | 1.00 60.29 | A1 |
| ATOM | 237 | OE1 | GLU | 34 | 33.483 | 57.186 | 8.412 | 1.00 63.26 | A1 |
| ATOM | 238 | OE2 | GLU | 34 | 31.724 | 58.504 | 8.459 | 1.00 60.44 | A1 |
| ATOM | 239 | C | GLU | 34 | 31.218 | 60.877 | 6.564 | 1.00 43.59 | A1 |
| ATOM | 240 | O | GLU | 34 | 30.175 | 60.631 | 7.161 | 1.00 44.87 | A1 |
| ATOM | 241 | N | LYS | 35 | 32.045 | 61.811 | 6.998 | 1.00 44.80 | A1 |
| ATOM | 242 | H | LYS | 35 | 32.923 | 61.931 | 6.569 | 1.00 0.00 | A1 |
| ATOM | 243 | CA | LYS | 35 | 31.674 | 62.634 | 8.134 | 1.00 45.43 | A1 |
| ATOM | 244 | CB | LYS | 35 | 32.881 | 63.364 | 8.686 | 1.00 47.67 | A1 |
| ATOM | 245 | CG | LYS | 35 | 33.701 | 62.414 | 9.510 | 1.00 52.75 | A1 |
| ATOM | 246 | CD | LYS | 35 | 35.084 | 63.021 | 9.548 | 1.00 57.55 | A1 |
| ATOM | 247 | CE | LYS | 35 | 36.067 | 62.099 | 10.238 | 1.00 60.35 | A1 |
| ATOM | 248 | NZ | LYS | 35 | 35.810 | 62.064 | 11.669 | 1.00 62.91 | A1 |
| ATOM | 249 | HZ1 | LYS | 35 | 34.838 | 61.733 | 11.840 | 1.00 0.00 | A1 |
| ATOM | 250 | HZ2 | LYS | 35 | 35.930 | 63.011 | 12.078 | 1.00 0.00 | A1 |
| ATOM | 251 | HZ3 | LYS | 35 | 36.477 | 61.405 | 12.119 | 1.00 0.00 | A1 |
| ATOM | 252 | C | LYS | 35 | 30.630 | 63.660 | 7.697 | 1.00 44.45 | A1 |
| ATOM | 253 | O | LYS | 35 | 29.730 | 63.999 | 8.478 | 1.00 44.61 | A1 |
| ATOM | 254 | N | LEU | 36 | 30.652 | 64.190 | 6.480 | 1.00 41.21 | A1 |
| ATOM | 255 | H | LEU | 36 | 31.343 | 63.930 | 5.836 | 1.00 0.00 | A1 |
| ATOM | 256 | CA | LEU | 36 | 29.647 | 65.157 | 6.144 | 1.00 40.25 | A1 |
| ATOM | 257 | CB | LEU | 36 | 30.070 | 65.899 | 4.889 | 1.00 39.03 | A1 |

FIG.5-4

| | | | | | | | | | |
|---|---|---|---|---|---|---|---|---|---|
| ATOM | 258 | CG | LEU | 36 | 31.253 | 66.834 | 4.935 | 1.00 33.99 | A1 |
| ATOM | 259 | CD1 | LEU | 36 | 31.438 | 67.404 | 3.571 | 1.00 32.08 | A1 |
| ATOM | 260 | CD2 | LEU | 36 | 31.034 | 67.939 | 5.928 | 1.00 35.05 | A1 |
| ATOM | 261 | C | LEU | 36 | 28.332 | 64.414 | 5.941 | 1.00 41.90 | A1 |
| ATOM | 262 | O | LEU | 36 | 27.267 | 64.828 | 6.431 | 1.00 42.30 | A1 |
| ATOM | 263 | N | CYS | 37 | 28.392 | 63.251 | 5.309 | 1.00 42.63 | A1 |
| ATOM | 264 | H | CYS | 37 | 29.250 | 62.904 | 5.020 | 1.00 0.00 | A1 |
| ATOM | 265 | CA | CYS | 37 | 27.216 | 62.469 | 5.084 | 1.00 43.53 | A1 |
| ATOM | 266 | C | CYS | 37 | 26.638 | 62.026 | 6.362 | 1.00 44.65 | A1 |
| ATOM | 267 | O | CYS | 37 | 25.426 | 61.997 | 6.459 | 1.00 46.40 | A1 |
| ATOM | 268 | CB | CYS | 37 | 27.474 | 61.240 | 4.313 | 1.00 44.60 | A1 |
| ATOM | 269 | SG | CYS | 37 | 26.133 | 60.038 | 4.530 | 1.00 43.86 | A1 |
| ATOM | 270 | N | ALA | 38 | 27.465 | 61.734 | 7.342 | 1.00 45.96 | A1 |
| ATOM | 271 | H | ALA | 38 | 28.433 | 61.707 | 7.202 | 1.00 0.00 | A1 |
| ATOM | 272 | CA | ALA | 38 | 26.932 | 61.261 | 8.592 | 1.00 48.03 | A1 |
| ATOM | 273 | CB | ALA | 38 | 27.869 | 60.140 | 9.108 | 1.00 48.64 | A1 |
| ATOM | 274 | C | ALA | 38 | 26.748 | 62.358 | 9.624 | 1.00 48.89 | A1 |
| ATOM | 275 | O | ALA | 38 | 26.103 | 62.085 | 10.621 | 1.00 50.72 | A1 |
| ATOM | 276 | N | THR | 39 | 27.256 | 63.590 | 9.512 | 1.00 50.66 | A1 |
| ATOM | 277 | H | THR | 39 | 27.858 | 63.780 | 8.770 | 1.00 0.00 | A1 |
| ATOM | 278 | CA | THR | 39 | 26.976 | 64.638 | 10.503 | 1.00 51.54 | A1 |
| ATOM | 279 | CB | THR | 39 | 28.179 | 65.593 | 10.690 | 1.00 51.76 | A1 |
| ATOM | 280 | OG1 | THR | 39 | 29.294 | 64.826 | 11.126 | 1.00 52.65 | A1 |
| ATOM | 281 | HG1 | THR | 39 | 29.749 | 64.481 | 10.355 | 1.00 0.00 | A1 |
| ATOM | 282 | CG2 | THR | 39 | 27.900 | 66.655 | 11.729 | 1.00 51.62 | A1 |
| ATOM | 283 | C | THR | 39 | 25.775 | 65.466 | 10.037 | 1.00 52.17 | A1 |
| ATOM | 284 | O | THR | 39 | 24.886 | 65.882 | 10.781 | 1.00 52.15 | A1 |
| ATOM | 285 | N | TYR | 40 | 25.751 | 65.720 | 8.738 | 1.00 52.83 | A1 |
| ATOM | 286 | H | TYR | 40 | 26.420 | 65.331 | 8.139 | 1.00 0.00 | A1 |
| ATOM | 287 | CA | TYR | 40 | 24.729 | 66.561 | 8.165 | 1.00 52.53 | A1 |
| ATOM | 288 | CB | TYR | 40 | 25.314 | 67.872 | 7.696 | 1.00 52.15 | A1 |
| ATOM | 289 | CG | TYR | 40 | 26.399 | 68.458 | 8.552 | 1.00 54.11 | A1 |
| ATOM | 290 | CD1 | TYR | 40 | 27.678 | 68.341 | 8.062 | 1.00 56.50 | A1 |
| ATOM | 291 | CE1 | TYR | 40 | 28.719 | 68.934 | 8.724 | 1.00 58.28 | A1 |
| ATOM | 292 | CD2 | TYR | 40 | 26.122 | 69.144 | 9.714 | 1.00 54.86 | A1 |
| ATOM | 293 | CE2 | TYR | 40 | 27.170 | 69.746 | 10.378 | 1.00 56.20 | A1 |
| ATOM | 294 | CZ | TYR | 40 | 28.453 | 69.642 | 9.872 | 1.00 58.26 | A1 |
| ATOM | 295 | OH | TYR | 40 | 29.513 | 70.310 | 10.463 | 1.00 61.00 | A1 |
| ATOM | 296 | HH | TYR | 40 | 30.179 | 70.443 | 9.782 | 1.00 0.00 | A1 |
| ATOM | 297 | C | TYR | 40 | 24.035 | 65.911 | 6.981 | 1.00 51.75 | A1 |
| ATOM | 298 | O | TYR | 40 | 23.662 | 66.578 | 6.024 | 1.00 52.52 | A1 |
| ATOM | 299 | N | LYS | 41 | 23.941 | 64.600 | 6.965 | 1.00 50.54 | A1 |
| ATOM | 300 | H | LYS | 41 | 24.474 | 64.064 | 7.583 | 1.00 0.00 | A1 |
| ATOM | 301 | CA | LYS | 41 | 23.112 | 63.885 | 6.029 | 1.00 50.48 | A1 |
| ATOM | 302 | CB | LYS | 41 | 21.641 | 63.989 | 6.540 | 1.00 50.62 | A1 |
| ATOM | 303 | CG | LYS | 41 | 21.387 | 63.326 | 7.911 | 1.00 52.11 | A1 |
| ATOM | 304 | CD | LYS | 41 | 20.112 | 63.878 | 8.574 | 1.00 55.54 | A1 |
| ATOM | 305 | CE | LYS | 41 | 19.578 | 63.087 | 9.820 | 1.00 58.79 | A1 |
| ATOM | 306 | NZ | LYS | 41 | 18.374 | 63.648 | 10.457 | 1.00 58.31 | A1 |
| ATOM | 307 | HZ1 | LYS | 41 | 17.605 | 63.688 | 9.757 | 1.00 0.00 | A1 |
| ATOM | 308 | HZ2 | LYS | 41 | 18.578 | 64.607 | 10.803 | 1.00 0.00 | A1 |
| ATOM | 309 | HZ3 | LYS | 41 | 18.084 | 63.043 | 11.252 | 1.00 0.00 | A1 |
| ATOM | 310 | C | LYS | 41 | 23.251 | 64.318 | 4.588 | 1.00 49.92 | A1 |
| ATOM | 311 | O | LYS | 41 | 22.312 | 64.124 | 3.793 | 1.00 51.49 | A1 |
| ATOM | 312 | N | LEU | 42 | 24.432 | 64.893 | 4.246 | 1.00 48.28 | A1 |
| ATOM | 313 | H | LEU | 42 | 25.103 | 65.050 | 4.937 | 1.00 0.00 | A1 |
| ATOM | 314 | CA | LEU | 42 | 24.742 | 65.286 | 2.859 | 1.00 46.61 | A1 |
| ATOM | 315 | CB | LEU | 42 | 25.565 | 66.574 | 2.757 | 1.00 44.69 | A1 |
| ATOM | 316 | CG | LEU | 42 | 24.807 | 67.802 | 3.218 | 1.00 42.63 | A1 |
| ATOM | 317 | CD1 | LEU | 42 | 25.718 | 68.580 | 4.097 | 1.00 43.29 | A1 |
| ATOM | 318 | CD2 | LEU | 42 | 24.283 | 68.590 | 2.045 | 1.00 41.26 | A1 |
| ATOM | 319 | C | LEU | 42 | 25.580 | 64.124 | 2.397 | 1.00 43.90 | A1 |
| ATOM | 320 | O | LEU | 42 | 26.766 | 64.017 | 2.711 | 1.00 46.32 | A1 |
| ATOM | 321 | N | CYS | 43 | 24.882 | 63.193 | 1.754 | 1.00 44.09 | A1 |
| ATOM | 322 | H | CYS | 43 | 23.925 | 63.353 | 1.619 | 1.00 0.00 | A1 |
| ATOM | 323 | CA | CYS | 43 | 25.480 | 61.951 | 1.358 | 1.00 42.87 | A1 |
| ATOM | 324 | C | CYS | 43 | 25.448 | 61.846 | -0.123 | 1.00 41.62 | A1 |
| ATOM | 325 | O | CYS | 43 | 25.762 | 60.805 | -0.666 | 1.00 41.99 | A1 |
| ATOM | 326 | CB | CYS | 43 | 24.716 | 60.796 | 2.026 | 1.00 41.77 | A1 |
| ATOM | 327 | SG | CYS | 43 | 24.523 | 61.011 | 3.835 | 1.00 45.91 | A1 |
| ATOM | 328 | N | HIS | 44 | 25.057 | 62.846 | -0.882 | 1.00 42.90 | A1 |
| ATOM | 329 | H | HIS | 44 | 24.841 | 63.721 | -0.491 | 1.00 0.00 | A1 |
| ATOM | 330 | CA | HIS | 44 | 25.069 | 62.680 | -2.320 | 1.00 44.60 | A1 |
| ATOM | 331 | CB | HIS | 44 | 23.653 | 62.264 | -2.825 | 1.00 48.40 | A1 |
| ATOM | 332 | CG | HIS | 44 | 23.085 | 60.935 | -2.310 | 1.00 50.37 | A1 |
| ATOM | 333 | CD2 | HIS | 44 | 22.178 | 60.844 | -1.272 | 1.00 50.52 | A1 |
| ATOM | 334 | ND1 | HIS | 44 | 23.358 | 59.689 | -2.713 | 1.00 52.28 | A1 |
| ATOM | 335 | HD1 | HIS | 44 | 24.130 | 59.394 | -3.251 | 1.00 0.00 | A1 |
| ATOM | 336 | CE1 | HIS | 44 | 22.652 | 58.873 | -1.955 | 1.00 51.92 | A1 |
| ATOM | 337 | NE2 | HIS | 44 | 21.947 | 59.565 | -1.091 | 1.00 50.53 | A1 |
| ATOM | 338 | HE2 | HIS | 44 | 21.290 | 59.189 | -0.466 | 1.00 0.00 | A1 |
| ATOM | 339 | C | HIS | 44 | 25.522 | 63.941 | -3.047 | 1.00 43.69 | A1 |
| ATOM | 340 | O | HIS | 44 | 24.765 | 64.906 | -3.108 | 1.00 43.00 | A1 |
| ATOM | 341 | N | PRO | 45 | 26.710 | 63.978 | -3.667 | 1.00 43.07 | A1 |
| ATOM | 342 | CD | PRO | 45 | 27.785 | 62.995 | -3.501 | 1.00 42.17 | A1 |
| ATOM | 343 | CA | PRO | 45 | 27.133 | 65.024 | -4.570 | 1.00 42.50 | A1 |

FIG.5-5

| | | | | | | | | | |
|---|---|---|---|---|---|---|---|---|---|
| ATOM | 344 | CB | PRO | 45 | 28.380 | 64.466 | -5.217 | 1.00 39.76 | A1 |
| ATOM | 345 | CG | PRO | 45 | 28.995 | 63.680 | -4.123 | 1.00 39.09 | A1 |
| ATOM | 346 | C | PRO | 45 | 26.071 | 65.423 | -5.585 | 1.00 44.49 | A1 |
| ATOM | 347 | O | PRO | 45 | 25.876 | 66.612 | -5.801 | 1.00 45.36 | A1 |
| ATOM | 348 | N | GLU | 46 | 25.334 | 64.501 | -6.225 | 1.00 45.36 | A1 |
| ATOM | 349 | H | GLU | 46 | 25.464 | 63.561 | -5.996 | 1.00 0.00 | A1 |
| ATOM | 350 | CA | GLU | 46 | 24.406 | 64.806 | -7.319 | 1.00 45.46 | A1 |
| ATOM | 351 | CB | GLU | 46 | 23.952 | 63.515 | -7.997 | 1.00 50.54 | A1 |
| ATOM | 352 | CG | GLU | 46 | 24.462 | 63.460 | -9.445 | 1.00 58.48 | A1 |
| ATOM | 353 | CD | GLU | 46 | 23.637 | 64.215 | -10.502 | 1.00 64.93 | A1 |
| ATOM | 354 | OE1 | GLU | 46 | 23.642 | 65.455 | -10.516 | 1.00 68.55 | A1 |
| ATOM | 355 | OE2 | GLU | 46 | 22.995 | 63.554 | -11.332 | 1.00 68.31 | A1 |
| ATOM | 356 | C | GLU | 46 | 23.181 | 65.584 | -6.937 | 1.00 42.96 | A1 |
| ATOM | 357 | O | GLU | 46 | 22.532 | 66.223 | -7.748 | 1.00 41.71 | A1 |
| ATOM | 358 | N | GLU | 47 | 22.919 | 65.563 | -5.654 | 1.00 41.96 | A1 |
| ATOM | 359 | H | GLU | 47 | 23.507 | 65.098 | -5.028 | 1.00 0.00 | A1 |
| ATOM | 360 | CA | GLU | 47 | 21.818 | 66.301 | -5.144 | 1.00 43.21 | A1 |
| ATOM | 361 | CB | GLU | 47 | 21.294 | 65.487 | -3.963 | 1.00 43.24 | A1 |
| ATOM | 362 | CG | GLU | 47 | 21.409 | 65.925 | -2.515 | 1.00 46.07 | A1 |
| ATOM | 363 | CD | GLU | 47 | 20.812 | 64.907 | -1.547 | 1.00 47.86 | A1 |
| ATOM | 364 | OE1 | GLU | 47 | 19.847 | 64.225 | -1.910 | 1.00 50.99 | A1 |
| ATOM | 365 | OE2 | GLU | 47 | 21.313 | 64.780 | -0.427 | 1.00 49.47 | A1 |
| ATOM | 366 | C | GLU | 47 | 22.295 | 67.718 | -4.809 | 1.00 44.04 | A1 |
| ATOM | 367 | O | GLU | 47 | 21.532 | 68.547 | -4.292 | 1.00 44.60 | A1 |
| ATOM | 368 | N | LEU | 48 | 23.567 | 68.015 | -5.121 | 1.00 43.05 | A1 |
| ATOM | 369 | H | LEU | 48 | 24.140 | 67.310 | -5.465 | 1.00 0.00 | A1 |
| ATOM | 370 | CA | LEU | 48 | 24.166 | 69.318 | -4.904 | 1.00 42.42 | A1 |
| ATOM | 371 | CB | LEU | 48 | 25.223 | 69.201 | -3.858 | 1.00 40.53 | A1 |
| ATOM | 372 | CG | LEU | 48 | 24.920 | 68.695 | -2.489 | 1.00 41.87 | A1 |
| ATOM | 373 | CD1 | LEU | 48 | 26.277 | 68.424 | -1.892 | 1.00 41.71 | A1 |
| ATOM | 374 | CD2 | LEU | 48 | 24.096 | 69.670 | -1.633 | 1.00 41.13 | A1 |
| ATOM | 375 | C | LEU | 48 | 24.792 | 69.937 | -6.166 | 1.00 42.37 | A1 |
| ATOM | 376 | O | LEU | 48 | 25.439 | 70.994 | -6.098 | 1.00 42.37 | A1 |
| ATOM | 377 | N | VAL | 49 | 24.566 | 69.366 | -7.347 | 1.00 41.52 | A1 |
| ATOM | 378 | H | VAL | 49 | 23.951 | 68.602 | -7.362 | 1.00 0.00 | A1 |
| ATOM | 379 | CA | VAL | 49 | 25.191 | 69.822 | -8.578 | 1.00 43.34 | A1 |
| ATOM | 380 | CB | VAL | 49 | 24.890 | 68.761 | -9.636 | 1.00 44.29 | A1 |
| ATOM | 381 | CG1 | VAL | 49 | 23.381 | 68.709 | -9.830 | 1.00 47.50 | A1 |
| ATOM | 382 | CG2 | VAL | 49 | 25.540 | 69.086 | -10.975 | 1.00 45.25 | A1 |
| ATOM | 383 | C | VAL | 49 | 24.740 | 71.214 | -9.028 | 1.00 44.98 | A1 |
| ATOM | 384 | O | VAL | 49 | 25.401 | 71.901 | -9.814 | 1.00 46.03 | A1 |
| ATOM | 385 | N | LEU | 50 | 23.565 | 71.602 | -8.530 | 1.00 46.16 | A1 |
| ATOM | 386 | H | LEU | 50 | 23.081 | 70.933 | -8.006 | 1.00 0.00 | A1 |
| ATOM | 387 | CA | LEU | 50 | 22.908 | 72.895 | -8.729 | 1.00 46.03 | A1 |
| ATOM | 388 | CB | LEU | 50 | 21.469 | 72.769 | -8.264 | 1.00 46.43 | A1 |
| ATOM | 389 | CG | LEU | 50 | 20.443 | 73.718 | -8.760 | 1.00 44.16 | A1 |
| ATOM | 390 | CD1 | LEU | 50 | 20.259 | 73.558 | -10.243 | 1.00 44.79 | A1 |
| ATOM | 391 | CD2 | LEU | 50 | 19.159 | 73.400 | -8.079 | 1.00 44.66 | A1 |
| ATOM | 392 | C | LEU | 50 | 23.632 | 73.968 | -7.917 | 1.00 45.85 | A1 |
| ATOM | 393 | O | LEU | 50 | 23.996 | 74.989 | -8.484 | 1.00 44.52 | A1 |
| ATOM | 394 | N | LEU | 51 | 23.853 | 73.764 | -6.606 | 1.00 45.44 | A1 |
| ATOM | 395 | H | LEU | 51 | 23.489 | 72.958 | -6.189 | 1.00 0.00 | A1 |
| ATOM | 396 | CA | LEU | 51 | 24.676 | 74.656 | -5.805 | 1.00 46.04 | A1 |
| ATOM | 397 | CB | LEU | 51 | 24.860 | 74.084 | -4.435 | 1.00 45.53 | A1 |
| ATOM | 398 | CG | LEU | 51 | 25.741 | 74.931 | -3.535 | 1.00 47.78 | A1 |
| ATOM | 399 | CD1 | LEU | 51 | 25.148 | 76.320 | -3.322 | 1.00 47.13 | A1 |
| ATOM | 400 | CD2 | LEU | 51 | 25.902 | 74.202 | -2.219 | 1.00 48.33 | A1 |
| ATOM | 401 | C | LEU | 51 | 26.064 | 74.845 | -6.436 | 1.00 46.27 | A1 |
| ATOM | 402 | O | LEU | 51 | 26.551 | 75.966 | -6.612 | 1.00 47.62 | A1 |
| ATOM | 403 | N | GLY | 52 | 26.702 | 73.736 | -6.809 | 1.00 44.84 | A1 |
| ATOM | 404 | H | GLY | 52 | 26.306 | 72.869 | -6.578 | 1.00 0.00 | A1 |
| ATOM | 405 | CA | GLY | 52 | 27.989 | 73.758 | -7.453 | 1.00 42.91 | A1 |
| ATOM | 406 | C | GLY | 52 | 27.984 | 74.533 | -8.750 | 1.00 42.47 | A1 |
| ATOM | 407 | O | GLY | 52 | 28.853 | 75.364 | -8.983 | 1.00 42.06 | A1 |
| ATOM | 408 | N | HIS | 53 | 27.047 | 74.307 | -9.653 | 1.00 42.02 | A1 |
| ATOM | 409 | H | HIS | 53 | 26.366 | 73.624 | -9.471 | 1.00 0.00 | A1 |
| ATOM | 410 | CA | HIS | 53 | 27.009 | 75.104 | -10.861 | 1.00 42.23 | A1 |
| ATOM | 411 | CB | HIS | 53 | 25.842 | 74.689 | -11.706 | 1.00 42.21 | A1 |
| ATOM | 412 | CG | HIS | 53 | 26.076 | 73.399 | -12.460 | 1.00 44.60 | A1 |
| ATOM | 413 | CD2 | HIS | 53 | 25.112 | 72.774 | -13.200 | 1.00 47.49 | A1 |
| ATOM | 414 | ND1 | HIS | 53 | 27.180 | 72.669 | -12.578 | 1.00 46.76 | A1 |
| ATOM | 415 | HD1 | HIS | 53 | 28.039 | 72.853 | -12.139 | 1.00 0.00 | A1 |
| ATOM | 416 | CE1 | HIS | 53 | 26.954 | 71.641 | -13.346 | 1.00 46.90 | A1 |
| ATOM | 417 | NE2 | HIS | 53 | 25.704 | 71.725 | -13.707 | 1.00 50.22 | A1 |
| ATOM | 418 | HE2 | HIS | 53 | 25.237 | 71.033 | -14.239 | 1.00 0.00 | A1 |
| ATOM | 419 | C | HIS | 53 | 26.893 | 76.585 | -10.536 | 1.00 42.72 | A1 |
| ATOM | 420 | O | HIS | 53 | 27.622 | 77.399 | -11.068 | 1.00 42.03 | A1 |
| ATOM | 421 | N | SER | 54 | 26.099 | 76.920 | -9.535 | 1.00 45.08 | A1 |
| ATOM | 422 | H | SER | 54 | 25.673 | 76.218 | -9.001 | 1.00 0.00 | A1 |
| ATOM | 423 | CA | SER | 54 | 25.792 | 78.278 | -9.177 | 1.00 46.92 | A1 |
| ATOM | 424 | CB | SER | 54 | 24.576 | 78.181 | -8.289 | 1.00 48.86 | A1 |
| ATOM | 425 | OG | SER | 54 | 23.521 | 77.616 | -9.112 | 1.00 53.06 | A1 |
| ATOM | 426 | HG | SER | 54 | 23.465 | 76.677 | -8.918 | 1.00 0.00 | A1 |
| ATOM | 427 | C | SER | 54 | 26.939 | 79.033 | -8.549 | 1.00 47.92 | A1 |
| ATOM | 428 | O | SER | 54 | 27.038 | 80.264 | -8.655 | 1.00 49.60 | A1 |
| ATOM | 429 | N | LEU | 55 | 27.837 | 78.273 | -7.933 | 1.00 47.59 | A1 |

FIG. 5-6

| | | | | | | | | | |
|---|---|---|---|---|---|---|---|---|---|
| ATOM | 430 | H | LEU | 55 | 27.638 | 77.322 | -7.791 | 1.00 0.00 | A1 |
| ATOM | 431 | CA | LEU | 55 | 29.075 | 78.810 | -7.401 | 1.00 45.27 | A1 |
| ATOM | 432 | CB | LEU | 55 | 29.552 | 77.913 | -6.243 | 1.00 45.49 | A1 |
| ATOM | 433 | CG | LEU | 55 | 28.840 | 77.992 | -4.874 | 1.00 47.30 | A1 |
| ATOM | 434 | CD1 | LEU | 55 | 28.876 | 76.596 | -4.299 | 1.00 49.52 | A1 |
| ATOM | 435 | CD2 | LEU | 55 | 29.530 | 78.921 | -3.862 | 1.00 45.69 | A1 |
| ATOM | 436 | C | LEU | 55 | 30.133 | 78.889 | -8.492 | 1.00 43.63 | A1 |
| ATOM | 437 | O | LEU | 55 | 31.247 | 79.350 | -8.272 | 1.00 43.24 | A1 |
| ATOM | 438 | N | GLY | 56 | 29.855 | 78.383 | -9.675 | 1.00 43.55 | A1 |
| ATOM | 439 | H | GLY | 56 | 28.984 | 77.975 | -9.828 | 1.00 0.00 | A1 |
| ATOM | 440 | CA | GLY | 56 | 30.814 | 78.390 | -10.753 | 1.00 45.59 | A1 |
| ATOM | 441 | C | GLY | 56 | 32.182 | 77.811 | -10.392 | 1.00 46.76 | A1 |
| ATOM | 442 | O | GLY | 56 | 33.171 | 78.213 | -11.015 | 1.00 47.31 | A1 |
| ATOM | 443 | N | ILE | 57 | 32.247 | 76.885 | -9.412 | 1.00 47.49 | A1 |
| ATOM | 444 | H | ILE | 57 | 31.392 | 76.594 | -9.042 | 1.00 0.00 | A1 |
| ATOM | 445 | CA | ILE | 57 | 33.486 | 76.249 | -8.950 | 1.00 48.28 | A1 |
| ATOM | 446 | CB | ILE | 57 | 33.144 | 75.172 | -7.863 | 1.00 47.79 | A1 |
| ATOM | 447 | CG2 | ILE | 57 | 34.457 | 74.591 | -7.348 | 1.00 46.85 | A1 |
| ATOM | 448 | CG1 | ILE | 57 | 32.338 | 75.764 | -6.701 | 1.00 45.09 | A1 |
| ATOM | 449 | CD | ILE | 57 | 31.859 | 74.739 | -5.659 | 1.00 41.23 | A1 |
| ATOM | 450 | C | ILE | 57 | 34.276 | 75.602 | -10.115 | 1.00 49.15 | A1 |
| ATOM | 451 | O | ILE | 57 | 33.678 | 74.935 | -10.968 | 1.00 49.04 | A1 |
| ATOM | 452 | N | PRO | 58 | 35.596 | 75.817 | -10.248 | 1.00 49.75 | A1 |
| ATOM | 453 | CD | PRO | 58 | 36.402 | 76.743 | -9.433 | 1.00 50.94 | A1 |
| ATOM | 454 | CA | PRO | 58 | 36.421 | 75.228 | -11.302 | 1.00 50.72 | A1 |
| ATOM | 455 | CB | PRO | 58 | 37.525 | 76.241 | -11.488 | 1.00 50.92 | A1 |
| ATOM | 456 | CG | PRO | 58 | 37.814 | 76.663 | -10.041 | 1.00 50.82 | A1 |
| ATOM | 457 | C | PRO | 58 | 36.916 | 73.845 | -10.875 | 1.00 50.36 | A1 |
| ATOM | 458 | O | PRO | 58 | 37.187 | 73.599 | -9.691 | 1.00 49.75 | A1 |
| ATOM | 459 | N | TRP | 59 | 37.030 | 72.927 | -11.816 | 1.00 50.37 | A1 |
| ATOM | 460 | H | TRP | 59 | 36.888 | 73.141 | -12.760 | 1.00 0.00 | A1 |
| ATOM | 461 | CA | TRP | 59 | 37.524 | 71.595 | -11.482 | 1.00 51.78 | A1 |
| ATOM | 462 | CB | TRP | 59 | 36.435 | 70.562 | -11.857 | 1.00 49.06 | A1 |
| ATOM | 463 | CG | TRP | 59 | 35.254 | 70.712 | -10.889 | 1.00 46.37 | A1 |
| ATOM | 464 | CD2 | TRP | 59 | 35.320 | 70.845 | -9.521 | 1.00 44.06 | A1 |
| ATOM | 465 | CE2 | TRP | 59 | 33.998 | 71.027 | -9.205 | 1.00 44.18 | A1 |
| ATOM | 466 | CE3 | TRP | 59 | 36.274 | 70.842 | -8.538 | 1.00 44.03 | A1 |
| ATOM | 467 | CD1 | TRP | 59 | 33.972 | 70.794 | -11.354 | 1.00 45.17 | A1 |
| ATOM | 468 | NE1 | TRP | 59 | 33.229 | 70.994 | -10.297 | 1.00 43.17 | A1 |
| ATOM | 469 | HE1 | TRP | 59 | 32.301 | 71.312 | -10.332 | 1.00 0.00 | A1 |
| ATOM | 470 | CZ2 | TRP | 59 | 33.598 | 71.215 | -7.916 | 1.00 45.60 | A1 |
| ATOM | 471 | CZ3 | TRP | 59 | 35.893 | 71.028 | -7.243 | 1.00 45.25 | A1 |
| ATOM | 472 | CH2 | TRP | 59 | 34.565 | 71.214 | -6.938 | 1.00 46.43 | A1 |
| ATOM | 473 | C | TRP | 59 | 38.815 | 71.435 | -12.256 | 1.00 52.84 | A1 |
| ATOM | 474 | O | TRP | 59 | 38.842 | 71.972 | -13.372 | 1.00 54.96 | A1 |
| ATOM | 475 | N | ALA | 60 | 39.912 | 70.834 | -11.777 | 1.00 51.97 | A1 |
| ATOM | 476 | H | ALA | 60 | 39.857 | 70.269 | -10.977 | 1.00 0.00 | A1 |
| ATOM | 477 | CA | ALA | 60 | 41.108 | 70.870 | -12.609 | 1.00 52.18 | A1 |
| ATOM | 478 | CB | ALA | 60 | 42.303 | 70.610 | -11.748 | 1.00 51.75 | A1 |
| ATOM | 479 | C | ALA | 60 | 41.055 | 69.857 | -13.746 | 1.00 52.16 | A1 |
| ATOM | 480 | O | ALA | 60 | 40.545 | 68.760 | -13.530 | 1.00 52.17 | A1 |
| ATOM | 481 | N | PRO | 61 | 41.435 | 70.145 | -14.986 | 1.00 53.34 | A1 |
| ATOM | 482 | CD | PRO | 61 | 41.370 | 71.458 | -15.622 | 1.00 54.76 | A1 |
| ATOM | 483 | CA | PRO | 61 | 41.691 | 69.145 | -15.993 | 1.00 55.57 | A1 |
| ATOM | 484 | CB | PRO | 61 | 41.792 | 69.918 | -17.310 | 1.00 54.95 | A1 |
| ATOM | 485 | CG | PRO | 61 | 42.211 | 71.297 | -16.901 | 1.00 54.05 | A1 |
| ATOM | 486 | C | PRO | 61 | 42.934 | 68.333 | -15.690 | 1.00 57.54 | A1 |
| ATOM | 487 | O | PRO | 61 | 43.757 | 68.661 | -14.834 | 1.00 57.20 | A1 |
| ATOM | 488 | N | LEU | 62 | 43.040 | 67.271 | -16.486 | 1.00 59.98 | A1 |
| ATOM | 489 | H | LEU | 62 | 42.285 | 67.067 | -17.077 | 1.00 0.00 | A1 |
| ATOM | 490 | CA | LEU | 62 | 44.184 | 66.370 | -16.471 | 1.00 63.64 | A1 |
| ATOM | 491 | CB | LEU | 62 | 44.062 | 65.417 | -15.260 | 1.00 63.72 | A1 |
| ATOM | 492 | CG | LEU | 62 | 45.323 | 64.691 | -14.865 | 1.00 64.43 | A1 |
| ATOM | 493 | CD1 | LEU | 62 | 46.394 | 65.704 | -14.488 | 1.00 64.02 | A1 |
| ATOM | 494 | CD2 | LEU | 62 | 45.016 | 63.764 | -13.717 | 1.00 64.98 | A1 |
| ATOM | 495 | C | LEU | 62 | 44.214 | 65.611 | -17.812 | 1.00 65.69 | A2 |
| ATOM | 496 | OT1 | LEU | 62 | 44.256 | 66.302 | -18.844 | 1.00 68.47 | A2 |
| ATOM | 497 | OT2 | LEU | 62 | 44.194 | 64.371 | -17.845 | 1.00 66.57 | A2 |
| ATOM | 498 | CB | LEU | 72 | 57.448 | 63.159 | -19.422 | 1.00 63.44 | A2 |
| ATOM | 499 | CG | LEU | 72 | 57.716 | 62.495 | -18.117 | 1.00 63.40 | A2 |
| ATOM | 500 | CD1 | LEU | 72 | 56.719 | 61.408 | -17.913 | 1.00 61.50 | A2 |
| ATOM | 501 | CD2 | LEU | 72 | 59.107 | 61.901 | -18.121 | 1.00 63.22 | A2 |
| ATOM | 502 | C | LEU | 72 | 55.897 | 65.084 | -18.876 | 1.00 65.40 | A2 |
| ATOM | 503 | O | LEU | 72 | 54.827 | 65.301 | -18.316 | 1.00 67.30 | A2 |
| ATOM | 504 | HT1 | LEU | 72 | 56.469 | 64.683 | -21.261 | 1.00 0.00 | A2 |
| ATOM | 505 | HT2 | LEU | 72 | 54.827 | 64.355 | -20.951 | 1.00 0.00 | A2 |
| ATOM | 506 | N | LEU | 72 | 55.795 | 63.983 | -20.899 | 1.00 66.29 | A2 |
| ATOM | 507 | HT3 | LEU | 72 | 55.866 | 63.098 | -21.439 | 1.00 0.00 | A2 |
| ATOM | 508 | CA | LEU | 72 | 56.064 | 63.714 | -19.512 | 1.00 64.91 | A2 |
| ATOM | 509 | N | ALA | 73 | 56.807 | 66.046 | -19.086 | 1.00 64.54 | A2 |
| ATOM | 510 | H | ALA | 73 | 57.690 | 65.804 | -19.432 | 1.00 0.00 | A2 |
| ATOM | 511 | CA | ALA | 73 | 56.707 | 67.433 | -18.615 | 1.00 62.55 | A2 |
| ATOM | 512 | CB | ALA | 73 | 57.553 | 68.314 | -19.529 | 1.00 64.84 | A2 |
| ATOM | 513 | C | ALA | 73 | 55.319 | 68.024 | -18.539 | 1.00 60.37 | A2 |
| ATOM | 514 | O | ALA | 73 | 54.801 | 68.180 | -17.456 | 1.00 59.42 | A2 |
| ATOM | 515 | N | GLY | 74 | 54.693 | 68.226 | -19.691 | 1.00 59.72 | A2 |

FIG.5-7

| | | | | | | | | | |
|---|---|---|---|---|---|---|---|---|---|
| ATOM | 516 | H | GLY | 74 | 55.212 | 68.174 | -20.514 | 1.00 0.00 | A2 |
| ATOM | 517 | CA | GLY | 74 | 53.336 | 68.728 | -19.816 | 1.00 59.99 | A2 |
| ATOM | 518 | C | GLY | 74 | 52.327 | 68.114 | -18.865 | 1.00 60.27 | A2 |
| ATOM | 519 | O | GLY | 74 | 51.880 | 68.796 | -17.935 | 1.00 60.80 | A2 |
| ATOM | 520 | N | CYS | 75 | 51.945 | 66.850 | -19.030 | 1.00 59.60 | A2 |
| ATOM | 521 | H | CYS | 75 | 52.160 | 66.358 | -19.839 | 1.00 0.00 | A2 |
| ATOM | 522 | CA | CYS | 75 | 51.002 | 66.276 | -18.078 | 1.00 60.17 | A2 |
| ATOM | 523 | CB | CYS | 75 | 50.670 | 64.801 | -18.464 | 1.00 64.08 | A2 |
| ATOM | 524 | SG | CYS | 75 | 49.832 | 64.732 | -20.096 | 1.00 73.47 | A2 |
| ATOM | 525 | C | CYS | 75 | 51.502 | 66.346 | -16.642 | 1.00 56.73 | A2 |
| ATOM | 526 | O | CYS | 75 | 50.734 | 66.748 | -15.765 | 1.00 55.82 | A2 |
| ATOM | 527 | N | LEU | 76 | 52.795 | 66.142 | -16.396 | 1.00 53.93 | A2 |
| ATOM | 528 | H | LEU | 76 | 53.423 | 66.043 | -17.137 | 1.00 0.00 | A2 |
| ATOM | 529 | CA | LEU | 76 | 53.325 | 66.156 | -15.044 | 1.00 52.94 | A2 |
| ATOM | 530 | CB | LEU | 76 | 54.798 | 65.754 | -15.181 | 1.00 50.81 | A2 |
| ATOM | 531 | CG | LEU | 76 | 55.575 | 65.011 | -14.090 | 1.00 49.02 | A2 |
| ATOM | 532 | CD1 | LEU | 76 | 54.852 | 63.740 | -13.698 | 1.00 46.76 | A2 |
| ATOM | 533 | CD2 | LEU | 76 | 56.951 | 64.633 | -14.623 | 1.00 47.67 | A2 |
| ATOM | 534 | C | LEU | 76 | 53.093 | 67.545 | -14.425 | 1.00 53.65 | A2 |
| ATOM | 535 | O | LEU | 76 | 52.731 | 67.716 | -13.244 | 1.00 53.50 | A2 |
| ATOM | 536 | N | SER | 77 | 53.137 | 68.553 | -15.301 | 1.00 53.91 | A2 |
| ATOM | 537 | H | SER | 77 | 53.322 | 68.361 | -16.242 | 1.00 0.00 | A2 |
| ATOM | 538 | CA | SER | 77 | 52.882 | 69.932 | -14.942 | 1.00 54.93 | A2 |
| ATOM | 539 | CB | SER | 77 | 53.425 | 70.835 | -16.040 | 1.00 58.32 | A2 |
| ATOM | 540 | OG | SER | 77 | 54.806 | 70.587 | -16.310 | 1.00 63.35 | A2 |
| ATOM | 541 | HG | SER | 77 | 54.949 | 69.637 | -16.315 | 1.00 0.00 | A2 |
| ATOM | 542 | C | SER | 77 | 51.382 | 70.172 | -14.759 | 1.00 53.47 | A2 |
| ATOM | 543 | O | SER | 77 | 50.982 | 70.965 | -13.899 | 1.00 53.54 | A2 |
| ATOM | 544 | N | GLN | 78 | 50.509 | 69.501 | -15.512 | 1.00 51.82 | A2 |
| ATOM | 545 | H | GLN | 78 | 50.857 | 68.901 | -16.207 | 1.00 0.00 | A2 |
| ATOM | 546 | CA | GLN | 78 | 49.074 | 69.619 | -15.349 | 1.00 50.74 | A2 |
| ATOM | 547 | CB | GLN | 78 | 48.402 | 68.877 | -16.451 | 1.00 54.31 | A2 |
| ATOM | 548 | CG | GLN | 78 | 47.420 | 69.784 | -17.160 | 1.00 58.59 | A2 |
| ATOM | 549 | CD | GLN | 78 | 46.557 | 68.940 | -18.071 | 1.00 62.32 | A2 |
| ATOM | 550 | OE1 | GLN | 78 | 47.005 | 68.260 | -18.998 | 1.00 65.94 | A2 |
| ATOM | 551 | NE2 | GLN | 78 | 45.269 | 68.889 | -17.800 | 1.00 63.17 | A2 |
| ATOM | 552 | HE21 | GLN | 78 | 44.973 | 69.327 | -16.972 | 1.00 0.00 | A2 |
| ATOM | 553 | HE22 | GLN | 78 | 44.704 | 68.444 | -18.456 | 1.00 0.00 | A2 |
| ATOM | 554 | C | GLN | 78 | 48.591 | 69.065 | -14.011 | 1.00 48.17 | A2 |
| ATOM | 555 | O | GLN | 78 | 47.691 | 69.618 | -13.368 | 1.00 46.31 | A2 |
| ATOM | 556 | N | LEU | 79 | 49.236 | 67.988 | -13.564 | 1.00 45.89 | A2 |
| ATOM | 557 | H | LEU | 79 | 49.920 | 67.584 | -14.140 | 1.00 0.00 | A2 |
| ATOM | 558 | CA | LEU | 79 | 48.919 | 67.359 | -12.294 | 1.00 44.54 | A2 |
| ATOM | 559 | CB | LEU | 79 | 49.617 | 66.015 | -12.259 | 1.00 45.06 | A2 |
| ATOM | 560 | CG | LEU | 79 | 49.154 | 64.895 | -11.351 | 1.00 45.18 | A2 |
| ATOM | 561 | CD1 | LEU | 79 | 49.634 | 63.594 | -11.957 | 1.00 48.06 | A2 |
| ATOM | 562 | CD2 | LEU | 79 | 49.766 | 64.986 | -9.969 | 1.00 46.03 | A2 |
| ATOM | 563 | C | LEU | 79 | 49.366 | 68.265 | -11.170 | 1.00 43.49 | A2 |
| ATOM | 564 | O | LEU | 79 | 48.645 | 68.509 | -10.199 | 1.00 43.20 | A2 |
| ATOM | 565 | N | HIS | 80 | 50.556 | 68.834 | -11.329 | 1.00 43.83 | A2 |
| ATOM | 566 | H | HIS | 80 | 51.115 | 68.548 | -12.085 | 1.00 0.00 | A2 |
| ATOM | 567 | CA | HIS | 80 | 51.060 | 69.788 | -10.360 | 1.00 43.79 | A2 |
| ATOM | 568 | CB | HIS | 80 | 52.456 | 70.221 | -10.810 | 1.00 43.58 | A2 |
| ATOM | 569 | CG | HIS | 80 | 53.030 | 71.031 | -9.690 | 1.00 43.75 | A2 |
| ATOM | 570 | CD2 | HIS | 80 | 53.484 | 70.497 | -8.517 | 1.00 47.48 | A2 |
| ATOM | 571 | ND1 | HIS | 80 | 53.083 | 72.343 | -9.567 | 1.00 44.24 | A2 |
| ATOM | 572 | HD1 | HIS | 80 | 52.842 | 73.004 | -10.255 | 1.00 0.00 | A2 |
| ATOM | 573 | CE1 | HIS | 80 | 53.530 | 72.641 | -8.376 | 1.00 44.47 | A2 |
| ATOM | 574 | NE2 | HIS | 80 | 53.772 | 71.520 | -7.748 | 1.00 48.16 | A2 |
| ATOM | 575 | HE2 | HIS | 80 | 54.103 | 71.444 | -6.824 | 1.00 0.00 | A2 |
| ATOM | 576 | C | HIS | 80 | 50.094 | 70.978 | -10.229 | 1.00 44.40 | A2 |
| ATOM | 577 | O | HIS | 80 | 49.643 | 71.294 | -9.131 | 1.00 44.28 | A2 |
| ATOM | 578 | N | SER | 81 | 49.733 | 71.670 | -11.309 | 1.00 45.13 | A2 |
| ATOM | 579 | H | SER | 81 | 50.136 | 71.459 | -12.176 | 1.00 0.00 | A2 |
| ATOM | 580 | CA | SER | 81 | 48.738 | 72.742 | -11.296 | 1.00 45.41 | A2 |
| ATOM | 581 | CB | SER | 81 | 48.612 | 73.347 | -12.682 | 1.00 45.59 | A2 |
| ATOM | 582 | OG | SER | 81 | 49.894 | 73.444 | -13.292 | 1.00 49.27 | A2 |
| ATOM | 583 | HG | SER | 81 | 50.058 | 72.670 | -13.843 | 1.00 0.00 | A2 |
| ATOM | 584 | C | SER | 81 | 47.344 | 72.266 | -10.856 | 1.00 44.85 | A2 |
| ATOM | 585 | O | SER | 81 | 46.604 | 73.064 | -10.256 | 1.00 46.83 | A2 |
| ATOM | 586 | N | GLY | 82 | 46.946 | 71.010 | -11.092 | 1.00 42.16 | A2 |
| ATOM | 587 | H | GLY | 82 | 47.513 | 70.411 | -11.614 | 1.00 0.00 | A2 |
| ATOM | 588 | CA | GLY | 82 | 45.663 | 70.500 | -10.650 | 1.00 39.39 | A2 |
| ATOM | 589 | C | GLY | 82 | 45.569 | 70.461 | -9.139 | 1.00 39.30 | A2 |
| ATOM | 590 | O | GLY | 82 | 44.542 | 70.843 | -8.544 | 1.00 39.64 | A2 |
| ATOM | 591 | N | LEU | 83 | 46.676 | 70.032 | -8.521 | 1.00 37.57 | A2 |
| ATOM | 592 | H | LEU | 83 | 47.413 | 69.695 | -9.075 | 1.00 0.00 | A2 |
| ATOM | 593 | CA | LEU | 83 | 46.826 | 70.007 | -7.057 | 1.00 38.07 | A2 |
| ATOM | 594 | CB | LEU | 83 | 48.133 | 69.202 | -6.748 | 1.00 35.67 | A2 |
| ATOM | 595 | CG | LEU | 83 | 48.071 | 67.736 | -7.225 | 1.00 32.51 | A2 |
| ATOM | 596 | CD1 | LEU | 83 | 49.442 | 67.145 | -7.319 | 1.00 29.77 | A2 |
| ATOM | 597 | CD2 | LEU | 83 | 47.180 | 66.973 | -6.288 | 1.00 28.71 | A2 |
| ATOM | 598 | C | LEU | 83 | 46.836 | 71.386 | -6.354 | 1.00 38.48 | A2 |
| ATOM | 599 | O | LEU | 83 | 46.392 | 71.627 | -5.219 | 1.00 38.05 | A2 |
| ATOM | 600 | N | PHE | 84 | 47.366 | 72.338 | -7.108 | 1.00 40.34 | A2 |
| ATOM | 601 | H | PHE | 84 | 47.804 | 72.078 | -7.944 | 1.00 0.00 | A2 |

FIG.5-8

| ATOM | 602 | CA | PHE | 84 | 47.414 | 73.703 | -6.688 | 1.00 | 41.54 | A2 |
|---|---|---|---|---|---|---|---|---|---|---|
| ATOM | 603 | CB | PHE | 84 | 48.163 | 74.531 | -7.693 | 1.00 | 46.88 | A2 |
| ATOM | 604 | CG | PHE | 84 | 48.715 | 75.777 | -6.988 | 1.00 | 55.09 | A2 |
| ATOM | 605 | CD1 | PHE | 84 | 49.521 | 75.622 | -5.849 | 1.00 | 55.31 | A2 |
| ATOM | 606 | CD2 | PHE | 84 | 48.396 | 77.053 | -7.469 | 1.00 | 55.79 | A2 |
| ATOM | 607 | CE1 | PHE | 84 | 50.004 | 76.737 | -5.195 | 1.00 | 57.60 | A2 |
| ATOM | 608 | CE2 | PHE | 84 | 48.892 | 78.156 | -6.796 | 1.00 | 57.25 | A2 |
| ATOM | 609 | CZ | PHE | 84 | 49.688 | 78.002 | -5.667 | 1.00 | 58.34 | A2 |
| ATOM | 610 | C | PHE | 84 | 45.994 | 74.191 | -6.591 | 1.00 | 40.47 | A2 |
| ATOM | 611 | O | PHE | 84 | 45.609 | 74.749 | -5.558 | 1.00 | 42.71 | A2 |
| ATOM | 612 | N | LEU | 85 | 45.190 | 73.953 | -7.624 | 1.00 | 38.64 | A2 |
| ATOM | 613 | H | LEU | 85 | 45.555 | 73.527 | -8.429 | 1.00 | 0.00 | A2 |
| ATOM | 614 | CA | LEU | 85 | 43.794 | 74.335 | -7.584 | 1.00 | 38.81 | A2 |
| ATOM | 615 | CB | LEU | 85 | 43.101 | 73.886 | -8.839 | 1.00 | 41.27 | A2 |
| ATOM | 616 | CG | LEU | 85 | 41.673 | 74.403 | -9.017 | 1.00 | 46.45 | A2 |
| ATOM | 617 | CD1 | LEU | 85 | 41.702 | 75.784 | -9.719 | 1.00 | 47.80 | A2 |
| ATOM | 618 | CD2 | LEU | 85 | 40.860 | 73.359 | -9.787 | 1.00 | 48.25 | A2 |
| ATOM | 619 | C | LEU | 85 | 43.079 | 73.731 | -6.386 | 1.00 | 38.20 | A2 |
| ATOM | 620 | O | LEU | 85 | 42.498 | 74.469 | -5.582 | 1.00 | 38.36 | A2 |
| ATOM | 621 | N | TYR | 86 | 43.150 | 72.405 | -6.198 | 1.00 | 37.92 | A2 |
| ATOM | 622 | H | TYR | 86 | 43.637 | 71.850 | -6.845 | 1.00 | 0.00 | A2 |
| ATOM | 623 | CA | TYR | 86 | 42.501 | 71.801 | -5.057 | 1.00 | 37.15 | A2 |
| ATOM | 624 | CB | TYR | 86 | 42.598 | 70.255 | -5.102 | 1.00 | 36.73 | A2 |
| ATOM | 625 | CG | TYR | 86 | 41.561 | 69.685 | -6.081 | 1.00 | 33.66 | A2 |
| ATOM | 626 | CD1 | TYR | 86 | 41.946 | 69.312 | -7.374 | 1.00 | 30.03 | A2 |
| ATOM | 627 | CE1 | TYR | 86 | 40.991 | 68.885 | -8.280 | 1.00 | 30.08 | A2 |
| ATOM | 628 | CD2 | TYR | 86 | 40.224 | 69.623 | -5.666 | 1.00 | 32.61 | A2 |
| ATOM | 629 | CE2 | TYR | 86 | 39.263 | 69.203 | -6.574 | 1.00 | 31.66 | A2 |
| ATOM | 630 | CZ | TYR | 86 | 39.656 | 68.838 | -7.868 | 1.00 | 30.57 | A2 |
| ATOM | 631 | OH | TYR | 86 | 38.670 | 68.428 | -8.751 | 1.00 | 28.18 | A2 |
| ATOM | 632 | HH | TYR | 86 | 39.107 | 67.994 | -9.485 | 1.00 | 0.00 | A2 |
| ATOM | 633 | C | TYR | 86 | 43.054 | 72.318 | -3.746 | 1.00 | 37.75 | A2 |
| ATOM | 634 | O | TYR | 86 | 42.173 | 72.469 | -2.889 | 1.00 | 39.52 | A2 |
| ATOM | 635 | N | GLN | 87 | 44.347 | 72.655 | -3.478 | 1.00 | 36.93 | A2 |
| ATOM | 636 | H | GLN | 87 | 45.044 | 72.463 | -4.140 | 1.00 | 0.00 | A2 |
| ATOM | 637 | CA | GLN | 87 | 44.749 | 73.332 | -2.205 | 1.00 | 36.40 | A2 |
| ATOM | 638 | CB | GLN | 87 | 46.210 | 73.668 | -2.255 | 1.00 | 39.56 | A2 |
| ATOM | 639 | CG | GLN | 87 | 47.126 | 72.993 | -1.237 | 1.00 | 46.99 | A2 |
| ATOM | 640 | CD | GLN | 87 | 48.641 | 73.062 | -1.576 | 1.00 | 50.96 | A2 |
| ATOM | 641 | OE1 | GLN | 87 | 49.144 | 72.623 | -2.627 | 1.00 | 52.15 | A2 |
| ATOM | 642 | NE2 | GLN | 87 | 49.446 | 73.608 | -0.663 | 1.00 | 52.96 | A2 |
| ATOM | 643 | HE21 | GLN | 87 | 49.055 | 73.957 | 0.164 | 1.00 | 0.00 | A2 |
| ATOM | 644 | HE22 | GLN | 87 | 50.396 | 73.621 | -0.888 | 1.00 | 0.00 | A2 |
| ATOM | 645 | C | GLN | 87 | 43.941 | 74.652 | -2.013 | 1.00 | 34.36 | A2 |
| ATOM | 646 | O | GLN | 87 | 43.414 | 74.990 | -0.935 | 1.00 | 31.55 | A2 |
| ATOM | 647 | N | GLY | 88 | 43.740 | 75.335 | -3.159 | 1.00 | 32.73 | A2 |
| ATOM | 648 | H | GLY | 88 | 44.165 | 75.005 | -3.981 | 1.00 | 0.00 | A2 |
| ATOM | 649 | CA | GLY | 88 | 42.948 | 76.546 | -3.232 | 1.00 | 30.81 | A2 |
| ATOM | 650 | C | GLY | 88 | 41.540 | 76.275 | -2.731 | 1.00 | 30.47 | A2 |
| ATOM | 651 | O | GLY | 88 | 41.130 | 76.819 | -1.703 | 1.00 | 30.27 | A2 |
| ATOM | 652 | N | LEU | 89 | 40.802 | 75.387 | -3.406 | 1.00 | 29.01 | A2 |
| ATOM | 653 | H | LEU | 89 | 41.220 | 74.912 | -4.154 | 1.00 | 0.00 | A2 |
| ATOM | 654 | CA | LEU | 89 | 39.447 | 75.102 | -3.009 | 1.00 | 27.60 | A2 |
| ATOM | 655 | CB | LEU | 89 | 38.922 | 74.073 | -3.935 | 1.00 | 28.13 | A2 |
| ATOM | 656 | CG | LEU | 89 | 38.764 | 74.583 | -5.340 | 1.00 | 29.51 | A2 |
| ATOM | 657 | CD1 | LEU | 89 | 38.363 | 73.530 | -6.364 | 1.00 | 24.13 | A2 |
| ATOM | 658 | CD2 | LEU | 89 | 37.673 | 75.637 | -5.220 | 1.00 | 32.87 | A2 |
| ATOM | 659 | C | LEU | 89 | 39.352 | 74.629 | -1.583 | 1.00 | 29.88 | A2 |
| ATOM | 660 | O | LEU | 89 | 38.427 | 75.012 | -0.860 | 1.00 | 30.81 | A2 |
| ATOM | 661 | N | LEU | 90 | 40.317 | 73.839 | -1.094 | 1.00 | 32.59 | A2 |
| ATOM | 662 | H | LEU | 90 | 41.101 | 73.626 | -1.643 | 1.00 | 0.00 | A2 |
| ATOM | 663 | CA | LEU | 90 | 40.182 | 73.274 | 0.235 | 1.00 | 33.41 | A2 |
| ATOM | 664 | CB | LEU | 90 | 41.207 | 72.234 | 0.503 | 1.00 | 36.15 | A2 |
| ATOM | 665 | CG | LEU | 90 | 41.075 | 70.971 | -0.343 | 1.00 | 38.76 | A2 |
| ATOM | 666 | CD1 | LEU | 90 | 42.431 | 70.267 | -0.456 | 1.00 | 37.21 | A2 |
| ATOM | 667 | CD2 | LEU | 90 | 39.995 | 70.099 | 0.279 | 1.00 | 40.54 | A2 |
| ATOM | 668 | C | LEU | 90 | 40.342 | 74.319 | 1.255 | 1.00 | 34.24 | A2 |
| ATOM | 669 | O | LEU | 90 | 39.711 | 74.256 | 2.313 | 1.00 | 35.57 | A2 |
| ATOM | 670 | N | GLN | 91 | 41.188 | 75.291 | 0.940 | 1.00 | 35.24 | A2 |
| ATOM | 671 | H | GLN | 91 | 41.663 | 75.284 | 0.078 | 1.00 | 0.00 | A2 |
| ATOM | 672 | CA | GLN | 91 | 41.397 | 76.373 | 1.883 | 1.00 | 37.60 | A2 |
| ATOM | 673 | CB | GLN | 91 | 42.557 | 77.182 | 1.363 | 1.00 | 39.65 | A2 |
| ATOM | 674 | CG | GLN | 91 | 43.155 | 78.237 | 2.284 | 1.00 | 44.32 | A2 |
| ATOM | 675 | CD | GLN | 91 | 44.348 | 78.799 | 1.542 | 1.00 | 46.96 | A2 |
| ATOM | 676 | OE1 | GLN | 91 | 45.235 | 78.083 | 1.068 | 1.00 | 47.42 | A2 |
| ATOM | 677 | NE2 | GLN | 91 | 44.376 | 80.092 | 1.341 | 1.00 | 46.82 | A2 |
| ATOM | 678 | HE21 | GLN | 91 | 43.690 | 80.685 | 1.700 | 1.00 | 0.00 | A2 |
| ATOM | 679 | HE22 | GLN | 91 | 45.108 | 80.331 | 0.741 | 1.00 | 0.00 | A2 |
| ATOM | 680 | C | GLN | 91 | 40.129 | 77.231 | 2.061 | 1.00 | 37.22 | A2 |
| ATOM | 681 | O | GLN | 91 | 39.718 | 77.530 | 3.186 | 1.00 | 36.21 | A2 |
| ATOM | 682 | N | ALA | 92 | 39.456 | 77.570 | 0.943 | 1.00 | 38.63 | A2 |
| ATOM | 683 | H | ALA | 92 | 39.808 | 77.205 | 0.098 | 1.00 | 0.00 | A2 |
| ATOM | 684 | CA | ALA | 92 | 38.243 | 78.402 | 0.880 | 1.00 | 38.10 | A2 |
| ATOM | 685 | CB | ALA | 92 | 37.657 | 78.436 | -0.511 | 1.00 | 36.76 | A2 |
| ATOM | 686 | C | ALA | 92 | 37.139 | 77.905 | 1.770 | 1.00 | 38.95 | A2 |
| ATOM | 687 | O | ALA | 92 | 36.294 | 78.687 | 2.194 | 1.00 | 42.45 | A2 |

FIG.5-9

| ATOM | 688 | N | LEU | 93 | 37.151 | 76.618 | 2.123 | 1.00 | 38.34 | A2 |
|------|-----|---|-----|----|--------|--------|-------|------|-------|-----|
| ATOM | 689 | H | LEU | 93 | 37.855 | 76.040 | 1.759 | 1.00 | 0.00 | A2 |
| ATOM | 690 | CA | LEU | 93 | 36.111 | 76.018 | 2.972 | 1.00 | 36.90 | A2 |
| ATOM | 691 | CB | LEU | 93 | 36.088 | 74.463 | 2.794 | 1.00 | 35.34 | A2 |
| ATOM | 692 | CG | LEU | 93 | 35.725 | 73.992 | 1.378 | 1.00 | 33.55 | A2 |
| ATOM | 693 | CD1 | LEU | 93 | 36.159 | 72.583 | 1.129 | 1.00 | 33.26 | A2 |
| ATOM | 694 | CD2 | LEU | 93 | 34.254 | 74.167 | 1.215 | 1.00 | 32.18 | A2 |
| ATOM | 695 | C | LEU | 93 | 36.264 | 76.353 | 4.426 | 1.00 | 36.44 | A2 |
| ATOM | 696 | O | LEU | 93 | 35.473 | 75.917 | 5.256 | 1.00 | 35.17 | A2 |
| ATOM | 697 | N | GLU | 94 | 37.357 | 77.019 | 4.736 | 1.00 | 38.19 | A2 |
| ATOM | 698 | H | GLU | 94 | 38.022 | 77.167 | 4.035 | 1.00 | 0.00 | A2 |
| ATOM | 699 | CA | GLU | 94 | 37.627 | 77.573 | 6.038 | 1.00 | 42.71 | A2 |
| ATOM | 700 | CB | GLU | 94 | 36.931 | 78.947 | 6.165 | 1.00 | 47.38 | A2 |
| ATOM | 701 | CG | GLU | 94 | 37.418 | 80.011 | 5.131 | 1.00 | 56.10 | A2 |
| ATOM | 702 | CD | GLU | 94 | 36.423 | 81.153 | 4.862 | 1.00 | 60.26 | A2 |
| ATOM | 703 | OE1 | GLU | 94 | 35.728 | 81.109 | 3.823 | 1.00 | 60.76 | A2 |
| ATOM | 704 | OE2 | GLU | 94 | 36.331 | 82.054 | 5.721 | 1.00 | 61.64 | A2 |
| ATOM | 705 | C | GLU | 94 | 37.245 | 76.701 | 7.198 | 1.00 | 43.90 | A2 |
| ATOM | 706 | O | GLU | 94 | 36.624 | 77.172 | 8.167 | 1.00 | 45.70 | A2 |
| ATOM | 707 | N | GLY | 95 | 37.641 | 75.410 | 7.001 | 1.00 | 44.03 | A2 |
| ATOM | 708 | H | GLY | 95 | 38.024 | 75.192 | 6.127 | 1.00 | 0.00 | A2 |
| ATOM | 709 | CA | GLY | 95 | 37.519 | 74.310 | 7.981 | 1.00 | 42.49 | A2 |
| ATOM | 710 | C | GLY | 95 | 36.162 | 73.612 | 8.061 | 1.00 | 42.24 | A2 |
| ATOM | 711 | O | GLY | 95 | 36.028 | 72.596 | 8.739 | 1.00 | 40.02 | A2 |
| ATOM | 712 | N | ILE | 96 | 35.160 | 74.123 | 7.328 | 1.00 | 42.82 | A2 |
| ATOM | 713 | H | ILE | 96 | 35.357 | 74.944 | 6.841 | 1.00 | 0.00 | A2 |
| ATOM | 714 | CA | ILE | 96 | 33.760 | 73.692 | 7.312 | 1.00 | 42.12 | A2 |
| ATOM | 715 | CB | ILE | 96 | 33.665 | 72.233 | 6.800 | 1.00 | 36.33 | A2 |
| ATOM | 716 | CG2 | ILE | 96 | 32.248 | 71.768 | 6.789 | 1.00 | 34.79 | A2 |
| ATOM | 717 | CG1 | ILE | 96 | 34.091 | 72.157 | 5.374 | 1.00 | 35.35 | A2 |
| ATOM | 718 | CD | ILE | 96 | 34.051 | 70.743 | 4.738 | 1.00 | 33.64 | A2 |
| ATOM | 719 | C | ILE | 96 | 33.106 | 73.863 | 8.709 | 1.00 | 44.74 | A2 |
| ATOM | 720 | O | ILE | 96 | 32.220 | 74.716 | 8.841 | 1.00 | 44.59 | A2 |
| ATOM | 721 | N | SER | 97 | 33.467 | 73.154 | 9.780 | 1.00 | 46.84 | A2 |
| ATOM | 722 | H | SER | 97 | 34.243 | 72.553 | 9.706 | 1.00 | 0.00 | A2 |
| ATOM | 723 | CA | SER | 97 | 32.900 | 73.359 | 11.105 | 1.00 | 48.91 | A2 |
| ATOM | 724 | CB | SER | 97 | 31.804 | 72.343 | 11.347 | 1.00 | 49.60 | A2 |
| ATOM | 725 | OG | SER | 97 | 32.211 | 71.120 | 11.954 | 1.00 | 52.85 | A2 |
| ATOM | 726 | HG | SER | 97 | 31.406 | 70.573 | 11.942 | 1.00 | 0.00 | A2 |
| ATOM | 727 | C | SER | 97 | 34.045 | 73.143 | 12.077 | 1.00 | 50.64 | A2 |
| ATOM | 728 | O | SER | 97 | 35.035 | 72.538 | 11.678 | 1.00 | 52.78 | A2 |
| ATOM | 729 | N | PRO | 98 | 34.063 | 73.474 | 13.348 | 1.00 | 52.12 | A2 |
| ATOM | 730 | CD | PRO | 98 | 33.002 | 74.170 | 14.016 | 1.00 | 52.90 | A2 |
| ATOM | 731 | CA | PRO | 98 | 35.195 | 73.200 | 14.257 | 1.00 | 54.94 | A2 |
| ATOM | 732 | CB | PRO | 98 | 34.750 | 73.717 | 15.600 | 1.00 | 54.78 | A2 |
| ATOM | 733 | CG | PRO | 98 | 33.772 | 74.777 | 15.182 | 1.00 | 55.48 | A2 |
| ATOM | 734 | C | PRO | 98 | 35.591 | 71.723 | 14.336 | 1.00 | 56.75 | A2 |
| ATOM | 735 | O | PRO | 98 | 36.738 | 71.274 | 14.468 | 1.00 | 57.85 | A2 |
| ATOM | 736 | N | GLU | 99 | 34.509 | 70.971 | 14.214 | 1.00 | 58.21 | A2 |
| ATOM | 737 | H | GLU | 99 | 33.652 | 71.400 | 14.028 | 1.00 | 0.00 | A2 |
| ATOM | 738 | CA | GLU | 99 | 34.543 | 69.537 | 14.281 | 1.00 | 58.48 | A2 |
| ATOM | 739 | CB | GLU | 99 | 33.111 | 69.104 | 14.304 | 1.00 | 63.30 | A2 |
| ATOM | 740 | CG | GLU | 99 | 32.958 | 67.702 | 14.852 | 1.00 | 71.04 | A2 |
| ATOM | 741 | CD | GLU | 99 | 32.076 | 66.838 | 13.962 | 1.00 | 76.95 | A2 |
| ATOM | 742 | OE1 | GLU | 99 | 32.209 | 65.608 | 14.079 | 1.00 | 80.63 | A2 |
| ATOM | 743 | OE2 | GLU | 99 | 31.295 | 67.382 | 13.153 | 1.00 | 77.99 | A2 |
| ATOM | 744 | C | GLU | 99 | 35.298 | 69.025 | 13.074 | 1.00 | 55.31 | A2 |
| ATOM | 745 | O | GLU | 99 | 36.251 | 68.270 | 13.210 | 1.00 | 55.96 | A2 |
| ATOM | 746 | N | LEU | 100 | 34.916 | 69.475 | 11.891 | 1.00 | 51.23 | A2 |
| ATOM | 747 | H | LEU | 100 | 34.214 | 70.159 | 11.841 | 1.00 | 0.00 | A2 |
| ATOM | 748 | CA | LEU | 100 | 35.577 | 69.052 | 10.678 | 1.00 | 48.08 | A2 |
| ATOM | 749 | CB | LEU | 100 | 34.627 | 69.341 | 9.574 | 1.00 | 45.52 | A2 |
| ATOM | 750 | CG | LEU | 100 | 33.544 | 68.337 | 9.674 | 1.00 | 45.39 | A2 |
| ATOM | 751 | CD1 | LEU | 100 | 32.207 | 68.972 | 9.458 | 1.00 | 46.40 | A2 |
| ATOM | 752 | CD2 | LEU | 100 | 33.851 | 67.245 | 8.677 | 1.00 | 47.48 | A2 |
| ATOM | 753 | C | LEU | 100 | 36.956 | 69.629 | 10.368 | 1.00 | 46.77 | A2 |
| ATOM | 754 | O | LEU | 100 | 37.578 | 69.244 | 9.357 | 1.00 | 46.62 | A2 |
| ATOM | 755 | N | GLY | 101 | 37.441 | 70.505 | 11.272 | 1.00 | 45.40 | A2 |
| ATOM | 756 | H | GLY | 101 | 36.893 | 70.704 | 12.056 | 1.00 | 0.00 | A2 |
| ATOM | 757 | CA | GLY | 101 | 38.703 | 71.238 | 11.126 | 1.00 | 42.52 | A2 |
| ATOM | 758 | C | GLY | 101 | 39.885 | 70.334 | 10.798 | 1.00 | 40.73 | A2 |
| ATOM | 759 | O | GLY | 101 | 40.475 | 70.402 | 9.710 | 1.00 | 40.69 | A2 |
| ATOM | 760 | N | PRO | 102 | 40.250 | 69.441 | 11.708 | 1.00 | 38.61 | A2 |
| ATOM | 761 | CD | PRO | 102 | 39.676 | 69.350 | 13.027 | 1.00 | 39.26 | A2 |
| ATOM | 762 | CA | PRO | 102 | 41.390 | 68.566 | 11.606 | 1.00 | 37.30 | A2 |
| ATOM | 763 | CB | PRO | 102 | 41.294 | 67.690 | 12.775 | 1.00 | 39.36 | A2 |
| ATOM | 764 | CG | PRO | 102 | 40.799 | 68.687 | 13.776 | 1.00 | 41.02 | A2 |
| ATOM | 765 | C | PRO | 102 | 41.364 | 67.795 | 10.331 | 1.00 | 37.15 | A2 |
| ATOM | 766 | O | PRO | 102 | 42.358 | 67.854 | 9.600 | 1.00 | 38.88 | A2 |
| ATOM | 767 | N | THR | 103 | 40.223 | 67.167 | 10.045 | 1.00 | 35.36 | A2 |
| ATOM | 768 | H | THR | 103 | 39.466 | 67.223 | 10.662 | 1.00 | 0.00 | A2 |
| ATOM | 769 | CA | THR | 103 | 40.051 | 66.386 | 8.843 | 1.00 | 34.62 | A2 |
| ATOM | 770 | CB | THR | 103 | 38.592 | 65.888 | 8.715 | 1.00 | 34.07 | A2 |
| ATOM | 771 | OG1 | THR | 103 | 38.356 | 65.240 | 9.936 | 1.00 | 35.43 | A2 |
| ATOM | 772 | HG1 | THR | 103 | 38.011 | 65.896 | 10.548 | 1.00 | 0.00 | A2 |
| ATOM | 773 | CG2 | THR | 103 | 38.312 | 64.896 | 7.594 | 1.00 | 31.29 | A2 |

FIG. 5-10

| | | | | | | | | | |
|---|---|---|---|---|---|---|---|---|---|
| ATOM | 774 | C | THR | 103 | 40.417 | 67.215 | 7.625 | 1.00 34.61 | A2 |
| ATOM | 775 | O | THR | 103 | 41.091 | 66.665 | 6.738 | 1.00 38.16 | A2 |
| ATOM | 776 | N | LEU | 104 | 40.054 | 68.498 | 7.529 | 1.00 32.49 | A2 |
| ATOM | 777 | H | LEU | 104 | 39.504 | 68.923 | 8.229 | 1.00 0.00 | A2 |
| ATOM | 778 | CA | LEU | 104 | 40.471 | 69.267 | 6.370 | 1.00 30.49 | A2 |
| ATOM | 779 | CB | LEU | 104 | 39.616 | 70.430 | 6.242 | 1.00 33.51 | A2 |
| ATOM | 780 | CG | LEU | 104 | 38.356 | 69.996 | 5.611 | 1.00 36.61 | A2 |
| ATOM | 781 | CD1 | LEU | 104 | 37.222 | 70.621 | 6.381 | 1.00 39.43 | A2 |
| ATOM | 782 | CD2 | LEU | 104 | 38.418 | 70.294 | 4.132 | 1.00 37.89 | A2 |
| ATOM | 783 | C | LEU | 104 | 41.904 | 69.727 | 6.414 | 1.00 28.48 | A2 |
| ATOM | 784 | O | LEU | 104 | 42.583 | 69.825 | 5.398 | 1.00 28.47 | A2 |
| ATOM | 785 | N | ASP | 105 | 42.449 | 69.949 | 7.574 | 1.00 26.99 | A2 |
| ATOM | 786 | H | ASP | 105 | 41.903 | 69.912 | 8.388 | 1.00 0.00 | A2 |
| ATOM | 787 | CA | ASP | 105 | 43.822 | 70.307 | 7.613 | 1.00 28.67 | A2 |
| ATOM | 788 | CB | ASP | 105 | 44.139 | 70.584 | 9.038 | 1.00 33.06 | A2 |
| ATOM | 789 | CG | ASP | 105 | 43.438 | 71.808 | 9.593 | 1.00 35.46 | A2 |
| ATOM | 790 | OD1 | ASP | 105 | 43.085 | 72.726 | 8.836 | 1.00 38.42 | A2 |
| ATOM | 791 | OD2 | ASP | 105 | 43.244 | 71.816 | 10.808 | 1.00 39.10 | A2 |
| ATOM | 792 | C | ASP | 105 | 44.701 | 69.206 | 7.032 | 1.00 28.90 | A2 |
| ATOM | 793 | O | ASP | 105 | 45.551 | 69.479 | 6.175 | 1.00 29.62 | A2 |
| ATOM | 794 | N | THR | 106 | 44.415 | 67.950 | 7.401 | 1.00 26.86 | A2 |
| ATOM | 795 | H | THR | 106 | 43.674 | 67.826 | 8.029 | 1.00 0.00 | A2 |
| ATOM | 796 | CA | THR | 106 | 45.143 | 66.770 | 6.935 | 1.00 24.81 | A2 |
| ATOM | 797 | CB | THR | 106 | 44.558 | 65.456 | 7.477 | 1.00 26.03 | A2 |
| ATOM | 798 | OG1 | THR | 106 | 44.680 | 65.566 | 8.894 | 1.00 31.53 | A2 |
| ATOM | 799 | HG1 | THR | 106 | 44.069 | 66.223 | 9.242 | 1.00 0.00 | A2 |
| ATOM | 800 | CG2 | THR | 106 | 45.258 | 64.220 | 7.011 | 1.00 20.90 | A2 |
| ATOM | 801 | C | THR | 106 | 45.073 | 66.684 | 5.460 | 1.00 23.75 | A2 |
| ATOM | 802 | O | THR | 106 | 46.065 | 66.411 | 4.812 | 1.00 24.68 | A2 |
| ATOM | 803 | N | LEU | 107 | 43.887 | 66.917 | 4.946 | 1.00 24.30 | A2 |
| ATOM | 804 | H | LEU | 107 | 43.145 | 67.176 | 5.528 | 1.00 0.00 | A2 |
| ATOM | 805 | CA | LEU | 107 | 43.668 | 66.783 | 3.531 | 1.00 27.29 | A2 |
| ATOM | 806 | CB | LEU | 107 | 42.158 | 66.913 | 3.273 | 1.00 25.45 | A2 |
| ATOM | 807 | CG | LEU | 107 | 41.642 | 66.888 | 1.863 | 1.00 26.24 | A2 |
| ATOM | 808 | CD1 | LEU | 107 | 42.095 | 65.649 | 1.158 | 1.00 26.41 | A2 |
| ATOM | 809 | CD2 | LEU | 107 | 40.140 | 66.925 | 1.914 | 1.00 27.62 | A2 |
| ATOM | 810 | C | LEU | 107 | 44.485 | 67.848 | 2.819 | 1.00 28.01 | A2 |
| ATOM | 811 | O | LEU | 107 | 45.154 | 67.555 | 1.823 | 1.00 30.72 | A2 |
| ATOM | 812 | N | GLN | 108 | 44.540 | 69.055 | 3.373 | 1.00 28.52 | A2 |
| ATOM | 813 | H | GLN | 108 | 44.030 | 69.221 | 4.194 | 1.00 0.00 | A2 |
| ATOM | 814 | CA | GLN | 108 | 45.343 | 70.132 | 2.792 | 1.00 28.38 | A2 |
| ATOM | 815 | CB | GLN | 108 | 45.138 | 71.363 | 3.630 | 1.00 30.15 | A2 |
| ATOM | 816 | CG | GLN | 108 | 43.711 | 71.787 | 3.542 | 1.00 32.67 | A2 |
| ATOM | 817 | CD | GLN | 108 | 43.606 | 73.192 | 4.048 | 1.00 35.24 | A2 |
| ATOM | 818 | OE1 | GLN | 108 | 43.085 | 73.484 | 5.125 | 1.00 36.07 | A2 |
| ATOM | 819 | NE2 | GLN | 108 | 44.189 | 74.044 | 3.213 | 1.00 33.58 | A2 |
| ATOM | 820 | HE21 | GLN | 108 | 44.582 | 73.701 | 2.386 | 1.00 0.00 | A2 |
| ATOM | 821 | HE22 | GLN | 108 | 44.195 | 74.986 | 3.471 | 1.00 0.00 | A2 |
| ATOM | 822 | C | GLN | 108 | 46.840 | 69.842 | 2.675 | 1.00 26.40 | A2 |
| ATOM | 823 | O | GLN | 108 | 47.450 | 69.955 | 1.597 | 1.00 27.57 | A2 |
| ATOM | 824 | N | LEU | 109 | 47.388 | 69.473 | 3.833 | 1.00 25.81 | A2 |
| ATOM | 825 | H | LEU | 109 | 46.795 | 69.495 | 4.615 | 1.00 0.00 | A2 |
| ATOM | 826 | CA | LEU | 109 | 48.764 | 69.003 | 4.043 | 1.00 27.96 | A2 |
| ATOM | 827 | CB | LEU | 109 | 48.951 | 68.637 | 5.513 | 1.00 29.41 | A2 |
| ATOM | 828 | CG | LEU | 109 | 48.712 | 69.771 | 6.520 | 1.00 31.78 | A2 |
| ATOM | 829 | CD1 | LEU | 109 | 48.750 | 69.188 | 7.933 | 1.00 29.16 | A2 |
| ATOM | 830 | CD2 | LEU | 109 | 49.724 | 70.889 | 6.285 | 1.00 32.19 | A2 |
| ATOM | 831 | C | LEU | 109 | 49.168 | 67.790 | 3.186 | 1.00 26.80 | A2 |
| ATOM | 832 | O | LEU | 109 | 50.214 | 67.721 | 2.544 | 1.00 26.81 | A2 |
| ATOM | 833 | N | ASP | 110 | 48.305 | 66.807 | 3.090 | 1.00 25.98 | A2 |
| ATOM | 834 | H | ASP | 110 | 47.471 | 66.835 | 3.600 | 1.00 0.00 | A2 |
| ATOM | 835 | CA | ASP | 110 | 48.590 | 65.684 | 2.250 | 1.00 23.32 | A2 |
| ATOM | 836 | CB | ASP | 110 | 47.577 | 64.570 | 2.553 | 1.00 26.34 | A2 |
| ATOM | 837 | CG | ASP | 110 | 47.905 | 63.878 | 3.894 | 1.00 31.10 | A2 |
| ATOM | 838 | OD1 | ASP | 110 | 47.070 | 63.093 | 4.323 | 1.00 34.98 | A2 |
| ATOM | 839 | OD2 | ASP | 110 | 48.958 | 64.107 | 4.535 | 1.00 34.06 | A2 |
| ATOM | 840 | C | ASP | 110 | 48.557 | 66.138 | 0.842 | 1.00 21.31 | A2 |
| ATOM | 841 | O | ASP | 110 | 49.493 | 65.711 | 0.165 | 1.00 20.63 | A2 |
| ATOM | 842 | N | VAL | 111 | 47.627 | 66.998 | 0.363 | 1.00 20.80 | A2 |
| ATOM | 843 | H | VAL | 111 | 46.900 | 67.310 | 0.944 | 1.00 0.00 | A2 |
| ATOM | 844 | CA | VAL | 111 | 47.711 | 67.454 | -1.019 | 1.00 20.44 | A2 |
| ATOM | 845 | CB | VAL | 111 | 46.531 | 68.364 | -1.376 | 1.00 23.60 | A2 |
| ATOM | 846 | CG1 | VAL | 111 | 46.615 | 68.946 | -2.808 | 1.00 23.04 | A2 |
| ATOM | 847 | CG2 | VAL | 111 | 45.289 | 67.497 | -1.371 | 1.00 24.30 | A2 |
| ATOM | 848 | C | VAL | 111 | 49.006 | 68.224 | -1.245 | 1.00 20.82 | A2 |
| ATOM | 849 | O | VAL | 111 | 49.617 | 68.006 | -2.303 | 1.00 19.22 | A2 |
| ATOM | 850 | N | ALA | 112 | 49.442 | 69.063 | -0.267 | 1.00 21.84 | A2 |
| ATOM | 851 | H | ALA | 112 | 48.839 | 69.190 | 0.492 | 1.00 0.00 | A2 |
| ATOM | 852 | CA | ALA | 112 | 50.708 | 69.805 | -0.295 | 1.00 24.16 | A2 |
| ATOM | 853 | CB | ALA | 112 | 50.861 | 70.561 | 1.011 | 1.00 22.69 | A2 |
| ATOM | 854 | C | ALA | 112 | 51.931 | 68.878 | -0.486 | 1.00 28.58 | A2 |
| ATOM | 855 | O | ALA | 112 | 52.778 | 69.026 | -1.390 | 1.00 32.53 | A2 |
| ATOM | 856 | N | ASP | 113 | 52.086 | 67.852 | 0.343 | 1.00 30.21 | A2 |
| ATOM | 857 | H | ASP | 113 | 51.507 | 67.817 | 1.130 | 1.00 0.00 | A2 |
| ATOM | 858 | CA | ASP | 113 | 53.084 | 66.846 | 0.166 | 1.00 31.70 | A2 |
| ATOM | 859 | CB | ASP | 113 | 52.706 | 65.659 | 0.953 | 1.00 36.31 | A2 |

FIG.5-11

| | | | | | | | | | |
|---|---|---|---|---|---|---|---|---|---|
| ATOM | 860 | CG | ASP | 113 | 53.170 | 65.758 | 2.357 | 1.00 42.27 | A2 |
| ATOM | 861 | OD1 | ASP | 113 | 52.559 | 65.109 | 3.203 | 1.00 46.37 | A2 |
| ATOM | 862 | OD2 | ASP | 113 | 54.160 | 66.461 | 2.589 | 1.00 48.93 | A2 |
| ATOM | 863 | C | ASP | 113 | 53.315 | 66.361 | -1.239 | 1.00 32.82 | A2 |
| ATOM | 864 | O | ASP | 113 | 54.433 | 66.308 | -1.754 | 1.00 36.25 | A2 |
| ATOM | 865 | N | PHE | 114 | 52.187 | 65.978 | -1.830 | 1.00 30.94 | A2 |
| ATOM | 866 | H | PHE | 114 | 51.344 | 66.164 | -1.361 | 1.00 0.00 | A2 |
| ATOM | 867 | CA | PHE | 114 | 52.109 | 65.328 | -3.103 | 1.00 27.84 | A2 |
| ATOM | 868 | CB | PHE | 114 | 50.708 | 64.794 | -3.226 | 1.00 23.18 | A2 |
| ATOM | 869 | CG | PHE | 114 | 50.565 | 63.928 | -4.420 | 1.00 21.04 | A2 |
| ATOM | 870 | CD1 | PHE | 114 | 51.623 | 63.225 | -4.938 | 1.00 24.05 | A2 |
| ATOM | 871 | CD2 | PHE | 114 | 49.369 | 63.914 | -5.046 | 1.00 22.37 | A2 |
| ATOM | 872 | CE1 | PHE | 114 | 51.476 | 62.514 | -6.102 | 1.00 24.54 | A2 |
| ATOM | 873 | CE2 | PHE | 114 | 49.211 | 63.207 | -6.212 | 1.00 21.33 | A2 |
| ATOM | 874 | CZ | PHE | 114 | 50.263 | 62.509 | -6.741 | 1.00 24.71 | A2 |
| ATOM | 875 | C | PHE | 114 | 52.453 | 66.291 | -4.190 | 1.00 29.20 | A2 |
| ATOM | 876 | O | PHE | 114 | 53.072 | 65.883 | -5.158 | 1.00 30.84 | A2 |
| ATOM | 877 | N | ALA | 115 | 52.057 | 67.554 | -4.058 | 1.00 31.99 | A2 |
| ATOM | 878 | H | ALA | 115 | 51.446 | 67.768 | -3.317 | 1.00 0.00 | A2 |
| ATOM | 879 | CA | ALA | 115 | 52.423 | 68.655 | -4.952 | 1.00 31.29 | A2 |
| ATOM | 880 | CB | ALA | 115 | 51.824 | 69.939 | -4.420 | 1.00 30.65 | A2 |
| ATOM | 881 | C | ALA | 115 | 53.936 | 68.787 | -4.976 | 1.00 31.31 | A2 |
| ATOM | 882 | O | ALA | 115 | 54.539 | 68.823 | -6.044 | 1.00 30.36 | A2 |
| ATOM | 883 | N | THR | 116 | 54.551 | 68.846 | -3.813 | 1.00 32.20 | A2 |
| ATOM | 884 | H | THR | 116 | 54.013 | 68.910 | -2.992 | 1.00 0.00 | A2 |
| ATOM | 885 | CA | THR | 116 | 55.998 | 68.897 | -3.656 | 1.00 34.91 | A2 |
| ATOM | 886 | CB | THR | 116 | 56.325 | 68.953 | -2.150 | 1.00 35.78 | A2 |
| ATOM | 887 | OG1 | THR | 116 | 55.564 | 70.038 | -1.576 | 1.00 35.58 | A2 |
| ATOM | 888 | HG1 | THR | 116 | 54.942 | 69.644 | -0.939 | 1.00 0.00 | A2 |
| ATOM | 889 | CG2 | THR | 116 | 57.816 | 69.050 | -1.921 | 1.00 35.38 | A2 |
| ATOM | 890 | C | THR | 116 | 56.714 | 67.726 | -4.304 | 1.00 37.14 | A2 |
| ATOM | 891 | O | THR | 116 | 57.641 | 67.937 | -5.066 | 1.00 39.27 | A2 |
| ATOM | 892 | N | THR | 117 | 56.318 | 66.485 | -4.045 | 1.00 39.05 | A2 |
| ATOM | 893 | H | THR | 117 | 55.615 | 66.383 | -3.369 | 1.00 0.00 | A2 |
| ATOM | 894 | CA | THR | 117 | 56.840 | 65.269 | -4.630 | 1.00 40.23 | A2 |
| ATOM | 895 | CB | THR | 117 | 55.909 | 64.090 | -4.216 | 1.00 39.99 | A2 |
| ATOM | 896 | OG1 | THR | 117 | 56.149 | 63.920 | -2.820 | 1.00 41.66 | A2 |
| ATOM | 897 | HG1 | THR | 117 | 55.653 | 64.559 | -2.286 | 1.00 0.00 | A2 |
| ATOM | 898 | CG2 | THR | 117 | 56.110 | 62.781 | -4.981 | 1.00 38.23 | A2 |
| ATOM | 899 | C | THR | 117 | 56.882 | 65.417 | -6.134 | 1.00 43.42 | A2 |
| ATOM | 900 | O | THR | 117 | 57.934 | 65.253 | -6.749 | 1.00 46.29 | A2 |
| ATOM | 901 | N | ILE | 118 | 55.763 | 65.777 | -6.741 | 1.00 45.87 | A2 |
| ATOM | 902 | H | ILE | 118 | 54.962 | 65.942 | -6.200 | 1.00 0.00 | A2 |
| ATOM | 903 | CA | ILE | 118 | 55.659 | 65.914 | -8.182 | 1.00 47.97 | A2 |
| ATOM | 904 | CB | ILE | 118 | 54.170 | 66.271 | -8.452 | 1.00 47.69 | A2 |
| ATOM | 905 | CG2 | ILE | 118 | 54.041 | 66.930 | -9.835 | 1.00 47.03 | A2 |
| ATOM | 906 | CG1 | ILE | 118 | 53.302 | 65.011 | -8.244 | 1.00 44.00 | A2 |
| ATOM | 907 | CD | ILE | 118 | 53.651 | 63.883 | -9.236 | 1.00 43.71 | A2 |
| ATOM | 908 | C | ILE | 118 | 56.647 | 66.932 | -8.724 | 1.00 50.69 | A2 |
| ATOM | 909 | O | ILE | 118 | 57.390 | 66.676 | -9.681 | 1.00 49.98 | A2 |
| ATOM | 910 | N | TRP | 119 | 56.697 | 68.061 | -8.015 | 1.00 54.68 | A2 |
| ATOM | 911 | H | TRP | 119 | 56.164 | 68.135 | -7.197 | 1.00 0.00 | A2 |
| ATOM | 912 | CA | TRP | 119 | 57.575 | 69.142 | -8.399 | 1.00 58.98 | A2 |
| ATOM | 913 | CB | TRP | 119 | 57.392 | 70.367 | -7.477 | 1.00 59.84 | A2 |
| ATOM | 914 | CG | TRP | 119 | 58.051 | 71.529 | -8.196 | 1.00 62.64 | A2 |
| ATOM | 915 | CD2 | TRP | 119 | 57.596 | 72.211 | -9.307 | 1.00 63.78 | A2 |
| ATOM | 916 | CE2 | TRP | 119 | 58.699 | 72.955 | -9.643 | 1.00 62.55 | A2 |
| ATOM | 917 | CE3 | TRP | 119 | 56.465 | 72.314 | -10.080 | 1.00 66.02 | A2 |
| ATOM | 918 | CD1 | TRP | 119 | 59.322 | 71.870 | -7.863 | 1.00 64.12 | A2 |
| ATOM | 919 | NE1 | TRP | 119 | 59.680 | 72.727 | -8.784 | 1.00 65.00 | A2 |
| ATOM | 920 | HE1 | TRP | 119 | 60.568 | 73.140 | -8.828 | 1.00 0.00 | A2 |
| ATOM | 921 | CZ2 | TRP | 119 | 58.726 | 73.794 | -10.714 | 1.00 62.90 | A2 |
| ATOM | 922 | CZ3 | TRP | 119 | 56.469 | 73.157 | -11.170 | 1.00 65.18 | A2 |
| ATOM | 923 | CH2 | TRP | 119 | 57.591 | 73.887 | -11.481 | 1.00 64.40 | A2 |
| ATOM | 924 | C | TRP | 119 | 59.021 | 68.664 | -8.352 | 1.00 61.26 | A2 |
| ATOM | 925 | O | TRP | 119 | 59.748 | 68.788 | -9.343 | 1.00 62.12 | A2 |
| ATOM | 926 | N | GLN | 120 | 59.447 | 68.065 | -7.249 | 1.00 62.91 | A2 |
| ATOM | 927 | H | GLN | 120 | 58.811 | 67.961 | -6.519 | 1.00 0.00 | A2 |
| ATOM | 928 | CA | GLN | 120 | 60.786 | 67.504 | -7.113 | 1.00 65.16 | A2 |
| ATOM | 929 | CB | GLN | 120 | 60.900 | 66.800 | -5.780 | 1.00 66.56 | A2 |
| ATOM | 930 | CG | GLN | 120 | 60.627 | 67.678 | -4.582 | 1.00 67.18 | A2 |
| ATOM | 931 | CD | GLN | 120 | 60.725 | 66.907 | -3.284 | 1.00 67.77 | A2 |
| ATOM | 932 | OE1 | GLN | 120 | 61.221 | 67.465 | -2.319 | 1.00 69.31 | A2 |
| ATOM | 933 | NE2 | GLN | 120 | 60.305 | 65.654 | -3.129 | 1.00 67.39 | A2 |
| ATOM | 934 | HE21 | GLN | 120 | 59.903 | 65.174 | -3.877 | 1.00 0.00 | A2 |
| ATOM | 935 | HE22 | GLN | 120 | 60.441 | 65.282 | -2.234 | 1.00 0.00 | A2 |
| ATOM | 936 | C | GLN | 120 | 61.169 | 66.509 | -8.222 | 1.00 66.22 | A2 |
| ATOM | 937 | O | GLN | 120 | 62.326 | 66.421 | -8.662 | 1.00 66.50 | A2 |
| ATOM | 938 | N | GLN | 121 | 60.202 | 65.745 | -8.706 | 1.00 67.10 | A2 |
| ATOM | 939 | H | GLN | 121 | 59.307 | 65.754 | -8.303 | 1.00 0.00 | A2 |
| ATOM | 940 | CA | GLN | 121 | 60.480 | 64.878 | -9.812 | 1.00 68.66 | A2 |
| ATOM | 941 | CB | GLN | 121 | 59.292 | 63.971 | -10.070 | 1.00 67.96 | A2 |
| ATOM | 942 | CG | GLN | 121 | 59.614 | 62.937 | -11.128 | 1.00 68.89 | A2 |
| ATOM | 943 | CD | GLN | 121 | 60.940 | 62.236 | -10.852 | 1.00 71.37 | A2 |
| ATOM | 944 | OE1 | GLN | 121 | 61.212 | 61.706 | -9.777 | 1.00 71.70 | A2 |
| ATOM | 945 | NE2 | GLN | 121 | 61.879 | 62.262 | -11.786 | 1.00 74.41 | A2 |

FIG.5-12

| ATOM | 946 | HE21 | GLN | 121 | 61.707 | 62.729 | -12.627 | 1.00 | 0.00 | A2 |
|---|---|---|---|---|---|---|---|---|---|---|
| ATOM | 947 | HE22 | GLN | 121 | 62.736 | 61.859 | -11.541 | 1.00 | 0.00 | A2 |
| ATOM | 948 | C | GLN | 121 | 60.760 | 65.743 | -11.045 | 1.00 | 70.48 | A2 |
| ATOM | 949 | O | GLN | 121 | 61.671 | 65.436 | -11.827 | 1.00 | 70.94 | A2 |
| ATOM | 950 | N | MET | 122 | 60.019 | 66.846 | -11.236 | 1.00 | 71.67 | A2 |
| ATOM | 951 | H | MET | 122 | 59.351 | 67.087 | -10.555 | 1.00 | 0.00 | A2 |
| ATOM | 952 | CA | MET | 122 | 60.190 | 67.688 | -12.412 | 1.00 | 72.62 | A2 |
| ATOM | 953 | CB | MET | 122 | 59.173 | 68.819 | -12.448 | 1.00 | 73.12 | A2 |
| ATOM | 954 | CG | MET | 122 | 57.880 | 68.343 | -13.083 | 1.00 | 73.64 | A2 |
| ATOM | 955 | SD | MET | 122 | 56.669 | 69.662 | -13.295 | 1.00 | 75.44 | A2 |
| ATOM | 956 | CE | MET | 122 | 55.695 | 69.349 | -11.861 | 1.00 | 76.43 | A2 |
| ATOM | 957 | C | MET | 122 | 61.566 | 68.281 | -12.411 | 1.00 | 73.22 | A2 |
| ATOM | 958 | O | MET | 122 | 62.240 | 68.287 | -13.441 | 1.00 | 73.03 | A2 |
| ATOM | 959 | N | GLU | 123 | 61.991 | 68.697 | -11.223 | 1.00 | 74.74 | A2 |
| ATOM | 960 | H | GLU | 123 | 61.372 | 68.617 | -10.466 | 1.00 | 0.00 | A2 |
| ATOM | 961 | CA | GLU | 123 | 63.305 | 69.262 | -11.018 | 1.00 | 75.95 | A2 |
| ATOM | 962 | CB | GLU | 123 | 63.484 | 69.665 | -9.597 | 1.00 | 75.72 | A2 |
| ATOM | 963 | CG | GLU | 123 | 62.644 | 70.906 | -9.500 | 1.00 | 79.11 | A2 |
| ATOM | 964 | CD | GLU | 123 | 62.651 | 71.529 | -8.122 | 1.00 | 83.02 | A2 |
| ATOM | 965 | OE1 | GLU | 123 | 62.741 | 72.763 | -8.057 | 1.00 | 84.15 | A2 |
| ATOM | 966 | OE2 | GLU | 123 | 62.543 | 70.789 | -7.133 | 1.00 | 84.45 | A2 |
| ATOM | 967 | C | GLU | 123 | 64.381 | 68.280 | -11.386 | 1.00 | 77.17 | A2 |
| ATOM | 968 | O | GLU | 123 | 65.092 | 68.558 | -12.356 | 1.00 | 78.22 | A2 |
| ATOM | 969 | N | GLU | 124 | 64.504 | 67.110 | -10.765 | 1.00 | 77.66 | A2 |
| ATOM | 970 | H | GLU | 124 | 63.867 | 66.852 | -10.060 | 1.00 | 0.00 | A2 |
| ATOM | 971 | CA | GLU | 124 | 65.574 | 66.215 | -11.167 | 1.00 | 78.47 | A2 |
| ATOM | 972 | CB | GLU | 124 | 65.600 | 65.051 | -10.195 | 1.00 | 80.79 | A2 |
| ATOM | 973 | CG | GLU | 124 | 64.387 | 64.132 | -10.150 | 1.00 | 83.29 | A2 |
| ATOM | 974 | CD | GLU | 124 | 64.375 | 63.248 | -8.908 | 1.00 | 85.51 | A2 |
| ATOM | 975 | OE1 | GLU | 124 | 64.733 | 63.729 | -7.824 | 1.00 | 86.84 | A2 |
| ATOM | 976 | OE2 | GLU | 124 | 64.006 | 62.075 | -9.024 | 1.00 | 86.39 | A2 |
| ATOM | 977 | C | GLU | 124 | 65.534 | 65.705 | -12.612 | 1.00 | 78.01 | A2 |
| ATOM | 978 | O | GLU | 124 | 66.480 | 65.057 | -13.060 | 1.00 | 78.91 | A2 |
| ATOM | 979 | N | LEU | 125 | 64.460 | 65.943 | -13.363 | 1.00 | 77.11 | A2 |
| ATOM | 980 | H | LEU | 125 | 63.666 | 66.340 | -12.945 | 1.00 | 0.00 | A2 |
| ATOM | 981 | CA | LEU | 125 | 64.387 | 65.583 | -14.771 | 1.00 | 76.23 | A2 |
| ATOM | 982 | CB | LEU | 125 | 63.061 | 64.832 | -14.952 | 1.00 | 76.88 | A2 |
| ATOM | 983 | CG | LEU | 125 | 62.392 | 64.382 | -16.263 | 1.00 | 76.63 | A2 |
| ATOM | 984 | CD1 | LEU | 125 | 63.350 | 63.754 | -17.276 | 1.00 | 76.67 | A2 |
| ATOM | 985 | CD2 | LEU | 125 | 61.309 | 63.402 | -15.839 | 1.00 | 75.89 | A2 |
| ATOM | 986 | C | LEU | 125 | 64.506 | 66.827 | -15.648 | 1.00 | 75.84 | A2 |
| ATOM | 987 | O | LEU | 125 | 64.360 | 66.788 | -16.871 | 1.00 | 75.36 | A2 |
| ATOM | 988 | N | GLY | 126 | 64.759 | 67.968 | -15.027 | 1.00 | 75.90 | A2 |
| ATOM | 989 | H | GLY | 126 | 64.741 | 67.976 | -14.056 | 1.00 | 0.00 | A2 |
| ATOM | 990 | CA | GLY | 126 | 64.968 | 69.213 | -15.736 | 1.00 | 77.58 | A2 |
| ATOM | 991 | C | GLY | 126 | 63.697 | 69.814 | -16.330 | 1.00 | 78.63 | A2 |
| ATOM | 992 | O | GLY | 126 | 63.735 | 70.736 | -17.146 | 1.00 | 78.55 | A2 |
| ATOM | 993 | N | MET | 127 | 62.524 | 69.343 | -15.933 | 1.00 | 80.08 | A2 |
| ATOM | 994 | H | MET | 127 | 62.522 | 68.603 | -15.293 | 1.00 | 0.00 | A2 |
| ATOM | 995 | CA | MET | 127 | 61.266 | 69.902 | -16.415 | 1.00 | 81.46 | A2 |
| ATOM | 996 | CB | MET | 127 | 60.191 | 68.802 | -16.361 | 1.00 | 81.86 | A2 |
| ATOM | 997 | CG | MET | 127 | 60.708 | 67.599 | -17.147 | 1.00 | 82.66 | A2 |
| ATOM | 998 | SD | MET | 127 | 59.682 | 66.115 | -17.282 | 1.00 | 83.70 | A2 |
| ATOM | 999 | CE | MET | 127 | 60.236 | 65.620 | -18.900 | 1.00 | 83.23 | A2 |
| ATOM | 1000 | C | MET | 127 | 60.847 | 71.131 | -15.599 | 1.00 | 82.18 | A2 |
| ATOM | 1001 | OT1 | MET | 127 | 60.116 | 71.958 | -16.142 | 1.00 | 83.86 | A2 |
| ATOM | 1002 | OT2 | MET | 127 | 61.267 | 71.285 | -14.446 | 1.00 | 82.04 | A2 |
| ATOM | 1003 | CB | MET | 138 | 39.323 | 80.595 | -4.492 | 1.00 | 59.39 | A3 |
| ATOM | 1004 | CG | MET | 138 | 40.123 | 79.298 | -4.421 | 1.00 | 57.97 | A3 |
| ATOM | 1005 | SD | MET | 138 | 40.561 | 78.973 | -6.145 | 1.00 | 60.85 | A3 |
| ATOM | 1006 | CE | MET | 138 | 41.129 | 77.310 | -6.351 | 1.00 | 61.48 | A3 |
| ATOM | 1007 | C | MET | 138 | 37.021 | 81.072 | -5.454 | 1.00 | 60.26 | A3 |
| ATOM | 1008 | O | MET | 138 | 36.832 | 82.262 | -5.181 | 1.00 | 62.98 | A3 |
| ATOM | 1009 | HT1 | MET | 138 | 38.497 | 82.600 | -6.075 | 1.00 | 0.00 | A3 |
| ATOM | 1010 | HT2 | MET | 138 | 38.313 | 81.757 | -7.529 | 1.00 | 0.00 | A3 |
| ATOM | 1011 | N | MET | 138 | 38.839 | 81.784 | -6.639 | 1.00 | 60.49 | A3 |
| ATOM | 1012 | HT3 | MET | 138 | 39.865 | 81.816 | -6.768 | 1.00 | 0.00 | A3 |
| ATOM | 1013 | CA | MET | 138 | 38.445 | 80.672 | -5.787 | 1.00 | 60.51 | A3 |
| ATOM | 1014 | N | PRO | 139 | 35.995 | 80.242 | -5.612 | 1.00 | 57.82 | A3 |
| ATOM | 1015 | CD | PRO | 139 | 36.028 | 79.060 | -6.448 | 1.00 | 58.10 | A3 |
| ATOM | 1016 | CA | PRO | 139 | 34.654 | 80.538 | -5.142 | 1.00 | 54.67 | A3 |
| ATOM | 1017 | CB | PRO | 139 | 33.870 | 79.323 | -5.525 | 1.00 | 54.54 | A3 |
| ATOM | 1018 | CG | PRO | 139 | 34.945 | 78.290 | -5.755 | 1.00 | 58.20 | A3 |
| ATOM | 1019 | C | PRO | 139 | 34.588 | 80.875 | -3.664 | 1.00 | 52.24 | A3 |
| ATOM | 1020 | O | PRO | 139 | 35.507 | 80.623 | -2.882 | 1.00 | 51.89 | A3 |
| ATOM | 1021 | N | ALA | 140 | 33.499 | 81.547 | -3.342 | 1.00 | 49.86 | A3 |
| ATOM | 1022 | H | ALA | 140 | 32.789 | 81.676 | -4.005 | 1.00 | 0.00 | A3 |
| ATOM | 1023 | CA | ALA | 140 | 33.234 | 81.926 | -1.994 | 1.00 | 49.39 | A3 |
| ATOM | 1024 | CB | ALA | 140 | 32.966 | 83.413 | -1.895 | 1.00 | 49.94 | A3 |
| ATOM | 1025 | C | ALA | 140 | 31.978 | 81.153 | -1.590 | 1.00 | 49.25 | A3 |
| ATOM | 1026 | O | ALA | 140 | 30.889 | 81.162 | -2.205 | 1.00 | 49.06 | A3 |
| ATOM | 1027 | N | PHE | 141 | 32.293 | 80.442 | -0.506 | 1.00 | 47.48 | A3 |
| ATOM | 1028 | H | PHE | 141 | 33.190 | 80.550 | -0.122 | 1.00 | 0.00 | A3 |
| ATOM | 1029 | CA | PHE | 141 | 31.401 | 79.552 | 0.208 | 1.00 | 45.66 | A3 |
| ATOM | 1030 | CB | PHE | 141 | 32.215 | 78.305 | 0.792 | 1.00 | 40.28 | A3 |
| ATOM | 1031 | CG | PHE | 141 | 32.684 | 77.404 | -0.349 | 1.00 | 35.35 | A3 |

FIG.5-13

| ATOM | 1032 | CD1 | PHE | 141 | 31.800 | 76.591 | -1.006 | 1.00 | 34.39 | A3 |
|------|------|-----|-----|-----|--------|--------|--------|------|-------|-----|
| ATOM | 1033 | CD2 | PHE | 141 | 33.966 | 77.497 | -0.830 | 1.00 | 37.69 | A3 |
| ATOM | 1034 | CE1 | PHE | 141 | 32.174 | 75.895 | -2.133 | 1.00 | 34.00 | A3 |
| ATOM | 1035 | CE2 | PHE | 141 | 34.358 | 76.807 | -1.956 | 1.00 | 36.69 | A3 |
| ATOM | 1036 | CZ  | PHE | 141 | 33.449 | 76.001 | -2.614 | 1.00 | 37.29 | A3 |
| ATOM | 1037 | C   | PHE | 141 | 31.003 | 80.580 | 1.242  | 1.00 | 46.54 | A3 |
| ATOM | 1038 | O   | PHE | 141 | 31.584 | 80.664 | 2.317  | 1.00 | 48.26 | A3 |
| ATOM | 1039 | N   | ALA | 142 | 30.067 | 81.452 | 0.843  | 1.00 | 47.38 | A3 |
| ATOM | 1040 | H   | ALA | 142 | 29.624 | 81.295 | -0.020 | 1.00 | 0.00  | A3 |
| ATOM | 1041 | CA  | ALA | 142 | 29.581 | 82.564 | 1.668  | 1.00 | 46.06 | A3 |
| ATOM | 1042 | CB  | ALA | 142 | 28.731 | 83.546 | 0.879  | 1.00 | 45.04 | A3 |
| ATOM | 1043 | C   | ALA | 142 | 28.703 | 82.132 | 2.802  | 1.00 | 45.27 | A3 |
| ATOM | 1044 | O   | ALA | 142 | 28.343 | 83.002 | 3.584  | 1.00 | 47.38 | A3 |
| ATOM | 1045 | N   | SER | 143 | 28.318 | 80.860 | 2.899  | 1.00 | 43.36 | A3 |
| ATOM | 1046 | H   | SER | 143 | 28.724 | 80.201 | 2.303  | 1.00 | 0.00  | A3 |
| ATOM | 1047 | CA  | SER | 143 | 27.377 | 80.392 | 3.897  | 1.00 | 41.94 | A3 |
| ATOM | 1048 | CB  | SER | 143 | 26.036 | 80.129 | 3.181  | 1.00 | 44.17 | A3 |
| ATOM | 1049 | OG  | SER | 143 | 25.323 | 78.918 | 3.536  | 1.00 | 48.18 | A3 |
| ATOM | 1050 | HG  | SER | 143 | 24.455 | 78.974 | 3.098  | 1.00 | 0.00  | A3 |
| ATOM | 1051 | C   | SER | 143 | 27.877 | 79.145 | 4.602  | 1.00 | 39.79 | A3 |
| ATOM | 1052 | O   | SER | 143 | 28.763 | 78.452 | 4.132  | 1.00 | 38.50 | A3 |
| ATOM | 1053 | N   | ALA | 144 | 27.218 | 78.775 | 5.683  | 1.00 | 39.10 | A3 |
| ATOM | 1054 | H   | ALA | 144 | 26.449 | 79.312 | 5.960  | 1.00 | 0.00  | A3 |
| ATOM | 1055 | CA  | ALA | 144 | 27.566 | 77.586 | 6.411  | 1.00 | 39.22 | A3 |
| ATOM | 1056 | CB  | ALA | 144 | 26.982 | 77.598 | 7.802  | 1.00 | 36.97 | A3 |
| ATOM | 1057 | C   | ALA | 144 | 26.964 | 76.420 | 5.627  | 1.00 | 41.58 | A3 |
| ATOM | 1058 | O   | ALA | 144 | 27.706 | 75.448 | 5.444  | 1.00 | 42.07 | A3 |
| ATOM | 1059 | N   | PHE | 145 | 25.719 | 76.407 | 5.076  | 1.00 | 40.77 | A3 |
| ATOM | 1060 | H   | PHE | 145 | 25.149 | 77.203 | 5.110  | 1.00 | 0.00  | A3 |
| ATOM | 1061 | CA  | PHE | 145 | 25.307 | 75.234 | 4.312  | 1.00 | 39.31 | A3 |
| ATOM | 1062 | CB  | PHE | 145 | 23.877 | 75.396 | 3.798  | 1.00 | 36.46 | A3 |
| ATOM | 1063 | CG  | PHE | 145 | 23.477 | 74.452 | 2.641  | 1.00 | 31.91 | A3 |
| ATOM | 1064 | CD1 | PHE | 145 | 23.579 | 74.900 | 1.323  | 1.00 | 29.02 | A3 |
| ATOM | 1065 | CD2 | PHE | 145 | 23.013 | 73.185 | 2.916  | 1.00 | 29.40 | A3 |
| ATOM | 1066 | CE1 | PHE | 145 | 23.225 | 74.100 | 0.277  | 1.00 | 28.34 | A3 |
| ATOM | 1067 | CE2 | PHE | 145 | 22.661 | 72.389 | 1.858  | 1.00 | 28.80 | A3 |
| ATOM | 1068 | CZ  | PHE | 145 | 22.764 | 72.831 | 0.549  | 1.00 | 30.58 | A3 |
| ATOM | 1069 | C   | PHE | 145 | 26.266 | 75.071 | 3.120  | 1.00 | 40.44 | A3 |
| ATOM | 1070 | O   | PHE | 145 | 26.556 | 73.938 | 2.697  | 1.00 | 40.55 | A3 |
| ATOM | 1071 | N   | GLN | 146 | 26.745 | 76.232 | 2.619  | 1.00 | 39.11 | A3 |
| ATOM | 1072 | H   | GLN | 146 | 26.437 | 77.073 | 3.015  | 1.00 | 0.00  | A3 |
| ATOM | 1073 | CA  | GLN | 146 | 27.660 | 76.263 | 1.511  | 1.00 | 38.01 | A3 |
| ATOM | 1074 | CB  | GLN | 146 | 27.907 | 77.644 | 1.054  | 1.00 | 38.92 | A3 |
| ATOM | 1075 | CG  | GLN | 146 | 26.884 | 78.066 | 0.049  | 1.00 | 43.26 | A3 |
| ATOM | 1076 | CD  | GLN | 146 | 27.171 | 79.440 | -0.522 | 1.00 | 45.37 | A3 |
| ATOM | 1077 | OE1 | GLN | 146 | 27.851 | 80.253 | 0.083  | 1.00 | 47.57 | A3 |
| ATOM | 1078 | NE2 | GLN | 146 | 26.689 | 79.793 | -1.692 | 1.00 | 47.50 | A3 |
| ATOM | 1079 | HE21| GLN | 146 | 26.149 | 79.149 | -2.190 | 1.00 | 0.00  | A3 |
| ATOM | 1080 | HE22| GLN | 146 | 26.913 | 80.690 | -2.021 | 1.00 | 0.00  | A3 |
| ATOM | 1081 | C   | GLN | 146 | 29.005 | 75.670 | 1.836  | 1.00 | 37.25 | A3 |
| ATOM | 1082 | O   | GLN | 146 | 29.634 | 75.093 | 0.950  | 1.00 | 38.28 | A3 |
| ATOM | 1083 | N   | ARG | 147 | 29.511 | 75.775 | 3.054  | 1.00 | 36.37 | A3 |
| ATOM | 1084 | H   | ARG | 147 | 29.044 | 76.300 | 3.738  | 1.00 | 0.00  | A3 |
| ATOM | 1085 | CA  | ARG | 147 | 30.798 | 75.180 | 3.357  | 1.00 | 35.68 | A3 |
| ATOM | 1086 | CB  | ARG | 147 | 31.299 | 75.574 | 4.713  | 1.00 | 37.12 | A3 |
| ATOM | 1087 | CG  | ARG | 147 | 31.730 | 77.016 | 4.697  | 1.00 | 42.68 | A3 |
| ATOM | 1088 | CD  | ARG | 147 | 32.034 | 77.494 | 6.093  | 1.00 | 49.54 | A3 |
| ATOM | 1089 | NE  | ARG | 147 | 32.674 | 78.774 | 5.877  | 1.00 | 58.21 | A3 |
| ATOM | 1090 | HE  | ARG | 147 | 32.475 | 79.252 | 5.045  | 1.00 | 0.00  | A3 |
| ATOM | 1091 | CZ  | ARG | 147 | 33.519 | 79.373 | 6.742  | 1.00 | 62.77 | A3 |
| ATOM | 1092 | NH1 | ARG | 147 | 33.905 | 78.868 | 7.936  | 1.00 | 63.96 | A3 |
| ATOM | 1093 | HH11| ARG | 147 | 34.545 | 79.379 | 8.510  | 1.00 | 0.00  | A3 |
| ATOM | 1094 | HH12| ARG | 147 | 33.561 | 77.980 | 8.239  | 1.00 | 0.00  | A3 |
| ATOM | 1095 | NH2 | ARG | 147 | 33.960 | 80.584 | 6.403  | 1.00 | 64.80 | A3 |
| ATOM | 1096 | HH21| ARG | 147 | 34.599 | 81.069 | 6.999  | 1.00 | 0.00  | A3 |
| ATOM | 1097 | HH22| ARG | 147 | 33.665 | 80.996 | 5.541  | 1.00 | 0.00  | A3 |
| ATOM | 1098 | C   | ARG | 147 | 30.570 | 73.702 | 3.337  | 1.00 | 34.91 | A3 |
| ATOM | 1099 | O   | ARG | 147 | 31.233 | 73.050 | 2.539  | 1.00 | 34.56 | A3 |
| ATOM | 1100 | N   | ALA | 148 | 29.544 | 73.194 | 4.040  | 1.00 | 33.44 | A3 |
| ATOM | 1101 | H   | ALA | 148 | 28.926 | 73.818 | 4.482  | 1.00 | 0.00  | A3 |
| ATOM | 1102 | CA  | ALA | 148 | 29.358 | 71.754 | 4.172  | 1.00 | 33.92 | A3 |
| ATOM | 1103 | CB  | ALA | 148 | 28.217 | 71.426 | 5.163  | 1.00 | 32.85 | A3 |
| ATOM | 1104 | C   | ALA | 148 | 29.077 | 71.095 | 2.843  | 1.00 | 33.40 | A3 |
| ATOM | 1105 | O   | ALA | 148 | 29.765 | 70.141 | 2.457  | 1.00 | 34.31 | A3 |
| ATOM | 1106 | N   | ALA | 149 | 28.169 | 71.657 | 2.077  | 1.00 | 32.60 | A3 |
| ATOM | 1107 | H   | ALA | 149 | 27.662 | 72.424 | 2.411  | 1.00 | 0.00  | A3 |
| ATOM | 1108 | CA  | ALA | 149 | 27.890 | 71.134 | 0.757  | 1.00 | 32.70 | A3 |
| ATOM | 1109 | CB  | ALA | 149 | 26.595 | 71.774 | 0.299  | 1.00 | 31.91 | A3 |
| ATOM | 1110 | C   | ALA | 149 | 29.032 | 71.381 | -0.258 | 1.00 | 33.75 | A3 |
| ATOM | 1111 | O   | ALA | 149 | 29.208 | 70.661 | -1.264 | 1.00 | 34.49 | A3 |
| ATOM | 1112 | N   | GLY | 150 | 29.867 | 72.401 | -0.052 | 1.00 | 33.58 | A3 |
| ATOM | 1113 | H   | GLY | 150 | 29.724 | 73.035 | 0.682  | 1.00 | 0.00  | A3 |
| ATOM | 1114 | CA  | GLY | 150 | 31.017 | 72.608 | -0.913 | 1.00 | 31.79 | A3 |
| ATOM | 1115 | C   | GLY | 150 | 32.113 | 71.629 | -0.478 | 1.00 | 31.39 | A3 |
| ATOM | 1116 | O   | GLY | 150 | 32.997 | 71.261 | -1.265 | 1.00 | 31.77 | A3 |
| ATOM | 1117 | N   | GLY | 151 | 32.075 | 71.161 | 0.773  | 1.00 | 29.83 | A3 |

FIG.5-14

| ATOM | 1118 | H | GLY | 151 | 31.412 | 71.524 | 1.394 | 1.00 | 0.00 | A3 |
|---|---|---|---|---|---|---|---|---|---|---|
| ATOM | 1119 | CA | GLY | 151 | 33.018 | 70.166 | 1.243 | 1.00 | 32.16 | A3 |
| ATOM | 1120 | C | GLY | 151 | 32.764 | 68.909 | 0.409 | 1.00 | 33.98 | A3 |
| ATOM | 1121 | O | GLY | 151 | 33.664 | 68.501 | -0.349 | 1.00 | 35.66 | A3 |
| ATOM | 1122 | N | VAL | 152 | 31.486 | 68.418 | 0.451 | 1.00 | 31.87 | A3 |
| ATOM | 1123 | H | VAL | 152 | 30.867 | 68.906 | 1.040 | 1.00 | 0.00 | A3 |
| ATOM | 1124 | CA | VAL | 152 | 30.978 | 67.240 | -0.275 | 1.00 | 29.61 | A3 |
| ATOM | 1125 | CB | VAL | 152 | 29.419 | 67.145 | -0.125 | 1.00 | 27.63 | A3 |
| ATOM | 1126 | CG1 | VAL | 152 | 28.883 | 66.035 | -0.976 | 1.00 | 27.37 | A3 |
| ATOM | 1127 | CG2 | VAL | 152 | 29.002 | 66.786 | 1.279 | 1.00 | 24.74 | A3 |
| ATOM | 1128 | C | VAL | 152 | 31.351 | 67.294 | -1.762 | 1.00 | 29.91 | A3 |
| ATOM | 1129 | O | VAL | 152 | 31.805 | 66.329 | -2.393 | 1.00 | 31.75 | A3 |
| ATOM | 1130 | N | LEU | 153 | 31.236 | 68.452 | -2.361 | 1.00 | 29.26 | A3 |
| ATOM | 1131 | H | LEU | 153 | 30.881 | 69.219 | -1.860 | 1.00 | 0.00 | A3 |
| ATOM | 1132 | CA | LEU | 153 | 31.559 | 68.607 | -3.756 | 1.00 | 26.77 | A3 |
| ATOM | 1133 | CB | LEU | 153 | 30.881 | 69.858 | -4.160 | 1.00 | 28.22 | A3 |
| ATOM | 1134 | CG | LEU | 153 | 29.943 | 69.894 | -5.316 | 1.00 | 30.67 | A3 |
| ATOM | 1135 | CD1 | LEU | 153 | 28.580 | 69.281 | -5.090 | 1.00 | 26.48 | A3 |
| ATOM | 1136 | CD2 | LEU | 153 | 29.741 | 71.365 | -5.496 | 1.00 | 34.46 | A3 |
| ATOM | 1137 | C | LEU | 153 | 33.032 | 68.628 | -4.111 | 1.00 | 26.08 | A3 |
| ATOM | 1138 | O | LEU | 153 | 33.419 | 68.187 | -5.212 | 1.00 | 26.78 | A3 |
| ATOM | 1139 | N | VAL | 154 | 33.902 | 69.180 | -3.269 | 1.00 | 26.12 | A3 |
| ATOM | 1140 | H | VAL | 154 | 33.589 | 69.557 | -2.416 | 1.00 | 0.00 | A3 |
| ATOM | 1141 | CA | VAL | 154 | 35.330 | 69.259 | -3.611 | 1.00 | 26.23 | A3 |
| ATOM | 1142 | CB | VAL | 154 | 36.057 | 70.299 | -2.692 | 1.00 | 26.51 | A3 |
| ATOM | 1143 | CG1 | VAL | 154 | 37.578 | 70.188 | -2.942 | 1.00 | 25.01 | A3 |
| ATOM | 1144 | CG2 | VAL | 154 | 35.528 | 71.728 | -2.945 | 1.00 | 27.82 | A3 |
| ATOM | 1145 | C | VAL | 154 | 35.933 | 67.850 | -3.375 | 1.00 | 26.80 | A3 |
| ATOM | 1146 | O | VAL | 154 | 36.678 | 67.363 | -4.229 | 1.00 | 26.27 | A3 |
| ATOM | 1147 | N | ALA | 155 | 35.635 | 67.241 | -2.199 | 1.00 | 24.76 | A3 |
| ATOM | 1148 | H | ALA | 155 | 35.084 | 67.758 | -1.570 | 1.00 | 0.00 | A3 |
| ATOM | 1149 | CA | ALA | 155 | 36.095 | 65.940 | -1.782 | 1.00 | 25.21 | A3 |
| ATOM | 1150 | CB | ALA | 155 | 35.463 | 65.572 | -0.457 | 1.00 | 25.25 | A3 |
| ATOM | 1151 | C | ALA | 155 | 35.708 | 64.946 | -2.841 | 1.00 | 26.94 | A3 |
| ATOM | 1152 | O | ALA | 155 | 36.594 | 64.288 | -3.398 | 1.00 | 26.76 | A3 |
| ATOM | 1153 | N | SER | 156 | 34.450 | 64.982 | -3.282 | 1.00 | 29.96 | A3 |
| ATOM | 1154 | H | SER | 156 | 33.790 | 65.577 | -2.868 | 1.00 | 0.00 | A3 |
| ATOM | 1155 | CA | SER | 156 | 34.034 | 64.105 | -4.354 | 1.00 | 32.17 | A3 |
| ATOM | 1156 | CB | SER | 156 | 32.531 | 64.319 | -4.544 | 1.00 | 34.23 | A3 |
| ATOM | 1157 | OG | SER | 156 | 32.000 | 64.195 | -5.879 | 1.00 | 39.35 | A3 |
| ATOM | 1158 | HG | SER | 156 | 31.120 | 63.815 | -5.851 | 1.00 | 0.00 | A3 |
| ATOM | 1159 | C | SER | 156 | 34.845 | 64.338 | -5.632 | 1.00 | 33.46 | A3 |
| ATOM | 1160 | O | SER | 156 | 35.411 | 63.380 | -6.174 | 1.00 | 34.62 | A3 |
| ATOM | 1161 | N | HIS | 157 | 35.054 | 65.576 | -6.133 | 1.00 | 33.90 | A3 |
| ATOM | 1162 | H | HIS | 157 | 34.771 | 66.349 | -5.605 | 1.00 | 0.00 | A3 |
| ATOM | 1163 | CA | HIS | 157 | 35.821 | 65.773 | -7.383 | 1.00 | 31.19 | A3 |
| ATOM | 1164 | CB | HIS | 157 | 35.707 | 67.209 | -7.900 | 1.00 | 32.59 | A3 |
| ATOM | 1165 | CG | HIS | 157 | 34.369 | 67.449 | -8.566 | 1.00 | 31.11 | A3 |
| ATOM | 1166 | CD2 | HIS | 157 | 34.127 | 67.394 | -9.928 | 1.00 | 30.78 | A3 |
| ATOM | 1167 | ND1 | HIS | 157 | 33.223 | 67.666 | -7.942 | 1.00 | 32.36 | A3 |
| ATOM | 1168 | HD1 | HIS | 157 | 33.080 | 67.773 | -6.979 | 1.00 | 0.00 | A3 |
| ATOM | 1169 | CE1 | HIS | 157 | 32.293 | 67.732 | -8.875 | 1.00 | 32.01 | A3 |
| ATOM | 1170 | NE2 | HIS | 157 | 32.838 | 67.571 | -10.060 | 1.00 | 29.18 | A3 |
| ATOM | 1171 | HE2 | HIS | 157 | 32.327 | 67.621 | -10.895 | 1.00 | 0.00 | A3 |
| ATOM | 1172 | C | HIS | 157 | 37.291 | 65.476 | -7.269 | 1.00 | 29.68 | A3 |
| ATOM | 1173 | O | HIS | 157 | 37.950 | 65.059 | -8.219 | 1.00 | 29.65 | A3 |
| ATOM | 1174 | N | LEU | 158 | 37.801 | 65.669 | -6.071 | 1.00 | 29.24 | A3 |
| ATOM | 1175 | H | LEU | 158 | 37.213 | 65.901 | -5.326 | 1.00 | 0.00 | A3 |
| ATOM | 1176 | CA | LEU | 158 | 39.216 | 65.479 | -5.826 | 1.00 | 31.94 | A3 |
| ATOM | 1177 | CB | LEU | 158 | 39.609 | 65.949 | -4.373 | 1.00 | 28.66 | A3 |
| ATOM | 1178 | CG | LEU | 158 | 41.008 | 65.751 | -3.859 | 1.00 | 24.32 | A3 |
| ATOM | 1179 | CD1 | LEU | 158 | 41.990 | 66.378 | -4.776 | 1.00 | 20.87 | A3 |
| ATOM | 1180 | CD2 | LEU | 158 | 41.099 | 66.330 | -2.477 | 1.00 | 24.86 | A3 |
| ATOM | 1181 | C | LEU | 158 | 39.468 | 63.994 | -6.027 | 1.00 | 31.46 | A3 |
| ATOM | 1182 | O | LEU | 158 | 40.298 | 63.609 | -6.844 | 1.00 | 30.58 | A3 |
| ATOM | 1183 | N | GLN | 159 | 38.652 | 63.225 | -5.340 | 1.00 | 33.54 | A3 |
| ATOM | 1184 | H | GLN | 159 | 38.011 | 63.676 | -4.748 | 1.00 | 0.00 | A3 |
| ATOM | 1185 | CA | GLN | 159 | 38.594 | 61.792 | -5.442 | 1.00 | 35.73 | A3 |
| ATOM | 1186 | CB | GLN | 159 | 37.308 | 61.492 | -4.813 | 1.00 | 37.26 | A3 |
| ATOM | 1187 | CG | GLN | 159 | 37.064 | 60.063 | -4.520 | 1.00 | 45.01 | A3 |
| ATOM | 1188 | CD | GLN | 159 | 37.755 | 59.611 | -3.256 | 1.00 | 46.24 | A3 |
| ATOM | 1189 | OE1 | GLN | 159 | 38.142 | 58.443 | -3.232 | 1.00 | 48.29 | A3 |
| ATOM | 1190 | NE2 | GLN | 159 | 37.936 | 60.456 | -2.224 | 1.00 | 47.82 | A3 |
| ATOM | 1191 | HE21 | GLN | 159 | 37.575 | 61.364 | -2.289 | 1.00 | 0.00 | A3 |
| ATOM | 1192 | HE22 | GLN | 159 | 38.412 | 60.101 | -1.447 | 1.00 | 0.00 | A3 |
| ATOM | 1193 | C | GLN | 159 | 38.686 | 61.381 | -6.921 | 1.00 | 36.24 | A3 |
| ATOM | 1194 | O | GLN | 159 | 39.632 | 60.690 | -7.324 | 1.00 | 38.97 | A3 |
| ATOM | 1195 | N | SER | 160 | 37.824 | 61.896 | -7.796 | 1.00 | 35.48 | A3 |
| ATOM | 1196 | H | SER | 160 | 37.142 | 62.540 | -7.498 | 1.00 | 0.00 | A3 |
| ATOM | 1197 | CA | SER | 160 | 37.869 | 61.564 | -9.203 | 1.00 | 34.96 | A3 |
| ATOM | 1198 | CB | SER | 160 | 36.645 | 62.100 | -9.863 | 1.00 | 37.54 | A3 |
| ATOM | 1199 | OG | SER | 160 | 35.587 | 62.434 | -8.942 | 1.00 | 44.81 | A3 |
| ATOM | 1200 | HG | SER | 160 | 35.340 | 61.689 | -8.387 | 1.00 | 0.00 | A3 |
| ATOM | 1201 | C | SER | 160 | 39.090 | 62.095 | -9.922 | 1.00 | 34.65 | A3 |
| ATOM | 1202 | O | SER | 160 | 39.605 | 61.382 | -10.785 | 1.00 | 35.42 | A3 |
| ATOM | 1203 | N | PHE | 161 | 39.615 | 63.293 | -9.595 | 1.00 | 33.82 | A3 |

FIG.5-15

| | | | | | | | |
|---|---|---|---|---|---|---|---|
| ATOM | 1204 | H | PHE | 161 | 39.203 63.796 -8.864 | 1.00 0.00 | A3 |
| ATOM | 1205 | CA | PHE | 161 | 40.820 63.850 -10.218 | 1.00 31.21 | A3 |
| ATOM | 1206 | CB | PHE | 161 | 41.110 65.264 -9.629 | 1.00 28.28 | A3 |
| ATOM | 1207 | CG | PHE | 161 | 42.455 65.881 -10.062 | 1.00 24.92 | A3 |
| ATOM | 1208 | CD1 | PHE | 161 | 42.696 66.228 -11.389 | 1.00 22.98 | A3 |
| ATOM | 1209 | CD2 | PHE | 161 | 43.464 66.021 -9.135 | 1.00 23.03 | A3 |
| ATOM | 1210 | CE1 | PHE | 161 | 43.941 66.495 -11.767 | 1.00 21.06 | A3 |
| ATOM | 1211 | CE2 | PHE | 161 | 44.701 66.495 -9.528 | 1.00 20.28 | A3 |
| ATOM | 1212 | CZ | PHE | 161 | 44.939 66.826 -10.832 | 1.00 17.03 | A3 |
| ATOM | 1213 | C | PHE | 161 | 42.008 62.907 -9.943 | 1.00 31.77 | A3 |
| ATOM | 1214 | O | PHE | 161 | 42.786 62.578 -10.845 | 1.00 32.63 | A3 |
| ATOM | 1215 | N | LEU | 162 | 42.117 62.434 -8.690 | 1.00 31.67 | A3 |
| ATOM | 1216 | H | LEU | 162 | 41.420 62.691 -8.054 | 1.00 0.00 | A3 |
| ATOM | 1217 | CA | LEU | 162 | 43.186 61.574 -8.232 | 1.00 31.29 | A3 |
| ATOM | 1218 | CB | LEU | 162 | 43.204 61.433 -6.743 | 1.00 25.84 | A3 |
| ATOM | 1219 | CG | LEU | 162 | 43.693 62.674 -6.003 | 1.00 26.02 | A3 |
| ATOM | 1220 | CD1 | LEU | 162 | 43.594 62.455 -4.516 | 1.00 25.24 | A3 |
| ATOM | 1221 | CD2 | LEU | 162 | 45.107 62.994 -6.415 | 1.00 27.04 | A3 |
| ATOM | 1222 | C | LEU | 162 | 43.061 60.212 -8.813 | 1.00 34.23 | A3 |
| ATOM | 1223 | O | LEU | 162 | 44.107 59.654 -9.070 | 1.00 36.51 | A3 |
| ATOM | 1224 | N | GLU | 163 | 41.926 59.589 -9.082 | 1.00 37.24 | A3 |
| ATOM | 1225 | H | GLU | 163 | 41.072 60.002 -8.826 | 1.00 0.00 | A3 |
| ATOM | 1226 | CA | GLU | 163 | 41.975 58.327 -9.771 | 1.00 40.47 | A3 |
| ATOM | 1227 | CB | GLU | 163 | 40.566 57.716 -9.835 | 1.00 45.38 | A3 |
| ATOM | 1228 | CG | GLU | 163 | 40.264 56.975 -8.526 | 1.00 51.84 | A3 |
| ATOM | 1229 | CD | GLU | 163 | 41.291 55.889 -8.126 | 1.00 57.97 | A3 |
| ATOM | 1230 | OE1 | GLU | 163 | 40.897 54.722 -8.092 | 1.00 62.01 | A3 |
| ATOM | 1231 | OE2 | GLU | 163 | 42.466 56.180 -7.832 | 1.00 59.17 | A3 |
| ATOM | 1232 | C | GLU | 163 | 42.586 58.430 -11.142 | 1.00 41.34 | A3 |
| ATOM | 1233 | O | GLU | 163 | 43.456 57.633 -11.486 | 1.00 42.17 | A3 |
| ATOM | 1234 | N | VAL | 164 | 42.257 59.436 -11.920 | 1.00 42.28 | A3 |
| ATOM | 1235 | H | VAL | 164 | 41.589 60.091 -11.615 | 1.00 0.00 | A3 |
| ATOM | 1236 | CA | VAL | 164 | 42.911 59.609 -13.187 | 1.00 44.13 | A3 |
| ATOM | 1237 | CB | VAL | 164 | 42.207 60.711 -13.940 | 1.00 45.52 | A3 |
| ATOM | 1238 | CG1 | VAL | 164 | 42.892 60.975 -15.278 | 1.00 48.79 | A3 |
| ATOM | 1239 | CG2 | VAL | 164 | 40.786 60.269 -14.226 | 1.00 46.09 | A3 |
| ATOM | 1240 | C | VAL | 164 | 44.386 59.933 -12.991 | 1.00 46.13 | A3 |
| ATOM | 1241 | O | VAL | 164 | 45.192 59.473 -13.794 | 1.00 45.99 | A3 |
| ATOM | 1242 | N | SER | 165 | 44.879 60.677 -12.006 | 1.00 49.51 | A3 |
| ATOM | 1243 | H | SER | 165 | 44.287 61.173 -11.396 | 1.00 0.00 | A3 |
| ATOM | 1244 | CA | SER | 165 | 46.325 60.845 -11.895 | 1.00 53.44 | A3 |
| ATOM | 1245 | CB | SER | 165 | 46.715 61.796 -10.775 | 1.00 54.77 | A3 |
| ATOM | 1246 | OG | SER | 165 | 46.049 61.618 -9.530 | 1.00 59.99 | A3 |
| ATOM | 1247 | HG | SER | 165 | 45.997 60.694 -9.261 | 1.00 0.00 | A3 |
| ATOM | 1248 | C | SER | 165 | 46.958 59.502 -11.630 | 1.00 55.15 | A3 |
| ATOM | 1249 | O | SER | 165 | 48.028 59.227 -12.148 | 1.00 55.02 | A3 |
| ATOM | 1250 | N | TYR | 166 | 46.239 58.645 -10.900 | 1.00 58.57 | A3 |
| ATOM | 1251 | H | TYR | 166 | 45.374 58.948 -10.549 | 1.00 0.00 | A3 |
| ATOM | 1252 | CA | TYR | 166 | 46.617 57.273 -10.625 | 1.00 61.42 | A3 |
| ATOM | 1253 | CB | TYR | 166 | 45.543 56.653 -9.680 | 1.00 64.05 | A3 |
| ATOM | 1254 | CG | TYR | 166 | 45.502 55.138 -9.682 | 1.00 69.00 | A3 |
| ATOM | 1255 | CD1 | TYR | 166 | 44.389 54.501 -10.185 | 1.00 71.64 | A3 |
| ATOM | 1256 | CE1 | TYR | 166 | 44.367 53.130 -10.283 | 1.00 73.15 | A3 |
| ATOM | 1257 | CD2 | TYR | 166 | 46.594 54.409 -9.257 | 1.00 71.27 | A3 |
| ATOM | 1258 | CE2 | TYR | 166 | 46.584 53.040 -9.346 | 1.00 72.92 | A3 |
| ATOM | 1259 | CZ | TYR | 166 | 45.468 52.417 -9.862 | 1.00 75.71 | A3 |
| ATOM | 1260 | OH | TYR | 166 | 45.474 51.038 -10.016 | 1.00 80.61 | A3 |
| ATOM | 1261 | HH | TYR | 166 | 44.571 50.736 -10.134 | 1.00 0.00 | A3 |
| ATOM | 1262 | C | TYR | 166 | 46.712 56.567 -11.987 | 1.00 62.34 | A3 |
| ATOM | 1263 | O | TYR | 166 | 47.766 55.981 -12.282 | 1.00 63.25 | A3 |
| ATOM | 1264 | N | ALA | 167 | 45.727 56.622 -12.884 | 1.00 61.27 | A3 |
| ATOM | 1265 | H | ALA | 167 | 44.893 57.089 -12.678 | 1.00 0.00 | A3 |
| ATOM | 1266 | CA | ALA | 167 | 45.933 55.982 -14.159 | 1.00 61.47 | A3 |
| ATOM | 1267 | CB | ALA | 167 | 44.608 55.904 -14.904 | 1.00 60.98 | A3 |
| ATOM | 1268 | C | ALA | 167 | 46.982 56.694 -15.020 | 1.00 62.19 | A3 |
| ATOM | 1269 | O | ALA | 167 | 47.719 56.000 -15.734 | 1.00 62.63 | A3 |
| ATOM | 1270 | N | VAL | 168 | 47.210 58.011 -14.991 | 1.00 63.37 | A3 |
| ATOM | 1271 | H | VAL | 168 | 46.756 58.570 -14.330 | 1.00 0.00 | A3 |
| ATOM | 1272 | CA | VAL | 168 | 48.174 58.593 -15.923 | 1.00 65.62 | A3 |
| ATOM | 1273 | CB | VAL | 168 | 48.061 60.121 -16.131 | 1.00 66.30 | A3 |
| ATOM | 1274 | CG1 | VAL | 168 | 46.687 60.431 -16.706 | 1.00 66.78 | A3 |
| ATOM | 1275 | CG2 | VAL | 168 | 48.278 60.879 -14.840 | 1.00 68.47 | A3 |
| ATOM | 1276 | C | VAL | 168 | 49.579 58.339 -15.469 | 1.00 66.45 | A3 |
| ATOM | 1277 | O | VAL | 168 | 50.458 58.183 -16.302 | 1.00 66.22 | A3 |
| ATOM | 1278 | N | LEU | 169 | 49.823 58.241 -14.177 | 1.00 68.83 | A3 |
| ATOM | 1279 | H | LEU | 169 | 49.102 58.404 -13.536 | 1.00 0.00 | A3 |
| ATOM | 1280 | CA | LEU | 169 | 51.141 57.899 -13.695 | 1.00 71.81 | A3 |
| ATOM | 1281 | CB | LEU | 169 | 51.249 58.228 -12.188 | 1.00 71.53 | A3 |
| ATOM | 1282 | CG | LEU | 169 | 51.137 59.732 -11.813 | 1.00 70.68 | A3 |
| ATOM | 1283 | CD1 | LEU | 169 | 51.187 59.826 -10.298 | 1.00 69.39 | A3 |
| ATOM | 1284 | CD2 | LEU | 169 | 52.223 60.580 -12.491 | 1.00 68.49 | A3 |
| ATOM | 1285 | C | LEU | 169 | 51.333 56.414 -13.979 | 1.00 73.61 | A3 |
| ATOM | 1286 | O | LEU | 169 | 52.408 56.013 -14.429 | 1.00 74.75 | A3 |
| ATOM | 1287 | N | ARG | 170 | 50.309 55.583 -13.819 | 1.00 75.45 | A3 |
| ATOM | 1288 | H | ARG | 170 | 49.488 55.923 -13.399 | 1.00 0.00 | A3 |
| ATOM | 1289 | CA | ARG | 170 | 50.364 54.179 -14.199 | 1.00 78.17 | A3 |

FIG.5 {

| ATOM | 1290 | CB | ARG | 170 | 48.944 | 53.642 | -14.004 | 1.00 | 78.45 | A3 |
|------|------|----|-----|-----|--------|--------|---------|------|-------|-----|
| ATOM | 1291 | CG | ARG | 170 | 48.394 | 52.506 | -14.871 | 1.00 | 78.17 | A3 |
| ATOM | 1292 | CD | ARG | 170 | 48.744 | 51.181 | -14.271 | 1.00 | 77.25 | A3 |
| ATOM | 1293 | NE | ARG | 170 | 48.123 | 51.120 | -12.970 | 1.00 | 76.15 | A3 |
| ATOM | 1294 | HE | ARG | 170 | 47.245 | 51.528 | -12.824 | 1.00 | 0.00 | A3 |
| ATOM | 1295 | CZ | ARG | 170 | 48.758 | 50.547 | -11.970 | 1.00 | 76.14 | A3 |
| ATOM | 1296 | NH1 | ARG | 170 | 49.973 | 50.017 | -12.112 | 1.00 | 76.84 | A3 |
| ATOM | 1297 | HH11 | ARG | 170 | 50.441 | 50.030 | -12.994 | 1.00 | 0.00 | A3 |
| ATOM | 1298 | HH12 | ARG | 170 | 49.570 | 50.030 | -11.329 | 1.00 | 0.00 | A3 |
| ATOM | 1299 | NH2 | ARG | 170 | 50.406 | 49.570 | -10.806 | 1.00 | 77.02 | A3 |
| ATOM | 1300 | HH21 | ARG | 170 | 48.147 | 50.492 | -10.806 | 1.00 | 0.00 | A3 |
| ATOM | 1301 | HH22 | ARG | 170 | 47.237 | 50.890 | -10.714 | 1.00 | 77.02 | A3 |
| ATOM | 1302 | C | ARG | 170 | 48.586 | 50.052 | -10.023 | 1.00 | 0.00 | A3 |
| ATOM | 1303 | O | ARG | 170 | 50.870 | 54.052 | -15.647 | 1.00 | 79.84 | A3 |
| ATOM | 1304 | N | HIS | 171 | 51.924 | 53.470 | -15.908 | 1.00 | 80.07 | A3 |
| ATOM | 1305 | H | HIS | 171 | 50.193 | 54.663 | -16.611 | 1.00 | 81.38 | A3 |
| ATOM | 1306 | CA | HIS | 171 | 49.433 | 55.234 | -16.359 | 1.00 | 0.00 | A3 |
| ATOM | 1307 | CB | HIS | 171 | 50.663 | 54.597 | -17.970 | 1.00 | 84.03 | A3 |
| ATOM | 1308 | CG | HIS | 171 | 49.590 | 55.054 | -18.902 | 1.00 | 86.82 | A3 |
| ATOM | 1309 | CD2 | HIS | 171 | 48.496 | 54.037 | -19.147 | 1.00 | 90.73 | A3 |
| ATOM | 1310 | ND1 | HIS | 171 | 47.467 | 53.765 | -18.272 | 1.00 | 91.35 | A3 |
| ATOM | 1311 | HD1 | HIS | 171 | 48.308 | 53.301 | -20.248 | 1.00 | 92.24 | A3 |
| ATOM | 1312 | CE1 | HIS | 171 | 48.887 | 53.287 | -21.044 | 1.00 | 92.41 | A3 |
| ATOM | 1313 | NE2 | HIS | 171 | 47.204 | 52.605 | -20.077 | 1.00 | 92.41 | A3 |
| ATOM | 1314 | HE2 | HIS | 171 | 46.711 | 52.892 | -18.891 | 1.00 | 92.59 | A3 |
| ATOM | 1315 | C | HIS | 171 | 45.884 | 52.511 | -18.518 | 1.00 | 0.00 | A3 |
| ATOM | 1316 | O | HIS | 171 | 51.907 | 55.446 | -18.232 | 1.00 | 85.42 | A3 |
| ATOM | 1317 | N | LEU | 172 | 52.440 | 55.352 | -19.344 | 1.00 | 85.98 | A3 |
| ATOM | 1318 | H | LEU | 172 | 52.359 | 56.307 | -17.302 | 1.00 | 86.13 | A3 |
| ATOM | 1319 | CA | LEU | 172 | 51.870 | 56.411 | -16.463 | 1.00 | 0.00 | A3 |
| ATOM | 1320 | CB | LEU | 172 | 53.550 | 57.133 | -17.496 | 1.00 | 86.02 | A3 |
| ATOM | 1321 | CG | LEU | 172 | 53.500 | 58.357 | -16.607 | 1.00 | 86.31 | A3 |
| ATOM | 1322 | CD1 | LEU | 172 | 54.022 | 59.658 | -17.203 | 1.00 | 87.48 | A3 |
| ATOM | 1323 | CD2 | LEU | 172 | 53.436 | 59.939 | -18.596 | 1.00 | 87.68 | A3 |
| ATOM | 1324 | C | LEU | 172 | 53.645 | 60.778 | -16.251 | 1.00 | 87.95 | A3 |
| ATOM | 1325 | O | LEU | 172 | 54.813 | 56.357 | -17.180 | 1.00 | 85.92 | A3 |
| ATOM | 1326 | N | ALA | 173 | 55.896 | 56.660 | -17.692 | 1.00 | 86.23 | A3 |
| ATOM | 1327 | H | ALA | 173 | 54.733 | 55.383 | -16.282 | 1.00 | 85.49 | A3 |
| ATOM | 1328 | CA | ALA | 173 | 53.899 | 55.276 | -15.769 | 1.00 | 0.00 | A3 |
| ATOM | 1329 | CB | ALA | 173 | 55.856 | 54.497 | -16.087 | 1.00 | 85.65 | A3 |
| ATOM | 1330 | C | ALA | 173 | 56.602 | 54.859 | -14.809 | 1.00 | 85.01 | A3 |
| ATOM | 1331 | OT1 | ALA | 173 | 55.330 | 53.073 | -16.008 | 1.00 | 86.54 | A3 |
| ATOM | 1332 | OT2 | ALA | 173 | 55.585 | 52.347 | -16.971 | 1.00 | 87.21 | A3 |
| ATOM | 1333 | CB | LEU | 210 | 54.650 | 52.707 | -15.036 | 1.00 | 87.31 | A3 |

| ATOM | 1333 | CB | LEU | 210 | 45.234 | 42.591 | 25.453 | 1.00 | 52.47 | B1 |
|------|------|----|-----|-----|--------|--------|--------|------|-------|-----|
| ATOM | 1334 | CG | LEU | 210 | 43.799 | 42.058 | 25.547 | 1.00 | 51.68 | B1 |
| ATOM | 1335 | CD1 | LEU | 210 | 43.123 | 42.562 | 26.804 | 1.00 | 53.37 | B1 |
| ATOM | 1336 | CD2 | LEU | 210 | 43.050 | 42.453 | 24.303 | 1.00 | 51.37 | B1 |
| ATOM | 1337 | C | LEU | 210 | 46.770 | 44.374 | 24.596 | 1.00 | 50.98 | B1 |
| ATOM | 1338 | O | LEU | 210 | 46.475 | 45.267 | 23.790 | 1.00 | 51.76 | B1 |
| ATOM | 1339 | HT1 | LEU | 210 | 44.382 | 44.922 | 24.421 | 1.00 | 0.00 | B1 |
| ATOM | 1340 | HT2 | LEU | 210 | 45.157 | 45.974 | 25.414 | 1.00 | 0.00 | B1 |
| ATOM | 1341 | N | LEU | 210 | 44.705 | 45.041 | 25.406 | 1.00 | 53.59 | B1 |
| ATOM | 1342 | HT3 | LEU | 210 | 43.855 | 45.012 | 25.997 | 1.00 | 0.00 | B1 |
| ATOM | 1343 | CA | LEU | 210 | 45.730 | 44.038 | 25.676 | 1.00 | 52.35 | B1 |
| ATOM | 1344 | N | PRO | 211 | 47.974 | 43.825 | 24.494 | 1.00 | 49.35 | B1 |
| ATOM | 1345 | CD | PRO | 211 | 48.621 | 43.024 | 25.532 | 1.00 | 49.52 | B1 |
| ATOM | 1346 | CA | PRO | 211 | 48.895 | 44.191 | 23.419 | 1.00 | 49.04 | B1 |
| ATOM | 1347 | CB | PRO | 211 | 50.209 | 43.571 | 23.865 | 1.00 | 49.02 | B1 |
| ATOM | 1348 | CG | PRO | 211 | 49.794 | 42.438 | 24.783 | 1.00 | 49.77 | B1 |
| ATOM | 1349 | C | PRO | 211 | 48.543 | 43.864 | 21.965 | 1.00 | 48.03 | B1 |
| ATOM | 1350 | O | PRO | 211 | 47.872 | 42.896 | 21.622 | 1.00 | 49.05 | B1 |
| ATOM | 1351 | N | GLN | 212 | 49.032 | 44.675 | 21.051 | 1.00 | 46.52 | B1 |
| ATOM | 1352 | H | GLN | 212 | 49.506 | 45.478 | 21.349 | 1.00 | 0.00 | B1 |
| ATOM | 1353 | CA | GLN | 212 | 48.839 | 44.461 | 19.641 | 1.00 | 45.47 | B1 |
| ATOM | 1354 | CB | GLN | 212 | 49.553 | 45.522 | 18.849 | 1.00 | 46.81 | B1 |
| ATOM | 1355 | CG | GLN | 212 | 48.482 | 46.139 | 17.999 | 1.00 | 49.55 | B1 |
| ATOM | 1356 | CD | GLN | 212 | 49.024 | 46.703 | 16.709 | 1.00 | 54.21 | B1 |
| ATOM | 1357 | OE1 | GLN | 212 | 48.429 | 47.672 | 16.232 | 1.00 | 57.72 | B1 |
| ATOM | 1358 | NE2 | GLN | 212 | 50.086 | 46.176 | 16.074 | 1.00 | 52.39 | B1 |
| ATOM | 1359 | HE21 | GLN | 212 | 50.530 | 45.383 | 16.430 | 1.00 | 0.00 | B1 |
| ATOM | 1360 | HE22 | GLN | 212 | 50.341 | 46.625 | 15.244 | 1.00 | 0.00 | B1 |
| ATOM | 1361 | C | GLN | 212 | 49.390 | 43.133 | 19.185 | 1.00 | 44.79 | B1 |
| ATOM | 1362 | O | GLN | 212 | 48.959 | 42.520 | 18.208 | 1.00 | 44.01 | B1 |
| ATOM | 1363 | N | SER | 213 | 50.401 | 42.671 | 19.893 | 1.00 | 44.72 | B1 |
| ATOM | 1364 | H | SER | 213 | 50.730 | 43.115 | 20.698 | 1.00 | 0.00 | B1 |
| ATOM | 1365 | CA | SER | 213 | 51.025 | 41.424 | 19.521 | 1.00 | 43.76 | B1 |
| ATOM | 1366 | CB | SER | 213 | 52.220 | 41.124 | 20.354 | 1.00 | 45.29 | B1 |
| ATOM | 1367 | OG | SER | 213 | 51.802 | 41.455 | 21.681 | 1.00 | 52.50 | B1 |
| ATOM | 1368 | HG | SER | 213 | 52.479 | 41.127 | 22.288 | 1.00 | 0.00 | B1 |
| ATOM | 1369 | C | SER | 213 | 50.014 | 40.376 | 19.784 | 1.00 | 40.92 | B1 |
| ATOM | 1370 | O | SER | 213 | 49.964 | 39.492 | 18.947 | 1.00 | 43.32 | B1 |
| ATOM | 1371 | N | PHE | 214 | 49.242 | 40.571 | 20.876 | 1.00 | 38.86 | B1 |
| ATOM | 1372 | H | PHE | 214 | 49.414 | 41.370 | 21.410 | 1.00 | 0.00 | B1 |
| ATOM | 1373 | CA | PHE | 214 | 48.210 | 39.664 | 21.336 | 1.00 | 37.40 | B1 |
| ATOM | 1374 | CB | PHE | 214 | 47.568 | 40.064 | 22.634 | 1.00 | 37.45 | B1 |
| ATOM | 1375 | CG | PHE | 214 | 46.494 | 39.080 | 23.035 | 1.00 | 41.01 | B1 |

| ATOM | 1376 | CD1 | PHE | 214 | 45.176 | 39.459 | 23.044 | 1.00 | 42.77 | B1 |
|---|---|---|---|---|---|---|---|---|---|---|
| ATOM | 1377 | CD2 | PHE | 214 | 46.818 | 37.794 | 23.400 | 1.00 | 42.02 | B1 |
| ATOM | 1378 | CE1 | PHE | 214 | 44.197 | 38.554 | 23.423 | 1.00 | 41.82 | B1 |
| ATOM | 1379 | CE2 | PHE | 214 | 45.834 | 36.898 | 23.776 | 1.00 | 41.70 | B1 |
| ATOM | 1380 | CZ | PHE | 214 | 44.519 | 37.277 | 23.791 | 1.00 | 41.05 | B1 |
| ATOM | 1381 | C | PHE | 214 | 47.109 | 39.656 | 20.321 | 1.00 | 36.54 | B1 |
| ATOM | 1382 | O | PHE | 214 | 46.735 | 38.566 | 19.889 | 1.00 | 37.99 | B1 |
| ATOM | 1383 | N | LEU | 215 | 46.616 | 40.812 | 19.893 | 1.00 | 33.27 | B1 |
| ATOM | 1384 | H | LEU | 215 | 47.008 | 41.642 | 20.238 | 1.00 | 0.00 | B1 |
| ATOM | 1385 | CA | LEU | 215 | 45.504 | 40.864 | 18.966 | 1.00 | 30.38 | B1 |
| ATOM | 1386 | CB | LEU | 215 | 45.099 | 42.282 | 18.701 | 1.00 | 31.82 | B1 |
| ATOM | 1387 | CG | LEU | 215 | 43.857 | 42.530 | 17.893 | 1.00 | 32.78 | B1 |
| ATOM | 1388 | CD1 | LEU | 215 | 42.727 | 41.963 | 18.737 | 1.00 | 32.95 | B1 |
| ATOM | 1389 | CD2 | LEU | 215 | 43.688 | 44.011 | 17.508 | 1.00 | 28.93 | B1 |
| ATOM | 1390 | C | LEU | 215 | 45.811 | 40.232 | 17.648 | 1.00 | 29.57 | B1 |
| ATOM | 1391 | O | LEU | 215 | 44.922 | 39.632 | 17.055 | 1.00 | 31.28 | B1 |
| ATOM | 1392 | N | LEU | 216 | 47.031 | 40.379 | 17.155 | 1.00 | 29.44 | B1 |
| ATOM | 1393 | H | LEU | 216 | 47.677 | 40.935 | 17.646 | 1.00 | 0.00 | B1 |
| ATOM | 1394 | CA | LEU | 216 | 47.465 | 39.790 | 15.893 | 1.00 | 29.89 | B1 |
| ATOM | 1395 | CB | LEU | 216 | 48.791 | 40.450 | 15.472 | 1.00 | 28.61 | B1 |
| ATOM | 1396 | CG | LEU | 216 | 48.682 | 41.877 | 14.939 | 1.00 | 26.83 | B1 |
| ATOM | 1397 | CD1 | LEU | 216 | 49.925 | 42.558 | 15.344 | 1.00 | 28.57 | B1 |
| ATOM | 1398 | CD2 | LEU | 216 | 48.446 | 41.950 | 13.452 | 1.00 | 24.09 | B1 |
| ATOM | 1399 | C | LEU | 216 | 47.613 | 38.274 | 16.062 | 1.00 | 31.23 | B1 |
| ATOM | 1400 | O | LEU | 216 | 47.328 | 37.514 | 15.138 | 1.00 | 29.20 | B1 |
| ATOM | 1401 | N | LYS | 217 | 47.999 | 37.826 | 17.261 | 1.00 | 32.50 | B1 |
| ATOM | 1402 | H | LYS | 217 | 48.305 | 38.482 | 17.926 | 1.00 | 0.00 | B1 |
| ATOM | 1403 | CA | LYS | 217 | 48.067 | 36.439 | 17.599 | 1.00 | 34.90 | B1 |
| ATOM | 1404 | CB | LYS | 217 | 48.645 | 36.280 | 19.002 | 1.00 | 38.07 | B1 |
| ATOM | 1405 | CG | LYS | 217 | 49.394 | 34.978 | 19.109 | 1.00 | 45.25 | B1 |
| ATOM | 1406 | CD | LYS | 217 | 49.714 | 34.491 | 20.521 | 1.00 | 53.27 | B1 |
| ATOM | 1407 | CE | LYS | 217 | 50.229 | 33.024 | 20.297 | 1.00 | 59.03 | B1 |
| ATOM | 1408 | NZ | LYS | 217 | 50.213 | 32.135 | 21.467 | 1.00 | 62.10 | B1 |
| ATOM | 1409 | HZ1 | LYS | 217 | 49.239 | 32.056 | 21.824 | 1.00 | 0.00 | B1 |
| ATOM | 1410 | HZ2 | LYS | 217 | 50.830 | 32.515 | 22.214 | 1.00 | 0.00 | B1 |
| ATOM | 1411 | HZ3 | LYS | 217 | 50.554 | 31.195 | 21.179 | 1.00 | 0.00 | B1 |
| ATOM | 1412 | C | LYS | 217 | 46.617 | 35.950 | 17.546 | 1.00 | 36.77 | B1 |
| ATOM | 1413 | O | LYS | 217 | 46.311 | 34.933 | 16.886 | 1.00 | 39.58 | B1 |
| ATOM | 1414 | N | CYS | 218 | 45.664 | 36.638 | 18.177 | 1.00 | 34.86 | B1 |
| ATOM | 1415 | H | CYS | 218 | 45.907 | 37.388 | 18.751 | 1.00 | 0.00 | B1 |
| ATOM | 1416 | CA | CYS | 218 | 44.277 | 36.238 | 18.076 | 1.00 | 33.61 | B1 |
| ATOM | 1417 | CB | CYS | 218 | 43.430 | 37.175 | 18.846 | 1.00 | 33.21 | B1 |
| ATOM | 1418 | SG | CYS | 218 | 43.856 | 36.710 | 20.515 | 1.00 | 35.92 | B1 |
| ATOM | 1419 | C | CYS | 218 | 43.766 | 36.189 | 16.652 | 1.00 | 32.89 | B1 |
| ATOM | 1420 | O | CYS | 218 | 43.155 | 35.169 | 16.323 | 1.00 | 34.71 | B1 |
| ATOM | 1421 | N | LEU | 219 | 44.035 | 37.169 | 15.777 | 1.00 | 29.52 | B1 |
| ATOM | 1422 | H | LEU | 219 | 44.512 | 37.960 | 16.104 | 1.00 | 0.00 | B1 |
| ATOM | 1423 | CA | LEU | 219 | 43.614 | 37.119 | 14.393 | 1.00 | 27.44 | B1 |
| ATOM | 1424 | CB | LEU | 219 | 44.116 | 38.412 | 13.727 | 1.00 | 26.24 | B1 |
| ATOM | 1425 | CG | LEU | 219 | 43.884 | 38.768 | 12.241 | 1.00 | 25.07 | B1 |
| ATOM | 1426 | CD1 | LEU | 219 | 42.402 | 38.975 | 11.996 | 1.00 | 26.24 | B1 |
| ATOM | 1427 | CD2 | LEU | 219 | 44.563 | 40.051 | 11.882 | 1.00 | 22.10 | B1 |
| ATOM | 1428 | C | LEU | 219 | 44.121 | 35.867 | 13.634 | 1.00 | 28.24 | B1 |
| ATOM | 1429 | O | LEU | 219 | 43.373 | 35.204 | 12.889 | 1.00 | 27.12 | B1 |
| ATOM | 1430 | N | GLU | 220 | 45.399 | 35.499 | 13.795 | 1.00 | 28.06 | B1 |
| ATOM | 1431 | H | GLU | 220 | 45.957 | 35.974 | 14.448 | 1.00 | 0.00 | B1 |
| ATOM | 1432 | CA | GLU | 220 | 45.963 | 34.411 | 13.048 | 1.00 | 28.38 | B1 |
| ATOM | 1433 | CB | GLU | 220 | 47.376 | 34.198 | 13.469 | 1.00 | 34.25 | B1 |
| ATOM | 1434 | CG | GLU | 220 | 48.049 | 33.079 | 12.666 | 1.00 | 46.36 | B1 |
| ATOM | 1435 | CD | GLU | 220 | 49.545 | 32.794 | 12.907 | 1.00 | 55.51 | B1 |
| ATOM | 1436 | OE1 | GLU | 220 | 50.113 | 32.133 | 12.021 | 1.00 | 58.95 | B1 |
| ATOM | 1437 | OE2 | GLU | 220 | 50.144 | 33.213 | 13.930 | 1.00 | 60.41 | B1 |
| ATOM | 1438 | C | GLU | 220 | 45.134 | 33.193 | 13.354 | 1.00 | 27.30 | B1 |
| ATOM | 1439 | O | GLU | 220 | 44.662 | 32.524 | 12.437 | 1.00 | 27.08 | B1 |
| ATOM | 1440 | N | GLN | 221 | 44.866 | 33.023 | 14.642 | 1.00 | 25.42 | B1 |
| ATOM | 1441 | H | GLN | 221 | 45.229 | 33.687 | 15.268 | 1.00 | 0.00 | B1 |
| ATOM | 1442 | CA | GLN | 221 | 44.074 | 31.940 | 15.176 | 1.00 | 26.28 | B1 |
| ATOM | 1443 | CB | GLN | 221 | 44.143 | 31.927 | 16.691 | 1.00 | 26.78 | B1 |
| ATOM | 1444 | CG | GLN | 221 | 45.555 | 31.456 | 17.011 | 1.00 | 29.19 | B1 |
| ATOM | 1445 | CD | GLN | 221 | 45.752 | 31.067 | 18.442 | 1.00 | 31.98 | B1 |
| ATOM | 1446 | OE1 | GLN | 221 | 46.472 | 30.162 | 18.808 | 1.00 | 35.98 | B1 |
| ATOM | 1447 | NE2 | GLN | 221 | 45.110 | 31.736 | 19.347 | 1.00 | 39.31 | B1 |
| ATOM | 1448 | HE21 | GLN | 221 | 45.263 | 31.423 | 20.246 | 1.00 | 0.00 | B1 |
| ATOM | 1449 | HE22 | GLN | 221 | 44.571 | 32.514 | 19.111 | 1.00 | 0.00 | B1 |
| ATOM | 1450 | C | GLN | 221 | 42.615 | 31.925 | 14.789 | 1.00 | 26.21 | B1 |
| ATOM | 1451 | O | GLN | 221 | 42.186 | 30.896 | 14.269 | 1.00 | 30.69 | B1 |
| ATOM | 1452 | N | VAL | 222 | 41.814 | 32.962 | 14.984 | 1.00 | 23.63 | B1 |
| ATOM | 1453 | H | VAL | 222 | 42.199 | 33.746 | 15.426 | 1.00 | 0.00 | B1 |
| ATOM | 1454 | CA | VAL | 222 | 40.429 | 33.034 | 14.537 | 1.00 | 21.92 | B1 |
| ATOM | 1455 | CB | VAL | 222 | 39.934 | 34.442 | 14.793 | 1.00 | 21.36 | B1 |
| ATOM | 1456 | CG1 | VAL | 222 | 38.706 | 34.831 | 14.027 | 1.00 | 17.72 | B1 |
| ATOM | 1457 | CG2 | VAL | 222 | 39.671 | 34.496 | 16.257 | 1.00 | 20.95 | B1 |
| ATOM | 1458 | C | VAL | 222 | 40.374 | 32.707 | 13.066 | 1.00 | 22.65 | B1 |
| ATOM | 1459 | O | VAL | 222 | 39.475 | 32.013 | 12.632 | 1.00 | 23.72 | B1 |
| ATOM | 1460 | N | ARG | 223 | 41.341 | 33.120 | 12.283 | 1.00 | 23.95 | B1 |
| ATOM | 1461 | H | ARG | 223 | 42.099 | 33.614 | 12.666 | 1.00 | 0.00 | B1 |

FIG.5-18

| | | | | | | | | | |
|---|---|---|---|---|---|---|---|---|---|
| ATOM | 1462 | CA | ARG | 223 | 41.309 | 32.939 | 10.844 | 1.00 27.19 | B1 |
| ATOM | 1463 | CB | ARG | 223 | 42.294 | 33.935 | 10.283 | 1.00 29.26 | B1 |
| ATOM | 1464 | CG | ARG | 223 | 42.102 | 34.364 | 8.869 | 1.00 35.23 | B1 |
| ATOM | 1465 | CD | ARG | 223 | 42.880 | 33.487 | 7.929 | 1.00 41.88 | B1 |
| ATOM | 1466 | NE | ARG | 223 | 41.972 | 32.676 | 7.096 | 1.00 47.42 | B1 |
| ATOM | 1467 | HE | ARG | 223 | 41.451 | 31.953 | 7.502 | 1.00 0.00 | B1 |
| ATOM | 1468 | CZ | ARG | 223 | 41.875 | 32.896 | 5.784 | 1.00 46.15 | B1 |
| ATOM | 1469 | NH1 | ARG | 223 | 42.575 | 33.837 | 5.246 | 1.00 49.54 | B1 |
| ATOM | 1470 | HH11 | ARG | 223 | 42.522 | 33.989 | 4.259 | 1.00 0.00 | B1 |
| ATOM | 1471 | HH12 | ARG | 223 | 43.156 | 34.428 | 5.805 | 1.00 0.00 | B1 |
| ATOM | 1472 | NH2 | ARG | 223 | 41.178 | 32.161 | 4.952 | 1.00 45.74 | B1 |
| ATOM | 1473 | HH21 | ARG | 223 | 40.697 | 31.353 | 5.290 | 1.00 0.00 | B1 |
| ATOM | 1474 | HH22 | ARG | 223 | 41.154 | 32.399 | 3.980 | 1.00 0.00 | B1 |
| ATOM | 1475 | C | ARG | 223 | 41.624 | 31.492 | 10.430 | 1.00 29.13 | B1 |
| ATOM | 1476 | O | ARG | 223 | 41.181 | 30.987 | 9.376 | 1.00 29.32 | B1 |
| ATOM | 1477 | N | LYS | 224 | 42.413 | 30.791 | 11.259 | 1.00 29.17 | B1 |
| ATOM | 1478 | H | LYS | 224 | 42.791 | 31.235 | 12.048 | 1.00 0.00 | B1 |
| ATOM | 1479 | CA | LYS | 224 | 42.714 | 29.411 | 10.994 | 1.00 27.70 | B1 |
| ATOM | 1480 | CB | LYS | 224 | 43.922 | 29.085 | 11.818 | 1.00 30.07 | B1 |
| ATOM | 1481 | CG | LYS | 224 | 44.372 | 27.660 | 11.706 | 1.00 36.70 | B1 |
| ATOM | 1482 | CD | LYS | 224 | 45.829 | 27.544 | 12.127 | 1.00 41.68 | B1 |
| ATOM | 1483 | CE | LYS | 224 | 46.303 | 26.478 | 11.131 | 1.00 48.18 | B1 |
| ATOM | 1484 | NZ | LYS | 224 | 47.750 | 26.492 | 10.913 | 1.00 53.57 | B1 |
| ATOM | 1485 | HZ1 | LYS | 224 | 48.230 | 26.241 | 11.801 | 1.00 0.00 | B1 |
| ATOM | 1486 | HZ2 | LYS | 224 | 48.057 | 27.436 | 10.606 | 1.00 0.00 | B1 |
| ATOM | 1487 | HZ3 | LYS | 224 | 47.998 | 25.792 | 10.183 | 1.00 0.00 | B1 |
| ATOM | 1488 | C | LYS | 224 | 41.464 | 28.598 | 11.347 | 1.00 26.27 | B1 |
| ATOM | 1489 | O | LYS | 224 | 40.970 | 27.810 | 10.510 | 1.00 24.82 | B1 |
| ATOM | 1490 | N | ILE | 225 | 40.892 | 28.835 | 12.547 | 1.00 24.75 | B1 |
| ATOM | 1491 | H | ILE | 225 | 41.308 | 29.487 | 13.151 | 1.00 0.00 | B1 |
| ATOM | 1492 | CA | ILE | 225 | 39.656 | 28.147 | 12.943 | 1.00 23.33 | B1 |
| ATOM | 1493 | CB | ILE | 225 | 39.146 | 28.622 | 14.296 | 1.00 18.08 | B1 |
| ATOM | 1494 | CG2 | ILE | 225 | 37.874 | 27.872 | 14.577 | 1.00 15.43 | B1 |
| ATOM | 1495 | CG1 | ILE | 225 | 40.161 | 28.400 | 15.380 | 1.00 13.38 | B1 |
| ATOM | 1496 | CD | ILE | 225 | 39.787 | 28.967 | 16.749 | 1.00 13.59 | B1 |
| ATOM | 1497 | C | ILE | 225 | 38.594 | 28.437 | 11.889 | 1.00 27.28 | B1 |
| ATOM | 1498 | O | ILE | 225 | 37.978 | 27.492 | 11.400 | 1.00 31.49 | B1 |
| ATOM | 1499 | N | GLN | 226 | 38.396 | 29.677 | 11.402 | 1.00 29.69 | B1 |
| ATOM | 1500 | H | GLN | 226 | 38.894 | 30.413 | 11.803 | 1.00 0.00 | B1 |
| ATOM | 1501 | CA | GLN | 226 | 37.450 | 29.969 | 10.313 | 1.00 29.12 | B1 |
| ATOM | 1502 | CB | GLN | 226 | 37.366 | 31.438 | 9.962 | 1.00 32.26 | B1 |
| ATOM | 1503 | CG | GLN | 226 | 36.682 | 32.156 | 11.108 | 1.00 36.28 | B1 |
| ATOM | 1504 | CD | GLN | 226 | 36.429 | 33.613 | 10.816 | 1.00 37.88 | B1 |
| ATOM | 1505 | OE1 | GLN | 226 | 37.158 | 34.281 | 10.076 | 1.00 36.34 | B1 |
| ATOM | 1506 | NE2 | GLN | 226 | 35.359 | 34.114 | 11.421 | 1.00 39.62 | B1 |
| ATOM | 1507 | HE21 | GLN | 226 | 34.823 | 33.501 | 11.971 | 1.00 0.00 | B1 |
| ATOM | 1508 | HE22 | GLN | 226 | 35.153 | 35.057 | 11.287 | 1.00 0.00 | B1 |
| ATOM | 1509 | C | GLN | 226 | 37.714 | 29.295 | 9.007 | 1.00 26.82 | B1 |
| ATOM | 1510 | O | GLN | 226 | 36.775 | 28.887 | 8.325 | 1.00 27.45 | B1 |
| ATOM | 1511 | N | GLY | 227 | 38.940 | 29.186 | 8.570 | 1.00 26.55 | B1 |
| ATOM | 1512 | H | GLY | 227 | 39.683 | 29.612 | 9.043 | 1.00 0.00 | B1 |
| ATOM | 1513 | CA | GLY | 227 | 39.195 | 28.427 | 7.348 | 1.00 27.27 | B1 |
| ATOM | 1514 | C | GLY | 227 | 38.832 | 26.949 | 7.574 | 1.00 27.65 | B1 |
| ATOM | 1515 | O | GLY | 227 | 38.287 | 26.291 | 6.656 | 1.00 26.79 | B1 |
| ATOM | 1516 | N | ASP | 228 | 39.025 | 26.429 | 8.819 | 1.00 27.03 | B1 |
| ATOM | 1517 | H | ASP | 228 | 39.460 | 26.957 | 9.523 | 1.00 0.00 | B1 |
| ATOM | 1518 | CA | ASP | 228 | 38.618 | 25.038 | 9.052 | 1.00 28.20 | B1 |
| ATOM | 1519 | CB | ASP | 228 | 38.986 | 24.492 | 10.391 | 1.00 26.04 | B1 |
| ATOM | 1520 | CG | ASP | 228 | 40.427 | 24.554 | 10.774 | 1.00 24.88 | B1 |
| ATOM | 1521 | OD1 | ASP | 228 | 40.627 | 24.521 | 11.977 | 1.00 23.37 | B1 |
| ATOM | 1522 | OD2 | ASP | 228 | 41.302 | 24.637 | 9.912 | 1.00 23.32 | B1 |
| ATOM | 1523 | C | ASP | 228 | 37.120 | 24.830 | 8.992 | 1.00 27.23 | B1 |
| ATOM | 1524 | O | ASP | 228 | 36.662 | 23.900 | 8.336 | 1.00 27.07 | B1 |
| ATOM | 1525 | N | GLY | 229 | 36.390 | 25.739 | 9.639 | 1.00 26.74 | B1 |
| ATOM | 1526 | H | GLY | 229 | 36.861 | 26.444 | 10.134 | 1.00 0.00 | B1 |
| ATOM | 1527 | CA | GLY | 229 | 34.946 | 25.723 | 9.673 | 1.00 25.87 | B1 |
| ATOM | 1528 | C | GLY | 229 | 34.393 | 25.825 | 8.274 | 1.00 24.95 | B1 |
| ATOM | 1529 | O | GLY | 229 | 33.370 | 25.222 | 7.956 | 1.00 25.73 | B1 |
| ATOM | 1530 | N | ALA | 230 | 35.058 | 26.541 | 7.391 | 1.00 23.97 | B1 |
| ATOM | 1531 | H | ALA | 230 | 35.871 | 27.026 | 7.654 | 1.00 0.00 | B1 |
| ATOM | 1532 | CA | ALA | 230 | 34.530 | 26.688 | 6.061 | 1.00 25.94 | B1 |
| ATOM | 1533 | CB | ALA | 230 | 35.193 | 27.852 | 5.312 | 1.00 19.76 | B1 |
| ATOM | 1534 | C | ALA | 230 | 34.794 | 25.403 | 5.304 | 1.00 29.42 | B1 |
| ATOM | 1535 | O | ALA | 230 | 34.014 | 25.061 | 4.423 | 1.00 32.07 | B1 |
| ATOM | 1536 | N | ALA | 231 | 35.878 | 24.671 | 5.572 | 1.00 32.16 | B1 |
| ATOM | 1537 | H | ALA | 231 | 36.556 | 25.045 | 6.175 | 1.00 0.00 | B1 |
| ATOM | 1538 | CA | ALA | 231 | 36.141 | 23.364 | 4.957 | 1.00 31.99 | B1 |
| ATOM | 1539 | CB | ALA | 231 | 37.489 | 22.847 | 5.428 | 1.00 32.77 | B1 |
| ATOM | 1540 | C | ALA | 231 | 35.060 | 22.361 | 5.386 | 1.00 32.99 | B1 |
| ATOM | 1541 | O | ALA | 231 | 34.599 | 21.575 | 4.576 | 1.00 34.12 | B1 |
| ATOM | 1542 | N | LEU | 232 | 34.662 | 22.309 | 6.652 | 1.00 33.30 | B1 |
| ATOM | 1543 | H | LEU | 232 | 35.174 | 22.861 | 7.284 | 1.00 0.00 | B1 |
| ATOM | 1544 | CA | LEU | 232 | 33.558 | 21.506 | 7.165 | 1.00 35.33 | B1 |
| ATOM | 1545 | CB | LEU | 232 | 33.279 | 21.783 | 8.626 | 1.00 34.22 | B1 |
| ATOM | 1546 | CG | LEU | 232 | 32.410 | 20.861 | 9.394 | 1.00 33.16 | B1 |
| ATOM | 1547 | CD1 | LEU | 232 | 33.191 | 19.545 | 9.451 | 1.00 34.59 | B1 |

FIG.5-19

```
ATOM   1548  CD2 LEU  232     32.107  21.381  10.800  1.00 31.32   B1
ATOM   1549  C   LEU  232     32.271  21.829   6.440  1.00 36.65   B1
ATOM   1550  O   LEU  232     31.703  20.986   5.749  1.00 38.89   B1
ATOM   1551  N   GLN  233     31.836  23.084   6.570  1.00 0.00    B1
ATOM   1552  H   GLN  233     32.378  23.719   7.087  1.00 0.00    B1
ATOM   1553  CA  GLN  233     30.637  23.579   5.933  1.00 40.02   B1
ATOM   1554  CB  GLN  233     30.572  25.072   6.162  1.00 42.25   B1
ATOM   1555  CG  GLN  233     30.290  25.398   7.626  1.00 48.22   B1
ATOM   1556  CD  GLN  233     30.021  26.879   7.983  1.00 53.75   B1
ATOM   1557  OE1 GLN  233     30.799  27.810   7.718  1.00 55.93   B1
ATOM   1558  NE2 GLN  233     28.909  27.215   8.634  1.00 56.51   B1
ATOM   1559  HE21 GLN 233     28.810  28.144   8.902  1.00 0.00    B1
ATOM   1560  HE22 GLN 233     28.205  26.533   8.710  1.00 0.00    B1
ATOM   1561  C   GLN  233     30.635  23.243   4.441  1.00 39.70   B1
ATOM   1562  O   GLN  233     29.631  22.777   3.898  1.00 40.20   B1
ATOM   1563  N   GLU  234     31.744  23.377   3.736  1.00 39.32   B1
ATOM   1564  H   GLU  234     32.544  23.750   4.163  1.00 0.00    B1
ATOM   1565  CA  GLU  234     31.809  23.025   2.329  1.00 39.23   B1
ATOM   1566  CB  GLU  234     33.155  23.434   1.811  1.00 40.25   B1
ATOM   1567  CG  GLU  234     33.292  23.028   0.383  1.00 47.69   B1
ATOM   1568  CD  GLU  234     34.733  23.056  -0.073  1.00 53.40   B1
ATOM   1569  OE1 GLU  234     34.986  23.721  -1.100  1.00 53.78   B1
ATOM   1570  OE2 GLU  234     35.568  22.400   0.590  1.00 57.55   B1
ATOM   1571  C   GLU  234     31.580  21.535   2.136  1.00 37.09   B1
ATOM   1572  O   GLU  234     30.884  21.217   1.188  1.00 36.67   B1
ATOM   1573  N   LYS  235     32.092  20.623   2.986  1.00 37.27   B1
ATOM   1574  H   LYS  235     32.668  20.965   3.706  1.00 0.00    B1
ATOM   1575  CA  LYS  235     31.832  19.177   2.942  1.00 36.27   B1
ATOM   1576  CB  LYS  235     32.516  18.365   3.997  1.00 34.92   B1
ATOM   1577  CG  LYS  235     33.978  18.483   4.107  1.00 38.47   B1
ATOM   1578  CD  LYS  235     34.762  17.999   2.921  1.00 38.07   B1
ATOM   1579  CE  LYS  235     36.192  18.051   3.460  1.00 39.15   B1
ATOM   1580  NZ  LYS  235     37.117  17.460   2.521  1.00 41.34   B1
ATOM   1581  HZ1 LYS  235     37.080  17.978   1.622  1.00 0.00    B1
ATOM   1582  HZ2 LYS  235     36.854  16.466   2.363  1.00 0.00    B1
ATOM   1583  HZ3 LYS  235     38.080  17.497   2.911  1.00 0.00    B1
ATOM   1584  C   LYS  235     30.363  18.847   3.204  1.00 35.20   B1
ATOM   1585  O   LYS  235     29.722  18.102   2.463  1.00 35.60   B1
ATOM   1586  N   LEU  236     29.807  19.332   4.301  1.00 33.53   B1
ATOM   1587  H   LEU  236     30.363  19.888   4.885  1.00 0.00    B1
ATOM   1588  CA  LEU  236     28.417  19.116   4.641  1.00 32.30   B1
ATOM   1589  CB  LEU  236     28.093  19.918   5.894  1.00 28.85   B1
ATOM   1590  CG  LEU  236     28.791  19.441   7.148  1.00 28.23   B1
ATOM   1591  CD1 LEU  236     28.703  20.460   8.268  1.00 24.14   B1
ATOM   1592  CD2 LEU  236     28.132  18.163   7.587  1.00 26.66   B1
ATOM   1593  C   LEU  236     27.590  19.574   3.453  1.00 33.69   B1
ATOM   1594  O   LEU  236     26.691  18.849   3.064  1.00 35.13   B1
ATOM   1595  N   CYS  237     27.870  20.670   2.753  1.00 34.49   B1
ATOM   1596  H   CYS  237     28.611  21.251   3.025  1.00 0.00    B1
ATOM   1597  CA  CYS  237     27.064  21.016   1.606  1.00 34.95   B1
ATOM   1598  C   CYS  237     27.324  20.090   0.451  1.00 35.97   B1
ATOM   1599  O   CYS  237     26.360  19.573  -0.089  1.00 36.09   B1
ATOM   1600  CB  CYS  237     27.334  22.413   1.130  1.00 35.18   B1
ATOM   1601  SG  CYS  237     26.409  22.880  -0.365  1.00 36.40   B1
ATOM   1602  N   ALA  238     28.571  19.804   0.074  1.00 37.29   B1
ATOM   1603  H   ALA  238     29.324  20.158   0.591  1.00 0.00    B1
ATOM   1604  CA  ALA  238     28.841  18.973  -1.090  1.00 36.80   B1
ATOM   1605  CB  ALA  238     30.274  18.684  -1.403  1.00 37.35   B1
ATOM   1606  C   ALA  238     28.320  17.617  -0.911  1.00 36.49   B1
ATOM   1607  O   ALA  238     27.645  17.198  -1.809  1.00 36.54   B1
ATOM   1608  N   THR  239     28.628  16.969   0.193  1.00 38.80   B1
ATOM   1609  H   THR  239     29.236  17.391   0.821  1.00 0.00    B1
ATOM   1610  CA  THR  239     28.230  15.587   0.464  1.00 41.33   B1
ATOM   1611  CB  THR  239     29.158  15.035   1.554  1.00 42.38   B1
ATOM   1612  OG1 THR  239     30.473  15.265   1.031  1.00 45.70   B1
ATOM   1613  HG1 THR  239     31.019  15.668   1.709  1.00 0.00    B1
ATOM   1614  CG2 THR  239     28.936  13.574   1.916  1.00 41.85   B1
ATOM   1615  C   THR  239     26.771  15.341   0.864  1.00 41.94   B1
ATOM   1616  O   THR  239     26.260  14.284   0.460  1.00 43.34   B1
ATOM   1617  N   TYR  240     26.095  16.207   1.669  1.00 40.07   B1
ATOM   1618  H   TYR  240     26.538  17.034   1.953  1.00 0.00    B1
ATOM   1619  CA  TYR  240     24.718  15.992   2.084  1.00 38.21   B1
ATOM   1620  CB  TYR  240     24.594  15.993   3.618  1.00 38.08   B1
ATOM   1621  CG  TYR  240     25.524  14.926   4.193  1.00 43.37   B1
ATOM   1622  CD1 TYR  240     26.475  15.243   5.149  1.00 45.06   B1
ATOM   1623  CE1 TYR  240     27.420  14.283   5.529  1.00 47.35   B1
ATOM   1624  CD2 TYR  240     25.518  13.643   3.641  1.00 43.89   B1
ATOM   1625  CE2 TYR  240     26.442  12.690   4.003  1.00 44.77   B1
ATOM   1626  CZ  TYR  240     27.410  13.005   4.943  1.00 47.96   B1
ATOM   1627  OH  TYR  240     28.390  12.047   5.244  1.00 46.59   B1
ATOM   1628  HH  TYR  240     28.027  11.187   4.992  1.00 0.00    B1
ATOM   1629  C   TYR  240     23.781  17.032   1.516  1.00 39.49   B1
ATOM   1630  O   TYR  240     22.587  16.934   1.775  1.00 42.76   B1
ATOM   1631  N   LYS  241     24.174  18.011   0.694  1.00 37.36   B1
ATOM   1632  H   LYS  241     25.091  18.023   0.345  1.00 0.00    B1
ATOM   1633  CA  LYS  241     23.314  19.115   0.275  1.00 36.37   B1
```

FIG.5-20

| ATOM | 1634 | CB | LYS | 241 | 22.173 | 18.648 | -0.595 | 1.00 | 38.38 | B1 |
|---|---|---|---|---|---|---|---|---|---|---|
| ATOM | 1635 | CG | LYS | 241 | 22.645 | 17.940 | -1.838 | 1.00 | 42.94 | B1 |
| ATOM | 1636 | CD | LYS | 241 | 23.468 | 18.809 | -2.737 | 1.00 | 46.97 | B1 |
| ATOM | 1637 | CE | LYS | 241 | 23.657 | 18.070 | -4.051 | 1.00 | 49.20 | B1 |
| ATOM | 1638 | NZ | LYS | 241 | 22.509 | 18.372 | -4.893 | 1.00 | 51.54 | B1 |
| ATOM | 1639 | HZ1 | LYS | 241 | 22.447 | 19.400 | -5.038 | 1.00 | 0.00 | B1 |
| ATOM | 1640 | HZ2 | LYS | 241 | 21.641 | 18.041 | -4.426 | 1.00 | 0.00 | B1 |
| ATOM | 1641 | HZ3 | LYS | 241 | 22.609 | 17.895 | -5.811 | 1.00 | 0.00 | B1 |
| ATOM | 1642 | C | LYS | 241 | 22.720 | 19.904 | 1.429 | 1.00 | 33.37 | B1 |
| ATOM | 1643 | O | LYS | 241 | 21.728 | 20.580 | 1.223 | 1.00 | 33.90 | B1 |
| ATOM | 1644 | N | LEU | 242 | 23.286 | 19.853 | 2.648 | 1.00 | 31.40 | B1 |
| ATOM | 1645 | H | LEU | 242 | 24.055 | 19.260 | 2.756 | 1.00 | 0.00 | B1 |
| ATOM | 1646 | CA | LEU | 242 | 22.904 | 20.682 | 3.758 | 1.00 | 31.09 | B1 |
| ATOM | 1647 | CB | LEU | 242 | 23.253 | 20.059 | 5.096 | 1.00 | 28.55 | B1 |
| ATOM | 1648 | CG | LEU | 242 | 22.571 | 18.798 | 5.641 | 1.00 | 30.36 | B1 |
| ATOM | 1649 | CD1 | LEU | 242 | 22.530 | 18.814 | 7.138 | 1.00 | 29.62 | B1 |
| ATOM | 1650 | CD2 | LEU | 242 | 21.086 | 18.861 | 5.443 | 1.00 | 31.94 | B1 |
| ATOM | 1651 | C | LEU | 242 | 23.778 | 21.933 | 3.550 | 1.00 | 34.03 | B1 |
| ATOM | 1652 | O | LEU | 242 | 24.903 | 22.027 | 4.058 | 1.00 | 35.53 | B1 |
| ATOM | 1653 | N | CYS | 243 | 23.316 | 22.883 | 2.722 | 1.00 | 34.89 | B1 |
| ATOM | 1654 | H | CYS | 243 | 22.491 | 22.665 | 2.238 | 1.00 | 0.00 | B1 |
| ATOM | 1655 | CA | CYS | 243 | 24.051 | 24.083 | 2.377 | 1.00 | 35.42 | B1 |
| ATOM | 1656 | C | CYS | 243 | 23.492 | 25.335 | 2.975 | 1.00 | 36.85 | B1 |
| ATOM | 1657 | O | CYS | 243 | 23.956 | 26.400 | 2.565 | 1.00 | 40.10 | B1 |
| ATOM | 1658 | CB | CYS | 243 | 24.046 | 24.383 | 0.929 | 1.00 | 33.12 | B1 |
| ATOM | 1659 | SG | CYS | 243 | 24.438 | 22.883 | 0.099 | 1.00 | 38.25 | B1 |
| ATOM | 1660 | N | HIS | 244 | 22.496 | 25.393 | 3.848 | 1.00 | 35.37 | B1 |
| ATOM | 1661 | H | HIS | 244 | 22.185 | 24.588 | 4.318 | 1.00 | 0.00 | B1 |
| ATOM | 1662 | CA | HIS | 244 | 21.939 | 26.676 | 4.191 | 1.00 | 33.29 | B1 |
| ATOM | 1663 | CB | HIS | 244 | 20.655 | 26.987 | 3.340 | 1.00 | 33.64 | B1 |
| ATOM | 1664 | CG | HIS | 244 | 20.915 | 27.205 | 1.857 | 1.00 | 33.12 | B1 |
| ATOM | 1665 | CD2 | HIS | 244 | 20.288 | 26.584 | 0.814 | 1.00 | 37.29 | B1 |
| ATOM | 1666 | ND1 | HIS | 244 | 21.874 | 27.902 | 1.298 | 1.00 | 36.85 | B1 |
| ATOM | 1667 | HD1 | HIS | 244 | 22.648 | 28.281 | 1.778 | 1.00 | 0.00 | B1 |
| ATOM | 1668 | CE1 | HIS | 244 | 21.874 | 27.722 | -0.013 | 1.00 | 35.95 | B1 |
| ATOM | 1669 | NE2 | HIS | 244 | 20.910 | 26.920 | -0.301 | 1.00 | 35.54 | B1 |
| ATOM | 1670 | HE2 | HIS | 244 | 20.616 | 26.706 | -1.214 | 1.00 | 0.00 | B1 |
| ATOM | 1671 | C | HIS | 244 | 21.621 | 26.565 | 5.650 | 1.00 | 33.38 | B1 |
| ATOM | 1672 | O | HIS | 244 | 20.546 | 26.105 | 6.029 | 1.00 | 33.23 | B1 |
| ATOM | 1673 | N | PRO | 245 | 22.539 | 27.018 | 6.499 | 1.00 | 33.21 | B1 |
| ATOM | 1674 | CD | PRO | 245 | 23.851 | 27.524 | 6.099 | 1.00 | 31.29 | B1 |
| ATOM | 1675 | CA | PRO | 245 | 22.373 | 26.979 | 7.948 | 1.00 | 34.16 | B1 |
| ATOM | 1676 | CB | PRO | 245 | 23.490 | 27.799 | 8.467 | 1.00 | 32.85 | B1 |
| ATOM | 1677 | CG | PRO | 245 | 24.564 | 27.549 | 7.428 | 1.00 | 31.74 | B1 |
| ATOM | 1678 | C | PRO | 245 | 21.032 | 27.470 | 8.407 | 1.00 | 36.26 | B1 |
| ATOM | 1679 | O | PRO | 245 | 20.478 | 26.878 | 9.315 | 1.00 | 38.13 | B1 |
| ATOM | 1680 | N | GLU | 246 | 20.529 | 28.463 | 7.640 | 1.00 | 39.64 | B1 |
| ATOM | 1681 | H | GLU | 246 | 21.134 | 28.747 | 6.934 | 1.00 | 0.00 | B1 |
| ATOM | 1682 | CA | GLU | 246 | 19.257 | 29.229 | 7.711 | 1.00 | 41.10 | B1 |
| ATOM | 1683 | CB | GLU | 246 | 19.044 | 30.107 | 6.438 | 1.00 | 43.15 | B1 |
| ATOM | 1684 | CG | GLU | 246 | 20.256 | 30.918 | 5.944 | 1.00 | 47.07 | B1 |
| ATOM | 1685 | CD | GLU | 246 | 20.813 | 30.539 | 4.558 | 1.00 | 52.63 | B1 |
| ATOM | 1686 | OE1 | GLU | 246 | 22.054 | 30.545 | 4.374 | 1.00 | 54.22 | B1 |
| ATOM | 1687 | OE2 | GLU | 246 | 20.002 | 30.250 | 3.656 | 1.00 | 53.39 | B1 |
| ATOM | 1688 | C | GLU | 246 | 18.071 | 28.298 | 7.819 | 1.00 | 40.57 | B1 |
| ATOM | 1689 | O | GLU | 246 | 17.308 | 28.338 | 8.791 | 1.00 | 39.90 | B1 |
| ATOM | 1690 | N | GLU | 247 | 18.025 | 27.388 | 6.840 | 1.00 | 40.32 | B1 |
| ATOM | 1691 | H | GLU | 247 | 18.750 | 27.334 | 6.190 | 1.00 | 0.00 | B1 |
| ATOM | 1692 | CA | GLU | 247 | 17.001 | 26.347 | 6.830 | 1.00 | 40.76 | B1 |
| ATOM | 1693 | CB | GLU | 247 | 17.139 | 25.423 | 5.642 | 1.00 | 44.03 | B1 |
| ATOM | 1694 | CG | GLU | 247 | 16.830 | 26.240 | 4.400 | 1.00 | 48.54 | B1 |
| ATOM | 1695 | CD | GLU | 247 | 17.163 | 25.628 | 3.050 | 1.00 | 50.24 | B1 |
| ATOM | 1696 | OE1 | GLU | 247 | 16.849 | 26.299 | 2.056 | 1.00 | 52.92 | B1 |
| ATOM | 1697 | OE2 | GLU | 247 | 17.744 | 24.533 | 2.987 | 1.00 | 50.84 | B1 |
| ATOM | 1698 | C | GLU | 247 | 16.966 | 25.444 | 8.034 | 1.00 | 39.24 | B1 |
| ATOM | 1699 | O | GLU | 247 | 15.915 | 24.888 | 8.329 | 1.00 | 39.40 | B1 |
| ATOM | 1700 | N | LEU | 248 | 18.066 | 25.280 | 8.760 | 1.00 | 37.92 | B1 |
| ATOM | 1701 | H | LEU | 248 | 18.864 | 25.814 | 8.576 | 1.00 | 0.00 | B1 |
| ATOM | 1702 | CA | LEU | 248 | 18.101 | 24.338 | 9.858 | 1.00 | 35.75 | B1 |
| ATOM | 1703 | CB | LEU | 248 | 19.458 | 23.623 | 9.796 | 1.00 | 34.13 | B1 |
| ATOM | 1704 | CG | LEU | 248 | 19.669 | 22.866 | 8.430 | 1.00 | 34.00 | B1 |
| ATOM | 1705 | CD1 | LEU | 248 | 20.997 | 22.149 | 8.306 | 1.00 | 33.97 | B1 |
| ATOM | 1706 | CD2 | LEU | 248 | 18.620 | 21.810 | 8.322 | 1.00 | 32.33 | B1 |
| ATOM | 1707 | C | LEU | 248 | 17.871 | 25.031 | 11.155 | 1.00 | 36.51 | B1 |
| ATOM | 1708 | O | LEU | 248 | 17.736 | 24.370 | 12.186 | 1.00 | 36.31 | B1 |
| ATOM | 1709 | N | VAL | 249 | 17.663 | 26.350 | 11.146 | 1.00 | 38.88 | B1 |
| ATOM | 1710 | H | VAL | 249 | 17.566 | 26.810 | 10.283 | 1.00 | 0.00 | B1 |
| ATOM | 1711 | CA | VAL | 249 | 17.573 | 27.133 | 12.371 | 1.00 | 41.39 | B1 |
| ATOM | 1712 | CB | VAL | 249 | 17.265 | 28.640 | 12.020 | 1.00 | 43.72 | B1 |
| ATOM | 1713 | CG1 | VAL | 249 | 15.804 | 28.985 | 11.776 | 1.00 | 44.70 | B1 |
| ATOM | 1714 | CG2 | VAL | 249 | 17.702 | 29.434 | 13.214 | 1.00 | 45.20 | B1 |
| ATOM | 1715 | C | VAL | 249 | 16.590 | 26.635 | 13.406 | 1.00 | 42.61 | B1 |
| ATOM | 1716 | O | VAL | 249 | 16.912 | 26.716 | 14.594 | 1.00 | 44.77 | B1 |
| ATOM | 1717 | N | LEU | 250 | 15.453 | 26.035 | 13.016 | 1.00 | 43.61 | B1 |
| ATOM | 1718 | H | LEU | 250 | 15.319 | 25.919 | 12.053 | 1.00 | 0.00 | B1 |
| ATOM | 1719 | CA | LEU | 250 | 14.457 | 25.537 | 13.987 | 1.00 | 43.96 | B1 |

FIG. 5-21

| | | | | | | | | | |
|---|---|---|---|---|---|---|---|---|---|
| ATOM | 1720 | CB | LEU | 250 | 13.102 | 25.296 | 13.373 | 1.00 | 43.88 | B1 |
| ATOM | 1721 | CG | LEU | 250 | 12.729 | 26.281 | 12.313 | 1.00 | 47.04 | B1 |
| ATOM | 1722 | CD1 | LEU | 250 | 13.092 | 25.577 | 11.011 | 1.00 | 47.30 | B1 |
| ATOM | 1723 | CD2 | LEU | 250 | 11.286 | 26.772 | 12.441 | 1.00 | 46.18 | B1 |
| ATOM | 1724 | C | LEU | 250 | 14.852 | 24.207 | 14.626 | 1.00 | 43.96 | B1 |
| ATOM | 1725 | O | LEU | 250 | 14.450 | 23.887 | 15.764 | 1.00 | 44.07 | B1 |
| ATOM | 1726 | N | LEU | 251 | 15.691 | 23.446 | 13.893 | 1.00 | 42.41 | B1 |
| ATOM | 1727 | H | LEU | 251 | 16.049 | 23.788 | 13.048 | 1.00 | 0.00 | B1 |
| ATOM | 1728 | CA | LEU | 251 | 16.155 | 22.159 | 14.362 | 1.00 | 40.63 | B1 |
| ATOM | 1729 | CB | LEU | 251 | 16.834 | 21.418 | 13.257 | 1.00 | 36.17 | B1 |
| ATOM | 1730 | CG | LEU | 251 | 15.996 | 20.629 | 12.267 | 1.00 | 33.16 | B1 |
| ATOM | 1731 | CD1 | LEU | 251 | 14.595 | 21.168 | 11.956 | 1.00 | 33.36 | B1 |
| ATOM | 1732 | CD2 | LEU | 251 | 16.875 | 20.619 | 11.050 | 1.00 | 34.71 | B1 |
| ATOM | 1733 | C | LEU | 251 | 17.104 | 22.372 | 15.493 | 1.00 | 42.78 | B1 |
| ATOM | 1734 | O | LEU | 251 | 17.124 | 21.554 | 16.395 | 1.00 | 45.44 | B1 |
| ATOM | 1735 | N | GLY | 252 | 17.826 | 23.477 | 15.610 | 1.00 | 44.86 | B1 |
| ATOM | 1736 | H | GLY | 252 | 17.750 | 24.160 | 14.910 | 1.00 | 0.00 | B1 |
| ATOM | 1737 | CA | GLY | 252 | 18.734 | 23.711 | 16.719 | 1.00 | 46.68 | B1 |
| ATOM | 1738 | C | GLY | 252 | 18.071 | 23.596 | 18.067 | 1.00 | 49.18 | B1 |
| ATOM | 1739 | O | GLY | 252 | 18.709 | 23.318 | 19.077 | 1.00 | 49.23 | B1 |
| ATOM | 1740 | N | HIS | 253 | 16.756 | 23.787 | 18.046 | 1.00 | 53.74 | B1 |
| ATOM | 1741 | H | HIS | 253 | 16.358 | 24.055 | 17.190 | 1.00 | 0.00 | B1 |
| ATOM | 1742 | CA | HIS | 253 | 15.859 | 23.649 | 19.197 | 1.00 | 57.46 | B1 |
| ATOM | 1743 | CB | HIS | 253 | 14.468 | 24.157 | 18.764 | 1.00 | 62.93 | B1 |
| ATOM | 1744 | CG | HIS | 253 | 13.212 | 23.813 | 19.577 | 1.00 | 68.75 | B1 |
| ATOM | 1745 | CD2 | HIS | 253 | 12.031 | 24.529 | 19.414 | 1.00 | 71.00 | B1 |
| ATOM | 1746 | ND1 | HIS | 253 | 12.980 | 22.854 | 20.479 | 1.00 | 70.67 | B1 |
| ATOM | 1747 | HD1 | HIS | 253 | 13.627 | 22.193 | 20.830 | 1.00 | 0.00 | B1 |
| ATOM | 1748 | CE1 | HIS | 253 | 11.723 | 22.966 | 20.845 | 1.00 | 73.40 | B1 |
| ATOM | 1749 | NE2 | HIS | 253 | 11.156 | 23.973 | 20.204 | 1.00 | 72.91 | B1 |
| ATOM | 1750 | HE2 | HIS | 253 | 10.218 | 24.260 | 20.311 | 1.00 | 0.00 | B1 |
| ATOM | 1751 | C | HIS | 253 | 15.771 | 22.209 | 19.691 | 1.00 | 56.06 | B1 |
| ATOM | 1752 | O | HIS | 253 | 15.880 | 21.827 | 20.857 | 1.00 | 56.17 | B1 |
| ATOM | 1753 | N | SER | 254 | 15.395 | 21.435 | 18.724 | 1.00 | 53.46 | B1 |
| ATOM | 1754 | H | SER | 254 | 15.278 | 21.783 | 17.813 | 1.00 | 0.00 | B1 |
| ATOM | 1755 | CA | SER | 254 | 15.177 | 20.034 | 18.898 | 1.00 | 52.61 | B1 |
| ATOM | 1756 | CB | SER | 254 | 14.613 | 19.595 | 17.576 | 1.00 | 53.04 | B1 |
| ATOM | 1757 | OG | SER | 254 | 13.793 | 20.686 | 17.158 | 1.00 | 56.04 | B1 |
| ATOM | 1758 | HG | SER | 254 | 13.369 | 20.467 | 16.319 | 1.00 | 0.00 | B1 |
| ATOM | 1759 | C | SER | 254 | 16.512 | 19.386 | 19.275 | 1.00 | 51.48 | B1 |
| ATOM | 1760 | O | SER | 254 | 16.596 | 18.639 | 20.245 | 1.00 | 51.90 | B1 |
| ATOM | 1761 | N | LEU | 255 | 17.577 | 19.790 | 18.562 | 1.00 | 49.31 | B1 |
| ATOM | 1762 | H | LEU | 255 | 17.430 | 20.480 | 17.889 | 1.00 | 0.00 | B1 |
| ATOM | 1763 | CA | LEU | 255 | 18.913 | 19.272 | 18.723 | 1.00 | 46.02 | B1 |
| ATOM | 1764 | CB | LEU | 255 | 19.706 | 19.723 | 17.537 | 1.00 | 44.66 | B1 |
| ATOM | 1765 | CG | LEU | 255 | 19.362 | 18.968 | 16.274 | 1.00 | 44.51 | B1 |
| ATOM | 1766 | CD1 | LEU | 255 | 19.810 | 19.679 | 15.006 | 1.00 | 43.16 | B1 |
| ATOM | 1767 | CD2 | LEU | 255 | 19.969 | 17.604 | 16.456 | 1.00 | 44.67 | B1 |
| ATOM | 1768 | C | LEU | 255 | 19.536 | 19.718 | 20.012 | 1.00 | 46.56 | B1 |
| ATOM | 1769 | O | LEU | 255 | 20.565 | 19.174 | 20.440 | 1.00 | 46.82 | B1 |
| ATOM | 1770 | N | GLY | 256 | 18.918 | 20.759 | 20.581 | 1.00 | 45.93 | B1 |
| ATOM | 1771 | H | GLY | 256 | 18.210 | 21.225 | 20.101 | 1.00 | 0.00 | B1 |
| ATOM | 1772 | CA | GLY | 256 | 19.277 | 21.273 | 21.890 | 1.00 | 46.68 | B1 |
| ATOM | 1773 | C | GLY | 256 | 20.669 | 21.866 | 21.970 | 1.00 | 47.28 | B1 |
| ATOM | 1774 | O | GLY | 256 | 21.273 | 21.844 | 23.056 | 1.00 | 49.64 | B1 |
| ATOM | 1775 | N | ILE | 257 | 21.143 | 22.441 | 20.849 | 1.00 | 45.74 | B1 |
| ATOM | 1776 | H | ILE | 257 | 20.497 | 22.589 | 20.128 | 1.00 | 0.00 | B1 |
| ATOM | 1777 | CA | ILE | 257 | 22.481 | 23.017 | 20.726 | 1.00 | 43.64 | B1 |
| ATOM | 1778 | CB | ILE | 257 | 22.684 | 23.363 | 19.257 | 1.00 | 42.54 | B1 |
| ATOM | 1779 | CG2 | ILE | 257 | 23.988 | 24.110 | 19.073 | 1.00 | 41.05 | B1 |
| ATOM | 1780 | CG1 | ILE | 257 | 22.694 | 22.088 | 18.437 | 1.00 | 40.55 | B1 |
| ATOM | 1781 | CD | ILE | 257 | 22.452 | 22.468 | 16.970 | 1.00 | 39.49 | B1 |
| ATOM | 1782 | C | ILE | 257 | 22.559 | 24.246 | 21.616 | 1.00 | 43.27 | B1 |
| ATOM | 1783 | O | ILE | 257 | 21.706 | 25.110 | 21.450 | 1.00 | 43.22 | B1 |
| ATOM | 1784 | N | PRO | 258 | 23.441 | 24.392 | 22.608 | 1.00 | 43.05 | B1 |
| ATOM | 1785 | CD | PRO | 258 | 24.133 | 23.321 | 23.296 | 1.00 | 43.29 | B1 |
| ATOM | 1786 | CA | PRO | 258 | 23.559 | 25.616 | 23.360 | 1.00 | 43.82 | B1 |
| ATOM | 1787 | CB | PRO | 258 | 24.295 | 25.236 | 24.612 | 1.00 | 41.97 | B1 |
| ATOM | 1788 | CG | PRO | 258 | 25.107 | 24.064 | 24.186 | 1.00 | 43.79 | B1 |
| ATOM | 1789 | C | PRO | 258 | 24.252 | 26.703 | 22.555 | 1.00 | 46.06 | B1 |
| ATOM | 1790 | O | PRO | 258 | 24.983 | 26.513 | 21.560 | 1.00 | 46.59 | B1 |
| ATOM | 1791 | N | TRP | 259 | 23.996 | 27.887 | 23.106 | 1.00 | 46.75 | B1 |
| ATOM | 1792 | H | TRP | 259 | 23.588 | 27.921 | 23.994 | 1.00 | 0.00 | B1 |
| ATOM | 1793 | CA | TRP | 259 | 24.427 | 29.143 | 22.517 | 1.00 | 45.77 | B1 |
| ATOM | 1794 | CB | TRP | 259 | 23.213 | 30.071 | 22.397 | 1.00 | 46.60 | B1 |
| ATOM | 1795 | CG | TRP | 259 | 23.556 | 31.372 | 21.749 | 1.00 | 47.51 | B1 |
| ATOM | 1796 | CD2 | TRP | 259 | 23.860 | 31.525 | 20.430 | 1.00 | 47.83 | B1 |
| ATOM | 1797 | CE2 | TRP | 259 | 24.154 | 32.888 | 20.392 | 1.00 | 48.47 | B1 |
| ATOM | 1798 | CE3 | TRP | 259 | 23.940 | 30.745 | 19.290 | 1.00 | 47.39 | B1 |
| ATOM | 1799 | CD1 | TRP | 259 | 23.639 | 32.520 | 22.493 | 1.00 | 48.60 | B1 |
| ATOM | 1800 | NE1 | TRP | 259 | 24.013 | 33.421 | 21.628 | 1.00 | 48.27 | B1 |
| ATOM | 1801 | HE1 | TRP | 259 | 24.224 | 34.344 | 21.870 | 1.00 | 0.00 | B1 |
| ATOM | 1802 | CZ2 | TRP | 259 | 24.531 | 33.486 | 19.195 | 1.00 | 47.40 | B1 |
| ATOM | 1803 | CZ3 | TRP | 259 | 24.317 | 31.344 | 18.097 | 1.00 | 49.07 | B1 |
| ATOM | 1804 | CH2 | TRP | 259 | 24.613 | 32.706 | 18.050 | 1.00 | 49.12 | B1 |
| ATOM | 1805 | C | TRP | 259 | 25.459 | 29.727 | 23.440 | 1.00 | 44.01 | B1 |

FIG.5-22

| | | | | | | | | | | |
|---|---|---|---|---|---|---|---|---|---|---|
| ATOM | 1806 | O | TRP | 259 | 25.340 | 29.664 | 24.671 | 1.00 | 43.25 | B1 |
| ATOM | 1807 | N | ALA | 260 | 26.469 | 30.247 | 22.777 | 1.00 | 43.01 | B1 |
| ATOM | 1808 | H | ALA | 260 | 26.523 | 30.198 | 21.796 | 1.00 | 0.00 | B1 |
| ATOM | 1809 | CA | ALA | 260 | 27.493 | 30.973 | 23.482 | 1.00 | 43.48 | B1 |
| ATOM | 1810 | CB | ALA | 260 | 28.874 | 30.549 | 22.969 | 1.00 | 43.33 | B1 |
| ATOM | 1811 | C | ALA | 260 | 27.249 | 32.486 | 23.216 | 1.00 | 43.41 | B1 |
| ATOM | 1812 | O | ALA | 260 | 27.315 | 32.946 | 22.054 | 1.00 | 40.55 | B1 |
| ATOM | 1813 | N | PRO | 261 | 26.853 | 33.267 | 24.253 | 1.00 | 42.61 | B1 |
| ATOM | 1814 | CD | PRO | 261 | 26.527 | 32.807 | 25.606 | 1.00 | 42.33 | B1 |
| ATOM | 1815 | CA | PRO | 261 | 26.720 | 34.701 | 24.199 | 1.00 | 42.37 | B1 |
| ATOM | 1816 | CB | PRO | 261 | 25.778 | 34.987 | 25.335 | 1.00 | 41.46 | B1 |
| ATOM | 1817 | CG | PRO | 261 | 26.251 | 34.060 | 26.411 | 1.00 | 40.00 | B1 |
| ATOM | 1818 | C | PRO | 261 | 28.087 | 35.369 | 24.311 | 1.00 | 42.22 | B1 |
| ATOM | 1819 | O | PRO | 261 | 28.998 | 34.956 | 25.037 | 1.00 | 38.82 | B1 |
| ATOM | 1820 | N | LEU | 262 | 28.234 | 36.403 | 23.486 | 1.00 | 45.20 | B1 |
| ATOM | 1821 | H | LEU | 262 | 27.513 | 36.610 | 22.853 | 1.00 | 0.00 | B1 |
| ATOM | 1822 | CA | LEU | 262 | 29.434 | 37.210 | 23.498 | 1.00 | 46.50 | B1 |
| ATOM | 1823 | CB | LEU | 262 | 30.531 | 36.609 | 22.610 | 1.00 | 45.09 | B1 |
| ATOM | 1824 | CG | LEU | 262 | 31.903 | 37.157 | 22.964 | 1.00 | 42.55 | B1 |
| ATOM | 1825 | CD1 | LEU | 262 | 32.344 | 36.695 | 24.338 | 1.00 | 41.52 | B1 |
| ATOM | 1826 | CD2 | LEU | 262 | 32.850 | 36.730 | 21.900 | 1.00 | 44.21 | B1 |
| ATOM | 1827 | C | LEU | 262 | 29.154 | 38.628 | 23.035 | 1.00 | 48.56 | B1 |
| ATOM | 1828 | O | LEU | 262 | 29.633 | 39.470 | 23.790 | 1.00 | 48.23 | B1 |
| ATOM | 1829 | N | SER | 263 | 28.388 | 38.956 | 21.960 | 1.00 | 51.33 | B1 |
| ATOM | 1830 | H | SER | 263 | 27.982 | 38.242 | 21.427 | 1.00 | 0.00 | B1 |
| ATOM | 1831 | CA | SER | 263 | 28.127 | 40.339 | 21.494 | 1.00 | 55.19 | B1 |
| ATOM | 1832 | CB | SER | 263 | 26.871 | 40.511 | 20.612 | 1.00 | 57.17 | B1 |
| ATOM | 1833 | OG | SER | 263 | 26.498 | 39.411 | 19.776 | 1.00 | 64.12 | B1 |
| ATOM | 1834 | HG | SER | 263 | 26.093 | 38.741 | 20.336 | 1.00 | 0.00 | B1 |
| ATOM | 1835 | C | SER | 263 | 27.909 | 41.354 | 22.600 | 1.00 | 56.15 | B1 |
| ATOM | 1836 | O | SER | 263 | 28.744 | 42.243 | 22.753 | 1.00 | 57.88 | B1 |
| ATOM | 1837 | N | SER | 264 | 26.899 | 41.231 | 23.452 | 1.00 | 56.52 | B1 |
| ATOM | 1838 | H | SER | 264 | 26.277 | 40.478 | 23.415 | 1.00 | 0.00 | B1 |
| ATOM | 1839 | CA | SER | 264 | 26.716 | 42.204 | 24.494 | 1.00 | 58.28 | B1 |
| ATOM | 1840 | CB | SER | 264 | 25.313 | 41.977 | 25.064 | 1.00 | 58.77 | B1 |
| ATOM | 1841 | OG | SER | 264 | 25.099 | 40.726 | 25.713 | 1.00 | 58.50 | B1 |
| ATOM | 1842 | HG | SER | 264 | 25.385 | 40.832 | 26.632 | 1.00 | 0.00 | B1 |
| ATOM | 1843 | C | SER | 264 | 27.800 | 42.168 | 25.584 | 1.00 | 59.95 | B1 |
| ATOM | 1844 | O | SER | 264 | 27.610 | 42.805 | 26.620 | 1.00 | 60.44 | B1 |
| ATOM | 1845 | N | CYS | 265 | 28.948 | 41.484 | 25.466 | 1.00 | 61.37 | B1 |
| ATOM | 1846 | H | CYS | 265 | 29.192 | 41.114 | 24.596 | 1.00 | 0.00 | B1 |
| ATOM | 1847 | CA | CYS | 265 | 29.958 | 41.502 | 26.509 | 1.00 | 62.57 | B1 |
| ATOM | 1848 | CB | CYS | 265 | 30.991 | 40.418 | 26.285 | 1.00 | 64.32 | B1 |
| ATOM | 1849 | SG | CYS | 265 | 32.322 | 40.638 | 27.504 | 1.00 | 71.40 | B1 |
| ATOM | 1850 | C | CYS | 265 | 30.667 | 42.860 | 26.515 | 1.00 | 63.12 | B1 |
| ATOM | 1851 | OT1 | CYS | 265 | 31.065 | 43.360 | 25.444 | 1.00 | 63.44 | B2 |
| ATOM | 1852 | OT2 | CYS | 265 | 30.809 | 43.408 | 27.610 | 1.00 | 61.72 | B2 |
| ATOM | 1853 | CB | ALA | 272 | 40.020 | 43.327 | 30.788 | 1.00 | 77.44 | B2 |
| ATOM | 1854 | C | ALA | 272 | 38.698 | 41.201 | 30.601 | 1.00 | 76.53 | B2 |
| ATOM | 1855 | O | ALA | 272 | 37.525 | 40.873 | 30.361 | 1.00 | 76.81 | B2 |
| ATOM | 1856 | HT1 | ALA | 272 | 37.486 | 43.550 | 30.261 | 1.00 | 0.00 | B2 |
| ATOM | 1857 | HT2 | ALA | 272 | 37.357 | 42.450 | 28.996 | 1.00 | 0.00 | B2 |
| ATOM | 1858 | N | ALA | 272 | 37.973 | 43.169 | 29.427 | 1.00 | 76.81 | B2 |
| ATOM | 1859 | HT3 | ALA | 272 | 38.195 | 43.924 | 28.752 | 1.00 | 0.00 | B2 |
| ATOM | 1860 | CA | ALA | 272 | 39.176 | 42.460 | 29.853 | 1.00 | 77.02 | B2 |
| ATOM | 1861 | N | ALA | 273 | 39.485 | 40.547 | 31.487 | 1.00 | 74.93 | B2 |
| ATOM | 1862 | H | ALA | 273 | 40.334 | 40.963 | 31.745 | 1.00 | 0.00 | B2 |
| ATOM | 1863 | CA | ALA | 273 | 39.244 | 39.241 | 32.119 | 1.00 | 72.64 | B2 |
| ATOM | 1864 | CB | ALA | 273 | 39.704 | 39.279 | 33.558 | 1.00 | 71.92 | B2 |
| ATOM | 1865 | C | ALA | 273 | 37.872 | 38.599 | 32.118 | 1.00 | 71.60 | B2 |
| ATOM | 1866 | O | ALA | 273 | 37.806 | 37.458 | 31.702 | 1.00 | 71.68 | B2 |
| ATOM | 1867 | N | GLY | 274 | 36.775 | 39.282 | 32.484 | 1.00 | 70.20 | B2 |
| ATOM | 1868 | H | GLY | 274 | 36.903 | 40.167 | 32.874 | 1.00 | 0.00 | B2 |
| ATOM | 1869 | CA | GLY | 274 | 35.412 | 38.758 | 32.425 | 1.00 | 66.78 | B2 |
| ATOM | 1870 | C | GLY | 274 | 35.050 | 38.437 | 30.990 | 1.00 | 65.05 | B2 |
| ATOM | 1871 | O | GLY | 274 | 34.627 | 37.320 | 30.709 | 1.00 | 66.44 | B2 |
| ATOM | 1872 | N | CYS | 275 | 35.301 | 39.364 | 30.048 | 1.00 | 62.77 | B2 |
| ATOM | 1873 | H | CYS | 275 | 35.634 | 40.223 | 30.357 | 1.00 | 0.00 | B2 |
| ATOM | 1874 | CA | CYS | 275 | 35.026 | 39.188 | 28.611 | 1.00 | 59.30 | B2 |
| ATOM | 1875 | C | CYS | 275 | 35.875 | 38.063 | 28.054 | 1.00 | 55.89 | B2 |
| ATOM | 1876 | O | CYS | 275 | 35.425 | 37.152 | 27.351 | 1.00 | 54.41 | B2 |
| ATOM | 1877 | CB | CYS | 275 | 35.349 | 40.466 | 27.827 | 1.00 | 61.50 | B2 |
| ATOM | 1878 | SG | CYS | 275 | 34.119 | 40.937 | 26.577 | 1.00 | 66.63 | B2 |
| ATOM | 1879 | N | LEU | 276 | 37.124 | 38.114 | 28.506 | 1.00 | 52.23 | B2 |
| ATOM | 1880 | H | LEU | 276 | 37.350 | 38.722 | 29.233 | 1.00 | 0.00 | B2 |
| ATOM | 1881 | CA | LEU | 276 | 38.091 | 37.163 | 28.066 | 1.00 | 48.93 | B2 |
| ATOM | 1882 | CB | LEU | 276 | 39.483 | 37.564 | 28.542 | 1.00 | 45.96 | B2 |
| ATOM | 1883 | CG | LEU | 276 | 40.241 | 38.557 | 27.670 | 1.00 | 43.20 | B2 |
| ATOM | 1884 | CD1 | LEU | 276 | 41.599 | 38.782 | 28.279 | 1.00 | 44.63 | B2 |
| ATOM | 1885 | CD2 | LEU | 276 | 40.429 | 38.033 | 26.271 | 1.00 | 40.55 | B2 |
| ATOM | 1886 | C | LEU | 276 | 37.673 | 35.833 | 28.638 | 1.00 | 47.84 | B2 |
| ATOM | 1887 | O | LEU | 276 | 37.784 | 34.803 | 27.964 | 1.00 | 48.51 | B2 |
| ATOM | 1888 | N | ALA | 277 | 37.074 | 35.840 | 29.804 | 1.00 | 45.56 | B2 |
| ATOM | 1889 | H | ALA | 277 | 36.898 | 36.662 | 30.289 | 1.00 | 0.00 | B2 |
| ATOM | 1890 | CA | ALA | 277 | 36.613 | 34.605 | 30.365 | 1.00 | 45.77 | B2 |
| ATOM | 1891 | CB | ALA | 277 | 36.147 | 34.810 | 31.783 | 1.00 | 47.87 | B2 |

FIG.5-23

| | | | | | | | | | | |
|---|---|---|---|---|---|---|---|---|---|---|
| ATOM | 1892 | C | ALA | 277 | 35.442 | 34.111 | 29.542 | 1.00 | 45.03 | B2 |
| ATOM | 1893 | O | ALA | 277 | 35.342 | 32.926 | 29.271 | 1.00 | 44.20 | B2 |
| ATOM | 1894 | N | GLN | 278 | 34.592 | 35.000 | 29.049 | 1.00 | 45.13 | B2 |
| ATOM | 1895 | H | GLN | 278 | 34.731 | 35.944 | 29.263 | 1.00 | 0.00 | B2 |
| ATOM | 1896 | CA | GLN | 278 | 33.435 | 34.601 | 28.284 | 1.00 | 45.27 | B2 |
| ATOM | 1897 | CB | GLN | 278 | 32.550 | 35.825 | 28.083 | 1.00 | 48.13 | B2 |
| ATOM | 1898 | CG | GLN | 278 | 31.140 | 35.442 | 28.484 | 1.00 | 56.00 | B2 |
| ATOM | 1899 | CD | GLN | 278 | 30.045 | 36.464 | 28.178 | 1.00 | 61.94 | B2 |
| ATOM | 1900 | OE1 | GLN | 278 | 29.048 | 36.530 | 28.896 | 1.00 | 65.95 | B2 |
| ATOM | 1901 | NE2 | GLN | 278 | 30.080 | 37.291 | 27.132 | 1.00 | 65.55 | B2 |
| ATOM | 1902 | HE21 | GLN | 278 | 30.829 | 37.221 | 26.510 | 1.00 | 0.00 | B2 |
| ATOM | 1903 | HE22 | GLN | 278 | 29.343 | 37.927 | 27.056 | 1.00 | 0.00 | B2 |
| ATOM | 1904 | C | GLN | 278 | 33.812 | 33.971 | 26.950 | 1.00 | 43.16 | B2 |
| ATOM | 1905 | O | GLN | 278 | 33.173 | 33.050 | 26.462 | 1.00 | 40.58 | B2 |
| ATOM | 1906 | N | LEU | 279 | 34.869 | 34.476 | 26.331 | 1.00 | 43.32 | B2 |
| ATOM | 1907 | H | LEU | 279 | 35.328 | 35.227 | 26.767 | 1.00 | 0.00 | B2 |
| ATOM | 1908 | CA | LEU | 279 | 35.398 | 33.966 | 25.069 | 1.00 | 42.80 | B2 |
| ATOM | 1909 | CB | LEU | 279 | 36.583 | 34.790 | 24.626 | 1.00 | 41.42 | B2 |
| ATOM | 1910 | CG | LEU | 279 | 36.885 | 35.014 | 23.190 | 1.00 | 40.76 | B2 |
| ATOM | 1911 | CD1 | LEU | 279 | 38.239 | 35.647 | 23.130 | 1.00 | 41.76 | B2 |
| ATOM | 1912 | CD2 | LEU | 279 | 36.943 | 33.753 | 22.411 | 1.00 | 40.01 | B2 |
| ATOM | 1913 | C | LEU | 279 | 35.876 | 32.554 | 25.341 | 1.00 | 42.92 | B2 |
| ATOM | 1914 | O | LEU | 279 | 35.572 | 31.598 | 24.640 | 1.00 | 42.57 | B2 |
| ATOM | 1915 | N | HIS | 280 | 36.654 | 32.463 | 26.403 | 1.00 | 43.93 | B2 |
| ATOM | 1916 | H | HIS | 280 | 36.837 | 33.282 | 26.917 | 1.00 | 0.00 | B2 |
| ATOM | 1917 | CA | HIS | 280 | 37.215 | 31.223 | 26.850 | 1.00 | 46.12 | B2 |
| ATOM | 1918 | CB | HIS | 280 | 38.029 | 31.506 | 28.101 | 1.00 | 48.74 | B2 |
| ATOM | 1919 | CG | HIS | 280 | 38.914 | 30.320 | 28.394 | 1.00 | 54.16 | B2 |
| ATOM | 1920 | CD2 | HIS | 280 | 40.041 | 30.069 | 27.650 | 1.00 | 56.02 | B2 |
| ATOM | 1921 | ND1 | HIS | 280 | 38.759 | 29.326 | 29.264 | 1.00 | 56.01 | B2 |
| ATOM | 1922 | HD1 | HIS | 280 | 38.012 | 29.203 | 29.890 | 1.00 | 56.00 | B2 |
| ATOM | 1923 | CE1 | HIS | 280 | 39.744 | 28.483 | 29.058 | 1.00 | 56.64 | B2 |
| ATOM | 1924 | NE2 | HIS | 280 | 40.507 | 28.937 | 28.088 | 1.00 | 56.64 | B2 |
| ATOM | 1925 | HE2 | HIS | 280 | 41.282 | 28.478 | 27.684 | 1.00 | 0.00 | B2 |
| ATOM | 1926 | C | HIS | 280 | 36.161 | 30.134 | 27.117 | 1.00 | 45.65 | B2 |
| ATOM | 1927 | O | HIS | 280 | 36.362 | 28.977 | 26.711 | 1.00 | 46.23 | B2 |
| ATOM | 1928 | N | SER | 281 | 35.086 | 30.473 | 27.822 | 1.00 | 43.91 | B2 |
| ATOM | 1929 | H | SER | 281 | 35.009 | 31.367 | 28.219 | 1.00 | 0.00 | B2 |
| ATOM | 1930 | CA | SER | 281 | 34.008 | 29.574 | 28.105 | 1.00 | 43.53 | B2 |
| ATOM | 1931 | CB | SER | 281 | 33.026 | 30.291 | 29.002 | 1.00 | 44.18 | B2 |
| ATOM | 1932 | OG | SER | 281 | 33.761 | 30.812 | 30.113 | 1.00 | 47.79 | B2 |
| ATOM | 1933 | HG | SER | 281 | 33.288 | 30.648 | 30.931 | 1.00 | 0.00 | B2 |
| ATOM | 1934 | C | SER | 281 | 33.382 | 29.169 | 26.787 | 1.00 | 43.35 | B2 |
| ATOM | 1935 | O | SER | 281 | 33.334 | 27.973 | 26.496 | 1.00 | 44.83 | B2 |
| ATOM | 1936 | N | GLY | 282 | 32.977 | 30.120 | 25.940 | 1.00 | 42.33 | B2 |
| ATOM | 1937 | H | GLY | 282 | 33.043 | 31.058 | 26.221 | 1.00 | 0.00 | B2 |
| ATOM | 1938 | CA | GLY | 282 | 32.363 | 29.869 | 24.632 | 1.00 | 40.65 | B2 |
| ATOM | 1939 | C | GLY | 282 | 33.175 | 28.937 | 23.755 | 1.00 | 39.06 | B2 |
| ATOM | 1940 | O | GLY | 282 | 32.584 | 28.075 | 23.107 | 1.00 | 40.10 | B2 |
| ATOM | 1941 | N | LEU | 283 | 34.514 | 29.066 | 23.776 | 1.00 | 37.39 | B2 |
| ATOM | 1942 | H | LEU | 283 | 34.880 | 29.807 | 24.304 | 1.00 | 0.00 | B2 |
| ATOM | 1943 | CA | LEU | 283 | 35.465 | 28.213 | 23.037 | 1.00 | 35.06 | B2 |
| ATOM | 1944 | CB | LEU | 283 | 36.902 | 28.718 | 23.089 | 1.00 | 30.20 | B2 |
| ATOM | 1945 | CG | LEU | 283 | 37.167 | 30.001 | 22.302 | 1.00 | 25.73 | B2 |
| ATOM | 1946 | CD1 | LEU | 283 | 38.539 | 30.461 | 22.664 | 1.00 | 24.38 | B2 |
| ATOM | 1947 | CD2 | LEU | 283 | 37.036 | 29.802 | 20.815 | 1.00 | 21.94 | B2 |
| ATOM | 1948 | C | LEU | 283 | 35.470 | 26.851 | 23.651 | 1.00 | 34.81 | B2 |
| ATOM | 1949 | O | LEU | 283 | 35.314 | 25.859 | 22.947 | 1.00 | 31.09 | B2 |
| ATOM | 1950 | N | PHE | 284 | 35.533 | 26.842 | 24.973 | 1.00 | 37.62 | B2 |
| ATOM | 1951 | H | PHE | 284 | 35.567 | 27.686 | 25.467 | 1.00 | 0.00 | B2 |
| ATOM | 1952 | CA | PHE | 284 | 35.485 | 25.596 | 25.710 | 1.00 | 42.51 | B2 |
| ATOM | 1953 | CB | PHE | 284 | 35.542 | 25.877 | 27.184 | 1.00 | 49.49 | B2 |
| ATOM | 1954 | CG | PHE | 284 | 36.221 | 24.770 | 27.968 | 1.00 | 58.39 | B2 |
| ATOM | 1955 | CD1 | PHE | 284 | 37.265 | 25.108 | 28.816 | 1.00 | 63.05 | B2 |
| ATOM | 1956 | CD2 | PHE | 284 | 35.810 | 23.453 | 27.861 | 1.00 | 60.84 | B2 |
| ATOM | 1957 | CE1 | PHE | 284 | 37.900 | 24.124 | 29.563 | 1.00 | 65.86 | B2 |
| ATOM | 1958 | CE2 | PHE | 284 | 36.444 | 22.480 | 28.605 | 1.00 | 64.49 | B2 |
| ATOM | 1959 | CZ | PHE | 284 | 37.486 | 22.810 | 29.455 | 1.00 | 66.32 | B2 |
| ATOM | 1960 | C | PHE | 284 | 34.204 | 24.849 | 25.384 | 1.00 | 41.44 | B2 |
| ATOM | 1961 | O | PHE | 284 | 34.257 | 23.630 | 25.306 | 1.00 | 41.42 | B2 |
| ATOM | 1962 | N | LEU | 285 | 33.100 | 25.563 | 25.101 | 1.00 | 41.24 | B2 |
| ATOM | 1963 | H | LEU | 285 | 33.192 | 26.534 | 25.174 | 1.00 | 0.00 | B2 |
| ATOM | 1964 | CA | LEU | 285 | 31.781 | 25.025 | 24.730 | 1.00 | 38.92 | B2 |
| ATOM | 1965 | CB | LEU | 285 | 30.727 | 26.139 | 24.807 | 1.00 | 39.05 | B2 |
| ATOM | 1966 | CG | LEU | 285 | 29.292 | 25.740 | 24.481 | 1.00 | 41.16 | B2 |
| ATOM | 1967 | CD1 | LEU | 285 | 28.711 | 24.981 | 25.662 | 1.00 | 41.12 | B2 |
| ATOM | 1968 | CD2 | LEU | 285 | 28.472 | 26.971 | 24.139 | 1.00 | 39.60 | B2 |
| ATOM | 1969 | C | LEU | 285 | 31.780 | 24.441 | 23.329 | 1.00 | 37.34 | B2 |
| ATOM | 1970 | O | LEU | 285 | 31.245 | 23.351 | 23.095 | 1.00 | 36.97 | B2 |
| ATOM | 1971 | N | TYR | 286 | 32.352 | 25.172 | 22.372 | 1.00 | 35.26 | B2 |
| ATOM | 1972 | H | TYR | 286 | 32.705 | 26.062 | 22.593 | 1.00 | 0.00 | B2 |
| ATOM | 1973 | CA | TYR | 286 | 32.455 | 24.660 | 21.033 | 1.00 | 35.04 | B2 |
| ATOM | 1974 | CB | TYR | 286 | 32.891 | 25.790 | 20.122 | 1.00 | 34.44 | B2 |
| ATOM | 1975 | CG | TYR | 286 | 31.690 | 26.684 | 19.808 | 1.00 | 34.75 | B2 |
| ATOM | 1976 | CD1 | TYR | 286 | 31.433 | 27.879 | 20.469 | 1.00 | 35.67 | B2 |
| ATOM | 1977 | CE1 | TYR | 286 | 30.313 | 28.620 | 20.158 | 1.00 | 36.90 | B2 |

FIG. 5-24

| | | | | | | | | | |
|---|---|---|---|---|---|---|---|---|---|
| ATOM | 1978 | CD2 TYR | 286 | 30.823 | 26.255 | 18.839 | 1.00 | 36.19 | B2 |
| ATOM | 1979 | CE2 TYR | 286 | 29.707 | 26.990 | 18.521 | 1.00 | 37.55 | B2 |
| ATOM | 1980 | CZ TYR | 286 | 29.449 | 28.164 | 19.178 | 1.00 | 37.73 | B2 |
| ATOM | 1981 | OH TYR | 286 | 28.285 | 28.826 | 18.823 | 1.00 | 38.04 | B2 |
| ATOM | 1982 | HH TYR | 286 | 28.289 | 29.707 | 19.243 | 1.00 | 0.00 | B2 |
| ATOM | 1983 | C TYR | 286 | 33.393 | 23.464 | 20.926 | 1.00 | 34.80 | B2 |
| ATOM | 1984 | O TYR | 286 | 33.071 | 22.537 | 20.180 | 1.00 | 35.35 | B2 |
| ATOM | 1985 | N ALA | 287 | 34.527 | 23.339 | 21.636 | 1.00 | 34.66 | B2 |
| ATOM | 1986 | H ALA | 287 | 34.803 | 24.088 | 22.206 | 1.00 | 0.00 | B2 |
| ATOM | 1987 | CA ALA | 287 | 35.350 | 22.108 | 21.565 | 1.00 | 34.28 | B2 |
| ATOM | 1988 | CB ALA | 287 | 36.617 | 22.291 | 22.415 | 1.00 | 33.63 | B2 |
| ATOM | 1989 | C ALA | 287 | 34.528 | 20.906 | 22.073 | 1.00 | 33.32 | B2 |
| ATOM | 1990 | O ALA | 287 | 34.535 | 19.827 | 21.478 | 1.00 | 33.07 | B2 |
| ATOM | 1991 | N GLY | 288 | 33.723 | 21.118 | 23.111 | 1.00 | 33.19 | B2 |
| ATOM | 1992 | H GLY | 288 | 33.791 | 21.985 | 23.564 | 1.00 | 0.00 | B2 |
| ATOM | 1993 | CA GLY | 288 | 32.761 | 20.162 | 23.655 | 1.00 | 35.62 | B2 |
| ATOM | 1994 | C GLY | 288 | 31.744 | 19.606 | 22.636 | 1.00 | 36.89 | B2 |
| ATOM | 1995 | O GLY | 288 | 31.624 | 18.379 | 22.444 | 1.00 | 34.97 | B2 |
| ATOM | 1996 | N LEU | 289 | 31.037 | 20.536 | 21.966 | 1.00 | 36.69 | B2 |
| ATOM | 1997 | H LEU | 289 | 31.200 | 21.476 | 22.201 | 1.00 | 0.00 | B2 |
| ATOM | 1998 | CA LEU | 289 | 30.018 | 20.249 | 20.954 | 1.00 | 35.05 | B2 |
| ATOM | 1999 | CB LEU | 289 | 29.351 | 21.576 | 20.502 | 1.00 | 36.32 | B2 |
| ATOM | 2000 | CG LEU | 289 | 28.552 | 22.450 | 21.464 | 1.00 | 35.76 | B2 |
| ATOM | 2001 | CD1 LEU | 289 | 28.256 | 23.821 | 20.890 | 1.00 | 32.66 | B2 |
| ATOM | 2002 | CD2 LEU | 289 | 27.246 | 21.780 | 21.697 | 1.00 | 35.35 | B2 |
| ATOM | 2003 | C LEU | 289 | 30.536 | 19.519 | 19.714 | 1.00 | 34.21 | B2 |
| ATOM | 2004 | O LEU | 289 | 29.871 | 18.694 | 19.078 | 1.00 | 33.28 | B2 |
| ATOM | 2005 | N LEU | 290 | 31.756 | 19.902 | 19.355 | 1.00 | 33.25 | B2 |
| ATOM | 2006 | H LEU | 290 | 32.183 | 20.634 | 19.850 | 1.00 | 0.00 | B2 |
| ATOM | 2007 | CA LEU | 290 | 32.448 | 19.345 | 18.230 | 1.00 | 32.44 | B2 |
| ATOM | 2008 | CB LEU | 290 | 33.729 | 20.159 | 18.000 | 1.00 | 32.62 | B2 |
| ATOM | 2009 | CG LEU | 290 | 33.560 | 21.509 | 17.315 | 1.00 | 32.05 | B2 |
| ATOM | 2010 | CD1 LEU | 290 | 34.889 | 22.189 | 17.349 | 1.00 | 32.58 | B2 |
| ATOM | 2011 | CD2 LEU | 290 | 33.068 | 21.374 | 15.879 | 1.00 | 31.74 | B2 |
| ATOM | 2012 | C LEU | 290 | 32.737 | 17.908 | 18.558 | 1.00 | 31.94 | B2 |
| ATOM | 2013 | O LEU | 290 | 32.432 | 17.020 | 17.772 | 1.00 | 30.50 | B2 |
| ATOM | 2014 | N GLN | 291 | 33.249 | 17.711 | 19.770 | 1.00 | 33.58 | B2 |
| ATOM | 2015 | H GLN | 291 | 33.512 | 18.494 | 20.298 | 1.00 | 0.00 | B2 |
| ATOM | 2016 | CA GLN | 291 | 33.499 | 16.372 | 20.311 | 1.00 | 36.39 | B2 |
| ATOM | 2017 | CB GLN | 291 | 33.988 | 16.490 | 21.702 | 1.00 | 36.86 | B2 |
| ATOM | 2018 | CG GLN | 291 | 34.926 | 15.367 | 21.950 | 1.00 | 39.48 | B2 |
| ATOM | 2019 | CD GLN | 291 | 35.658 | 15.503 | 23.252 | 1.00 | 40.79 | B2 |
| ATOM | 2020 | OE1 GLN | 291 | 36.457 | 14.626 | 23.549 | 1.00 | 44.80 | B2 |
| ATOM | 2021 | NE2 GLN | 291 | 35.494 | 16.535 | 24.072 | 1.00 | 42.59 | B2 |
| ATOM | 2022 | HE21 GLN | 291 | 34.928 | 17.287 | 23.817 | 1.00 | 0.00 | B2 |
| ATOM | 2023 | HE22 GLN | 291 | 35.910 | 16.463 | 24.958 | 1.00 | 0.00 | B2 |
| ATOM | 2024 | C GLN | 291 | 32.233 | 15.536 | 20.307 | 1.00 | 36.66 | B2 |
| ATOM | 2025 | O GLN | 291 | 32.220 | 14.478 | 19.707 | 1.00 | 37.46 | B2 |
| ATOM | 2026 | N ALA | 292 | 31.143 | 16.023 | 20.913 | 1.00 | 38.37 | B2 |
| ATOM | 2027 | H ALA | 292 | 31.255 | 16.849 | 21.418 | 1.00 | 0.00 | B2 |
| ATOM | 2028 | CA ALA | 292 | 29.778 | 15.451 | 20.857 | 1.00 | 39.25 | B2 |
| ATOM | 2029 | CB ALA | 292 | 28.818 | 16.485 | 21.444 | 1.00 | 40.28 | B2 |
| ATOM | 2030 | C ALA | 292 | 29.215 | 14.999 | 19.484 | 1.00 | 38.65 | B2 |
| ATOM | 2031 | O ALA | 292 | 28.411 | 14.067 | 19.356 | 1.00 | 37.58 | B2 |
| ATOM | 2032 | N LEU | 293 | 29.614 | 15.702 | 18.430 | 1.00 | 39.00 | B2 |
| ATOM | 2033 | H LEU | 293 | 30.149 | 16.513 | 18.574 | 1.00 | 0.00 | B2 |
| ATOM | 2034 | CA LEU | 293 | 29.265 | 15.335 | 17.077 | 1.00 | 39.74 | B2 |
| ATOM | 2035 | CB LEU | 293 | 29.662 | 16.418 | 16.106 | 1.00 | 37.53 | B2 |
| ATOM | 2036 | CG LEU | 293 | 28.969 | 17.701 | 16.138 | 1.00 | 34.34 | B2 |
| ATOM | 2037 | CD1 LEU | 293 | 29.547 | 18.582 | 15.053 | 1.00 | 33.88 | B2 |
| ATOM | 2038 | CD2 LEU | 293 | 27.503 | 17.462 | 15.918 | 1.00 | 35.69 | B2 |
| ATOM | 2039 | C LEU | 293 | 29.933 | 14.060 | 16.596 | 1.00 | 40.86 | B2 |
| ATOM | 2040 | O LEU | 293 | 29.686 | 13.669 | 15.449 | 1.00 | 40.58 | B2 |
| ATOM | 2041 | N GLU | 294 | 30.887 | 13.495 | 17.365 | 1.00 | 42.12 | B2 |
| ATOM | 2042 | H GLU | 294 | 31.131 | 13.963 | 18.190 | 1.00 | 0.00 | B2 |
| ATOM | 2043 | CA GLU | 294 | 31.598 | 12.255 | 17.076 | 1.00 | 42.89 | B2 |
| ATOM | 2044 | CB GLU | 294 | 30.806 | 10.984 | 17.485 | 1.00 | 48.38 | B2 |
| ATOM | 2045 | CG GLU | 294 | 30.715 | 10.614 | 18.972 | 1.00 | 56.26 | B2 |
| ATOM | 2046 | CD GLU | 294 | 29.271 | 10.408 | 19.486 | 1.00 | 63.70 | B2 |
| ATOM | 2047 | OE1 GLU | 294 | 29.058 | 10.603 | 20.702 | 1.00 | 67.72 | B2 |
| ATOM | 2048 | OE2 GLU | 294 | 28.363 | 10.074 | 18.692 | 1.00 | 64.81 | B2 |
| ATOM | 2049 | C GLU | 294 | 31.972 | 12.068 | 15.632 | 1.00 | 41.53 | B2 |
| ATOM | 2050 | O GLU | 294 | 31.804 | 11.007 | 15.021 | 1.00 | 40.29 | B2 |
| ATOM | 2051 | N GLY | 295 | 32.424 | 13.203 | 15.106 | 1.00 | 40.93 | B2 |
| ATOM | 2052 | H GLY | 295 | 32.357 | 14.033 | 15.621 | 1.00 | 0.00 | B2 |
| ATOM | 2053 | CA GLY | 295 | 32.998 | 13.236 | 13.783 | 1.00 | 39.95 | B2 |
| ATOM | 2054 | C GLY | 295 | 32.027 | 13.230 | 12.634 | 1.00 | 40.60 | B2 |
| ATOM | 2055 | O GLY | 295 | 32.477 | 13.216 | 11.487 | 1.00 | 40.96 | B2 |
| ATOM | 2056 | N ILE | 296 | 30.728 | 13.296 | 12.898 | 1.00 | 41.18 | B2 |
| ATOM | 2057 | H ILE | 296 | 30.446 | 13.210 | 13.825 | 1.00 | 0.00 | B2 |
| ATOM | 2058 | CA ILE | 296 | 29.687 | 13.306 | 11.888 | 1.00 | 44.02 | B2 |
| ATOM | 2059 | CB ILE | 296 | 29.683 | 14.580 | 11.009 | 1.00 | 43.49 | B2 |
| ATOM | 2060 | CG2 ILE | 296 | 28.288 | 14.685 | 10.421 | 1.00 | 40.56 | B2 |
| ATOM | 2061 | CG1 ILE | 296 | 30.047 | 15.831 | 11.793 | 1.00 | 45.11 | B2 |
| ATOM | 2062 | CD ILE | 296 | 30.039 | 17.189 | 11.062 | 1.00 | 46.06 | B2 |
| ATOM | 2063 | C ILE | 296 | 29.820 | 12.107 | 10.949 | 1.00 | 46.71 | B2 |

FIG. 5-25

| | | | | | | | | | |
|---|---|---|---|---|---|---|---|---|---|
| ATOM | 2064 | O | ILE | 296 | 28.918 | 11.279 | 11.060 | 1.00 50.61 | B2 |
| ATOM | 2065 | N | SER | 297 | 30.767 | 11.875 | 10.019 | 1.00 47.21 | B2 |
| ATOM | 2066 | H | SER | 297 | 31.526 | 12.491 | 9.936 | 1.00 0.00 | B2 |
| ATOM | 2067 | CA | SER | 297 | 30.810 | 10.646 | 9.234 | 1.00 46.73 | B2 |
| ATOM | 2068 | CB | SER | 297 | 30.239 | 10.884 | 7.865 | 1.00 45.48 | B2 |
| ATOM | 2069 | OG | SER | 297 | 30.988 | 11.782 | 7.072 | 1.00 46.27 | B2 |
| ATOM | 2070 | HG | SER | 297 | 30.321 | 12.200 | 6.503 | 1.00 0.00 | B2 |
| ATOM | 2071 | C | SER | 297 | 32.263 | 10.269 | 9.123 | 1.00 48.72 | B2 |
| ATOM | 2072 | O | SER | 297 | 33.120 | 11.122 | 9.391 | 1.00 50.55 | B2 |
| ATOM | 2073 | N | PRO | 298 | 32.655 | 9.069 | 8.697 | 1.00 49.68 | B2 |
| ATOM | 2074 | CD | PRO | 298 | 31.782 | 7.964 | 8.334 | 1.00 50.62 | B2 |
| ATOM | 2075 | CA | PRO | 298 | 34.049 | 8.701 | 8.458 | 1.00 50.33 | B2 |
| ATOM | 2076 | CB | PRO | 298 | 33.948 | 7.308 | 7.856 | 1.00 51.53 | B2 |
| ATOM | 2077 | CG | PRO | 298 | 32.576 | 7.266 | 7.231 | 1.00 50.43 | B2 |
| ATOM | 2078 | C | PRO | 298 | 34.795 | 9.692 | 7.579 | 1.00 50.08 | B2 |
| ATOM | 2079 | O | PRO | 298 | 35.883 | 10.137 | 7.930 | 1.00 50.50 | B2 |
| ATOM | 2080 | N | GLN | 299 | 34.173 | 10.086 | 6.469 | 1.00 50.48 | B2 |
| ATOM | 2081 | H | GLN | 299 | 33.279 | 9.729 | 6.296 | 1.00 0.00 | B2 |
| ATOM | 2082 | CA | GLN | 299 | 34.749 | 11.050 | 5.550 | 1.00 51.74 | B2 |
| ATOM | 2083 | CB | GLN | 299 | 33.898 | 11.236 | 4.301 | 1.00 54.33 | B2 |
| ATOM | 2084 | CG | GLN | 299 | 33.095 | 10.067 | 3.725 | 1.00 58.11 | B2 |
| ATOM | 2085 | CD | GLN | 299 | 31.658 | 10.086 | 4.259 | 1.00 61.49 | B2 |
| ATOM | 2086 | OE1 | GLN | 299 | 31.160 | 9.083 | 4.776 | 1.00 61.00 | B2 |
| ATOM | 2087 | NE2 | GLN | 299 | 30.942 | 11.217 | 4.204 | 1.00 62.12 | B2 |
| ATOM | 2088 | HE21 | GLN | 299 | 31.345 | 12.012 | 3.800 | 1.00 0.00 | B2 |
| ATOM | 2089 | HE22 | GLN | 299 | 30.034 | 11.191 | 4.566 | 1.00 0.00 | B2 |
| ATOM | 2090 | C | GLN | 299 | 34.923 | 12.453 | 6.160 | 1.00 51.04 | B2 |
| ATOM | 2091 | O | GLN | 299 | 35.796 | 13.186 | 5.718 | 1.00 53.38 | B2 |
| ATOM | 2092 | N | LEU | 300 | 34.118 | 12.918 | 7.120 | 1.00 48.15 | B2 |
| ATOM | 2093 | H | LEU | 300 | 33.383 | 12.351 | 7.437 | 1.00 0.00 | B2 |
| ATOM | 2094 | CA | LEU | 300 | 34.272 | 14.220 | 7.745 | 1.00 43.32 | B2 |
| ATOM | 2095 | CB | LEU | 300 | 32.856 | 14.719 | 8.021 | 1.00 41.39 | B2 |
| ATOM | 2096 | CG | LEU | 300 | 32.073 | 15.546 | 6.974 | 1.00 37.99 | B2 |
| ATOM | 2097 | CD1 | LEU | 300 | 31.872 | 14.824 | 5.688 | 1.00 38.34 | B2 |
| ATOM | 2098 | CD2 | LEU | 300 | 30.705 | 15.809 | 7.522 | 1.00 37.67 | B2 |
| ATOM | 2099 | C | LEU | 300 | 35.142 | 14.220 | 9.019 | 1.00 42.84 | B2 |
| ATOM | 2100 | O | LEU | 300 | 35.558 | 15.278 | 9.541 | 1.00 41.56 | B2 |
| ATOM | 2101 | N | GLY | 301 | 35.467 | 13.016 | 9.528 | 1.00 40.83 | B2 |
| ATOM | 2102 | H | GLY | 301 | 35.157 | 12.221 | 9.046 | 1.00 0.00 | B2 |
| ATOM | 2103 | CA | GLY | 301 | 36.199 | 12.826 | 10.779 | 1.00 38.72 | B2 |
| ATOM | 2104 | C | GLY | 301 | 37.500 | 13.607 | 10.887 | 1.00 37.69 | B2 |
| ATOM | 2105 | O | GLY | 301 | 37.665 | 14.406 | 11.809 | 1.00 37.31 | B2 |
| ATOM | 2106 | N | PRO | 302 | 38.468 | 13.452 | 9.985 | 1.00 37.33 | B2 |
| ATOM | 2107 | CD | PRO | 302 | 38.353 | 12.630 | 8.790 | 1.00 37.77 | B2 |
| ATOM | 2108 | CA | PRO | 302 | 39.676 | 14.281 | 9.884 | 1.00 37.60 | B2 |
| ATOM | 2109 | CB | PRO | 302 | 40.256 | 13.907 | 8.541 | 1.00 36.62 | B2 |
| ATOM | 2110 | CG | PRO | 302 | 39.047 | 13.487 | 7.745 | 1.00 37.94 | B2 |
| ATOM | 2111 | C | PRO | 302 | 39.486 | 15.782 | 10.033 | 1.00 37.45 | B2 |
| ATOM | 2112 | O | PRO | 302 | 40.132 | 16.398 | 10.901 | 1.00 38.33 | B2 |
| ATOM | 2113 | N | THR | 303 | 38.547 | 16.311 | 9.204 | 1.00 37.05 | B2 |
| ATOM | 2114 | H | THR | 303 | 38.085 | 15.727 | 8.567 | 1.00 0.00 | B2 |
| ATOM | 2115 | CA | THR | 303 | 38.119 | 17.705 | 9.128 | 1.00 35.81 | B2 |
| ATOM | 2116 | CB | THR | 303 | 36.963 | 17.770 | 8.123 | 1.00 37.26 | B2 |
| ATOM | 2117 | OG1 | THR | 303 | 37.416 | 17.161 | 6.909 | 1.00 39.64 | B2 |
| ATOM | 2118 | HG1 | THR | 303 | 37.369 | 17.785 | 6.178 | 1.00 0.00 | B2 |
| ATOM | 2119 | CG2 | THR | 303 | 36.469 | 19.204 | 7.927 | 1.00 38.55 | B2 |
| ATOM | 2120 | C | THR | 303 | 37.687 | 18.223 | 10.506 | 1.00 34.93 | B2 |
| ATOM | 2121 | O | THR | 303 | 38.085 | 19.263 | 11.063 | 1.00 35.11 | B2 |
| ATOM | 2122 | N | LEU | 304 | 36.928 | 17.366 | 11.150 | 1.00 33.76 | B2 |
| ATOM | 2123 | H | LEU | 304 | 36.672 | 16.500 | 10.762 | 1.00 0.00 | B2 |
| ATOM | 2124 | CA | LEU | 304 | 36.436 | 17.746 | 12.418 | 1.00 31.01 | B2 |
| ATOM | 2125 | CB | LEU | 304 | 35.345 | 16.803 | 12.708 | 1.00 30.31 | B2 |
| ATOM | 2126 | CG | LEU | 304 | 34.234 | 17.567 | 13.320 | 1.00 31.32 | B2 |
| ATOM | 2127 | CD1 | LEU | 304 | 33.121 | 17.626 | 12.309 | 1.00 28.87 | B2 |
| ATOM | 2128 | CD2 | LEU | 304 | 33.921 | 16.970 | 14.692 | 1.00 34.23 | B2 |
| ATOM | 2129 | C | LEU | 304 | 37.553 | 17.726 | 13.421 | 1.00 31.86 | B2 |
| ATOM | 2130 | O | LEU | 304 | 37.615 | 18.623 | 14.259 | 1.00 34.21 | B2 |
| ATOM | 2131 | N | ASP | 305 | 38.510 | 16.811 | 13.326 | 1.00 30.56 | B2 |
| ATOM | 2132 | H | ASP | 305 | 38.456 | 16.117 | 12.635 | 1.00 0.00 | B2 |
| ATOM | 2133 | CA | ASP | 305 | 39.576 | 16.797 | 14.303 | 1.00 30.72 | B2 |
| ATOM | 2134 | CB | ASP | 305 | 40.504 | 15.608 | 14.114 | 1.00 36.20 | B2 |
| ATOM | 2135 | CG | ASP | 305 | 39.912 | 14.201 | 14.288 | 1.00 40.64 | B2 |
| ATOM | 2136 | OD1 | ASP | 305 | 38.976 | 14.040 | 15.103 | 1.00 37.52 | B2 |
| ATOM | 2137 | OD2 | ASP | 305 | 40.426 | 13.304 | 13.581 | 1.00 42.39 | B2 |
| ATOM | 2138 | C | ASP | 305 | 40.435 | 18.034 | 14.238 | 1.00 27.56 | B2 |
| ATOM | 2139 | O | ASP | 305 | 40.775 | 18.575 | 15.311 | 1.00 24.61 | B2 |
| ATOM | 2140 | N | THR | 306 | 40.781 | 18.417 | 12.979 | 1.00 24.77 | B2 |
| ATOM | 2141 | H | THR | 306 | 40.469 | 17.875 | 12.230 | 1.00 0.00 | B2 |
| ATOM | 2142 | CA | THR | 306 | 41.553 | 19.633 | 12.751 | 1.00 24.39 | B2 |
| ATOM | 2143 | CB | THR | 306 | 41.665 | 19.931 | 11.318 | 1.00 24.58 | B2 |
| ATOM | 2144 | OG1 | THR | 306 | 42.074 | 18.753 | 10.665 | 1.00 25.13 | B2 |
| ATOM | 2145 | HG1 | THR | 306 | 41.447 | 18.029 | 10.768 | 1.00 0.00 | B2 |
| ATOM | 2146 | CG2 | THR | 306 | 42.690 | 21.027 | 11.089 | 1.00 25.77 | B2 |
| ATOM | 2147 | C | THR | 306 | 40.893 | 20.844 | 13.419 | 1.00 25.24 | B2 |
| ATOM | 2148 | O | THR | 306 | 41.488 | 21.472 | 14.296 | 1.00 27.24 | B2 |
| ATOM | 2149 | N | LEU | 307 | 39.615 | 21.134 | 13.139 | 1.00 25.91 | B2 |

FIG.5-26

| ATOM | 2150 | H | LEU | 307 | 39.125 | 20.547 | 12.520 | 1.00 | 0.00 | B2 |
|---|---|---|---|---|---|---|---|---|---|---|
| ATOM | 2151 | CA | LEU | 307 | 38.900 | 22.228 | 13.764 | 1.00 | 25.53 | B2 |
| ATOM | 2152 | CB | LEU | 307 | 37.571 | 22.170 | 13.142 | 1.00 | 25.09 | B2 |
| ATOM | 2153 | CG | LEU | 307 | 36.530 | 23.097 | 13.588 | 1.00 | 27.93 | B2 |
| ATOM | 2154 | CD1 | LEU | 307 | 37.008 | 24.515 | 13.484 | 1.00 | 29.87 | B2 |
| ATOM | 2155 | CD2 | LEU | 307 | 35.311 | 22.846 | 12.728 | 1.00 | 28.93 | B2 |
| ATOM | 2156 | C | LEU | 307 | 38.850 | 22.214 | 15.269 | 1.00 | 27.09 | B2 |
| ATOM | 2157 | O | LEU | 307 | 38.854 | 23.253 | 15.925 | 1.00 | 30.03 | B2 |
| ATOM | 2158 | N | GLN | 308 | 38.875 | 21.044 | 15.879 | 1.00 | 29.09 | B2 |
| ATOM | 2159 | H | GLN | 308 | 38.883 | 20.239 | 15.319 | 1.00 | 0.00 | B2 |
| ATOM | 2160 | CA | GLN | 308 | 38.824 | 20.848 | 17.340 | 1.00 | 29.36 | B2 |
| ATOM | 2161 | CB | GLN | 308 | 38.379 | 19.399 | 17.562 | 1.00 | 29.41 | B2 |
| ATOM | 2162 | CG | GLN | 308 | 37.862 | 19.140 | 18.935 | 1.00 | 32.24 | B2 |
| ATOM | 2163 | CD | GLN | 308 | 37.586 | 17.672 | 19.165 | 1.00 | 34.03 | B2 |
| ATOM | 2164 | OE1 | GLN | 308 | 36.973 | 17.023 | 18.311 | 1.00 | 33.48 | B2 |
| ATOM | 2165 | NE2 | GLN | 308 | 38.053 | 17.127 | 20.299 | 1.00 | 31.67 | B2 |
| ATOM | 2166 | HE21 | GLN | 308 | 38.547 | 17.697 | 20.917 | 1.00 | 0.00 | B2 |
| ATOM | 2167 | HE22 | GLN | 308 | 37.875 | 16.174 | 20.436 | 1.00 | 0.00 | B2 |
| ATOM | 2168 | C | GLN | 308 | 40.154 | 21.138 | 18.051 | 1.00 | 28.94 | B2 |
| ATOM | 2169 | O | GLN | 308 | 40.196 | 21.796 | 19.101 | 1.00 | 28.44 | B2 |
| ATOM | 2170 | N | LEU | 309 | 41.269 | 20.671 | 17.460 | 1.00 | 28.78 | B2 |
| ATOM | 2171 | H | LEU | 309 | 41.157 | 20.120 | 16.655 | 1.00 | 0.00 | B2 |
| ATOM | 2172 | CA | LEU | 309 | 42.632 | 20.923 | 17.967 | 1.00 | 28.56 | B2 |
| ATOM | 2173 | CB | LEU | 309 | 43.671 | 20.154 | 17.106 | 1.00 | 26.54 | B2 |
| ATOM | 2174 | CG | LEU | 309 | 43.632 | 18.636 | 17.241 | 1.00 | 24.98 | B2 |
| ATOM | 2175 | CD1 | LEU | 309 | 44.595 | 17.935 | 16.353 | 1.00 | 24.17 | B2 |
| ATOM | 2176 | CD2 | LEU | 309 | 43.992 | 18.310 | 18.621 | 1.00 | 23.45 | B2 |
| ATOM | 2177 | C | LEU | 309 | 42.893 | 22.416 | 17.909 | 1.00 | 27.99 | B2 |
| ATOM | 2178 | O | LEU | 309 | 43.370 | 22.957 | 18.907 | 1.00 | 30.32 | B2 |
| ATOM | 2179 | N | ASP | 310 | 42.548 | 23.027 | 16.749 | 1.00 | 26.58 | B2 |
| ATOM | 2180 | H | ASP | 310 | 42.296 | 22.437 | 16.007 | 1.00 | 0.00 | B2 |
| ATOM | 2181 | CA | ASP | 310 | 42.495 | 24.477 | 16.495 | 1.00 | 27.90 | B2 |
| ATOM | 2182 | CB | ASP | 310 | 42.025 | 24.659 | 15.076 | 1.00 | 28.41 | B2 |
| ATOM | 2183 | CG | ASP | 310 | 43.162 | 24.556 | 14.096 | 1.00 | 31.84 | B2 |
| ATOM | 2184 | OD1 | ASP | 310 | 42.959 | 24.766 | 12.905 | 1.00 | 31.54 | B2 |
| ATOM | 2185 | OD2 | ASP | 310 | 44.297 | 24.314 | 14.514 | 1.00 | 37.32 | B2 |
| ATOM | 2186 | C | ASP | 310 | 41.666 | 25.410 | 17.422 | 1.00 | 27.99 | B2 |
| ATOM | 2187 | O | ASP | 310 | 42.219 | 26.429 | 17.876 | 1.00 | 27.23 | B2 |
| ATOM | 2188 | N | VAL | 311 | 40.374 | 25.086 | 17.725 | 1.00 | 26.29 | B2 |
| ATOM | 2189 | H | VAL | 311 | 39.961 | 24.347 | 17.225 | 1.00 | 0.00 | B2 |
| ATOM | 2190 | CA | VAL | 311 | 39.546 | 25.803 | 18.706 | 1.00 | 24.29 | B2 |
| ATOM | 2191 | CB | VAL | 311 | 38.098 | 25.217 | 18.869 | 1.00 | 21.47 | B2 |
| ATOM | 2192 | CG1 | VAL | 311 | 37.341 | 25.915 | 19.949 | 1.00 | 19.01 | B2 |
| ATOM | 2193 | CG2 | VAL | 311 | 37.261 | 25.488 | 17.667 | 1.00 | 18.56 | B2 |
| ATOM | 2194 | C | VAL | 311 | 40.270 | 25.638 | 20.020 | 1.00 | 27.21 | B2 |
| ATOM | 2195 | O | VAL | 311 | 40.437 | 26.647 | 20.719 | 1.00 | 29.71 | B2 |
| ATOM | 2196 | N | ALA | 312 | 40.762 | 24.428 | 20.357 | 1.00 | 27.97 | B2 |
| ATOM | 2197 | H | ALA | 312 | 40.585 | 23.674 | 19.756 | 1.00 | 0.00 | B2 |
| ATOM | 2198 | CA | ALA | 312 | 41.515 | 24.157 | 21.583 | 1.00 | 29.24 | B2 |
| ATOM | 2199 | CB | ALA | 312 | 41.855 | 22.688 | 21.532 | 1.00 | 30.53 | B2 |
| ATOM | 2200 | C | ALA | 312 | 42.778 | 25.026 | 21.784 | 1.00 | 30.06 | B2 |
| ATOM | 2201 | O | ALA | 312 | 43.057 | 25.508 | 22.886 | 1.00 | 30.04 | B2 |
| ATOM | 2202 | N | ASP | 313 | 43.554 | 25.286 | 20.735 | 1.00 | 31.33 | B2 |
| ATOM | 2203 | H | ASP | 313 | 43.433 | 24.730 | 19.935 | 1.00 | 0.00 | B2 |
| ATOM | 2204 | CA | ASP | 313 | 44.610 | 26.275 | 20.743 | 1.00 | 34.22 | B2 |
| ATOM | 2205 | CB | ASP | 313 | 45.279 | 26.512 | 19.447 | 1.00 | 38.87 | B2 |
| ATOM | 2206 | CG | ASP | 313 | 46.071 | 25.404 | 18.866 | 1.00 | 44.55 | B2 |
| ATOM | 2207 | OD1 | ASP | 313 | 46.225 | 25.439 | 17.636 | 1.00 | 48.67 | B2 |
| ATOM | 2208 | OD2 | ASP | 313 | 46.521 | 24.553 | 19.647 | 1.00 | 49.25 | B2 |
| ATOM | 2209 | C | ASP | 313 | 44.187 | 27.699 | 21.059 | 1.00 | 35.12 | B2 |
| ATOM | 2210 | O | ASP | 313 | 44.807 | 28.390 | 21.894 | 1.00 | 38.60 | B2 |
| ATOM | 2211 | N | PHE | 314 | 43.192 | 28.216 | 20.339 | 1.00 | 33.36 | B2 |
| ATOM | 2212 | H | PHE | 314 | 42.784 | 27.683 | 19.619 | 1.00 | 0.00 | B2 |
| ATOM | 2213 | CA | PHE | 314 | 42.715 | 29.548 | 20.600 | 1.00 | 31.09 | B2 |
| ATOM | 2214 | CB | PHE | 314 | 41.572 | 29.860 | 19.631 | 1.00 | 32.06 | B2 |
| ATOM | 2215 | CG | PHE | 314 | 41.074 | 31.303 | 19.636 | 1.00 | 33.37 | B2 |
| ATOM | 2216 | CD1 | PHE | 314 | 39.780 | 31.568 | 19.247 | 1.00 | 31.81 | B2 |
| ATOM | 2217 | CD2 | PHE | 314 | 41.907 | 32.354 | 20.021 | 1.00 | 35.65 | B2 |
| ATOM | 2218 | CE1 | PHE | 314 | 39.318 | 32.857 | 19.240 | 1.00 | 29.15 | B2 |
| ATOM | 2219 | CE2 | PHE | 314 | 41.455 | 33.648 | 20.017 | 1.00 | 32.48 | B2 |
| ATOM | 2220 | CZ | PHE | 314 | 40.154 | 33.870 | 19.622 | 1.00 | 32.81 | B2 |
| ATOM | 2221 | C | PHE | 314 | 42.282 | 29.601 | 22.057 | 1.00 | 29.90 | B2 |
| ATOM | 2222 | O | PHE | 314 | 42.658 | 30.550 | 22.764 | 1.00 | 26.87 | B2 |
| ATOM | 2223 | N | ALA | 315 | 41.686 | 28.532 | 22.584 | 1.00 | 29.29 | B2 |
| ATOM | 2224 | H | ALA | 315 | 41.448 | 27.764 | 22.022 | 1.00 | 0.00 | B2 |
| ATOM | 2225 | CA | ALA | 315 | 41.300 | 28.583 | 23.961 | 1.00 | 31.61 | B2 |
| ATOM | 2226 | CB | ALA | 315 | 40.632 | 27.358 | 24.451 | 1.00 | 32.23 | B2 |
| ATOM | 2227 | C | ALA | 315 | 42.482 | 28.751 | 24.836 | 1.00 | 34.41 | B2 |
| ATOM | 2228 | O | ALA | 315 | 42.361 | 29.437 | 25.853 | 1.00 | 37.66 | B2 |
| ATOM | 2229 | N | THR | 316 | 43.646 | 28.250 | 24.476 | 1.00 | 36.16 | B2 |
| ATOM | 2230 | H | THR | 316 | 43.745 | 27.778 | 23.625 | 1.00 | 0.00 | B2 |
| ATOM | 2231 | CA | THR | 316 | 44.780 | 28.388 | 25.374 | 1.00 | 37.99 | B2 |
| ATOM | 2232 | CB | THR | 316 | 45.795 | 27.255 | 25.156 | 1.00 | 41.16 | B2 |
| ATOM | 2233 | OG1 | THR | 316 | 45.049 | 26.081 | 25.521 | 1.00 | 45.50 | B2 |
| ATOM | 2234 | HG1 | THR | 316 | 44.316 | 25.900 | 24.913 | 1.00 | 0.00 | B2 |
| ATOM | 2235 | CG2 | THR | 316 | 47.152 | 27.415 | 25.888 | 1.00 | 40.31 | B2 |

FIG.5-27

```
ATOM  2236 C   THR 316    45.458 29.710 25.177 1.00 38.47  B2
ATOM  2237 O   THR 316    45.903 30.189 26.217 1.00 39.63  B2
ATOM  2238 N   THR 317    45.620 30.287 23.970 1.00 36.53  B2
ATOM  2239 H   THR 317    45.351 29.800 23.164 1.00 0.00   B2
ATOM  2240 CA  THR 317    46.092 31.657 23.844 1.00 37.07  B2
ATOM  2241 CB  THR 317    45.866 32.098 22.392 1.00 36.01  B2
ATOM  2242 OG1 THR 317    46.752 31.352 21.575 1.00 35.31  B2
ATOM  2243 HG1 THR 317    46.489 30.441 21.389 1.00 0.00   B2
ATOM  2244 CG2 THR 317    46.109 33.566 22.156 1.00 34.30  B2
ATOM  2245 C   THR 317    45.338 32.597 24.832 1.00 39.30  B2
ATOM  2246 O   THR 317    45.941 33.378 25.583 1.00 40.17  B2
ATOM  2247 N   ILE 318    44.003 32.481 24.912 1.00 40.83  B2
ATOM  2248 H   ILE 318    43.554 31.819 24.342 1.00 0.00   B2
ATOM  2249 CA  ILE 318    43.172 33.317 25.788 1.00 40.75  B2
ATOM  2250 CB  ILE 318    41.621 32.979 25.567 1.00 37.17  B2
ATOM  2251 CG2 ILE 318    40.742 33.706 26.545 1.00 34.29  B2
ATOM  2252 CG1 ILE 318    41.216 33.310 24.160 1.00 31.39  B2
ATOM  2253 CD  ILE 318    41.626 34.657 23.614 1.00 29.66  B2
ATOM  2254 C   ILE 318    43.624 33.019 27.217 1.00 42.43  B2
ATOM  2255 O   ILE 318    44.064 33.963 27.856 1.00 42.54  B2
ATOM  2256 N   TRP 319    43.662 31.784 27.744 1.00 44.17  B2
ATOM  2257 H   TRP 319    43.537 31.008 27.163 1.00 0.00   B2
ATOM  2258 CA  TRP 319    43.994 31.633 29.142 1.00 46.90  B2
ATOM  2259 CB  TRP 319    43.892 30.179 29.597 1.00 50.64  B2
ATOM  2260 CG  TRP 319    43.998 30.094 31.131 1.00 56.05  B2
ATOM  2261 CD2 TRP 319    43.005 30.397 32.038 1.00 58.61  B2
ATOM  2262 CE2 TRP 319    43.685 30.281 33.251 1.00 60.50  B2
ATOM  2263 CE3 TRP 319    41.668 30.740 32.005 1.00 60.12  B2
ATOM  2264 CD1 TRP 319    45.188 29.788 31.760 1.00 58.07  B2
ATOM  2265 NE1 TRP 319    44.968 29.921 33.042 1.00 60.07  B2
ATOM  2266 HE1 TRP 319    45.637 29.765 33.740 1.00 0.00   B2
ATOM  2267 CZ2 TRP 319    43.044 30.512 34.456 1.00 61.00  B2
ATOM  2268 CZ3 TRP 319    41.022 30.967 33.210 1.00 61.58  B2
ATOM  2269 CH2 TRP 319    41.704 30.854 34.417 1.00 62.04  B2
ATOM  2270 C   TRP 319    45.398 32.136 29.456 1.00 47.85  B2
ATOM  2271 O   TRP 319    45.635 32.772 30.490 1.00 47.99  B2
ATOM  2272 N   GLN 320    46.339 31.915 28.550 1.00 48.63  B2
ATOM  2273 H   GLN 320    46.091 31.482 27.708 1.00 0.00   B2
ATOM  2274 CA  GLN 320    47.706 32.319 28.767 1.00 49.45  B2
ATOM  2275 CB  GLN 320    48.567 31.988 27.589 1.00 51.44  B2
ATOM  2276 CG  GLN 320    48.828 30.494 27.444 1.00 55.03  B2
ATOM  2277 CD  GLN 320    49.958 30.349 26.438 1.00 60.17  B2
ATOM  2278 OE1 GLN 320    51.116 30.465 26.834 1.00 65.26  B2
ATOM  2279 NE2 GLN 320    49.771 30.145 25.131 1.00 59.32  B2
ATOM  2280 HE21 GLN 320   48.859 30.087 24.789 1.00 0.00   B2
ATOM  2281 HE22 GLN 320   50.582 30.083 24.590 1.00 0.00   B2
ATOM  2282 C   GLN 320    47.717 33.790 28.983 1.00 49.62  B2
ATOM  2283 O   GLN 320    48.251 34.209 29.987 1.00 49.91  B2
ATOM  2284 N   GLN 321    46.998 34.538 28.150 1.00 51.76  B2
ATOM  2285 H   GLN 321    46.535 34.102 27.403 1.00 0.00   B2
ATOM  2286 CA  GLN 321    46.837 35.988 28.278 1.00 52.08  B2
ATOM  2287 CB  GLN 321    46.015 36.571 27.151 1.00 49.72  B2
ATOM  2288 CG  GLN 321    45.873 38.058 27.166 1.00 51.19  B2
ATOM  2289 CD  GLN 321    47.211 38.781 27.201 1.00 53.13  B2
ATOM  2290 OE1 GLN 321    48.090 38.622 26.364 1.00 55.36  B2
ATOM  2291 NE2 GLN 321    47.468 39.618 28.177 1.00 53.21  B2
ATOM  2292 HE21 GLN 321   46.800 39.713 28.889 1.00 0.00   B2
ATOM  2293 HE22 GLN 321   48.338 40.057 28.168 1.00 0.00   B2
ATOM  2294 C   GLN 321    46.112 36.315 29.562 1.00 53.30  B2
ATOM  2295 O   GLN 321    46.293 37.422 30.058 1.00 54.39  B2
ATOM  2296 N   MET 322    45.269 35.441 30.117 1.00 54.50  B2
ATOM  2297 H   MET 322    45.098 34.592 29.662 1.00 0.00   B2
ATOM  2298 CA  MET 322    44.619 35.748 31.375 1.00 55.42  B2
ATOM  2299 CB  MET 322    43.595 34.690 31.713 1.00 52.93  B2
ATOM  2300 CG  MET 322    42.527 34.865 30.658 1.00 51.76  B2
ATOM  2301 SD  MET 322    40.861 34.428 31.189 1.00 54.19  B2
ATOM  2302 CE  MET 322    40.293 33.192 30.069 1.00 52.53  B2
ATOM  2303 C   MET 322    45.700 35.811 32.432 1.00 57.69  B2
ATOM  2304 O   MET 322    45.781 36.739 33.248 1.00 57.85  B2
ATOM  2305 N   GLU 323    46.652 34.900 32.319 1.00 60.28  B2
ATOM  2306 H   GLU 323    46.637 34.296 31.544 1.00 0.00   B2
ATOM  2307 CA  GLU 323    47.741 34.875 33.273 1.00 62.99  B2
ATOM  2308 CB  GLU 323    48.558 33.635 32.957 1.00 65.81  B2
ATOM  2309 CG  GLU 323    47.640 32.423 32.918 1.00 68.36  B2
ATOM  2310 CD  GLU 323    48.303 31.125 33.310 1.00 71.21  B2
ATOM  2311 OE1 GLU 323    47.651 30.364 34.044 1.00 71.19  B2
ATOM  2312 OE2 GLU 323    49.451 30.900 32.884 1.00 72.43  B2
ATOM  2313 C   GLU 323    48.648 36.124 33.418 1.00 63.96  B2
ATOM  2314 OT1 GLU 323    48.782 36.492 34.584 1.00 64.11  B2
ATOM  2315 OT2 GLU 323    49.169 36.725 32.449 1.00 62.96  B2
ATOM  2316 CB  MET 338    27.559 17.690 25.056 1.00 62.56  B3
ATOM  2317 CG  MET 338    28.087 18.862 24.222 1.00 63.85  B3
ATOM  2318 SD  MET 338    28.738 20.224 25.219 1.00 66.95  B3
ATOM  2319 CE  MET 338    27.328 21.252 25.515 1.00 65.50  B3
ATOM  2320 C   MET 338    24.988 17.301 25.122 1.00 57.55  B3
ATOM  2321 O   MET 338    24.417 16.347 25.667 1.00 56.47  B3
```

FIG.5-28

| ATOM | 2322 | HT1 | MET | 338 | 26.255 | 16.010 | 26.594 | 1.00 | 0.00 | B3 |
|---|---|---|---|---|---|---|---|---|---|---|
| ATOM | 2323 | HT2 | MET | 338 | 25.375 | 17.061 | 27.500 | 1.00 | 0.00 | B3 |
| ATOM | 2324 | N | MET | 338 | 26.286 | 16.971 | 27.009 | 1.00 | 61.55 | B3 |
| ATOM | 2325 | HT3 | MET | 338 | 27.108 | 17.107 | 27.620 | 1.00 | 60.35 | B3 |
| ATOM | 2326 | CA | MET | 338 | 26.226 | 17.853 | 25.851 | 1.00 | 55.58 | B3 |
| ATOM | 2327 | N | PRO | 339 | 24.493 | 17.830 | 23.998 | 1.00 | 54.39 | B3 |
| ATOM | 2328 | CD | PRO | 339 | 24.914 | 19.075 | 23.375 | 1.00 | 54.62 | B3 |
| ATOM | 2329 | CA | PRO | 339 | 23.453 | 17.226 | 23.164 | 1.00 | 53.52 | B3 |
| ATOM | 2330 | CB | PRO | 339 | 23.463 | 18.098 | 21.903 | 1.00 | 53.04 | B3 |
| ATOM | 2331 | CG | PRO | 339 | 24.845 | 18.711 | 21.909 | 1.00 | 53.61 | B3 |
| ATOM | 2332 | C | PRO | 339 | 23.666 | 15.748 | 22.881 | 1.00 | 53.61 | B3 |
| ATOM | 2333 | O | PRO | 339 | 24.730 | 15.222 | 23.169 | 1.00 | 53.35 | B3 |
| ATOM | 2334 | N | ALA | 340 | 22.704 | 15.045 | 22.333 | 1.00 | 54.32 | B3 |
| ATOM | 2335 | H | ALA | 340 | 21.844 | 15.460 | 22.111 | 1.00 | 0.00 | B3 |
| ATOM | 2336 | CA | ALA | 340 | 22.909 | 13.651 | 21.968 | 1.00 | 56.04 | B3 |
| ATOM | 2337 | CB | ALA | 340 | 21.867 | 12.713 | 22.625 | 1.00 | 57.60 | B3 |
| ATOM | 2338 | C | ALA | 340 | 22.617 | 13.713 | 20.495 | 1.00 | 55.61 | B3 |
| ATOM | 2339 | O | ALA | 340 | 21.426 | 13.783 | 20.196 | 1.00 | 58.64 | B3 |
| ATOM | 2340 | N | PHE | 341 | 23.516 | 13.734 | 19.514 | 1.00 | 53.34 | B3 |
| ATOM | 2341 | H | PHE | 341 | 24.472 | 13.607 | 19.685 | 1.00 | 0.00 | B3 |
| ATOM | 2342 | CA | PHE | 341 | 23.016 | 13.900 | 18.158 | 1.00 | 49.92 | B3 |
| ATOM | 2343 | CB | PHE | 341 | 24.050 | 14.541 | 17.244 | 1.00 | 48.16 | B3 |
| ATOM | 2344 | CG | PHE | 341 | 24.382 | 15.940 | 17.658 | 1.00 | 45.00 | B3 |
| ATOM | 2345 | CD1 | PHE | 341 | 23.510 | 16.923 | 17.359 | 1.00 | 43.44 | B3 |
| ATOM | 2346 | CD2 | PHE | 341 | 25.527 | 16.175 | 18.388 | 1.00 | 47.03 | B3 |
| ATOM | 2347 | CE1 | PHE | 341 | 23.812 | 18.172 | 17.831 | 1.00 | 49.15 | B3 |
| ATOM | 2348 | CE2 | PHE | 341 | 25.827 | 17.426 | 18.862 | 1.00 | 47.86 | B3 |
| ATOM | 2349 | CZ | PHE | 341 | 24.952 | 18.437 | 18.580 | 1.00 | 48.36 | B3 |
| ATOM | 2350 | C | PHE | 341 | 22.684 | 12.510 | 17.672 | 1.00 | 49.56 | B3 |
| ATOM | 2351 | O | PHE | 341 | 23.309 | 11.938 | 16.781 | 1.00 | 51.46 | B3 |
| ATOM | 2352 | N | ALA | 342 | 21.625 | 11.985 | 18.245 | 1.00 | 47.40 | B3 |
| ATOM | 2353 | H | ALA | 342 | 21.026 | 12.585 | 18.741 | 1.00 | 0.00 | B3 |
| ATOM | 2354 | CA | ALA | 342 | 21.167 | 10.650 | 17.997 | 1.00 | 46.11 | B3 |
| ATOM | 2355 | CB | ALA | 342 | 19.874 | 10.531 | 18.804 | 1.00 | 47.10 | B3 |
| ATOM | 2356 | C | ALA | 342 | 20.962 | 10.149 | 16.556 | 1.00 | 44.37 | B3 |
| ATOM | 2357 | O | ALA | 342 | 20.138 | 9.247 | 16.418 | 1.00 | 45.65 | B3 |
| ATOM | 2358 | N | SER | 343 | 21.537 | 10.573 | 15.423 | 1.00 | 41.37 | B3 |
| ATOM | 2359 | H | SER | 343 | 22.191 | 11.301 | 15.428 | 1.00 | 0.00 | B3 |
| ATOM | 2360 | CA | SER | 343 | 21.274 | 9.923 | 14.145 | 1.00 | 38.80 | B3 |
| ATOM | 2361 | CB | SER | 343 | 19.842 | 10.138 | 13.656 | 1.00 | 38.79 | B3 |
| ATOM | 2362 | OG | SER | 343 | 19.205 | 11.300 | 14.182 | 1.00 | 37.75 | B3 |
| ATOM | 2363 | HG | SER | 343 | 18.963 | 11.059 | 15.092 | 1.00 | 0.00 | B3 |
| ATOM | 2364 | C | SER | 343 | 22.172 | 10.467 | 13.088 | 1.00 | 38.22 | B3 |
| ATOM | 2365 | O | SER | 343 | 22.810 | 11.471 | 13.382 | 1.00 | 38.30 | B3 |
| ATOM | 2366 | N | ALA | 344 | 22.206 | 9.845 | 11.888 | 1.00 | 36.73 | B3 |
| ATOM | 2367 | H | ALA | 344 | 21.762 | 8.978 | 11.805 | 1.00 | 0.00 | B3 |
| ATOM | 2368 | CA | ALA | 344 | 22.914 | 10.384 | 10.715 | 1.00 | 38.09 | B3 |
| ATOM | 2369 | CB | ALA | 344 | 22.583 | 9.640 | 9.422 | 1.00 | 36.78 | B3 |
| ATOM | 2370 | C | ALA | 344 | 22.472 | 11.842 | 10.496 | 1.00 | 37.72 | B3 |
| ATOM | 2371 | O | ALA | 344 | 23.271 | 12.765 | 10.676 | 1.00 | 38.42 | B3 |
| ATOM | 2372 | N | PHE | 345 | 21.194 | 12.042 | 10.163 | 1.00 | 36.10 | B3 |
| ATOM | 2373 | H | PHE | 345 | 20.668 | 11.298 | 9.811 | 1.00 | 0.00 | B3 |
| ATOM | 2374 | CA | PHE | 345 | 20.564 | 13.338 | 10.195 | 1.00 | 34.69 | B3 |
| ATOM | 2375 | CB | PHE | 345 | 19.040 | 13.254 | 10.128 | 1.00 | 33.24 | B3 |
| ATOM | 2376 | CG | PHE | 345 | 18.462 | 14.656 | 9.918 | 1.00 | 31.72 | B3 |
| ATOM | 2377 | CD1 | PHE | 345 | 17.715 | 15.223 | 10.905 | 1.00 | 26.64 | B3 |
| ATOM | 2378 | CD2 | PHE | 345 | 18.767 | 15.343 | 8.745 | 1.00 | 29.99 | B3 |
| ATOM | 2379 | CE1 | PHE | 345 | 17.284 | 16.503 | 10.682 | 1.00 | 33.56 | B3 |
| ATOM | 2380 | CE2 | PHE | 345 | 18.333 | 16.619 | 8.537 | 1.00 | 30.81 | B3 |
| ATOM | 2381 | CZ | PHE | 345 | 17.581 | 17.201 | 9.520 | 1.00 | 31.44 | B3 |
| ATOM | 2382 | C | PHE | 345 | 20.888 | 14.145 | 11.458 | 1.00 | 35.02 | B3 |
| ATOM | 2383 | O | PHE | 345 | 21.246 | 15.319 | 11.292 | 1.00 | 37.81 | B3 |
| ATOM | 2384 | N | GLN | 346 | 20.814 | 13.688 | 12.691 | 1.00 | 32.53 | B3 |
| ATOM | 2385 | H | GLN | 346 | 20.516 | 12.778 | 12.894 | 1.00 | 0.00 | B3 |
| ATOM | 2386 | CA | GLN | 346 | 21.156 | 14.586 | 13.758 | 1.00 | 33.46 | B3 |
| ATOM | 2387 | CB | GLN | 346 | 20.899 | 13.985 | 15.061 | 1.00 | 33.80 | B3 |
| ATOM | 2388 | CG | GLN | 346 | 19.459 | 14.284 | 15.174 | 1.00 | 35.68 | B3 |
| ATOM | 2389 | CD | GLN | 346 | 18.788 | 13.658 | 16.344 | 1.00 | 38.48 | B3 |
| ATOM | 2390 | OE1 | GLN | 346 | 19.358 | 13.328 | 17.374 | 1.00 | 41.78 | B3 |
| ATOM | 2391 | NE2 | GLN | 346 | 17.508 | 13.463 | 16.167 | 1.00 | 41.08 | B3 |
| ATOM | 2392 | HE21 | GLN | 346 | 17.088 | 13.724 | 15.323 | 1.00 | 0.00 | B3 |
| ATOM | 2393 | HE22 | GLN | 346 | 17.026 | 13.063 | 16.919 | 1.00 | 0.00 | B3 |
| ATOM | 2394 | C | GLN | 346 | 22.564 | 15.051 | 13.773 | 1.00 | 35.73 | B3 |
| ATOM | 2395 | O | GLN | 346 | 22.766 | 16.231 | 14.051 | 1.00 | 38.18 | B3 |
| ATOM | 2396 | N | ARG | 347 | 23.507 | 14.190 | 13.431 | 1.00 | 35.57 | B3 |
| ATOM | 2397 | H | ARG | 347 | 23.248 | 13.289 | 13.157 | 1.00 | 0.00 | B3 |
| ATOM | 2398 | CA | ARG | 347 | 24.907 | 14.538 | 13.396 | 1.00 | 35.95 | B3 |
| ATOM | 2399 | CB | ARG | 347 | 25.760 | 13.236 | 13.222 | 1.00 | 36.20 | B3 |
| ATOM | 2400 | CG | ARG | 347 | 26.198 | 12.549 | 14.540 | 1.00 | 37.41 | B3 |
| ATOM | 2401 | CD | ARG | 347 | 26.986 | 11.246 | 14.373 | 1.00 | 39.70 | B3 |
| ATOM | 2402 | NE | ARG | 347 | 26.072 | 10.167 | 14.028 | 1.00 | 47.18 | B3 |
| ATOM | 2403 | HE | ARG | 347 | 25.416 | 9.893 | 14.701 | 1.00 | 0.00 | B3 |
| ATOM | 2404 | CZ | ARG | 347 | 26.071 | 9.516 | 12.846 | 1.00 | 48.49 | B3 |
| ATOM | 2405 | NH1 | ARG | 347 | 26.938 | 9.802 | 11.882 | 1.00 | 50.22 | B3 |
| ATOM | 2406 | HH11 | ARG | 347 | 27.602 | 10.528 | 12.031 | 1.00 | 0.00 | B3 |
| ATOM | 2407 | HH12 | ARG | 347 | 26.905 | 9.313 | 11.011 | 1.00 | 0.00 | B3 |

FIG. 5-29

| ATOM | 2408 | NH2 | ARG | 347 | 25.130 | 8.608 | 12.574 | 1.00 | 48.46 | B3 |
|---|---|---|---|---|---|---|---|---|---|---|
| ATOM | 2409 | HH21 | ARG | 347 | 24.423 | 8.408 | 13.252 | 1.00 | 0.00 | B3 |
| ATOM | 2410 | HH22 | ARG | 347 | 25.126 | 8.131 | 11.697 | 1.00 | 0.00 | B3 |
| ATOM | 2411 | C | ARG | 347 | 25.183 | 15.544 | 12.267 | 1.00 | 35.54 | B3 |
| ATOM | 2412 | O | ARG | 347 | 25.877 | 16.549 | 12.445 | 1.00 | 36.73 | B3 |
| ATOM | 2413 | N | ARG | 348 | 24.611 | 15.353 | 11.096 | 1.00 | 34.74 | B3 |
| ATOM | 2414 | H | ARG | 348 | 24.043 | 14.559 | 11.005 | 1.00 | 0.00 | B3 |
| ATOM | 2415 | CA | ARG | 348 | 24.802 | 16.225 | 9.954 | 1.00 | 35.24 | B3 |
| ATOM | 2416 | CB | ARG | 348 | 24.091 | 15.623 | 8.751 | 1.00 | 36.76 | B3 |
| ATOM | 2417 | CG | ARG | 348 | 24.778 | 14.303 | 8.450 | 1.00 | 44.22 | B3 |
| ATOM | 2418 | CD | ARG | 348 | 24.014 | 13.379 | 7.529 | 1.00 | 49.23 | B3 |
| ATOM | 2419 | NE | ARG | 348 | 24.705 | 12.090 | 7.457 | 1.00 | 54.27 | B3 |
| ATOM | 2420 | HE | ARG | 348 | 25.300 | 11.836 | 8.193 | 1.00 | 0.00 | B3 |
| ATOM | 2421 | CZ | ARG | 348 | 24.557 | 11.226 | 6.430 | 1.00 | 53.75 | B3 |
| ATOM | 2422 | NH1 | ARG | 348 | 23.758 | 11.479 | 5.381 | 1.00 | 51.85 | B3 |
| ATOM | 2423 | HH11 | ARG | 348 | 23.234 | 12.329 | 5.339 | 1.00 | 0.00 | B3 |
| ATOM | 2424 | HH12 | ARG | 348 | 23.680 | 10.807 | 4.645 | 1.00 | 0.00 | B3 |
| ATOM | 2425 | NH2 | ARG | 348 | 25.252 | 10.083 | 6.462 | 1.00 | 54.51 | B3 |
| ATOM | 2426 | HH21 | ARG | 348 | 25.169 | 9.424 | 5.714 | 1.00 | 0.00 | B3 |
| ATOM | 2427 | HH22 | ARG | 348 | 25.860 | 9.894 | 7.232 | 1.00 | 0.00 | B3 |
| ATOM | 2428 | C | ARG | 348 | 24.283 | 17.629 | 10.237 | 1.00 | 34.80 | B3 |
| ATOM | 2429 | O | ARG | 348 | 25.078 | 18.564 | 10.219 | 1.00 | 35.16 | B3 |
| ATOM | 2430 | N | ALA | 349 | 23.008 | 17.795 | 10.607 | 1.00 | 33.85 | B3 |
| ATOM | 2431 | H | ALA | 349 | 22.470 | 16.984 | 10.755 | 1.00 | 0.00 | B3 |
| ATOM | 2432 | CA | ALA | 349 | 22.352 | 19.083 | 10.853 | 1.00 | 32.96 | B3 |
| ATOM | 2433 | CB | ALA | 349 | 20.809 | 18.894 | 11.070 | 1.00 | 33.36 | B3 |
| ATOM | 2434 | C | ALA | 349 | 22.945 | 19.746 | 12.083 | 1.00 | 31.84 | B3 |
| ATOM | 2435 | O | ALA | 349 | 22.981 | 20.969 | 12.210 | 1.00 | 30.69 | B3 |
| ATOM | 2436 | N | GLY | 350 | 23.444 | 18.954 | 13.018 | 1.00 | 31.30 | B3 |
| ATOM | 2437 | H | GLY | 350 | 23.308 | 17.984 | 12.976 | 1.00 | 0.00 | B3 |
| ATOM | 2438 | CA | GLY | 350 | 24.117 | 19.505 | 14.181 | 1.00 | 31.08 | B3 |
| ATOM | 2439 | C | GLY | 350 | 25.462 | 20.025 | 13.753 | 1.00 | 30.79 | B3 |
| ATOM | 2440 | O | GLY | 350 | 25.974 | 21.010 | 14.280 | 1.00 | 31.38 | B3 |
| ATOM | 2441 | N | GLY | 351 | 25.991 | 19.374 | 12.731 | 1.00 | 30.03 | B3 |
| ATOM | 2442 | H | GLY | 351 | 25.546 | 18.582 | 12.367 | 1.00 | 0.00 | B3 |
| ATOM | 2443 | CA | GLY | 351 | 27.263 | 19.735 | 12.184 | 1.00 | 29.95 | B3 |
| ATOM | 2444 | C | GLY | 351 | 27.182 | 21.097 | 11.534 | 1.00 | 29.25 | B3 |
| ATOM | 2445 | O | GLY | 351 | 27.937 | 21.974 | 11.919 | 1.00 | 28.73 | B3 |
| ATOM | 2446 | N | VAL | 352 | 26.336 | 21.285 | 10.522 | 1.00 | 28.92 | B3 |
| ATOM | 2447 | H | VAL | 352 | 25.859 | 20.484 | 10.214 | 1.00 | 0.00 | B3 |
| ATOM | 2448 | CA | VAL | 352 | 26.079 | 22.567 | 9.881 | 1.00 | 28.59 | B3 |
| ATOM | 2449 | CB | VAL | 352 | 24.845 | 22.452 | 9.004 | 1.00 | 28.96 | B3 |
| ATOM | 2450 | CG1 | VAL | 352 | 24.627 | 23.785 | 8.346 | 1.00 | 30.86 | B3 |
| ATOM | 2451 | CG2 | VAL | 352 | 25.021 | 21.475 | 7.875 | 1.00 | 26.94 | B3 |
| ATOM | 2452 | C | VAL | 352 | 25.849 | 23.709 | 10.890 | 1.00 | 29.29 | B3 |
| ATOM | 2453 | O | VAL | 352 | 26.520 | 24.747 | 10.853 | 1.00 | 31.02 | B3 |
| ATOM | 2454 | N | LEU | 353 | 24.923 | 23.543 | 11.819 | 1.00 | 27.52 | B3 |
| ATOM | 2455 | H | LEU | 353 | 24.404 | 22.709 | 11.838 | 1.00 | 0.00 | B3 |
| ATOM | 2456 | CA | LEU | 353 | 24.635 | 24.548 | 12.817 | 1.00 | 26.18 | B3 |
| ATOM | 2457 | CB | LEU | 353 | 23.434 | 24.113 | 13.636 | 1.00 | 27.87 | B3 |
| ATOM | 2458 | CG | LEU | 353 | 22.098 | 24.034 | 12.931 | 1.00 | 26.54 | B3 |
| ATOM | 2459 | CD1 | LEU | 353 | 21.064 | 23.617 | 13.924 | 1.00 | 25.49 | B3 |
| ATOM | 2460 | CD2 | LEU | 353 | 21.750 | 25.372 | 12.320 | 1.00 | 28.23 | B3 |
| ATOM | 2461 | C | LEU | 353 | 25.742 | 24.905 | 13.772 | 1.00 | 27.17 | B3 |
| ATOM | 2462 | O | LEU | 353 | 25.838 | 26.093 | 14.088 | 1.00 | 28.00 | B3 |
| ATOM | 2463 | N | VAL | 354 | 26.539 | 23.949 | 14.318 | 1.00 | 27.20 | B3 |
| ATOM | 2464 | H | VAL | 354 | 26.321 | 23.006 | 14.139 | 1.00 | 0.00 | B3 |
| ATOM | 2465 | CA | VAL | 354 | 27.712 | 24.212 | 15.157 | 1.00 | 24.62 | B3 |
| ATOM | 2466 | CB | VAL | 354 | 28.236 | 22.910 | 15.745 | 1.00 | 22.01 | B3 |
| ATOM | 2467 | CG1 | VAL | 354 | 29.568 | 23.089 | 16.406 | 1.00 | 19.82 | B3 |
| ATOM | 2468 | CG2 | VAL | 354 | 27.276 | 22.467 | 16.802 | 1.00 | 23.96 | B3 |
| ATOM | 2469 | C | VAL | 354 | 28.812 | 24.893 | 14.332 | 1.00 | 25.46 | B3 |
| ATOM | 2470 | O | VAL | 354 | 29.439 | 25.832 | 14.798 | 1.00 | 26.23 | B3 |
| ATOM | 2471 | N | ALA | 355 | 29.059 | 24.530 | 13.089 | 1.00 | 26.12 | B3 |
| ATOM | 2472 | H | ALA | 355 | 28.579 | 23.745 | 12.744 | 1.00 | 0.00 | B3 |
| ATOM | 2473 | CA | ALA | 355 | 30.025 | 25.180 | 12.235 | 1.00 | 26.54 | B3 |
| ATOM | 2474 | CB | ALA | 355 | 30.034 | 24.591 | 10.869 | 1.00 | 22.08 | B3 |
| ATOM | 2475 | C | ALA | 355 | 29.533 | 26.601 | 12.096 | 1.00 | 28.51 | B3 |
| ATOM | 2476 | O | ALA | 355 | 30.315 | 27.498 | 12.344 | 1.00 | 31.93 | B3 |
| ATOM | 2477 | N | SER | 356 | 28.271 | 26.884 | 11.802 | 1.00 | 30.30 | B3 |
| ATOM | 2478 | H | SER | 356 | 27.654 | 26.134 | 11.665 | 1.00 | 0.00 | B3 |
| ATOM | 2479 | CA | SER | 356 | 27.778 | 28.249 | 11.625 | 1.00 | 31.10 | B3 |
| ATOM | 2480 | CB | SER | 356 | 26.401 | 28.147 | 11.016 | 1.00 | 35.23 | B3 |
| ATOM | 2481 | OG | SER | 356 | 25.679 | 29.380 | 10.905 | 1.00 | 43.82 | B3 |
| ATOM | 2482 | HG | SER | 356 | 26.250 | 30.004 | 10.429 | 1.00 | 0.00 | B3 |
| ATOM | 2483 | C | SER | 356 | 27.763 | 29.095 | 12.901 | 1.00 | 29.75 | B3 |
| ATOM | 2484 | O | SER | 356 | 28.115 | 30.289 | 12.898 | 1.00 | 28.35 | B3 |
| ATOM | 2485 | N | HIS | 357 | 27.465 | 28.464 | 14.025 | 1.00 | 27.82 | B3 |
| ATOM | 2486 | H | HIS | 357 | 27.301 | 27.498 | 14.019 | 1.00 | 0.00 | B3 |
| ATOM | 2487 | CA | HIS | 357 | 27.434 | 29.194 | 15.259 | 1.00 | 26.58 | B3 |
| ATOM | 2488 | CB | HIS | 357 | 26.735 | 28.365 | 16.305 | 1.00 | 25.77 | B3 |
| ATOM | 2489 | CG | HIS | 357 | 25.219 | 28.360 | 16.063 | 1.00 | 27.67 | B3 |
| ATOM | 2490 | CD2 | HIS | 357 | 24.563 | 28.767 | 14.915 | 1.00 | 28.94 | B3 |
| ATOM | 2491 | ND1 | HIS | 357 | 24.277 | 27.963 | 16.915 | 1.00 | 28.43 | B3 |
| ATOM | 2492 | HD1 | HIS | 357 | 24.456 | 27.622 | 17.828 | 1.00 | 0.00 | B3 |
| ATOM | 2493 | CE1 | HIS | 357 | 23.112 | 28.103 | 16.337 | 1.00 | 28.64 | B3 |

FIG. 5-30

| ATOM | 2494 | NE2 | HIS | 357 | 23.298 | 28.589 | 15.130 | 1.00 | 29.48 | B3 |
|---|---|---|---|---|---|---|---|---|---|---|
| ATOM | 2495 | HE2 | HIS | 357 | 22.576 | 28.801 | 14.495 | 1.00 | 0.00 | B3 |
| ATOM | 2496 | C | HIS | 357 | 28.852 | 29.506 | 15.645 | 1.00 | 27.93 | B3 |
| ATOM | 2497 | O | HIS | 357 | 29.119 | 30.606 | 16.115 | 1.00 | 29.15 | B3 |
| ATOM | 2498 | N | LEU | 358 | 29.830 | 28.637 | 15.383 | 1.00 | 28.33 | B3 |
| ATOM | 2499 | H | LEU | 358 | 29.624 | 27.761 | 14.997 | 1.00 | 0.00 | B3 |
| ATOM | 2500 | CA | LEU | 358 | 31.211 | 28.940 | 15.721 | 1.00 | 26.39 | B3 |
| ATOM | 2501 | CB | LEU | 358 | 32.030 | 27.702 | 15.547 | 1.00 | 21.42 | B3 |
| ATOM | 2502 | CG | LEU | 358 | 33.457 | 27.878 | 15.734 | 1.00 | 20.42 | B3 |
| ATOM | 2503 | CD1 | LEU | 358 | 33.805 | 28.078 | 17.165 | 1.00 | 16.79 | B3 |
| ATOM | 2504 | CD2 | LEU | 358 | 34.075 | 26.714 | 15.072 | 1.00 | 22.89 | B3 |
| ATOM | 2505 | C | LEU | 358 | 31.721 | 30.067 | 14.822 | 1.00 | 26.45 | B3 |
| ATOM | 2506 | O | LEU | 358 | 32.372 | 30.939 | 15.378 | 1.00 | 27.12 | B3 |
| ATOM | 2507 | N | GLN | 359 | 31.460 | 30.130 | 13.518 | 1.00 | 26.41 | B3 |
| ATOM | 2508 | H | GLN | 359 | 31.048 | 29.337 | 13.114 | 1.00 | 0.00 | B3 |
| ATOM | 2509 | CA | GLN | 359 | 31.863 | 31.254 | 12.671 | 1.00 | 29.10 | B3 |
| ATOM | 2510 | CB | GLN | 359 | 31.204 | 31.209 | 11.292 | 1.00 | 30.49 | B3 |
| ATOM | 2511 | CG | GLN | 359 | 31.395 | 29.952 | 10.455 | 1.00 | 38.94 | B3 |
| ATOM | 2512 | CD | GLN | 359 | 32.842 | 29.636 | 10.091 | 1.00 | 42.09 | B3 |
| ATOM | 2513 | OE1 | GLN | 359 | 33.774 | 29.979 | 10.821 | 1.00 | 46.15 | B3 |
| ATOM | 2514 | NE2 | GLN | 359 | 33.103 | 28.987 | 8.967 | 1.00 | 41.34 | B3 |
| ATOM | 2515 | HE21 | GLN | 359 | 32.341 | 28.706 | 8.412 | 1.00 | 0.00 | B3 |
| ATOM | 2516 | HE22 | GLN | 359 | 34.039 | 28.838 | 8.740 | 1.00 | 0.00 | B3 |
| ATOM | 2517 | C | GLN | 359 | 31.512 | 32.621 | 13.254 | 1.00 | 29.39 | B3 |
| ATOM | 2518 | O | GLN | 359 | 32.427 | 33.427 | 13.484 | 1.00 | 30.06 | B3 |
| ATOM | 2519 | N | SER | 360 | 30.201 | 32.810 | 13.528 | 1.00 | 28.66 | B3 |
| ATOM | 2520 | H | SER | 360 | 29.595 | 32.061 | 13.343 | 1.00 | 0.00 | B3 |
| ATOM | 2521 | CA | SER | 360 | 29.570 | 34.003 | 14.071 | 1.00 | 27.31 | B3 |
| ATOM | 2522 | CB | SER | 360 | 28.121 | 33.761 | 14.336 | 1.00 | 26.70 | B3 |
| ATOM | 2523 | OG | SER | 360 | 27.493 | 33.539 | 13.078 | 1.00 | 29.72 | B3 |
| ATOM | 2524 | HG | SER | 360 | 26.637 | 33.112 | 13.288 | 1.00 | 0.00 | B3 |
| ATOM | 2525 | C | SER | 360 | 30.202 | 34.387 | 15.353 | 1.00 | 27.15 | B3 |
| ATOM | 2526 | O | SER | 360 | 30.575 | 35.550 | 15.498 | 1.00 | 26.93 | B3 |
| ATOM | 2527 | N | PHE | 361 | 30.383 | 33.403 | 16.246 | 1.00 | 25.38 | B3 |
| ATOM | 2528 | H | PHE | 361 | 30.055 | 32.499 | 16.040 | 1.00 | 0.00 | B3 |
| ATOM | 2529 | CA | PHE | 361 | 31.066 | 33.626 | 17.517 | 1.00 | 25.20 | B3 |
| ATOM | 2530 | CB | PHE | 361 | 31.092 | 32.335 | 18.302 | 1.00 | 23.30 | B3 |
| ATOM | 2531 | CG | PHE | 361 | 31.796 | 32.394 | 19.655 | 1.00 | 23.63 | B3 |
| ATOM | 2532 | CD1 | PHE | 361 | 31.127 | 32.854 | 20.777 | 1.00 | 22.44 | B3 |
| ATOM | 2533 | CD2 | PHE | 361 | 33.098 | 31.931 | 19.770 | 1.00 | 23.35 | B3 |
| ATOM | 2534 | CE1 | PHE | 361 | 31.772 | 32.834 | 22.000 | 1.00 | 22.78 | B3 |
| ATOM | 2535 | CE2 | PHE | 361 | 33.719 | 31.921 | 21.002 | 1.00 | 21.26 | B3 |
| ATOM | 2536 | CZ | PHE | 361 | 33.058 | 32.368 | 22.114 | 1.00 | 19.54 | B3 |
| ATOM | 2537 | C | PHE | 361 | 32.505 | 34.143 | 17.385 | 1.00 | 26.56 | B3 |
| ATOM | 2538 | O | PHE | 361 | 32.914 | 34.979 | 18.183 | 1.00 | 26.76 | B3 |
| ATOM | 2539 | N | LEU | 362 | 33.309 | 33.645 | 16.441 | 1.00 | 28.17 | B3 |
| ATOM | 2540 | H | LEU | 362 | 32.962 | 32.921 | 15.874 | 1.00 | 0.00 | B3 |
| ATOM | 2541 | CA | LEU | 362 | 34.679 | 34.089 | 16.222 | 1.00 | 28.89 | B3 |
| ATOM | 2542 | CB | LEU | 362 | 35.452 | 33.125 | 15.338 | 1.00 | 28.18 | B3 |
| ATOM | 2543 | CG | LEU | 362 | 35.603 | 31.656 | 15.781 | 1.00 | 29.61 | B3 |
| ATOM | 2544 | CD1 | LEU | 362 | 36.306 | 30.996 | 14.633 | 1.00 | 31.63 | B3 |
| ATOM | 2545 | CD2 | LEU | 362 | 36.374 | 31.433 | 17.055 | 1.00 | 26.38 | B3 |
| ATOM | 2546 | C | LEU | 362 | 34.692 | 35.449 | 15.536 | 1.00 | 29.18 | B3 |
| ATOM | 2547 | O | LEU | 362 | 35.649 | 36.202 | 15.748 | 1.00 | 27.43 | B3 |
| ATOM | 2548 | N | GLU | 363 | 33.664 | 35.763 | 14.710 | 1.00 | 29.54 | B3 |
| ATOM | 2549 | H | GLU | 363 | 33.009 | 35.066 | 14.495 | 1.00 | 0.00 | B3 |
| ATOM | 2550 | CA | GLU | 363 | 33.496 | 37.090 | 14.145 | 1.00 | 30.30 | B3 |
| ATOM | 2551 | CB | GLU | 363 | 32.357 | 37.147 | 13.228 | 1.00 | 30.90 | B3 |
| ATOM | 2552 | CG | GLU | 363 | 32.763 | 36.735 | 11.849 | 1.00 | 38.69 | B3 |
| ATOM | 2553 | CD | GLU | 363 | 33.642 | 37.662 | 11.013 | 1.00 | 42.62 | B3 |
| ATOM | 2554 | OE1 | GLU | 363 | 33.896 | 37.282 | 9.860 | 1.00 | 46.58 | B3 |
| ATOM | 2555 | OE2 | GLU | 363 | 34.051 | 38.734 | 11.488 | 1.00 | 46.47 | B3 |
| ATOM | 2556 | C | GLU | 363 | 33.229 | 38.098 | 15.244 | 1.00 | 30.19 | B3 |
| ATOM | 2557 | O | GLU | 363 | 33.837 | 39.167 | 15.239 | 1.00 | 30.26 | B3 |
| ATOM | 2558 | N | VAL | 364 | 32.397 | 37.726 | 16.217 | 1.00 | 30.04 | B3 |
| ATOM | 2559 | H | VAL | 364 | 31.888 | 36.898 | 16.100 | 1.00 | 0.00 | B3 |
| ATOM | 2560 | CA | VAL | 364 | 32.178 | 38.522 | 17.400 | 1.00 | 31.90 | B3 |
| ATOM | 2561 | CB | VAL | 364 | 31.014 | 38.021 | 18.269 | 1.00 | 31.41 | B3 |
| ATOM | 2562 | CG1 | VAL | 364 | 30.860 | 38.811 | 19.562 | 1.00 | 30.73 | B3 |
| ATOM | 2563 | CG2 | VAL | 364 | 29.750 | 38.200 | 17.497 | 1.00 | 29.96 | B3 |
| ATOM | 2564 | C | VAL | 364 | 33.402 | 38.493 | 18.275 | 1.00 | 35.89 | B3 |
| ATOM | 2565 | O | VAL | 364 | 33.683 | 39.535 | 18.855 | 1.00 | 37.54 | B3 |
| ATOM | 2566 | N | SER | 365 | 34.173 | 37.421 | 18.477 | 1.00 | 38.25 | B3 |
| ATOM | 2567 | H | SER | 365 | 33.971 | 36.577 | 18.030 | 1.00 | 0.00 | B3 |
| ATOM | 2568 | CA | SER | 365 | 35.337 | 37.478 | 19.375 | 1.00 | 39.61 | B3 |
| ATOM | 2569 | CB | SER | 365 | 36.041 | 36.113 | 19.555 | 1.00 | 43.00 | B3 |
| ATOM | 2570 | OG | SER | 365 | 35.201 | 34.953 | 19.575 | 1.00 | 46.29 | B3 |
| ATOM | 2571 | HG | SER | 365 | 34.270 | 35.189 | 19.644 | 1.00 | 0.00 | B3 |
| ATOM | 2572 | C | SER | 365 | 36.398 | 38.418 | 18.840 | 1.00 | 38.21 | B3 |
| ATOM | 2573 | O | SER | 365 | 37.103 | 38.989 | 19.662 | 1.00 | 36.91 | B3 |
| ATOM | 2574 | N | TYR | 366 | 36.575 | 38.540 | 17.514 | 1.00 | 38.00 | B3 |
| ATOM | 2575 | H | TYR | 366 | 36.079 | 37.945 | 16.910 | 1.00 | 0.00 | B3 |
| ATOM | 2576 | CA | TYR | 366 | 37.568 | 39.463 | 16.969 | 1.00 | 39.85 | B3 |
| ATOM | 2577 | CB | TYR | 366 | 37.776 | 39.330 | 15.436 | 1.00 | 38.53 | B3 |
| ATOM | 2578 | CG | TYR | 366 | 38.662 | 40.447 | 14.879 | 1.00 | 38.21 | B3 |
| ATOM | 2579 | CD1 | TYR | 366 | 38.104 | 41.464 | 14.129 | 1.00 | 37.18 | B3 |

FIG.5-31

| | | | | | | | | | |
|---|---|---|---|---|---|---|---|---|---|
| ATOM | 2580 | CE1 | TYR | 366 | 38.918 | 42.495 | 13.678 | 1.00 41.77 | B3 |
| ATOM | 2581 | CD2 | TYR | 366 | 40.021 | 40.443 | 15.182 | 1.00 40.21 | B3 |
| ATOM | 2582 | CE2 | TYR | 366 | 40.849 | 41.466 | 14.739 | 1.00 40.76 | B3 |
| ATOM | 2583 | CZ | TYR | 366 | 40.297 | 42.504 | 13.976 | 1.00 42.82 | B3 |
| ATOM | 2584 | OH | TYR | 366 | 41.151 | 43.522 | 13.493 | 1.00 41.30 | B3 |
| ATOM | 2585 | HH | TYR | 366 | 40.743 | 43.977 | 12.755 | 1.00 0.00 | B3 |
| ATOM | 2586 | C | TYR | 366 | 37.133 | 40.893 | 17.241 | 1.00 40.55 | B3 |
| ATOM | 2587 | O | TYR | 366 | 37.917 | 41.647 | 17.798 | 1.00 40.92 | B3 |
| ATOM | 2588 | N | ARG | 366 | 35.933 | 41.309 | 16.853 | 1.00 41.88 | B3 |
| ATOM | 2589 | H | ARG | 367 | 35.360 | 40.682 | 16.360 | 1.00 0.00 | B3 |
| ATOM | 2590 | CA | ARG | 367 | 35.442 | 42.653 | 17.139 | 1.00 43.32 | B3 |
| ATOM | 2591 | CB | ARG | 367 | 34.013 | 42.709 | 16.650 | 1.00 46.82 | B3 |
| ATOM | 2592 | CG | ARG | 367 | 33.528 | 44.130 | 16.650 | 1.00 56.74 | B3 |
| ATOM | 2593 | CD | ARG | 367 | 32.069 | 44.267 | 16.248 | 1.00 61.81 | B3 |
| ATOM | 2594 | NE | ARG | 367 | 31.723 | 45.687 | 16.229 | 1.00 66.59 | B3 |
| ATOM | 2595 | HE | ARG | 367 | 32.438 | 46.356 | 16.172 | 1.00 0.00 | B3 |
| ATOM | 2596 | CZ | ARG | 367 | 30.458 | 46.091 | 16.308 | 1.00 69.75 | B3 |
| ATOM | 2597 | NH1 | ARG | 367 | 29.448 | 45.220 | 16.413 | 1.00 72.65 | B3 |
| ATOM | 2598 | HH11 | ARG | 367 | 29.631 | 44.236 | 16.410 | 1.00 0.00 | B3 |
| ATOM | 2599 | HH12 | ARG | 367 | 28.503 | 45.548 | 16.445 | 1.00 0.00 | B3 |
| ATOM | 2600 | NH2 | ARG | 367 | 30.160 | 47.375 | 16.162 | 1.00 71.64 | B3 |
| ATOM | 2601 | HH21 | ARG | 367 | 29.204 | 47.665 | 16.222 | 1.00 0.00 | B3 |
| ATOM | 2602 | HH22 | ARG | 367 | 30.888 | 48.043 | 16.013 | 1.00 0.00 | B3 |
| ATOM | 2603 | C | ARG | 367 | 35.551 | 43.011 | 18.635 | 1.00 40.96 | B3 |
| ATOM | 2604 | O | ARG | 367 | 35.994 | 44.090 | 19.012 | 1.00 41.10 | B3 |
| ATOM | 2605 | N | VAL | 368 | 35.160 | 42.135 | 19.542 | 1.00 39.83 | B3 |
| ATOM | 2606 | H | VAL | 368 | 34.726 | 41.316 | 19.217 | 1.00 0.00 | B3 |
| ATOM | 2607 | CA | VAL | 368 | 35.331 | 42.292 | 20.968 | 1.00 37.33 | B3 |
| ATOM | 2608 | CB | VAL | 368 | 34.748 | 41.043 | 21.664 | 1.00 35.75 | B3 |
| ATOM | 2609 | CG1 | VAL | 368 | 35.087 | 40.867 | 23.140 | 1.00 35.10 | B3 |
| ATOM | 2610 | CG2 | VAL | 368 | 33.259 | 41.230 | 21.586 | 1.00 33.28 | B3 |
| ATOM | 2611 | C | VAL | 368 | 36.813 | 42.459 | 21.223 | 1.00 38.75 | B3 |
| ATOM | 2612 | O | VAL | 368 | 37.144 | 43.498 | 21.772 | 1.00 40.11 | B3 |
| ATOM | 2613 | N | LEU | 369 | 37.759 | 41.600 | 20.835 | 1.00 39.59 | B3 |
| ATOM | 2614 | H | LEU | 369 | 37.492 | 40.818 | 20.308 | 1.00 0.00 | B3 |
| ATOM | 2615 | CA | LEU | 369 | 39.180 | 41.780 | 21.148 | 1.00 40.05 | B3 |
| ATOM | 2616 | CB | LEU | 369 | 39.984 | 40.601 | 20.679 | 1.00 37.15 | B3 |
| ATOM | 2617 | CG | LEU | 369 | 39.831 | 39.335 | 21.426 | 1.00 37.54 | B3 |
| ATOM | 2618 | CD1 | LEU | 369 | 40.349 | 38.238 | 20.528 | 1.00 39.70 | B3 |
| ATOM | 2619 | CD2 | LEU | 369 | 40.563 | 39.394 | 22.747 | 1.00 36.86 | B3 |
| ATOM | 2620 | C | LEU | 369 | 39.817 | 43.031 | 20.542 | 1.00 41.88 | B3 |
| ATOM | 2621 | O | LEU | 369 | 40.711 | 43.654 | 21.144 | 1.00 41.30 | B3 |
| ATOM | 2622 | N | ARG | 370 | 39.333 | 43.413 | 19.354 | 1.00 42.80 | B3 |
| ATOM | 2623 | H | ARG | 370 | 38.619 | 42.884 | 18.957 | 1.00 0.00 | B3 |
| ATOM | 2624 | CA | ARG | 370 | 39.819 | 44.577 | 18.663 | 1.00 44.96 | B3 |
| ATOM | 2625 | CB | ARG | 370 | 39.184 | 44.569 | 17.316 | 1.00 42.06 | B3 |
| ATOM | 2626 | CG | ARG | 370 | 39.424 | 45.719 | 16.371 | 1.00 43.93 | B3 |
| ATOM | 2627 | CD | ARG | 370 | 40.894 | 45.910 | 16.169 | 1.00 45.37 | B3 |
| ATOM | 2628 | NE | ARG | 370 | 41.219 | 46.681 | 14.976 | 1.00 48.00 | B3 |
| ATOM | 2629 | HE | ARG | 370 | 40.524 | 46.867 | 14.312 | 1.00 0.00 | B3 |
| ATOM | 2630 | CZ | ARG | 370 | 42.469 | 47.153 | 14.791 | 1.00 48.45 | B3 |
| ATOM | 2631 | NH1 | ARG | 370 | 43.443 | 46.961 | 15.691 | 1.00 49.13 | B3 |
| ATOM | 2632 | HH11 | ARG | 370 | 43.262 | 46.456 | 16.534 | 1.00 0.00 | B3 |
| ATOM | 2633 | HH12 | ARG | 370 | 44.357 | 47.326 | 15.520 | 1.00 0.00 | B3 |
| ATOM | 2634 | NH2 | ARG | 370 | 42.821 | 47.710 | 13.635 | 1.00 47.59 | B3 |
| ATOM | 2635 | HH21 | ARG | 370 | 42.163 | 47.785 | 12.889 | 1.00 0.00 | B3 |
| ATOM | 2636 | HH22 | ARG | 370 | 43.751 | 48.057 | 13.516 | 1.00 0.00 | B3 |
| ATOM | 2637 | C | ARG | 370 | 39.386 | 45.740 | 19.558 | 1.00 49.12 | B3 |
| ATOM | 2638 | O | ARG | 370 | 40.216 | 46.615 | 19.826 | 1.00 49.67 | B3 |
| ATOM | 2639 | N | HIS | 371 | 38.162 | 45.728 | 20.123 | 1.00 52.30 | B3 |
| ATOM | 2640 | H | HIS | 371 | 37.581 | 44.955 | 19.949 | 1.00 0.00 | B3 |
| ATOM | 2641 | CA | HIS | 371 | 37.745 | 46.738 | 21.080 | 1.00 56.65 | B3 |
| ATOM | 2642 | CB | HIS | 371 | 36.284 | 46.604 | 21.459 | 1.00 62.15 | B3 |
| ATOM | 2643 | CG | HIS | 371 | 35.320 | 46.991 | 20.346 | 1.00 71.70 | B3 |
| ATOM | 2644 | CD2 | HIS | 371 | 35.596 | 47.877 | 19.313 | 1.00 75.03 | B3 |
| ATOM | 2645 | ND1 | HIS | 371 | 34.067 | 46.546 | 20.166 | 1.00 75.91 | B3 |
| ATOM | 2646 | HD1 | HIS | 371 | 33.594 | 45.897 | 20.732 | 1.00 0.00 | B3 |
| ATOM | 2647 | CE1 | HIS | 371 | 33.580 | 47.116 | 19.077 | 1.00 77.30 | B3 |
| ATOM | 2648 | NE2 | HIS | 371 | 34.507 | 47.914 | 18.573 | 1.00 77.52 | B3 |
| ATOM | 2649 | HE2 | HIS | 371 | 34.401 | 48.460 | 17.764 | 1.00 0.00 | B3 |
| ATOM | 2650 | C | HIS | 371 | 38.533 | 46.669 | 22.382 | 1.00 56.97 | B3 |
| ATOM | 2651 | O | HIS | 371 | 38.458 | 47.592 | 23.176 | 1.00 58.12 | B3 |
| ATOM | 2652 | N | LEU | 372 | 39.271 | 45.632 | 22.715 | 1.00 56.98 | B3 |
| ATOM | 2653 | H | LEU | 372 | 39.302 | 44.855 | 22.122 | 1.00 0.00 | B3 |
| ATOM | 2654 | CA | LEU | 372 | 40.048 | 45.597 | 23.939 | 1.00 57.77 | B3 |
| ATOM | 2655 | CB | LEU | 372 | 39.725 | 44.272 | 24.633 | 1.00 57.29 | B3 |
| ATOM | 2656 | CG | LEU | 372 | 38.566 | 44.144 | 25.611 | 1.00 55.87 | B3 |
| ATOM | 2657 | CD1 | LEU | 372 | 37.358 | 44.892 | 25.123 | 1.00 55.77 | B3 |
| ATOM | 2658 | CD2 | LEU | 372 | 38.211 | 42.675 | 25.749 | 1.00 55.33 | B3 |
| ATOM | 2659 | C | LEU | 372 | 41.554 | 45.755 | 23.647 | 1.00 58.81 | B3 |
| ATOM | 2660 | O | LEU | 372 | 42.447 | 45.475 | 24.476 | 1.00 59.12 | B3 |
| ATOM | 2661 | N | ALA | 373 | 41.942 | 46.168 | 22.447 | 1.00 59.27 | B3 |
| ATOM | 2662 | H | ALA | 373 | 41.271 | 46.255 | 21.731 | 1.00 0.00 | B3 |
| ATOM | 2663 | CA | ALA | 373 | 43.336 | 46.425 | 22.147 | 1.00 60.03 | B3 |
| ATOM | 2664 | CB | ALA | 373 | 43.755 | 45.485 | 21.021 | 1.00 59.87 | B3 |
| ATOM | 2665 | C | ALA | 373 | 43.616 | 47.895 | 21.762 | 1.00 61.22 | B3 |

FIG. 5-32

| | | | | | | | | | | |
|---|---|---|---|---|---|---|---|---|---|---|
| ATOM | 2666 | OT1 | ALA | 373 | 44.798 | 48.243 | 21.697 | 1.00 | 62.45 | B3 |
| ATOM | 2667 | OT2 | ALA | 373 | 42.682 | 48.700 | 21.583 | 1.00 | 61.55 | B3 |
| ATOM | 2668 | CB  | LEU | 410 | 23.866 | 49.243 | 1.118  | 1.00 | 53.10 | C1 |
| ATOM | 2669 | CG  | LEU | 410 | 23.982 | 47.812 | 0.738  | 1.00 | 51.85 | C1 |
| ATOM | 2670 | CD1 | LEU | 410 | 25.074 | 47.596 | -0.330 | 1.00 | 52.64 | C1 |
| ATOM | 2671 | CD2 | LEU | 410 | 24.125 | 47.081 | 2.058  | 1.00 | 49.28 | C1 |
| ATOM | 2672 | C   | LEU | 410 | 22.381 | 51.214 | 1.635  | 1.00 | 52.99 | C1 |
| ATOM | 2673 | O   | LEU | 410 | 22.242 | 52.166 | 0.845  | 1.00 | 53.00 | C1 |
| ATOM | 2674 | HT1 | LEU | 410 | 22.721 | 50.836 | -0.665 | 1.00 | 0.00  | C1 |
| ATOM | 2675 | HT2 | LEU | 410 | 21.194 | 50.178 | -0.557 | 1.00 | 0.00  | C1 |
| ATOM | 2676 | N   | LEU | 410 | 22.198 | 49.968 | -0.415 | 1.00 | 54.31 | C1 |
| ATOM | 2677 | HT3 | LEU | 410 | 22.529 | 49.174 | -0.998 | 1.00 | 0.00  | C1 |
| ATOM | 2678 | CA  | LEU | 410 | 22.478 | 49.815 | 1.004  | 1.00 | 53.64 | C1 |
| ATOM | 2679 | N   | PRO | 411 | 22.450 | 51.433 | 2.965  | 1.00 | 52.95 | C1 |
| ATOM | 2680 | CD  | PRO | 411 | 22.466 | 50.407 | 4.022  | 1.00 | 52.54 | C1 |
| ATOM | 2681 | CA  | PRO | 411 | 22.666 | 52.766 | 3.548  | 1.00 | 53.25 | C1 |
| ATOM | 2682 | CB  | PRO | 411 | 22.688 | 52.541 | 5.068  | 1.00 | 52.85 | C1 |
| ATOM | 2683 | CG  | PRO | 411 | 23.163 | 51.108 | 5.203  | 1.00 | 52.83 | C1 |
| ATOM | 2684 | C   | PRO | 411 | 23.958 | 53.413 | 3.023  | 1.00 | 53.47 | C1 |
| ATOM | 2685 | O   | PRO | 411 | 25.073 | 52.878 | 3.167  | 1.00 | 54.02 | C1 |
| ATOM | 2686 | N   | GLN | 412 | 23.787 | 54.599 | 2.411  | 1.00 | 52.79 | C1 |
| ATOM | 2687 | H   | GLN | 412 | 22.863 | 54.900 | 2.294  | 1.00 | 0.00  | C1 |
| ATOM | 2688 | CA  | GLN | 412 | 24.873 | 55.413 | 1.871  | 1.00 | 50.44 | C1 |
| ATOM | 2689 | CB  | GLN | 412 | 24.387 | 56.762 | 1.413  | 1.00 | 52.47 | C1 |
| ATOM | 2690 | CG  | GLN | 412 | 25.364 | 57.408 | 0.437  | 1.00 | 56.51 | C1 |
| ATOM | 2691 | CD  | GLN | 412 | 25.228 | 56.954 | -1.017 | 1.00 | 59.40 | C1 |
| ATOM | 2692 | OE1 | GLN | 412 | 25.869 | 57.506 | -1.913 | 1.00 | 59.67 | C1 |
| ATOM | 2693 | NE2 | GLN | 412 | 24.336 | 56.022 | -1.389 | 1.00 | 60.12 | C1 |
| ATOM | 2694 | HE21| GLN | 412 | 23.734 | 55.616 | -0.737 | 1.00 | 0.00  | C1 |
| ATOM | 2695 | HE22| GLN | 412 | 24.396 | 55.748 | -2.328 | 1.00 | 0.00  | C1 |
| ATOM | 2696 | C   | GLN | 412 | 25.930 | 55.646 | 2.916  | 1.00 | 48.22 | C1 |
| ATOM | 2697 | O   | GLN | 412 | 27.089 | 55.591 | 2.545  | 1.00 | 46.78 | C1 |
| ATOM | 2698 | N   | SER | 413 | 25.614 | 55.842 | 4.201  | 1.00 | 47.90 | C1 |
| ATOM | 2699 | H   | SER | 413 | 24.693 | 55.976 | 4.492  | 1.00 | 0.00  | C1 |
| ATOM | 2700 | CA  | SER | 413 | 26.696 | 55.984 | 5.144  | 1.00 | 48.75 | C1 |
| ATOM | 2701 | CB  | SER | 413 | 26.261 | 56.344 | 6.548  | 1.00 | 50.61 | C1 |
| ATOM | 2702 | OG  | SER | 413 | 27.378 | 56.872 | 7.301  | 1.00 | 53.05 | C1 |
| ATOM | 2703 | HG  | SER | 413 | 28.178 | 56.355 | 7.145  | 1.00 | 0.00  | C1 |
| ATOM | 2704 | C   | SER | 413 | 27.480 | 54.684 | 5.267  | 1.00 | 48.71 | C1 |
| ATOM | 2705 | O   | SER | 413 | 28.698 | 54.839 | 5.392  | 1.00 | 50.77 | C1 |
| ATOM | 2706 | N   | PHE | 414 | 26.947 | 53.440 | 5.208  | 1.00 | 46.01 | C1 |
| ATOM | 2707 | H   | PHE | 414 | 25.996 | 53.323 | 5.015  | 1.00 | 0.00  | C1 |
| ATOM | 2708 | CA  | PHE | 414 | 27.787 | 52.233 | 5.274  | 1.00 | 42.92 | C1 |
| ATOM | 2709 | CB  | PHE | 414 | 26.959 | 50.915 | 5.232  | 1.00 | 40.76 | C1 |
| ATOM | 2710 | CG  | PHE | 414 | 27.633 | 49.627 | 4.757  | 1.00 | 35.06 | C1 |
| ATOM | 2711 | CD1 | PHE | 414 | 27.583 | 49.256 | 3.425  | 1.00 | 34.71 | C1 |
| ATOM | 2712 | CD2 | PHE | 414 | 28.262 | 48.800 | 5.663  | 1.00 | 34.81 | C1 |
| ATOM | 2713 | CE1 | PHE | 414 | 28.156 | 48.056 | 3.014  | 1.00 | 36.16 | C1 |
| ATOM | 2714 | CE2 | PHE | 414 | 28.832 | 47.602 | 5.247  | 1.00 | 33.40 | C1 |
| ATOM | 2715 | CZ  | PHE | 414 | 28.781 | 47.223 | 3.923  | 1.00 | 34.22 | C1 |
| ATOM | 2716 | C   | PHE | 414 | 28.667 | 52.271 | 4.044  | 1.00 | 41.25 | C1 |
| ATOM | 2717 | O   | PHE | 414 | 29.831 | 51.902 | 4.110  | 1.00 | 41.47 | C1 |
| ATOM | 2718 | N   | LEU | 415 | 28.122 | 52.748 | 2.942  | 1.00 | 39.50 | C1 |
| ATOM | 2719 | H   | LEU | 415 | 27.188 | 53.044 | 2.946  | 1.00 | 0.00  | C1 |
| ATOM | 2720 | CA  | LEU | 415 | 28.865 | 52.769 | 1.721  | 1.00 | 39.91 | C1 |
| ATOM | 2721 | CB  | LEU | 415 | 27.946 | 53.205 | 0.641  | 1.00 | 41.98 | C1 |
| ATOM | 2722 | CG  | LEU | 415 | 27.903 | 52.274 | -0.526 | 1.00 | 44.75 | C1 |
| ATOM | 2723 | CD1 | LEU | 415 | 26.430 | 51.951 | -0.780 | 1.00 | 42.93 | C1 |
| ATOM | 2724 | CD2 | LEU | 415 | 28.793 | 52.853 | -1.648 | 1.00 | 45.91 | C1 |
| ATOM | 2725 | C   | LEU | 415 | 30.081 | 53.669 | 1.755  | 1.00 | 40.03 | C1 |
| ATOM | 2726 | O   | LEU | 415 | 31.142 | 53.348 | 1.183  | 1.00 | 40.28 | C1 |
| ATOM | 2727 | N   | LEU | 416 | 29.901 | 54.779 | 2.487  | 1.00 | 37.46 | C1 |
| ATOM | 2728 | H   | LEU | 416 | 29.028 | 54.948 | 2.899  | 1.00 | 0.00  | C1 |
| ATOM | 2729 | CA  | LEU | 416 | 30.942 | 55.756 | 2.602  | 1.00 | 34.05 | C1 |
| ATOM | 2730 | CB  | LEU | 416 | 30.294 | 57.089 | 2.998  | 1.00 | 34.67 | C1 |
| ATOM | 2731 | CG  | LEU | 416 | 29.438 | 57.704 | 1.851  | 1.00 | 35.24 | C1 |
| ATOM | 2732 | CD1 | LEU | 416 | 28.770 | 58.948 | 2.358  | 1.00 | 31.87 | C1 |
| ATOM | 2733 | CD2 | LEU | 416 | 30.310 | 57.948 | 0.593  | 1.00 | 35.50 | C1 |
| ATOM | 2734 | C   | LEU | 416 | 31.952 | 55.258 | 3.586  | 1.00 | 31.97 | C1 |
| ATOM | 2735 | O   | LEU | 416 | 33.131 | 55.427 | 3.270  | 1.00 | 33.32 | C1 |
| ATOM | 2736 | N   | ALA | 417 | 31.573 | 54.619 | 4.695  | 1.00 | 29.05 | C1 |
| ATOM | 2737 | H   | ALA | 417 | 30.621 | 54.616 | 4.927  | 1.00 | 0.00  | C1 |
| ATOM | 2738 | CA  | ALA | 417 | 32.524 | 53.882 | 5.561  | 1.00 | 29.64 | C1 |
| ATOM | 2739 | CB  | ALA | 417 | 31.853 | 53.087 | 6.680  | 1.00 | 25.16 | C1 |
| ATOM | 2740 | C   | ALA | 417 | 33.319 | 52.827 | 4.777  | 1.00 | 30.68 | C1 |
| ATOM | 2741 | O   | ALA | 417 | 34.536 | 52.721 | 4.877  | 1.00 | 31.52 | C1 |
| ATOM | 2742 | N   | CYS | 418 | 32.726 | 52.041 | 3.905  | 1.00 | 32.19 | C1 |
| ATOM | 2743 | H   | CYS | 418 | 31.748 | 52.017 | 3.860  | 1.00 | 0.00  | C1 |
| ATOM | 2744 | CA  | CYS | 418 | 33.499 | 51.119 | 3.103  | 1.00 | 33.67 | C1 |
| ATOM | 2745 | CB  | CYS | 418 | 32.657 | 50.250 | 2.226  | 1.00 | 33.85 | C1 |
| ATOM | 2746 | SG  | CYS | 418 | 31.623 | 49.208 | 3.246  | 1.00 | 37.80 | C1 |
| ATOM | 2747 | C   | CYS | 418 | 34.446 | 51.818 | 2.170  | 1.00 | 34.80 | C1 |
| ATOM | 2748 | O   | CYS | 418 | 35.626 | 51.441 | 2.173  | 1.00 | 36.47 | C1 |
| ATOM | 2749 | N   | LEU | 419 | 34.009 | 52.820 | 1.377  | 1.00 | 35.00 | C1 |
| ATOM | 2750 | H   | LEU | 419 | 33.082 | 53.131 | 1.460  | 1.00 | 0.00  | C1 |
| ATOM | 2751 | CA  | LEU | 419 | 34.886 | 53.446 | 0.375  | 1.00 | 34.14 | C1 |

FIG.5-33

```
ATOM  2752 CB  LEU 419      34.062 54.484 -0.413 1.00 37.09      C1
ATOM  2753 CG  LEU 419      32.866 53.853 -1.244 1.00 39.61      C1
ATOM  2754 CD1 LEU 419      31.866 54.918 -1.609 1.00 39.24      C1
ATOM  2755 CD2 LEU 419      33.349 53.207 -2.553 1.00 40.02      C1
ATOM  2756 C   LEU 419      36.102 54.041  1.047 1.00 32.33      C1
ATOM  2757 O   LEU 419      37.198 53.973  0.549 1.00 31.60      C1
ATOM  2758 N   GLU 420      35.974 54.483  2.273 1.00 31.92      C1
ATOM  2759 H   GLU 420      35.068 54.528  2.648 1.00  0.00      C1
ATOM  2760 CA  GLU 420      37.078 54.905  3.092 1.00 31.79      C1
ATOM  2761 CB  GLU 420      36.477 55.462  4.344 1.00 34.29      C1
ATOM  2762 CG  GLU 420      37.430 56.240  5.185 1.00 38.66      C1
ATOM  2763 CD  GLU 420      36.952 56.499  6.609 1.00 45.20      C1
ATOM  2764 OE1 GLU 420      37.873 56.849  7.367 1.00 45.67      C1
ATOM  2765 OE2 GLU 420      35.745 56.345  6.954 1.00 44.21      C1
ATOM  2766 C   GLU 420      38.043 53.763  3.423 1.00 31.87      C1
ATOM  2767 O   GLU 420      39.253 53.949  3.270 1.00 32.82      C1
ATOM  2768 N   GLN 421      37.553 52.624  3.954 1.00 30.46      C1
ATOM  2769 H   GLN 421      36.583 52.556  4.098 1.00  0.00      C1
ATOM  2770 CA  GLN 421      38.366 51.461  4.283 1.00 29.34      C1
ATOM  2771 CB  GLN 421      37.545 50.389  4.984 1.00 30.88      C1
ATOM  2772 CG  GLN 421      37.308 50.634  6.463 1.00 33.58      C1
ATOM  2773 CD  GLN 421      36.320 49.625  7.058 1.00 37.89      C1
ATOM  2774 OE1 GLN 421      35.357 49.236  6.398 1.00 43.18      C1
ATOM  2775 NE2 GLN 421      36.427 49.095  8.275 1.00 37.13      C1
ATOM  2776 HE21 GLN 421     35.695 48.505  8.556 1.00 21.56      C1
ATOM  2777 HE22 GLN 421     37.207 49.330  8.812 1.00  0.00      C1
ATOM  2778 C   GLN 421      38.991 50.862  3.026 1.00 27.36      C1
ATOM  2779 O   GLN 421      40.152 50.445  3.099 1.00 29.09      C1
ATOM  2780 N   VAL 422      38.379 50.845  1.847 1.00 23.57      C1
ATOM  2781 H   VAL 422      37.448 51.138  1.803 1.00  0.00      C1
ATOM  2782 CA  VAL 422      39.077 50.420  0.651 1.00 23.52      C1
ATOM  2783 CB  VAL 422      38.163 50.636 -0.556 1.00 22.67      C1
ATOM  2784 CG1 VAL 422      38.873 50.455 -1.868 1.00 21.56      C1
ATOM  2785 CG2 VAL 422      37.057 49.610 -0.465 1.00 26.79      C1
ATOM  2786 C   VAL 422      40.353 51.254  0.514 1.00 26.22      C1
ATOM  2787 O   VAL 422      41.458 50.708  0.508 1.00 28.77      C1
ATOM  2788 N   ARG 423      40.275 52.599  0.575 1.00 27.49      C1
ATOM  2789 H   ARG 423      39.402 53.016  0.735 1.00  0.00      C1
ATOM  2790 CA  ARG 423      41.436 53.456  0.346 1.00 25.91      C1
ATOM  2791 CB  ARG 423      41.098 54.943  0.312 1.00 24.39      C1
ATOM  2792 CG  ARG 423      40.167 55.366 -0.807 1.00 22.81      C1
ATOM  2793 CD  ARG 423      40.525 54.798 -2.172 1.00 25.55      C1
ATOM  2794 NE  ARG 423      39.707 55.387 -3.216 1.00 25.38      C1
ATOM  2795 HE  ARG 423      39.168 56.173 -2.989 1.00  0.00      C1
ATOM  2796 CZ  ARG 423      39.629 54.928 -4.466 1.00 27.32      C1
ATOM  2797 NH1 ARG 423      40.264 53.857 -4.949 1.00 26.37      C1
ATOM  2798 HH11 ARG 423     40.884 53.341 -4.365 1.00  0.00      C1
ATOM  2799 HH12 ARG 423     40.150 53.595 -5.907 1.00  0.00      C1
ATOM  2800 NH2 ARG 423      38.960 55.682 -5.325 1.00 30.38      C1
ATOM  2801 HH21 ARG 423     38.539 56.537 -5.023 1.00  0.00      C1
ATOM  2802 HH22 ARG 423     38.865 55.385 -6.275 1.00  0.00      C1
ATOM  2803 C   ARG 423      42.429 53.241  1.432 1.00 23.60      C1
ATOM  2804 O   ARG 423      43.594 53.147  1.127 1.00 24.37      C1
ATOM  2805 N   LYS 424      42.065 53.050  2.668 1.00 24.38      C1
ATOM  2806 H   LYS 424      41.109 53.051  2.890 1.00  0.00      C1
ATOM  2807 CA  LYS 424      43.043 52.855  3.722 1.00 25.12      C1
ATOM  2808 CB  LYS 424      42.352 52.791  5.051 1.00 23.89      C1
ATOM  2809 CG  LYS 424      43.312 52.936  6.190 1.00 28.56      C1
ATOM  2810 CD  LYS 424      42.579 52.580  7.486 1.00 35.51      C1
ATOM  2811 CE  LYS 424      41.338 53.425  7.853 1.00 40.33      C1
ATOM  2812 NZ  LYS 424      40.519 52.722  8.834 1.00 42.23      C1
ATOM  2813 HZ1 LYS 424      41.079 52.559  9.695 1.00  0.00      C1
ATOM  2814 HZ2 LYS 424      40.208 51.814  8.435 1.00  0.00      C1
ATOM  2815 HZ3 LYS 424      39.689 53.306  9.065 1.00  0.00      C1
ATOM  2816 C   LYS 424      43.761 51.547  3.462 1.00 27.10      C1
ATOM  2817 O   LYS 424      44.923 51.425  3.848 1.00 30.64      C1
ATOM  2818 N   ILE 425      43.190 50.542  2.794 1.00 26.83      C1
ATOM  2819 H   ILE 425      42.260 50.607  2.488 1.00  0.00      C1
ATOM  2820 CA  ILE 425      43.949 49.312  2.561 1.00 25.46      C1
ATOM  2821 CB  ILE 425      42.965 48.093  2.336 1.00 24.91      C1
ATOM  2822 CG2 ILE 425      43.654 46.786  1.995 1.00 22.01      C1
ATOM  2823 CG1 ILE 425      42.229 47.909  3.633 1.00 25.34      C1
ATOM  2824 CD  ILE 425      40.885 47.169  3.432 1.00 25.68      C1
ATOM  2825 C   ILE 425      44.824 49.549  1.346 1.00 23.84      C1
ATOM  2826 O   ILE 425      45.959 49.069  1.316 1.00 24.57      C1
ATOM  2827 N   GLN 426      44.361 50.267  0.323 1.00 23.28      C1
ATOM  2828 H   GLN 426      43.451 50.630  0.393 1.00  0.00      C1
ATOM  2829 CA  GLN 426      45.164 50.531 -0.871 1.00 24.13      C1
ATOM  2830 CB  GLN 426      44.421 51.344 -1.896 1.00 24.04      C1
ATOM  2831 CG  GLN 426      43.275 50.539 -2.396 1.00 23.56      C1
ATOM  2832 CD  GLN 426      42.446 51.105 -3.511 1.00 23.92      C1
ATOM  2833 OE1 GLN 426      41.704 52.047 -3.345 1.00 25.34      C1
ATOM  2834 NE2 GLN 426      42.337 50.509 -4.672 1.00 27.55      C1
ATOM  2835 HE21 GLN 426     41.755 50.948 -5.323 1.00  0.00      C1
ATOM  2836 HE22 GLN 426     42.850 49.696 -4.851 1.00  0.00      C1
ATOM  2837 C   GLN 426      46.404 51.312 -0.488 1.00 26.69      C1
```

FIG.5-34

| | | | | | | | | | |
|---|---|---|---|---|---|---|---|---|---|
| ATOM | 2838 | O | GLN | 426 | 47.486 | 51.109 | -1.046 | 1.00 29.73 | C1 |
| ATOM | 2839 | N | GLY | 427 | 46.300 | 52.204 | 0.499 | 1.00 26.49 | C1 |
| ATOM | 2840 | H | GLY | 427 | 45.410 | 52.414 | 0.854 | 1.00 0.00 | C1 |
| ATOM | 2841 | CA | GLY | 427 | 47.446 | 52.894 | 1.022 | 1.00 24.25 | C1 |
| ATOM | 2842 | C | GLY | 427 | 48.467 | 51.913 | 1.589 | 1.00 23.08 | C1 |
| ATOM | 2843 | O | GLY | 427 | 49.597 | 51.921 | 1.106 | 1.00 22.28 | C1 |
| ATOM | 2844 | N | ASP | 428 | 48.107 | 51.073 | 2.575 | 1.00 22.75 | C1 |
| ATOM | 2845 | H | ASP | 428 | 47.189 | 51.111 | 2.918 | 1.00 0.00 | C1 |
| ATOM | 2846 | CA | ASP | 428 | 49.039 | 50.108 | 3.131 | 1.00 23.87 | C1 |
| ATOM | 2847 | CB | ASP | 428 | 48.415 | 49.199 | 4.117 | 1.00 26.52 | C1 |
| ATOM | 2848 | CG | ASP | 428 | 47.437 | 49.779 | 5.097 | 1.00 28.84 | C1 |
| ATOM | 2849 | OD1 | ASP | 428 | 46.420 | 49.151 | 5.265 | 1.00 31.81 | C1 |
| ATOM | 2850 | OD2 | ASP | 428 | 47.662 | 50.804 | 5.716 | 1.00 30.77 | C1 |
| ATOM | 2851 | C | ASP | 428 | 49.626 | 49.191 | 2.063 | 1.00 24.16 | C1 |
| ATOM | 2852 | O | ASP | 428 | 50.812 | 48.896 | 2.088 | 1.00 26.17 | C1 |
| ATOM | 2853 | N | GLY | 429 | 48.840 | 48.822 | 1.069 | 1.00 23.01 | C1 |
| ATOM | 2854 | H | GLY | 429 | 47.905 | 49.113 | 1.071 | 1.00 0.00 | C1 |
| ATOM | 2855 | CA | GLY | 429 | 49.289 | 47.964 | 0.029 | 1.00 25.44 | C1 |
| ATOM | 2856 | C | GLY | 429 | 50.405 | 48.649 | -0.716 | 1.00 27.39 | C1 |
| ATOM | 2857 | O | GLY | 429 | 51.528 | 48.135 | -0.741 | 1.00 28.51 | C1 |
| ATOM | 2858 | N | ALA | 430 | 50.127 | 49.840 | -1.271 | 1.00 28.26 | C1 |
| ATOM | 2859 | H | ALA | 430 | 49.216 | 50.185 | -1.172 | 1.00 0.00 | C1 |
| ATOM | 2860 | CA | ALA | 430 | 51.094 | 50.643 | -2.015 | 1.00 26.04 | C1 |
| ATOM | 2861 | CB | ALA | 430 | 50.490 | 51.976 | -2.407 | 1.00 27.93 | C1 |
| ATOM | 2862 | C | ALA | 430 | 52.300 | 50.927 | -1.133 | 1.00 25.19 | C1 |
| ATOM | 2863 | O | ALA | 430 | 53.393 | 51.053 | -1.655 | 1.00 25.43 | C1 |
| ATOM | 2864 | N | ALA | 431 | 52.171 | 50.979 | 0.186 | 1.00 24.05 | C1 |
| ATOM | 2865 | H | ALA | 431 | 51.279 | 50.872 | 0.579 | 1.00 0.00 | C1 |
| ATOM | 2866 | CA | ALA | 431 | 53.295 | 51.213 | 1.035 | 1.00 26.29 | C1 |
| ATOM | 2867 | CB | ALA | 431 | 52.874 | 51.522 | 2.458 | 1.00 24.14 | C1 |
| ATOM | 2868 | C | ALA | 431 | 54.139 | 49.972 | 1.073 | 1.00 29.82 | C1 |
| ATOM | 2869 | O | ALA | 431 | 55.360 | 50.085 | 0.959 | 1.00 31.97 | C1 |
| ATOM | 2870 | N | LEU | 432 | 53.562 | 48.777 | 1.203 | 1.00 31.87 | C1 |
| ATOM | 2871 | H | LEU | 432 | 52.585 | 48.726 | 1.279 | 1.00 0.00 | C1 |
| ATOM | 2872 | CA | LEU | 432 | 54.337 | 47.540 | 1.165 | 1.00 33.92 | C1 |
| ATOM | 2873 | CB | LEU | 432 | 53.430 | 46.315 | 1.301 | 1.00 37.42 | C1 |
| ATOM | 2874 | CG | LEU | 432 | 54.063 | 44.952 | 1.574 | 1.00 37.40 | C1 |
| ATOM | 2875 | CD1 | LEU | 432 | 54.751 | 44.949 | 2.950 | 1.00 38.10 | C1 |
| ATOM | 2876 | CD2 | LEU | 432 | 52.966 | 43.901 | 1.492 | 1.00 36.27 | C1 |
| ATOM | 2877 | C | LEU | 432 | 55.096 | 47.404 | -0.146 | 1.00 33.74 | C1 |
| ATOM | 2878 | O | LEU | 432 | 56.306 | 47.179 | -0.138 | 1.00 33.29 | C1 |
| ATOM | 2879 | N | GLN | 433 | 54.402 | 47.564 | -1.276 | 1.00 34.57 | C1 |
| ATOM | 2880 | H | GLN | 433 | 53.439 | 47.733 | -1.186 | 1.00 0.00 | C1 |
| ATOM | 2881 | CA | GLN | 433 | 55.002 | 47.526 | -2.600 | 1.00 35.83 | C1 |
| ATOM | 2882 | CB | GLN | 433 | 53.999 | 47.892 | -3.664 | 1.00 35.52 | C1 |
| ATOM | 2883 | CG | GLN | 433 | 52.996 | 46.823 | -3.832 | 1.00 39.40 | C1 |
| ATOM | 2884 | CD | GLN | 433 | 52.049 | 47.097 | -4.973 | 1.00 42.46 | C1 |
| ATOM | 2885 | OE1 | GLN | 433 | 50.924 | 47.526 | -4.786 | 1.00 48.22 | C1 |
| ATOM | 2886 | NE2 | GLN | 433 | 52.376 | 46.878 | -6.225 | 1.00 44.77 | C1 |
| ATOM | 2887 | HE21 | GLN | 433 | 53.271 | 46.540 | -6.433 | 1.00 0.00 | C1 |
| ATOM | 2888 | HE22 | GLN | 433 | 51.693 | 47.087 | -6.892 | 1.00 0.00 | C1 |
| ATOM | 2889 | C | GLN | 433 | 56.177 | 48.485 | -2.757 | 1.00 36.48 | C1 |
| ATOM | 2890 | O | GLN | 433 | 57.214 | 48.118 | -3.312 | 1.00 38.08 | C1 |
| ATOM | 2891 | N | GLU | 434 | 56.055 | 49.719 | -2.287 | 1.00 36.11 | C1 |
| ATOM | 2892 | H | GLU | 434 | 55.210 | 49.978 | -1.854 | 1.00 0.00 | C1 |
| ATOM | 2893 | CA | GLU | 434 | 57.089 | 50.719 | -2.426 | 1.00 35.93 | C1 |
| ATOM | 2894 | CB | GLU | 434 | 56.408 | 52.030 | -2.068 | 1.00 41.28 | C1 |
| ATOM | 2895 | CG | GLU | 434 | 57.126 | 53.356 | -2.019 | 1.00 43.07 | C1 |
| ATOM | 2896 | CD | GLU | 434 | 57.832 | 53.516 | -0.698 | 1.00 45.70 | C1 |
| ATOM | 2897 | OE1 | GLU | 434 | 57.190 | 53.538 | 0.367 | 1.00 49.33 | C1 |
| ATOM | 2898 | OE2 | GLU | 434 | 59.051 | 53.579 | -0.760 | 1.00 45.45 | C1 |
| ATOM | 2899 | C | GLU | 434 | 58.257 | 50.348 | -1.548 | 1.00 34.00 | C1 |
| ATOM | 2900 | O | GLU | 434 | 59.388 | 50.481 | -1.983 | 1.00 32.93 | C1 |
| ATOM | 2901 | N | LYS | 435 | 58.067 | 49.860 | -0.330 | 1.00 34.34 | C1 |
| ATOM | 2902 | H | LYS | 435 | 57.146 | 49.837 | 0.014 | 1.00 0.00 | C1 |
| ATOM | 2903 | CA | LYS | 435 | 59.151 | 49.358 | 0.511 | 1.00 34.56 | C1 |
| ATOM | 2904 | CB | LYS | 435 | 58.577 | 49.010 | 1.847 | 1.00 33.89 | C1 |
| ATOM | 2905 | CG | LYS | 435 | 58.357 | 50.231 | 2.709 | 1.00 36.71 | C1 |
| ATOM | 2906 | CD | LYS | 435 | 58.244 | 49.748 | 4.137 | 1.00 40.31 | C1 |
| ATOM | 2907 | CE | LYS | 435 | 58.293 | 50.861 | 5.213 | 1.00 45.32 | C1 |
| ATOM | 2908 | NZ | LYS | 435 | 58.494 | 50.325 | 6.575 | 1.00 47.31 | C1 |
| ATOM | 2909 | HZ1 | LYS | 435 | 59.388 | 49.795 | 6.611 | 1.00 0.00 | C1 |
| ATOM | 2910 | HZ2 | LYS | 435 | 57.708 | 49.689 | 6.818 | 1.00 0.00 | C1 |
| ATOM | 2911 | HZ3 | LYS | 435 | 58.534 | 51.109 | 7.257 | 1.00 0.00 | C1 |
| ATOM | 2912 | C | LYS | 435 | 59.906 | 48.135 | -0.065 | 1.00 36.10 | C1 |
| ATOM | 2913 | O | LYS | 435 | 61.139 | 48.036 | -0.012 | 1.00 37.08 | C1 |
| ATOM | 2914 | N | LEU | 436 | 59.215 | 47.168 | -0.665 | 1.00 36.28 | C1 |
| ATOM | 2915 | H | LEU | 436 | 58.235 | 47.245 | -0.651 | 1.00 0.00 | C1 |
| ATOM | 2916 | CA | LEU | 436 | 59.793 | 45.994 | -1.304 | 1.00 34.25 | C1 |
| ATOM | 2917 | CB | LEU | 436 | 58.655 | 45.076 | -1.753 | 1.00 33.41 | C1 |
| ATOM | 2918 | CG | LEU | 436 | 57.920 | 44.327 | -0.610 | 1.00 34.72 | C1 |
| ATOM | 2919 | CD1 | LEU | 436 | 56.764 | 43.538 | -1.181 | 1.00 33.50 | C1 |
| ATOM | 2920 | CD2 | LEU | 436 | 58.880 | 43.375 | 0.117 | 1.00 36.39 | C1 |
| ATOM | 2921 | C | LEU | 436 | 60.669 | 46.383 | -2.467 | 1.00 33.31 | C1 |
| ATOM | 2922 | O | LEU | 436 | 61.756 | 45.825 | -2.647 | 1.00 33.94 | C1 |
| ATOM | 2923 | N | CYS | 437 | 60.220 | 47.374 | -3.222 | 1.00 32.34 | C1 |

FIG.5-35

| ATOM | 2924 | H | CYS | 437 | 59.290 | 47.661 | -3.097 | 1.00 | 0.00 | | ATOM | 2967 | HZ1 | LYS | 441 | 65.568 | 49.549 | -4.506 | 1.00 | 0.00 | C1 |
|------|------|---|-----|-----|--------|--------|--------|------|------|---|------|------|---|-----|-----|--------|--------|--------|------|------|-----|
| ATOM | 2925 | CA | CYS | 437 | 60.978 | 47.949 | -4.301 | 1.00 | 32.01 | C1 | ATOM | 2968 | HZ2 | LYS | 441 | 65.885 | 49.525 | -6.173 | 1.00 | 0.00 | C1 |
| ATOM | 2926 | C | CYS | 437 | 62.214 | 48.704 | -3.857 | 1.00 | 34.70 | C1 | ATOM | 2969 | HZ3 | LYS | 441 | 66.468 | 50.801 | -5.219 | 1.00 | 0.00 | C1 |
| ATOM | 2927 | O | CYS | 437 | 63.313 | 48.599 | -4.412 | 1.00 | 36.26 | C1 | ATOM | 2970 | C | LYS | 441 | 63.629 | 45.015 | -6.425 | 1.00 | 28.86 | C1 |
| ATOM | 2928 | CB | CYS | 437 | 60.094 | 48.840 | -5.008 | 1.00 | 30.97 | C1 | ATOM | 2971 | O | LYS | 441 | 63.791 | 44.688 | -7.603 | 1.00 | 29.95 | C1 |
| ATOM | 2929 | SG | CYS | 437 | 61.003 | 49.666 | -6.319 | 1.00 | 36.22 | C1 | ATOM | 2972 | N | LEU | 442 | 62.556 | 44.601 | -5.749 | 1.00 | 27.58 | C1 |
| ATOM | 2930 | N | ALA | 438 | 62.016 | 49.463 | -2.785 | 1.00 | 36.35 | C1 | ATOM | 2973 | H | LEU | 442 | 62.392 | 44.924 | -4.837 | 1.00 | 0.00 | C1 |
| ATOM | 2931 | H | ALA | 438 | 61.108 | 49.547 | -2.431 | 1.00 | 0.00 | C1 | ATOM | 2974 | CA | LEU | 442 | 61.554 | 43.780 | -6.402 | 1.00 | 28.82 | C1 |
| ATOM | 2932 | CA | ALA | 438 | 63.060 | 50.226 | -2.170 | 1.00 | 35.83 | C1 | ATOM | 2975 | CB | LEU | 442 | 60.947 | 42.694 | -5.466 | 1.00 | 26.98 | C1 |
| ATOM | 2933 | CB | ALA | 438 | 62.440 | 51.107 | -1.153 | 1.00 | 36.38 | C1 | ATOM | 2976 | CG | LEU | 442 | 61.905 | 41.634 | -4.847 | 1.00 | 27.75 | C1 |
| ATOM | 2934 | C | ALA | 438 | 64.065 | 49.294 | -1.527 | 1.00 | 37.01 | C1 | ATOM | 2977 | CD1 | LEU | 442 | 61.133 | 40.643 | -4.009 | 1.00 | 24.29 | C1 |
| ATOM | 2935 | O | ALA | 438 | 65.132 | 49.168 | -2.092 | 1.00 | 39.39 | C1 | ATOM | 2978 | CD2 | LEU | 442 | 62.667 | 40.932 | -5.963 | 1.00 | 19.72 | C1 |
| ATOM | 2936 | N | THR | 439 | 63.808 | 48.591 | -0.422 | 1.00 | 36.59 | C1 | ATOM | 2979 | C | LEU | 442 | 60.575 | 44.892 | -6.635 | 1.00 | 30.59 | C1 |
| ATOM | 2937 | H | THR | 439 | 62.947 | 48.723 | 0.014 | 1.00 | 0.00 | C1 | ATOM | 2980 | O | LEU | 442 | 59.811 | 45.261 | -5.741 | 1.00 | 32.36 | C1 |
| ATOM | 2938 | CA | THR | 439 | 64.742 | 47.669 | 0.223 | 1.00 | 35.70 | C1 | ATOM | 2981 | N | CYS | 443 | 60.700 | 45.506 | -7.804 | 1.00 | 32.15 | C1 |
| ATOM | 2939 | CB | THR | 439 | 64.073 | 47.042 | 1.400 | 1.00 | 35.34 | C1 | ATOM | 2982 | H | CYS | 443 | 61.423 | 45.199 | -8.389 | 1.00 | 0.00 | C1 |
| ATOM | 2940 | OG1 | THR | 439 | 63.323 | 48.048 | 2.040 | 1.00 | 38.31 | C1 | ATOM | 2983 | CA | CYS | 443 | 59.866 | 46.645 | -8.191 | 1.00 | 32.69 | C1 |
| ATOM | 2941 | HG1 | THR | 439 | 62.419 | 47.999 | 1.706 | 1.00 | 0.00 | C1 | ATOM | 2984 | C | CYS | 443 | 58.807 | 46.380 | -9.217 | 1.00 | 33.43 | C1 |
| ATOM | 2942 | CG2 | THR | 439 | 65.039 | 46.479 | 2.369 | 1.00 | 36.50 | C1 | ATOM | 2985 | O | CYS | 443 | 58.051 | 47.288 | -9.465 | 1.00 | 34.10 | C1 |
| ATOM | 2943 | C | THR | 439 | 65.331 | 46.517 | -0.590 | 1.00 | 36.10 | C1 | ATOM | 2986 | CB | CYS | 443 | 60.715 | 47.800 | -8.743 | 1.00 | 30.74 | C1 |
| ATOM | 2944 | O | THR | 439 | 66.448 | 46.093 | -0.312 | 1.00 | 36.51 | C1 | ATOM | 2987 | SG | CYS | 443 | 61.938 | 48.345 | -7.519 | 1.00 | 32.96 | C1 |
| ATOM | 2945 | N | TYR | 440 | 64.603 | 45.917 | -1.548 | 1.00 | 36.02 | C1 | ATOM | 2988 | N | HIS | 444 | 58.649 | 45.260 | -9.911 | 1.00 | 35.65 | C1 |
| ATOM | 2946 | H | TYR | 440 | 63.751 | 46.319 | -1.822 | 1.00 | 0.00 | C1 | ATOM | 2989 | H | HIS | 444 | 59.147 | 44.445 | -9.659 | 1.00 | 0.00 | C1 |
| ATOM | 2947 | CA | TYR | 440 | 65.057 | 44.691 | -2.198 | 1.00 | 34.28 | C1 | ATOM | 2990 | CA | HIS | 444 | 57.662 | 45.172 | -10.975 | 1.00 | 37.75 | C1 |
| ATOM | 2948 | CB | TYR | 440 | 64.175 | 43.480 | -1.878 | 1.00 | 33.99 | C1 | ATOM | 2991 | CB | HIS | 444 | 58.329 | 45.224 | -12.330 | 1.00 | 37.09 | C1 |
| ATOM | 2949 | CG | TYR | 440 | 64.016 | 43.240 | -0.397 | 1.00 | 34.14 | C1 | ATOM | 2992 | CG | HIS | 444 | 59.149 | 46.476 | -12.560 | 1.00 | 41.36 | C1 |
| ATOM | 2950 | CD1 | TYR | 440 | 62.773 | 43.230 | 0.169 | 1.00 | 35.16 | C1 | ATOM | 2993 | CD2 | HIS | 444 | 60.434 | 46.664 | -12.075 | 1.00 | 41.40 | C1 |
| ATOM | 2951 | CE1 | TYR | 440 | 62.625 | 43.037 | 1.532 | 1.00 | 36.66 | C1 | ATOM | 2994 | ND1 | HIS | 444 | 58.811 | 47.563 | -13.261 | 1.00 | 41.74 | C1 |
| ATOM | 2952 | CD2 | TYR | 440 | 65.126 | 43.064 | 0.385 | 1.00 | 37.83 | C1 | ATOM | 2995 | HD1 | HIS | 444 | 57.892 | 47.890 | -13.410 | 1.00 | 0.00 | C1 |
| ATOM | 2953 | CE2 | TYR | 440 | 64.992 | 42.881 | 1.752 | 1.00 | 39.02 | C1 | ATOM | 2996 | CE1 | HIS | 444 | 59.850 | 48.372 | -13.217 | 1.00 | 42.00 | C1 |
| ATOM | 2954 | CZ | TYR | 440 | 63.741 | 42.864 | 2.317 | 1.00 | 37.34 | C1 | ATOM | 2997 | NE2 | HIS | 444 | 60.817 | 47.832 | -12.502 | 1.00 | 41.38 | C1 |
| ATOM | 2955 | OH | TYR | 440 | 63.637 | 42.649 | 3.678 | 1.00 | 37.56 | C1 | ATOM | 2998 | HE2 | HIS | 444 | 61.690 | 48.248 | -12.334 | 1.00 | 0.00 | C1 |
| ATOM | 2956 | HH | TYR | 440 | 64.498 | 42.343 | 3.988 | 1.00 | 0.00 | C1 | ATOM | 2999 | C | HIS | 444 | 56.889 | 43.871 | -10.878 | 1.00 | 40.10 | C1 |
| ATOM | 2957 | C | TYR | 440 | 65.088 | 44.768 | -3.681 | 1.00 | 34.07 | C1 | ATOM | 3000 | O | HIS | 444 | 57.461 | 42.867 | -11.309 | 1.00 | 40.15 | C1 |
| ATOM | 2958 | O | TYR | 440 | 65.598 | 43.823 | -4.267 | 1.00 | 35.54 | C1 | ATOM | 3001 | N | PRO | 445 | 55.615 | 43.752 | -10.406 | 1.00 | 42.06 | C1 |
| ATOM | 2959 | N | LYS | 441 | 64.627 | 45.833 | -4.330 | 1.00 | 33.18 | C1 | ATOM | 3002 | CD | PRO | 445 | 54.738 | 44.836 | -9.937 | 1.00 | 41.56 | C1 |
| ATOM | 2960 | H | LYS | 441 | 64.345 | 46.623 | -3.822 | 1.00 | 0.00 | C1 | ATOM | 3003 | CA | PRO | 445 | 54.913 | 42.497 | -10.276 | 1.00 | 40.90 | C1 |
| ATOM | 2961 | CA | LYS | 441 | 64.595 | 45.957 | -5.763 | 1.00 | 30.44 | C1 | ATOM | 3004 | CB | PRO | 445 | 53.569 | 42.882 | -9.730 | 1.00 | 39.35 | C1 |
| ATOM | 2962 | CB | LYS | 441 | 65.983 | 45.759 | -6.364 | 1.00 | 33.76 | C1 | ATOM | 3005 | CG | PRO | 445 | 53.364 | 44.274 | -10.215 | 1.00 | 39.35 | C1 |
| ATOM | 2963 | CG | LYS | 441 | 66.729 | 47.080 | -6.407 | 1.00 | 39.59 | C1 | ATOM | 3006 | C | PRO | 445 | 54.868 | 41.782 | -11.600 | 1.00 | 42.18 | C1 |
| ATOM | 2964 | CD | LYS | 441 | 67.273 | 47.497 | -5.045 | 1.00 | 47.69 | C1 | ATOM | 3007 | O | PRO | 445 | 54.769 | 40.571 | -11.569 | 1.00 | 45.69 | C1 |
| ATOM | 2965 | CE | LYS | 441 | 67.503 | 49.028 | -4.984 | 1.00 | 53.37 | C1 | ATOM | 3008 | N | GLU | 446 | 55.082 | 42.380 | -12.769 | 1.00 | 41.64 | C1 |
| ATOM | 2966 | NZ | LYS | 441 | 66.267 | 49.780 | -5.240 | 1.00 | 57.64 | C1 | ATOM | 3009 | H | GLU | 446 | 55.320 | 43.320 | -12.761 | 1.00 | 0.00 | C1 |

FIG.5-36

| | | | | | | | | |
|---|---|---|---|---|---|---|---|---|
| ATOM | 3010 | CA | GLU | 446 | 55.025 | 41.656 | -14.029 | 1.00 42.05 | C1 |
| ATOM | 3011 | CB | GLU | 446 | 54.967 | 42.639 | -15.183 | 1.00 47.06 | C1 |
| ATOM | 3012 | CG | GLU | 446 | 54.109 | 43.925 | -14.992 | 1.00 56.71 | C1 |
| ATOM | 3013 | CD | GLU | 446 | 54.728 | 45.083 | -14.162 | 1.00 62.28 | C1 |
| ATOM | 3014 | OE1 | GLU | 446 | 54.100 | 45.472 | -13.178 | 1.00 66.26 | C1 |
| ATOM | 3015 | OE2 | GLU | 446 | 55.818 | 45.604 | -14.473 | 1.00 65.55 | C1 |
| ATOM | 3016 | C | GLU | 446 | 56.237 | 40.722 | -14.197 | 1.00 40.44 | C1 |
| ATOM | 3017 | O | GLU | 446 | 56.186 | 39.708 | -14.904 | 1.00 41.66 | C1 |
| ATOM | 3018 | N | GLU | 447 | 57.360 | 40.995 | -13.538 | 1.00 37.89 | C1 |
| ATOM | 3019 | H | GLU | 447 | 57.394 | 41.809 | -12.999 | 1.00 0.00 | C1 |
| ATOM | 3020 | CA | GLU | 447 | 58.519 | 40.096 | -13.509 | 1.00 36.73 | C1 |
| ATOM | 3021 | CB | GLU | 447 | 59.750 | 40.810 | -12.976 | 1.00 34.60 | C1 |
| ATOM | 3022 | CG | GLU | 447 | 60.320 | 41.883 | -13.850 | 1.00 35.27 | C1 |
| ATOM | 3023 | CD | GLU | 447 | 61.450 | 42.699 | -13.197 | 1.00 36.14 | C1 |
| ATOM | 3024 | OE1 | GLU | 447 | 62.240 | 43.286 | -13.939 | 1.00 37.31 | C1 |
| ATOM | 3025 | OE2 | GLU | 447 | 61.541 | 42.782 | -11.970 | 1.00 32.80 | C1 |
| ATOM | 3026 | C | GLU | 447 | 58.311 | 38.850 | -12.599 | 1.00 36.31 | C1 |
| ATOM | 3027 | O | GLU | 447 | 59.113 | 37.911 | -12.592 | 1.00 36.33 | C1 |
| ATOM | 3028 | N | LEU | 448 | 57.273 | 38.763 | -11.769 | 1.00 33.81 | C1 |
| ATOM | 3029 | H | LEU | 448 | 56.554 | 39.431 | -11.802 | 1.00 0.00 | C1 |
| ATOM | 3030 | CA | LEU | 448 | 57.145 | 37.691 | -10.839 | 1.00 31.88 | C1 |
| ATOM | 3031 | CB | LEU | 448 | 57.080 | 38.299 | -9.484 | 1.00 29.29 | C1 |
| ATOM | 3032 | CG | LEU | 448 | 58.008 | 39.432 | -9.140 | 1.00 29.81 | C1 |
| ATOM | 3033 | CD1 | LEU | 448 | 57.907 | 39.863 | -7.684 | 1.00 26.02 | C1 |
| ATOM | 3034 | CD2 | LEU | 448 | 59.396 | 38.931 | -9.392 | 1.00 31.13 | C1 |
| ATOM | 3035 | C | LEU | 448 | 55.863 | 36.977 | -11.165 | 1.00 33.75 | C1 |
| ATOM | 3036 | O | LEU | 448 | 55.436 | 36.145 | -10.382 | 1.00 33.96 | C1 |
| ATOM | 3037 | N | VAL | 449 | 55.166 | 37.233 | -12.263 | 1.00 36.99 | C1 |
| ATOM | 3038 | H | VAL | 449 | 55.580 | 37.800 | -12.942 | 1.00 0.00 | C1 |
| ATOM | 3039 | CA | VAL | 449 | 53.819 | 36.701 | -12.472 | 1.00 41.46 | C1 |
| ATOM | 3040 | CB | VAL | 449 | 53.157 | 37.546 | -13.625 | 1.00 41.56 | C1 |
| ATOM | 3041 | CG1 | VAL | 449 | 54.002 | 37.614 | -14.880 | 1.00 42.22 | C1 |
| ATOM | 3042 | CG2 | VAL | 449 | 51.921 | 36.858 | -14.112 | 1.00 42.01 | C1 |
| ATOM | 3043 | C | VAL | 449 | 53.760 | 35.192 | -12.733 | 1.00 44.81 | C1 |
| ATOM | 3044 | O | VAL | 449 | 52.866 | 34.469 | -12.227 | 1.00 44.54 | C1 |
| ATOM | 3045 | N | LEU | 450 | 54.716 | 34.669 | -13.515 | 1.00 47.21 | C1 |
| ATOM | 3046 | H | LEU | 450 | 55.416 | 35.260 | -13.870 | 1.00 0.00 | C1 |
| ATOM | 3047 | CA | LEU | 450 | 54.771 | 33.243 | -13.781 | 1.00 50.57 | C1 |
| ATOM | 3048 | CB | LEU | 450 | 55.942 | 32.894 | -14.628 | 1.00 50.75 | C1 |
| ATOM | 3049 | CG | LEU | 450 | 56.148 | 33.488 | -15.994 | 1.00 52.39 | C1 |
| ATOM | 3050 | CD1 | LEU | 450 | 57.152 | 32.586 | -16.673 | 1.00 53.05 | C1 |
| ATOM | 3051 | CD2 | LEU | 450 | 54.882 | 33.534 | -16.833 | 1.00 54.10 | C1 |
| ATOM | 3052 | C | LEU | 450 | 54.911 | 32.468 | -12.471 | 1.00 53.83 | C1 |
| ATOM | 3053 | O | LEU | 450 | 54.297 | 31.406 | -12.266 | 1.00 55.62 | C1 |
| ATOM | 3054 | N | LEU | 451 | 55.685 | 33.097 | -11.575 | 1.00 55.46 | C1 |
| ATOM | 3055 | H | LEU | 451 | 56.073 | 33.954 | -11.849 | 1.00 0.00 | C1 |
| ATOM | 3056 | CA | LEU | 451 | 55.998 | 32.654 | -10.223 | 1.00 56.01 | C1 |
| ATOM | 3057 | CB | LEU | 451 | 57.137 | 33.542 | -9.731 | 1.00 55.80 | C1 |
| ATOM | 3058 | CG | LEU | 451 | 57.745 | 33.278 | -8.394 | 1.00 56.96 | C1 |
| ATOM | 3059 | CD1 | LEU | 451 | 58.833 | 32.284 | -8.653 | 1.00 59.12 | C1 |
| ATOM | 3060 | CD2 | LEU | 451 | 58.369 | 34.511 | -7.751 | 1.00 58.27 | C1 |
| ATOM | 3061 | C | LEU | 451 | 54.785 | 32.700 | -9.280 | 1.00 55.96 | C1 |
| ATOM | 3062 | O | LEU | 451 | 54.717 | 31.935 | -8.319 | 1.00 53.74 | C1 |
| ATOM | 3063 | N | GLY | 452 | 53.774 | 33.533 | -9.522 | 1.00 57.52 | C1 |
| ATOM | 3064 | H | GLY | 452 | 53.889 | 34.241 | -10.191 | 1.00 0.00 | C1 |
| ATOM | 3065 | CA | GLY | 452 | 52.567 | 33.515 | -8.710 | 1.00 60.66 | C1 |
| ATOM | 3066 | C | GLY | 452 | 51.942 | 32.137 | -8.772 | 1.00 63.64 | C1 |
| ATOM | 3067 | O | GLY | 452 | 51.476 | 31.593 | -7.782 | 1.00 62.60 | C1 |
| ATOM | 3068 | N | HIS | 453 | 52.089 | 31.545 | -9.969 | 1.00 68.46 | C1 |
| ATOM | 3069 | H | HIS | 453 | 52.628 | 32.040 | -10.618 | 1.00 0.00 | C1 |
| ATOM | 3070 | CA | HIS | 453 | 51.606 | 30.205 | -10.326 | 1.00 72.27 | C1 |
| ATOM | 3071 | CB | HIS | 453 | 51.785 | 29.908 | -11.828 | 1.00 73.84 | C1 |
| ATOM | 3072 | CG | HIS | 453 | 51.421 | 31.061 | -12.777 | 1.00 77.81 | C1 |
| ATOM | 3073 | CD2 | HIS | 453 | 50.599 | 32.148 | -12.498 | 1.00 79.29 | C1 |
| ATOM | 3074 | ND1 | HIS | 453 | 51.886 | 31.244 | -14.012 | 1.00 79.84 | C1 |
| ATOM | 3075 | HD1 | HIS | 453 | 52.617 | 30.739 | -14.425 | 1.00 0.00 | C1 |
| ATOM | 3076 | CE1 | HIS | 453 | 51.385 | 32.382 | -14.470 | 1.00 81.11 | C1 |
| ATOM | 3077 | NE2 | HIS | 453 | 50.613 | 32.923 | -13.551 | 1.00 79.85 | C1 |
| ATOM | 3078 | HE2 | HIS | 453 | 50.230 | 33.825 | -13.586 | 1.00 0.00 | C1 |
| ATOM | 3079 | C | HIS | 453 | 52.454 | 29.235 | -9.515 | 1.00 73.43 | C1 |
| ATOM | 3080 | O | HIS | 453 | 51.875 | 28.531 | -8.692 | 1.00 73.56 | C1 |
| ATOM | 3081 | N | SER | 454 | 53.785 | 29.207 | -9.651 | 1.00 74.64 | C1 |
| ATOM | 3082 | H | SER | 454 | 54.214 | 29.739 | -10.351 | 1.00 0.00 | C1 |
| ATOM | 3083 | CA | SER | 454 | 54.639 | 28.411 | -8.765 | 1.00 77.07 | C1 |
| ATOM | 3084 | CB | SER | 454 | 56.123 | 28.762 | -8.980 | 1.00 77.34 | C1 |
| ATOM | 3085 | OG | SER | 454 | 57.095 | 27.715 | -9.124 | 1.00 75.28 | C1 |
| ATOM | 3086 | HG | SER | 454 | 57.149 | 27.211 | -8.306 | 1.00 0.00 | C1 |
| ATOM | 3087 | C | SER | 454 | 54.332 | 28.608 | -7.262 | 1.00 78.84 | C1 |
| ATOM | 3088 | O | SER | 454 | 54.270 | 27.617 | -6.535 | 1.00 80.57 | C1 |
| ATOM | 3089 | N | LEU | 455 | 54.070 | 29.789 | -6.693 | 1.00 79.72 | C1 |
| ATOM | 3090 | H | LEU | 455 | 53.956 | 30.582 | -7.250 | 1.00 0.00 | C1 |
| ATOM | 3091 | CA | LEU | 455 | 53.849 | 29.915 | -5.257 | 1.00 80.43 | C1 |
| ATOM | 3092 | CB | LEU | 455 | 54.085 | 31.347 | -4.838 | 1.00 80.20 | C1 |
| ATOM | 3093 | CG | LEU | 455 | 55.389 | 31.981 | -5.269 | 1.00 81.67 | C1 |
| ATOM | 3094 | CD1 | LEU | 455 | 55.254 | 33.494 | -5.419 | 1.00 81.36 | C1 |
| ATOM | 3095 | CD2 | LEU | 455 | 56.431 | 31.579 | -4.264 | 1.00 82.26 | C1 |

FIG.5-37

| ATOM | 3096 | C   | LEU | 455 | 52.438 | 29.510 | -4.848  | 1.00 | 81.56 | C1 |
|------|------|-----|-----|-----|--------|--------|---------|------|-------|----|
| ATOM | 3097 | O   | LEU | 455 | 52.038 | 29.893 | -3.741  | 1.00 | 82.22 | C1 |
| ATOM | 3098 | N   | GLY | 456 | 51.653 | 28.816 | -5.708  | 1.00 | 81.89 | C1 |
| ATOM | 3099 | H   | GLY | 456 | 52.026 | 28.592 | -6.584  | 1.00 | 0.00  | C1 |
| ATOM | 3100 | CA  | GLY | 456 | 50.269 | 28.361 | -5.467  | 1.00 | 82.22 | C1 |
| ATOM | 3101 | C   | GLY | 456 | 49.220 | 29.386 | -4.973  | 1.00 | 82.56 | C1 |
| ATOM | 3102 | O   | GLY | 456 | 48.268 | 28.989 | -4.276  | 1.00 | 82.38 | C1 |
| ATOM | 3103 | N   | ILE | 457 | 49.342 | 30.697 | -5.286  | 1.00 | 82.54 | C1 |
| ATOM | 3104 | H   | ILE | 457 | 50.075 | 30.942 | -5.894  | 1.00 | 0.00  | C1 |
| ATOM | 3105 | CA  | ILE | 457 | 48.435 | 31.761 | -4.824  | 1.00 | 81.63 | C1 |
| ATOM | 3106 | CB  | ILE | 457 | 49.110 | 33.157 | -5.086  | 1.00 | 80.69 | C1 |
| ATOM | 3107 | CG2 | ILE | 457 | 48.218 | 34.305 | -4.662  | 1.00 | 79.76 | C1 |
| ATOM | 3108 | CG1 | ILE | 457 | 50.369 | 33.275 | -4.253  | 1.00 | 79.82 | C1 |
| ATOM | 3109 | CD  | ILE | 457 | 51.506 | 33.868 | -5.081  | 1.00 | 77.89 | C1 |
| ATOM | 3110 | C   | ILE | 457 | 47.048 | 31.698 | -5.472  | 1.00 | 81.70 | C1 |
| ATOM | 3111 | O   | ILE | 457 | 46.903 | 31.761 | -6.700  | 1.00 | 82.57 | C1 |
| ATOM | 3112 | N   | PRO | 458 | 45.963 | 31.583 | -4.705  | 1.00 | 81.40 | C1 |
| ATOM | 3113 | CD  | PRO | 458 | 45.959 | 31.225 | -3.278  | 1.00 | 81.21 | C1 |
| ATOM | 3114 | CA  | PRO | 458 | 44.607 | 31.643 | -5.264  | 1.00 | 80.74 | C1 |
| ATOM | 3115 | CB  | PRO | 458 | 43.779 | 30.942 | -4.157  | 1.00 | 81.12 | C1 |
| ATOM | 3116 | CG  | PRO | 458 | 44.757 | 30.293 | -3.173  | 1.00 | 80.47 | C1 |
| ATOM | 3117 | C   | PRO | 458 | 44.120 | 33.063 | -5.648  | 1.00 | 79.70 | C1 |
| ATOM | 3118 | O   | PRO | 458 | 43.674 | 33.736 | -4.718  | 1.00 | 80.10 | C1 |
| ATOM | 3119 | N   | TRP | 459 | 44.171 | 33.662 | -6.861  | 1.00 | 78.19 | C1 |
| ATOM | 3120 | H   | TRP | 459 | 44.614 | 33.185 | -7.591  | 1.00 | 0.00  | C1 |
| ATOM | 3121 | CA  | TRP | 459 | 43.543 | 34.986 | -7.092  | 1.00 | 77.73 | C1 |
| ATOM | 3122 | CB  | TRP | 459 | 43.802 | 35.428 | -8.522  | 1.00 | 78.71 | C1 |
| ATOM | 3123 | CG  | TRP | 459 | 43.054 | 36.677 | -9.017  | 1.00 | 81.37 | C1 |
| ATOM | 3124 | CD2 | TRP | 459 | 41.802 | 36.771 | -9.618  | 1.00 | 82.89 | C1 |
| ATOM | 3125 | CE2 | TRP | 459 | 41.717 | 38.139 | -9.883  | 1.00 | 84.21 | C1 |
| ATOM | 3126 | CE3 | TRP | 459 | 40.738 | 35.960 | -9.983  | 1.00 | 84.28 | C1 |
| ATOM | 3127 | CD1 | TRP | 459 | 43.661 | 37.899 | -8.925  | 1.00 | 83.89 | C1 |
| ATOM | 3128 | NE1 | TRP | 459 | 42.828 | 38.765 | -9.460  | 1.00 | 85.23 | C1 |
| ATOM | 3129 | HE1 | TRP | 459 | 42.944 | 39.738 | -9.483  | 1.00 | 0.00  | C1 |
| ATOM | 3130 | CZ2 | TRP | 459 | 40.615 | 38.727 | -10.494 | 1.00 | 84.17 | C1 |
| ATOM | 3131 | CZ3 | TRP | 459 | 39.630 | 36.538 | -10.597 | 1.00 | 84.56 | C1 |
| ATOM | 3132 | CH2 | TRP | 459 | 39.562 | 37.904 | -10.852 | 1.00 | 84.83 | C1 |
| ATOM | 3133 | C   | TRP | 459 | 42.009 | 35.013 | -6.827  | 1.00 | 77.31 | C1 |
| ATOM | 3134 | O   | TRP | 459 | 41.202 | 34.244 | -7.376  | 1.00 | 76.38 | C1 |
| ATOM | 3135 | N   | ALA | 460 | 41.557 | 35.969 | -6.020  | 1.00 | 76.81 | C1 |
| ATOM | 3136 | H   | ALA | 460 | 42.187 | 36.640 | -5.689  | 1.00 | 0.00  | C1 |
| ATOM | 3137 | CA  | ALA | 460 | 40.158 | 36.044 | -5.613  | 1.00 | 76.44 | C1 |
| ATOM | 3138 | CB  | ALA | 460 | 40.072 | 36.724 | -4.243  | 1.00 | 75.51 | C1 |
| ATOM | 3139 | C   | ALA | 460 | 39.237 | 36.784 | -6.588  | 1.00 | 76.29 | C1 |
| ATOM | 3140 | O   | ALA | 460 | 39.449 | 37.976 | -6.833  | 1.00 | 76.98 | C1 |
| ATOM | 3141 | N   | PRO | 461 | 38.217 | 36.147 | -7.187  | 1.00 | 76.26 | C1 |
| ATOM | 3142 | CD  | PRO | 461 | 38.104 | 34.684 | -7.245  | 1.00 | 75.88 | C1 |
| ATOM | 3143 | CA  | PRO | 461 | 37.242 | 36.793 | -8.068  | 1.00 | 75.46 | C1 |
| ATOM | 3144 | CB  | PRO | 461 | 36.605 | 35.605 | -8.755  | 1.00 | 75.71 | C1 |
| ATOM | 3145 | CG  | PRO | 461 | 36.703 | 34.458 | -7.767  | 1.00 | 75.60 | C1 |
| ATOM | 3146 | C   | PRO | 461 | 36.221 | 37.803 | -7.545  | 1.00 | 75.72 | C1 |
| ATOM | 3147 | O   | PRO | 461 | 35.677 | 37.734 | -6.440  | 1.00 | 73.66 | C1 |
| ATOM | 3148 | N   | LEU | 462 | 35.996 | 38.767 | -8.449  | 1.00 | 77.19 | C1 |
| ATOM | 3149 | H   | LEU | 462 | 36.516 | 38.723 | -9.277  | 1.00 | 0.00  | C1 |
| ATOM | 3150 | CA  | LEU | 462 | 35.069 | 39.891 | -8.275  | 1.00 | 78.87 | C1 |
| ATOM | 3151 | CB  | LEU | 462 | 35.674 | 40.984 | -7.360  | 1.00 | 78.32 | C1 |
| ATOM | 3152 | CG  | LEU | 462 | 34.786 | 41.959 | -6.558  | 1.00 | 78.09 | C1 |
| ATOM | 3153 | CD1 | LEU | 462 | 34.051 | 42.987 | -7.406  | 1.00 | 78.32 | C1 |
| ATOM | 3154 | CD2 | LEU | 462 | 33.767 | 41.092 | -5.828  | 1.00 | 78.62 | C1 |
| ATOM | 3155 | C   | LEU | 462 | 34.701 | 40.565 | -9.611  | 1.00 | 80.63 | C1 |
| ATOM | 3156 | OT1 | LEU | 462 | 33.507 | 40.842 | -9.808  | 1.00 | 81.74 | C1 |
| ATOM | 3157 | OT2 | LEU | 462 | 35.606 | 40.847 | -10.417 | 1.00 | 81.39 | C1 |
| ATOM | 3158 | CB  | LEU | 472 | 22.074 | 42.654 | -1.426  | 1.00 | 62.24 | C2 |
| ATOM | 3159 | CG  | LEU | 472 | 22.278 | 44.145 | -1.189  | 1.00 | 59.98 | C2 |
| ATOM | 3160 | CD1 | LEU | 472 | 23.496 | 44.325 | -0.328  | 1.00 | 59.13 | C2 |
| ATOM | 3161 | CD2 | LEU | 472 | 22.501 | 44.883 | -2.486  | 1.00 | 56.85 | C2 |
| ATOM | 3162 | C   | LEU | 472 | 23.504 | 40.625 | -1.996  | 1.00 | 63.91 | C2 |
| ATOM | 3163 | O   | LEU | 472 | 23.738 | 39.874 | -2.949  | 1.00 | 64.90 | C2 |
| ATOM | 3164 | HT1 | LEU | 472 | 21.563 | 41.441 | -3.595  | 1.00 | 0.00  | C2 |
| ATOM | 3165 | HT2 | LEU | 472 | 23.091 | 41.291 | -4.237  | 1.00 | 0.00  | C2 |
| ATOM | 3166 | N   | LEU | 472 | 22.472 | 41.930 | -3.693  | 1.00 | 64.29 | C2 |
| ATOM | 3167 | HT3 | LEU | 472 | 22.358 | 42.849 | -4.160  | 1.00 | 0.00  | C2 |
| ATOM | 3168 | CA  | LEU | 472 | 23.092 | 42.037 | -2.386  | 1.00 | 63.85 | C2 |
| ATOM | 3169 | N   | ALA | 473 | 23.652 | 40.229 | -0.733  | 1.00 | 63.02 | C2 |
| ATOM | 3170 | H   | ALA | 473 | 23.533 | 40.867 | 0.002   | 1.00 | 0.00  | C2 |
| ATOM | 3171 | CA  | ALA | 473 | 24.023 | 38.881 | -0.353  | 1.00 | 62.37 | C2 |
| ATOM | 3172 | CB  | ALA | 473 | 22.870 | 37.939 | -0.558  | 1.00 | 63.65 | C2 |
| ATOM | 3173 | C   | ALA | 473 | 25.196 | 38.354 | -1.126  | 1.00 | 62.01 | C2 |
| ATOM | 3174 | O   | ALA | 473 | 26.301 | 38.651 | -0.715  | 1.00 | 63.36 | C2 |
| ATOM | 3175 | N   | GLY | 474 | 25.032 | 37.784 | -2.306  | 1.00 | 61.43 | C2 |
| ATOM | 3176 | H   | GLY | 474 | 24.148 | 37.818 | -2.722  | 1.00 | 0.00  | C2 |
| ATOM | 3177 | CA  | GLY | 474 | 26.101 | 37.137 | -3.047  | 1.00 | 63.80 | C2 |
| ATOM | 3178 | C   | GLY | 474 | 27.354 | 37.950 | -3.356  | 1.00 | 65.13 | C2 |
| ATOM | 3179 | O   | GLY | 474 | 28.482 | 37.417 | -3.257  | 1.00 | 66.24 | C2 |
| ATOM | 3180 | N   | CYS | 475 | 27.175 | 39.237 | -3.757  | 1.00 | 64.88 | C2 |
| ATOM | 3181 | H   | CYS | 475 | 26.261 | 39.550 | -3.885  | 1.00 | 0.00  | C2 |

FIG.5-38

| | | | | | | | | | | |
|---|---|---|---|---|---|---|---|---|---|---|
| ATOM | 3182 | CA | CYS | 475 | 28.308 | 40.127 | -4.068 | 1.00 | 61.84 | C2 |
| ATOM | 3183 | CB | CYS | 475 | 27.925 | 41.413 | -4.806 | 1.00 | 63.74 | C2 |
| ATOM | 3184 | SG | CYS | 475 | 29.494 | 42.075 | -5.437 | 1.00 | 68.86 | C2 |
| ATOM | 3185 | C | CYS | 475 | 28.995 | 40.567 | -2.795 | 1.00 | 57.30 | C2 |
| ATOM | 3186 | O | CYS | 475 | 30.214 | 40.449 | -2.724 | 1.00 | 57.14 | C2 |
| ATOM | 3187 | N | LEU | 476 | 28.230 | 40.983 | -1.779 | 1.00 | 53.29 | C2 |
| ATOM | 3188 | H | LEU | 476 | 27.264 | 41.024 | -1.885 | 1.00 | 0.00 | C2 |
| ATOM | 3189 | CA | LEU | 476 | 28.797 | 41.315 | -0.493 | 1.00 | 50.43 | C2 |
| ATOM | 3190 | CB | LEU | 476 | 27.719 | 41.723 | 0.523 | 1.00 | 45.68 | C2 |
| ATOM | 3191 | CG | LEU | 476 | 27.130 | 43.165 | 0.497 | 1.00 | 42.80 | C2 |
| ATOM | 3192 | CD1 | LEU | 476 | 26.670 | 43.559 | 1.896 | 1.00 | 36.25 | C2 |
| ATOM | 3193 | CD2 | LEU | 476 | 28.180 | 44.180 | 0.057 | 1.00 | 40.22 | C2 |
| ATOM | 3194 | C | LEU | 476 | 29.546 | 40.108 | 0.042 | 1.00 | 50.42 | C2 |
| ATOM | 3195 | O | LEU | 476 | 30.614 | 40.222 | 0.646 | 1.00 | 50.61 | C2 |
| ATOM | 3196 | N | SER | 477 | 29.053 | 38.922 | -0.270 | 1.00 | 50.62 | C2 |
| ATOM | 3197 | H | SER | 477 | 28.196 | 38.860 | -0.729 | 1.00 | 0.00 | C2 |
| ATOM | 3198 | CA | SER | 477 | 29.721 | 37.712 | 0.125 | 1.00 | 51.41 | C2 |
| ATOM | 3199 | CB | SER | 477 | 28.778 | 36.524 | -0.051 | 1.00 | 53.45 | C2 |
| ATOM | 3200 | OG | SER | 477 | 27.732 | 36.616 | 0.926 | 1.00 | 57.65 | C2 |
| ATOM | 3201 | HG | SER | 477 | 27.280 | 37.462 | 0.828 | 1.00 | 0.00 | C2 |
| ATOM | 3202 | C | SER | 477 | 30.978 | 37.525 | -0.681 | 1.00 | 50.75 | C2 |
| ATOM | 3203 | O | SER | 477 | 31.980 | 37.143 | -0.068 | 1.00 | 51.41 | C2 |
| ATOM | 3204 | N | GLN | 478 | 31.037 | 37.788 | -1.984 | 1.00 | 50.21 | C2 |
| ATOM | 3205 | H | GLN | 478 | 30.222 | 38.056 | -2.457 | 1.00 | 0.00 | C2 |
| ATOM | 3206 | CA | GLN | 478 | 32.307 | 37.697 | -2.715 | 1.00 | 51.37 | C2 |
| ATOM | 3207 | CB | GLN | 478 | 32.064 | 37.929 | -4.166 | 1.00 | 53.65 | C2 |
| ATOM | 3208 | CG | GLN | 478 | 31.983 | 36.570 | -4.788 | 1.00 | 57.32 | C2 |
| ATOM | 3209 | CD | GLN | 478 | 31.354 | 36.649 | -6.160 | 1.00 | 60.47 | C2 |
| ATOM | 3210 | OE1 | GLN | 478 | 31.999 | 36.504 | -7.205 | 1.00 | 62.26 | C2 |
| ATOM | 3211 | NE2 | GLN | 478 | 30.045 | 36.878 | -6.167 | 1.00 | 62.16 | C2 |
| ATOM | 3212 | HE21 | GLN | 478 | 29.569 | 36.972 | -5.317 | 1.00 | 0.00 | C2 |
| ATOM | 3213 | HE22 | GLN | 478 | 29.641 | 36.928 | -7.054 | 1.00 | 0.00 | C2 |
| ATOM | 3214 | C | GLN | 478 | 33.398 | 38.670 | -2.249 | 1.00 | 50.66 | C2 |
| ATOM | 3215 | O | GLN | 478 | 34.584 | 38.314 | -2.217 | 1.00 | 50.13 | C2 |
| ATOM | 3216 | N | LEU | 479 | 33.045 | 39.909 | -1.859 | 1.00 | 48.78 | C2 |
| ATOM | 3217 | H | LEU | 479 | 32.131 | 40.223 | -2.039 | 1.00 | 0.00 | C2 |
| ATOM | 3218 | CA | LEU | 479 | 34.015 | 40.800 | -1.235 | 1.00 | 45.87 | C2 |
| ATOM | 3219 | CB | LEU | 479 | 33.434 | 42.141 | -0.827 | 1.00 | 47.03 | C2 |
| ATOM | 3220 | CG | LEU | 479 | 32.853 | 43.083 | -1.818 | 1.00 | 49.40 | C2 |
| ATOM | 3221 | CD1 | LEU | 479 | 32.596 | 44.393 | -1.078 | 1.00 | 48.15 | C2 |
| ATOM | 3222 | CD2 | LEU | 479 | 33.779 | 43.258 | -3.000 | 1.00 | 48.59 | C2 |
| ATOM | 3223 | C | LEU | 479 | 34.505 | 40.146 | 0.056 | 1.00 | 42.13 | C2 |
| ATOM | 3224 | O | LEU | 479 | 35.695 | 39.955 | 0.262 | 1.00 | 40.90 | C2 |
| ATOM | 3225 | N | HIS | 480 | 33.609 | 39.766 | 0.950 | 1.00 | 39.56 | C2 |
| ATOM | 3226 | H | HIS | 480 | 32.658 | 39.935 | 0.763 | 1.00 | 0.00 | C2 |
| ATOM | 3227 | CA | HIS | 480 | 33.979 | 39.108 | 2.179 | 1.00 | 37.81 | C2 |
| ATOM | 3228 | CB | HIS | 480 | 32.742 | 38.714 | 2.922 | 1.00 | 34.29 | C2 |
| ATOM | 3229 | CG | HIS | 480 | 33.094 | 38.241 | 4.309 | 1.00 | 33.82 | C2 |
| ATOM | 3230 | CD2 | HIS | 480 | 33.123 | 36.932 | 4.709 | 1.00 | 33.44 | C2 |
| ATOM | 3231 | ND1 | HIS | 480 | 33.450 | 38.995 | 5.344 | 1.00 | 34.27 | C2 |
| ATOM | 3232 | HD1 | HIS | 480 | 33.505 | 39.976 | 5.362 | 1.00 | 0.00 | C2 |
| ATOM | 3233 | CE1 | HIS | 480 | 33.706 | 38.223 | 6.365 | 1.00 | 33.80 | C2 |
| ATOM | 3234 | NE2 | HIS | 480 | 33.504 | 36.986 | 5.965 | 1.00 | 37.12 | C2 |
| ATOM | 3235 | HE2 | HIS | 480 | 33.637 | 36.202 | 6.544 | 1.00 | 0.00 | C2 |
| ATOM | 3236 | C | HIS | 480 | 34.836 | 37.860 | 1.961 | 1.00 | 39.08 | C2 |
| ATOM | 3237 | O | HIS | 480 | 35.716 | 37.631 | 2.791 | 1.00 | 40.93 | C2 |
| ATOM | 3238 | N | SER | 481 | 34.615 | 37.029 | 0.935 | 1.00 | 39.24 | C2 |
| ATOM | 3239 | H | SER | 481 | 33.900 | 37.241 | 0.305 | 1.00 | 0.00 | C2 |
| ATOM | 3240 | CA | SER | 481 | 35.391 | 35.818 | 0.683 | 1.00 | 38.17 | C2 |
| ATOM | 3241 | CB | SER | 481 | 34.813 | 34.943 | -0.420 | 1.00 | 40.42 | C2 |
| ATOM | 3242 | OG | SER | 481 | 33.454 | 34.597 | -0.137 | 1.00 | 47.61 | C2 |
| ATOM | 3243 | HG | SER | 481 | 32.898 | 35.385 | -0.162 | 1.00 | 0.00 | C2 |
| ATOM | 3244 | C | SER | 481 | 36.724 | 36.272 | 0.211 | 1.00 | 36.12 | C2 |
| ATOM | 3245 | O | SER | 481 | 37.692 | 35.793 | 0.765 | 1.00 | 36.23 | C2 |
| ATOM | 3246 | N | GLY | 482 | 36.786 | 37.206 | -0.744 | 1.00 | 36.21 | C2 |
| ATOM | 3247 | H | GLY | 482 | 35.956 | 37.498 | -1.168 | 1.00 | 0.00 | C2 |
| ATOM | 3248 | CA | GLY | 482 | 38.028 | 37.792 | -1.266 | 1.00 | 36.50 | C2 |
| ATOM | 3249 | C | GLY | 482 | 38.958 | 38.296 | -0.151 | 1.00 | 36.14 | C2 |
| ATOM | 3250 | O | GLY | 482 | 40.142 | 37.936 | -0.055 | 1.00 | 36.65 | C2 |
| ATOM | 3251 | N | LEU | 483 | 38.381 | 39.084 | 0.750 | 1.00 | 34.04 | C2 |
| ATOM | 3252 | H | LEU | 483 | 37.445 | 39.326 | 0.608 | 1.00 | 0.00 | C2 |
| ATOM | 3253 | CA | LEU | 483 | 39.073 | 39.593 | 1.900 | 1.00 | 32.07 | C2 |
| ATOM | 3254 | CB | LEU | 483 | 38.134 | 40.442 | 2.731 | 1.00 | 31.17 | C2 |
| ATOM | 3255 | CG | LEU | 483 | 37.535 | 41.687 | 2.081 | 1.00 | 31.11 | C2 |
| ATOM | 3256 | CD1 | LEU | 483 | 36.757 | 42.411 | 3.156 | 1.00 | 30.82 | C2 |
| ATOM | 3257 | CD2 | LEU | 483 | 38.599 | 42.593 | 1.480 | 1.00 | 29.50 | C2 |
| ATOM | 3258 | C | LEU | 483 | 39.600 | 38.461 | 2.745 | 1.00 | 32.91 | C2 |
| ATOM | 3259 | O | LEU | 483 | 40.752 | 38.498 | 3.199 | 1.00 | 31.25 | C2 |
| ATOM | 3260 | N | PHE | 484 | 38.767 | 37.422 | 2.925 | 1.00 | 34.08 | C2 |
| ATOM | 3261 | H | PHE | 484 | 37.900 | 37.408 | 2.471 | 1.00 | 0.00 | C2 |
| ATOM | 3262 | CA | PHE | 484 | 39.105 | 36.298 | 3.788 | 1.00 | 34.60 | C2 |
| ATOM | 3263 | CB | PHE | 484 | 37.975 | 35.300 | 3.925 | 1.00 | 37.46 | C2 |
| ATOM | 3264 | CG | PHE | 484 | 38.268 | 34.183 | 4.897 | 1.00 | 40.86 | C2 |
| ATOM | 3265 | CD1 | PHE | 484 | 38.219 | 32.884 | 4.482 | 1.00 | 45.62 | C2 |
| ATOM | 3266 | CD2 | PHE | 484 | 38.528 | 34.445 | 6.210 | 1.00 | 43.62 | C2 |
| ATOM | 3267 | CE1 | PHE | 484 | 38.421 | 31.858 | 5.395 | 1.00 | 47.98 | C2 |

FIG.5-39

| | | | | | | | | | |
|---|---|---|---|---|---|---|---|---|---|
| ATOM | 3268 | CE2 | PHE | 484 | 38.731 | 33.427 | 7.119 | 1.00 46.78 | C2 |
| ATOM | 3269 | CZ | PHE | 484 | 38.677 | 32.119 | 6.720 | 1.00 48.06 | C2 |
| ATOM | 3270 | C | PHE | 484 | 40.245 | 35.602 | 3.113 | 1.00 33.92 | C2 |
| ATOM | 3271 | O | PHE | 484 | 41.162 | 35.289 | 3.826 | 1.00 34.25 | C2 |
| ATOM | 3272 | N | LEU | 485 | 40.326 | 35.413 | 1.799 | 1.00 32.75 | C2 |
| ATOM | 3273 | H | LEU | 485 | 39.577 | 35.717 | 1.250 | 1.00 0.00 | C2 |
| ATOM | 3274 | CA | LEU | 485 | 41.475 | 34.778 | 1.163 | 1.00 33.74 | C2 |
| ATOM | 3275 | CB | LEU | 485 | 41.183 | 34.629 | -0.305 | 1.00 35.35 | C2 |
| ATOM | 3276 | CG | LEU | 485 | 42.101 | 33.962 | -1.275 | 1.00 37.80 | C2 |
| ATOM | 3277 | CD1 | LEU | 485 | 41.181 | 33.404 | -2.345 | 1.00 41.44 | C2 |
| ATOM | 3278 | CD2 | LEU | 485 | 43.125 | 34.903 | -1.899 | 1.00 40.07 | C2 |
| ATOM | 3279 | C | LEU | 485 | 42.740 | 35.585 | 1.376 | 1.00 33.95 | C2 |
| ATOM | 3280 | O | LEU | 485 | 43.766 | 35.060 | 1.850 | 1.00 33.84 | C2 |
| ATOM | 3281 | N | TYR | 486 | 42.609 | 36.885 | 1.034 | 1.00 33.67 | C2 |
| ATOM | 3282 | H | TYR | 486 | 41.757 | 37.186 | 0.659 | 1.00 0.00 | C2 |
| ATOM | 3283 | CA | TYR | 486 | 43.662 | 37.862 | 1.242 | 1.00 31.33 | C2 |
| ATOM | 3284 | CB | TYR | 486 | 43.210 | 39.290 | 0.714 | 1.00 35.33 | C2 |
| ATOM | 3285 | CG | TYR | 486 | 43.300 | 39.325 | -0.825 | 1.00 33.37 | C2 |
| ATOM | 3286 | CD1 | TYR | 486 | 42.154 | 39.405 | -1.579 | 1.00 32.79 | C2 |
| ATOM | 3287 | CE1 | TYR | 486 | 42.228 | 39.290 | -2.944 | 1.00 33.73 | C2 |
| ATOM | 3288 | CD2 | TYR | 486 | 44.533 | 39.153 | -1.445 | 1.00 34.59 | C2 |
| ATOM | 3289 | CE2 | TYR | 486 | 44.618 | 39.033 | -2.818 | 1.00 34.63 | C2 |
| ATOM | 3290 | CZ | TYR | 486 | 43.451 | 39.096 | -3.562 | 1.00 35.58 | C2 |
| ATOM | 3291 | OH | TYR | 486 | 43.484 | 38.880 | -4.942 | 1.00 38.24 | C2 |
| ATOM | 3292 | HH | TYR | 486 | 42.614 | 39.086 | -5.306 | 1.00 0.00 | C2 |
| ATOM | 3293 | C | TYR | 486 | 44.068 | 37.905 | 2.697 | 1.00 27.39 | C2 |
| ATOM | 3294 | O | TYR | 486 | 45.258 | 38.007 | 2.942 | 1.00 26.06 | C2 |
| ATOM | 3295 | N | GLN | 487 | 43.270 | 37.691 | 3.708 | 1.00 26.95 | C2 |
| ATOM | 3296 | H | GLN | 487 | 42.315 | 37.545 | 3.565 | 1.00 0.00 | C2 |
| ATOM | 3297 | CA | GLN | 487 | 43.835 | 37.646 | 5.031 | 1.00 28.33 | C2 |
| ATOM | 3298 | CB | GLN | 487 | 42.690 | 37.578 | 6.050 | 1.00 32.66 | C2 |
| ATOM | 3299 | CG | GLN | 487 | 43.092 | 37.979 | 7.485 | 1.00 38.24 | C2 |
| ATOM | 3300 | CD | GLN | 487 | 43.966 | 39.252 | 7.469 | 1.00 40.54 | C2 |
| ATOM | 3301 | OE1 | GLN | 487 | 43.441 | 40.346 | 7.292 | 1.00 40.45 | C2 |
| ATOM | 3302 | NE2 | GLN | 487 | 45.305 | 39.206 | 7.549 | 1.00 38.19 | C2 |
| ATOM | 3303 | HE21 | GLN | 487 | 45.755 | 40.057 | 7.452 | 1.00 0.00 | C2 |
| ATOM | 3304 | HE22 | GLN | 487 | 45.736 | 38.340 | 7.702 | 1.00 0.00 | C2 |
| ATOM | 3305 | C | GLN | 487 | 44.791 | 36.455 | 5.207 | 1.00 28.53 | C2 |
| ATOM | 3306 | O | GLN | 487 | 45.774 | 36.542 | 5.964 | 1.00 28.72 | C2 |
| ATOM | 3307 | N | GLY | 488 | 44.550 | 35.363 | 4.454 | 1.00 28.32 | C2 |
| ATOM | 3308 | H | GLY | 488 | 43.799 | 35.400 | 3.824 | 1.00 0.00 | C2 |
| ATOM | 3309 | CA | GLY | 488 | 45.291 | 34.120 | 4.557 | 1.00 26.04 | C2 |
| ATOM | 3310 | C | GLY | 488 | 46.660 | 34.264 | 4.033 | 1.00 25.75 | C2 |
| ATOM | 3311 | O | GLY | 488 | 47.660 | 33.946 | 4.712 | 1.00 25.86 | C2 |
| ATOM | 3312 | N | LEU | 489 | 46.655 | 34.798 | 2.818 | 1.00 25.05 | C2 |
| ATOM | 3313 | H | LEU | 489 | 45.798 | 35.062 | 2.416 | 1.00 0.00 | C2 |
| ATOM | 3314 | CA | LEU | 489 | 47.911 | 34.990 | 2.099 | 1.00 25.63 | C2 |
| ATOM | 3315 | CB | LEU | 489 | 47.708 | 35.570 | 0.725 | 1.00 27.66 | C2 |
| ATOM | 3316 | CG | LEU | 489 | 46.761 | 34.755 | -0.189 | 1.00 30.83 | C2 |
| ATOM | 3317 | CD1 | LEU | 489 | 46.373 | 35.506 | -1.471 | 1.00 30.43 | C2 |
| ATOM | 3318 | CD2 | LEU | 489 | 47.472 | 33.454 | -0.502 | 1.00 32.62 | C2 |
| ATOM | 3319 | C | LEU | 489 | 48.783 | 35.936 | 2.853 | 1.00 25.28 | C2 |
| ATOM | 3320 | O | LEU | 489 | 49.973 | 35.705 | 2.914 | 1.00 27.37 | C2 |
| ATOM | 3321 | N | LEU | 490 | 48.237 | 36.935 | 3.534 | 1.00 25.79 | C2 |
| ATOM | 3322 | H | LEU | 490 | 47.267 | 37.079 | 3.515 | 1.00 0.00 | C2 |
| ATOM | 3323 | CA | LEU | 490 | 49.072 | 37.868 | 4.220 | 1.00 25.96 | C2 |
| ATOM | 3324 | CB | LEU | 490 | 48.274 | 39.139 | 4.567 | 1.00 27.96 | C2 |
| ATOM | 3325 | CG | LEU | 490 | 47.823 | 40.131 | 3.474 | 1.00 27.89 | C2 |
| ATOM | 3326 | CD1 | LEU | 490 | 46.772 | 41.019 | 4.123 | 1.00 28.03 | C2 |
| ATOM | 3327 | CD2 | LEU | 490 | 48.988 | 40.942 | 2.899 | 1.00 28.15 | C2 |
| ATOM | 3328 | C | LEU | 490 | 49.619 | 37.243 | 5.459 | 1.00 27.33 | C2 |
| ATOM | 3329 | O | LEU | 490 | 50.740 | 37.528 | 5.865 | 1.00 26.73 | C2 |
| ATOM | 3330 | N | GLN | 491 | 48.883 | 36.370 | 6.111 | 1.00 29.88 | C2 |
| ATOM | 3331 | H | GLN | 491 | 47.984 | 36.127 | 5.799 | 1.00 0.00 | C2 |
| ATOM | 3332 | CA | GLN | 491 | 49.430 | 35.809 | 7.314 | 1.00 33.01 | C2 |
| ATOM | 3333 | CB | GLN | 491 | 48.305 | 35.113 | 8.027 | 1.00 38.68 | C2 |
| ATOM | 3334 | CG | GLN | 491 | 47.856 | 35.963 | 9.197 | 1.00 46.07 | C2 |
| ATOM | 3335 | CD | GLN | 491 | 46.348 | 36.262 | 9.278 | 1.00 50.83 | C2 |
| ATOM | 3336 | OE1 | GLN | 491 | 45.965 | 37.436 | 9.402 | 1.00 51.92 | C2 |
| ATOM | 3337 | NE2 | GLN | 491 | 45.425 | 35.294 | 9.278 | 1.00 51.67 | C2 |
| ATOM | 3338 | HE21 | GLN | 491 | 45.723 | 34.353 | 9.288 | 1.00 0.00 | C2 |
| ATOM | 3339 | HE22 | GLN | 491 | 44.489 | 35.560 | 9.286 | 1.00 0.00 | C2 |
| ATOM | 3340 | C | GLN | 491 | 50.582 | 34.867 | 6.986 | 1.00 33.58 | C2 |
| ATOM | 3341 | O | GLN | 491 | 51.582 | 34.828 | 7.715 | 1.00 34.65 | C2 |
| ATOM | 3342 | N | ALA | 492 | 50.482 | 34.191 | 5.824 | 1.00 34.15 | C2 |
| ATOM | 3343 | H | ALA | 492 | 49.701 | 34.382 | 5.264 | 1.00 0.00 | C2 |
| ATOM | 3344 | CA | ALA | 492 | 51.416 | 33.177 | 5.321 | 1.00 33.64 | C2 |
| ATOM | 3345 | CB | ALA | 492 | 50.818 | 32.500 | 4.081 | 1.00 31.67 | C2 |
| ATOM | 3346 | C | ALA | 492 | 52.802 | 33.678 | 4.959 | 1.00 34.79 | C2 |
| ATOM | 3347 | O | ALA | 492 | 53.789 | 32.943 | 4.879 | 1.00 36.03 | C2 |
| ATOM | 3348 | N | LEU | 493 | 52.885 | 34.981 | 4.728 | 1.00 35.94 | C2 |
| ATOM | 3349 | H | LEU | 493 | 52.060 | 35.510 | 4.721 | 1.00 0.00 | C2 |
| ATOM | 3350 | CA | LEU | 493 | 54.139 | 35.634 | 4.426 | 1.00 34.86 | C2 |
| ATOM | 3351 | CB | LEU | 493 | 53.898 | 36.990 | 3.747 | 1.00 31.36 | C2 |
| ATOM | 3352 | CG | LEU | 493 | 53.127 | 37.065 | 2.443 | 1.00 28.27 | C2 |
| ATOM | 3353 | CD1 | LEU | 493 | 52.715 | 38.495 | 2.214 | 1.00 31.74 | C2 |

FIG. 5-40

| ATOM | 3354 | CD2 | LEU | 493 | 53.977 | 36.608 | 1.285 | 1.00 | 28.79 | C2 |
|---|---|---|---|---|---|---|---|---|---|---|
| ATOM | 3355 | C | LEU | 493 | 54.879 | 35.843 | 5.721 | 1.00 | 36.15 | C2 |
| ATOM | 3356 | O | LEU | 493 | 55.985 | 36.374 | 5.694 | 1.00 | 36.70 | C2 |
| ATOM | 3357 | N | GLU | 494 | 54.300 | 35.497 | 6.855 | 1.00 | 38.35 | C2 |
| ATOM | 3358 | H | GLU | 494 | 53.395 | 35.130 | 6.836 | 1.00 | 0.00 | C2 |
| ATOM | 3359 | CA | GLU | 494 | 54.910 | 35.648 | 8.157 | 1.00 | 43.14 | C2 |
| ATOM | 3360 | CB | GLU | 494 | 55.621 | 34.340 | 8.545 | 1.00 | 46.61 | C2 |
| ATOM | 3361 | CG | GLU | 494 | 54.711 | 33.471 | 9.419 | 1.00 | 53.71 | C2 |
| ATOM | 3362 | CD | GLU | 494 | 54.195 | 32.160 | 8.785 | 1.00 | 60.27 | C2 |
| ATOM | 3363 | OE1 | GLU | 494 | 53.146 | 31.653 | 9.230 | 1.00 | 63.52 | C2 |
| ATOM | 3364 | OE2 | GLU | 494 | 54.839 | 31.630 | 7.862 | 1.00 | 62.76 | C2 |
| ATOM | 3365 | C | GLU | 494 | 55.865 | 36.825 | 8.343 | 1.00 | 44.32 | C2 |
| ATOM | 3366 | O | GLU | 494 | 57.055 | 36.678 | 8.610 | 1.00 | 46.91 | C2 |
| ATOM | 3367 | N | GLY | 495 | 55.358 | 38.046 | 8.114 | 1.00 | 44.32 | C2 |
| ATOM | 3368 | H | GLY | 495 | 54.450 | 38.112 | 7.753 | 1.00 | 0.00 | C2 |
| ATOM | 3369 | CA | GLY | 495 | 56.104 | 39.272 | 8.368 | 1.00 | 42.36 | C2 |
| ATOM | 3370 | C | GLY | 495 | 57.015 | 39.695 | 7.238 | 1.00 | 42.33 | C2 |
| ATOM | 3371 | O | GLY | 495 | 57.397 | 40.866 | 7.220 | 1.00 | 42.42 | C2 |
| ATOM | 3372 | N | ILE | 496 | 57.310 | 38.802 | 6.279 | 1.00 | 41.04 | C2 |
| ATOM | 3373 | H | ILE | 496 | 56.927 | 37.906 | 6.374 | 1.00 | 0.00 | C2 |
| ATOM | 3374 | CA | ILE | 496 | 58.259 | 38.993 | 5.192 | 1.00 | 41.15 | C2 |
| ATOM | 3375 | CB | ILE | 496 | 57.929 | 40.216 | 4.253 | 1.00 | 38.60 | C2 |
| ATOM | 3376 | CG2 | ILE | 496 | 59.077 | 40.437 | 3.248 | 1.00 | 37.62 | C2 |
| ATOM | 3377 | CG1 | ILE | 496 | 56.662 | 39.964 | 3.480 | 1.00 | 36.39 | C2 |
| ATOM | 3378 | CD | ILE | 496 | 56.314 | 41.071 | 2.470 | 1.00 | 35.27 | C2 |
| ATOM | 3379 | C | ILE | 496 | 59.672 | 39.203 | 5.749 | 1.00 | 42.91 | C2 |
| ATOM | 3380 | O | ILE | 496 | 60.541 | 38.396 | 5.448 | 1.00 | 44.22 | C2 |
| ATOM | 3381 | N | SER | 497 | 59.998 | 40.228 | 6.533 | 1.00 | 44.31 | C2 |
| ATOM | 3382 | H | SER | 497 | 59.297 | 40.852 | 6.827 | 1.00 | 0.00 | C2 |
| ATOM | 3383 | CA | SER | 497 | 61.346 | 40.501 | 6.992 | 1.00 | 44.86 | C2 |
| ATOM | 3384 | CB | SER | 497 | 62.204 | 41.254 | 5.938 | 1.00 | 44.13 | C2 |
| ATOM | 3385 | OG | SER | 497 | 62.181 | 42.673 | 6.033 | 1.00 | 40.74 | C2 |
| ATOM | 3386 | HG | SER | 497 | 62.531 | 42.964 | 5.170 | 1.00 | 0.00 | C2 |
| ATOM | 3387 | C | SER | 497 | 61.164 | 41.413 | 8.185 | 1.00 | 45.85 | C2 |
| ATOM | 3388 | O | SER | 497 | 60.132 | 42.110 | 8.288 | 1.00 | 47.55 | C2 |
| ATOM | 3389 | N | PRO | 498 | 62.164 | 41.490 | 9.071 | 1.00 | 44.96 | C2 |
| ATOM | 3390 | CD | PRO | 498 | 63.338 | 40.621 | 9.126 | 1.00 | 42.33 | C2 |
| ATOM | 3391 | CA | PRO | 498 | 62.086 | 42.327 | 10.250 | 1.00 | 44.88 | C2 |
| ATOM | 3392 | CB | PRO | 498 | 63.431 | 42.038 | 10.885 | 1.00 | 45.13 | C2 |
| ATOM | 3393 | CG | PRO | 498 | 63.629 | 40.581 | 10.603 | 1.00 | 42.00 | C2 |
| ATOM | 3394 | C | PRO | 498 | 61.760 | 43.799 | 9.983 | 1.00 | 45.22 | C2 |
| ATOM | 3395 | O | PRO | 498 | 61.215 | 44.446 | 10.869 | 1.00 | 45.24 | C2 |
| ATOM | 3396 | N | GLU | 499 | 62.017 | 44.314 | 8.777 | 1.00 | 46.16 | C2 |
| ATOM | 3397 | H | GLU | 499 | 62.362 | 43.716 | 8.081 | 1.00 | 0.00 | C2 |
| ATOM | 3398 | CA | GLU | 499 | 61.731 | 45.699 | 8.391 | 1.00 | 48.06 | C2 |
| ATOM | 3399 | CB | GLU | 499 | 62.498 | 46.193 | 7.155 | 1.00 | 52.19 | C2 |
| ATOM | 3400 | CG | GLU | 499 | 64.001 | 46.187 | 7.100 | 1.00 | 57.51 | C2 |
| ATOM | 3401 | CD | GLU | 499 | 64.544 | 44.777 | 7.076 | 1.00 | 60.61 | C2 |
| ATOM | 3402 | OE1 | GLU | 499 | 64.755 | 44.231 | 8.162 | 1.00 | 62.96 | C2 |
| ATOM | 3403 | OE2 | GLU | 499 | 64.739 | 44.234 | 5.984 | 1.00 | 62.79 | C2 |
| ATOM | 3404 | C | GLU | 499 | 60.269 | 45.896 | 7.981 | 1.00 | 46.94 | C2 |
| ATOM | 3405 | O | GLU | 499 | 59.600 | 46.895 | 8.272 | 1.00 | 48.15 | C2 |
| ATOM | 3406 | N | LEU | 500 | 59.806 | 44.934 | 7.193 | 1.00 | 44.38 | C2 |
| ATOM | 3407 | H | LEU | 500 | 60.351 | 44.137 | 7.027 | 1.00 | 0.00 | C2 |
| ATOM | 3408 | CA | LEU | 500 | 58.491 | 44.997 | 6.651 | 1.00 | 41.08 | C2 |
| ATOM | 3409 | CB | LEU | 500 | 58.519 | 44.197 | 5.445 | 1.00 | 41.37 | C2 |
| ATOM | 3410 | CG | LEU | 500 | 59.303 | 44.862 | 4.351 | 1.00 | 42.70 | C2 |
| ATOM | 3411 | CD1 | LEU | 500 | 59.776 | 43.828 | 3.351 | 1.00 | 43.98 | C2 |
| ATOM | 3412 | CD2 | LEU | 500 | 58.427 | 45.874 | 3.671 | 1.00 | 45.04 | C2 |
| ATOM | 3413 | C | LEU | 500 | 57.455 | 44.521 | 7.628 | 1.00 | 40.59 | C2 |
| ATOM | 3414 | O | LEU | 500 | 56.274 | 44.835 | 7.463 | 1.00 | 40.69 | C2 |
| ATOM | 3415 | N | GLY | 501 | 57.866 | 43.835 | 8.685 | 1.00 | 39.37 | C2 |
| ATOM | 3416 | H | GLY | 501 | 58.808 | 43.579 | 8.730 | 1.00 | 0.00 | C2 |
| ATOM | 3417 | CA | GLY | 501 | 56.974 | 43.386 | 9.734 | 1.00 | 39.59 | C2 |
| ATOM | 3418 | C | GLY | 501 | 55.816 | 44.324 | 10.092 | 1.00 | 39.66 | C2 |
| ATOM | 3419 | O | GLY | 501 | 54.661 | 44.034 | 9.777 | 1.00 | 40.66 | C2 |
| ATOM | 3420 | N | PRO | 502 | 55.986 | 45.462 | 10.742 | 1.00 | 39.90 | C2 |
| ATOM | 3421 | CD | PRO | 502 | 57.227 | 45.908 | 11.335 | 1.00 | 41.18 | C2 |
| ATOM | 3422 | CA | PRO | 502 | 54.912 | 46.387 | 11.045 | 1.00 | 38.67 | C2 |
| ATOM | 3423 | CB | PRO | 502 | 55.594 | 47.494 | 11.791 | 1.00 | 39.23 | C2 |
| ATOM | 3424 | CG | PRO | 502 | 56.989 | 47.405 | 11.221 | 1.00 | 41.36 | C2 |
| ATOM | 3425 | C | PRO | 502 | 54.158 | 46.849 | 9.817 | 1.00 | 37.54 | C2 |
| ATOM | 3426 | O | PRO | 502 | 52.966 | 47.139 | 9.961 | 1.00 | 38.36 | C2 |
| ATOM | 3427 | N | THR | 503 | 54.728 | 46.887 | 8.609 | 1.00 | 35.13 | C2 |
| ATOM | 3428 | H | THR | 503 | 55.663 | 46.638 | 8.449 | 1.00 | 0.00 | C2 |
| ATOM | 3429 | CA | THR | 503 | 53.940 | 47.283 | 7.462 | 1.00 | 35.09 | C2 |
| ATOM | 3430 | CB | THR | 503 | 54.832 | 47.376 | 6.245 | 1.00 | 34.48 | C2 |
| ATOM | 3431 | OG1 | THR | 503 | 56.025 | 48.018 | 6.668 | 1.00 | 38.23 | C2 |
| ATOM | 3432 | HG1 | THR | 503 | 55.857 | 48.946 | 6.845 | 1.00 | 0.00 | C2 |
| ATOM | 3433 | CG2 | THR | 503 | 54.197 | 48.162 | 5.126 | 1.00 | 35.56 | C2 |
| ATOM | 3434 | C | THR | 503 | 52.836 | 46.252 | 7.215 | 1.00 | 35.37 | C2 |
| ATOM | 3435 | O | THR | 503 | 51.671 | 46.552 | 6.915 | 1.00 | 37.11 | C2 |
| ATOM | 3436 | N | LEU | 504 | 53.218 | 44.996 | 7.380 | 1.00 | 34.02 | C2 |
| ATOM | 3437 | H | LEU | 504 | 54.146 | 44.799 | 7.647 | 1.00 | 0.00 | C2 |
| ATOM | 3438 | CA | LEU | 504 | 52.301 | 43.912 | 7.173 | 1.00 | 32.50 | C2 |
| ATOM | 3439 | CB | LEU | 504 | 53.127 | 42.650 | 7.002 | 1.00 | 34.78 | C2 |

FIG.5-41

| | | | | | | | | | |
|---|---|---|---|---|---|---|---|---|---|
| ATOM | 3440 | CG | LEU | 504 | 53.464 | 42.256 | 5.601 | 1.00 34.07 | C2 |
| ATOM | 3441 | CD1 | LEU | 504 | 54.163 | 40.977 | 5.667 | 1.00 37.97 | C2 |
| ATOM | 3442 | CD2 | LEU | 504 | 52.254 | 41.865 | 4.809 | 1.00 37.34 | C2 |
| ATOM | 3443 | C | LEU | 504 | 51.324 | 43.821 | 8.328 | 1.00 29.54 | C2 |
| ATOM | 3444 | O | LEU | 504 | 50.141 | 43.562 | 8.078 | 1.00 30.40 | C2 |
| ATOM | 3445 | N | ASP | 505 | 51.736 | 44.106 | 9.551 | 1.00 26.09 | C2 |
| ATOM | 3446 | H | ASP | 505 | 52.689 | 44.269 | 9.699 | 1.00 0.00 | C2 |
| ATOM | 3447 | CA | ASP | 505 | 50.798 | 44.084 | 10.643 | 1.00 27.88 | C2 |
| ATOM | 3448 | CB | ASP | 505 | 51.446 | 44.345 | 11.926 | 1.00 29.86 | C2 |
| ATOM | 3449 | CG | ASP | 505 | 52.500 | 43.312 | 12.239 | 1.00 34.64 | C2 |
| ATOM | 3450 | OD1 | ASP | 505 | 52.663 | 42.298 | 11.534 | 1.00 41.04 | C2 |
| ATOM | 3451 | OD2 | ASP | 505 | 53.179 | 43.542 | 13.224 | 1.00 37.40 | C2 |
| ATOM | 3452 | C | ASP | 505 | 49.661 | 45.060 | 10.568 | 1.00 28.61 | C2 |
| ATOM | 3453 | O | ASP | 505 | 48.566 | 44.739 | 11.039 | 1.00 30.30 | C2 |
| ATOM | 3454 | N | THR | 506 | 49.894 | 46.242 | 10.002 | 1.00 28.29 | C2 |
| ATOM | 3455 | H | THR | 506 | 50.823 | 46.493 | 9.804 | 1.00 0.00 | C2 |
| ATOM | 3456 | CA | THR | 506 | 48.860 | 47.225 | 9.731 | 1.00 25.74 | C2 |
| ATOM | 3457 | CB | THR | 506 | 49.497 | 48.556 | 9.336 | 1.00 26.14 | C2 |
| ATOM | 3458 | OG1 | THR | 506 | 49.944 | 49.099 | 10.588 | 1.00 31.63 | C2 |
| ATOM | 3459 | HG1 | THR | 506 | 49.243 | 49.072 | 11.246 | 1.00 0.00 | C2 |
| ATOM | 3460 | CG2 | THR | 506 | 48.594 | 49.517 | 8.619 | 1.00 24.46 | C2 |
| ATOM | 3461 | C | THR | 506 | 48.022 | 46.735 | 8.615 | 1.00 24.00 | C2 |
| ATOM | 3462 | O | THR | 506 | 46.817 | 46.864 | 8.719 | 1.00 25.85 | C2 |
| ATOM | 3463 | N | LEU | 507 | 48.554 | 46.196 | 7.525 | 1.00 23.51 | C2 |
| ATOM | 3464 | H | LEU | 507 | 49.527 | 46.073 | 7.453 | 1.00 0.00 | C2 |
| ATOM | 3465 | CA | LEU | 507 | 47.682 | 45.770 | 6.434 | 1.00 23.85 | C2 |
| ATOM | 3466 | CB | LEU | 507 | 48.574 | 45.408 | 5.196 | 1.00 25.85 | C2 |
| ATOM | 3467 | CG | LEU | 507 | 48.010 | 44.919 | 3.858 | 1.00 20.85 | C2 |
| ATOM | 3468 | CD1 | LEU | 507 | 46.771 | 45.650 | 3.455 | 1.00 24.13 | C2 |
| ATOM | 3469 | CD2 | LEU | 507 | 49.074 | 45.055 | 2.842 | 1.00 20.13 | C2 |
| ATOM | 3470 | C | LEU | 507 | 46.766 | 44.640 | 6.880 | 1.00 24.09 | C2 |
| ATOM | 3471 | O | LEU | 507 | 45.600 | 44.764 | 6.541 | 1.00 25.80 | C2 |
| ATOM | 3472 | N | GLN | 508 | 47.152 | 43.618 | 7.661 | 1.00 24.01 | C2 |
| ATOM | 3473 | H | GLN | 508 | 48.112 | 43.555 | 7.866 | 1.00 0.00 | C2 |
| ATOM | 3474 | CA | GLN | 508 | 46.228 | 42.625 | 8.214 | 1.00 23.71 | C2 |
| ATOM | 3475 | CB | GLN | 508 | 46.961 | 41.627 | 9.036 | 1.00 23.83 | C2 |
| ATOM | 3476 | CG | GLN | 508 | 47.937 | 40.899 | 8.173 | 1.00 31.64 | C2 |
| ATOM | 3477 | CD | GLN | 508 | 48.842 | 40.080 | 9.054 | 1.00 34.00 | C2 |
| ATOM | 3478 | OE1 | GLN | 508 | 50.031 | 40.346 | 9.161 | 1.00 38.32 | C2 |
| ATOM | 3479 | NE2 | GLN | 508 | 48.321 | 39.090 | 9.748 | 1.00 36.30 | C2 |
| ATOM | 3480 | HE21 | GLN | 508 | 47.373 | 38.880 | 9.639 | 1.00 0.00 | C2 |
| ATOM | 3481 | HE22 | GLN | 508 | 48.891 | 38.636 | 10.406 | 1.00 0.00 | C2 |
| ATOM | 3482 | C | GLN | 508 | 45.105 | 43.123 | 9.111 | 1.00 24.24 | C2 |
| ATOM | 3483 | O | GLN | 508 | 43.978 | 42.650 | 9.014 | 1.00 24.06 | C2 |
| ATOM | 3484 | N | LEU | 509 | 45.375 | 44.019 | 10.090 | 1.00 26.07 | C2 |
| ATOM | 3485 | H | LEU | 509 | 46.316 | 44.262 | 10.222 | 1.00 0.00 | C2 |
| ATOM | 3486 | CA | LEU | 509 | 44.378 | 44.640 | 10.977 | 1.00 25.71 | C2 |
| ATOM | 3487 | CB | LEU | 509 | 44.993 | 45.555 | 12.031 | 1.00 25.60 | C2 |
| ATOM | 3488 | CG | LEU | 509 | 45.838 | 44.757 | 13.042 | 1.00 29.00 | C2 |
| ATOM | 3489 | CD1 | LEU | 509 | 46.658 | 45.705 | 13.886 | 1.00 28.93 | C2 |
| ATOM | 3490 | CD2 | LEU | 509 | 44.950 | 43.919 | 13.937 | 1.00 27.94 | C2 |
| ATOM | 3491 | C | LEU | 509 | 43.465 | 45.471 | 10.130 | 1.00 25.17 | C2 |
| ATOM | 3492 | O | LEU | 509 | 42.274 | 45.411 | 10.408 | 1.00 27.22 | C2 |
| ATOM | 3493 | N | ASP | 510 | 43.899 | 46.208 | 9.101 | 1.00 23.77 | C2 |
| ATOM | 3494 | H | ASP | 510 | 44.865 | 46.277 | 8.930 | 1.00 0.00 | C2 |
| ATOM | 3495 | CA | ASP | 510 | 42.955 | 46.898 | 8.240 | 1.00 22.66 | C2 |
| ATOM | 3496 | CB | ASP | 510 | 43.652 | 47.829 | 7.306 | 1.00 25.21 | C2 |
| ATOM | 3497 | CG | ASP | 510 | 44.316 | 48.966 | 8.068 | 1.00 33.01 | C2 |
| ATOM | 3498 | OD1 | ASP | 510 | 45.178 | 49.621 | 7.477 | 1.00 34.28 | C2 |
| ATOM | 3499 | OD2 | ASP | 510 | 43.988 | 49.209 | 9.250 | 1.00 34.44 | C2 |
| ATOM | 3500 | C | ASP | 510 | 42.104 | 45.980 | 7.398 | 1.00 23.72 | C2 |
| ATOM | 3501 | O | ASP | 510 | 40.897 | 46.220 | 7.387 | 1.00 24.80 | C2 |
| ATOM | 3502 | N | VAL | 511 | 42.632 | 44.984 | 6.659 | 1.00 22.38 | C2 |
| ATOM | 3503 | H | VAL | 511 | 43.611 | 44.900 | 6.620 | 1.00 0.00 | C2 |
| ATOM | 3504 | CA | VAL | 511 | 41.823 | 44.010 | 5.961 | 1.00 21.89 | C2 |
| ATOM | 3505 | CB | VAL | 511 | 42.752 | 42.924 | 5.366 | 1.00 22.71 | C2 |
| ATOM | 3506 | CG1 | VAL | 511 | 41.954 | 41.756 | 4.792 | 1.00 20.43 | C2 |
| ATOM | 3507 | CG2 | VAL | 511 | 43.529 | 43.524 | 4.210 | 1.00 16.19 | C2 |
| ATOM | 3508 | C | VAL | 511 | 40.827 | 43.403 | 6.960 | 1.00 21.92 | C2 |
| ATOM | 3509 | O | VAL | 511 | 39.625 | 43.447 | 6.719 | 1.00 23.46 | C2 |
| ATOM | 3510 | N | ALA | 512 | 41.258 | 43.017 | 8.163 | 1.00 20.49 | C2 |
| ATOM | 3511 | H | ALA | 512 | 42.216 | 43.063 | 8.361 | 1.00 0.00 | C2 |
| ATOM | 3512 | CA | ALA | 512 | 40.388 | 42.357 | 9.108 | 1.00 20.83 | C2 |
| ATOM | 3513 | CB | ALA | 512 | 41.103 | 41.974 | 10.344 | 1.00 17.89 | C2 |
| ATOM | 3514 | C | ALA | 512 | 39.250 | 43.205 | 9.550 | 1.00 23.89 | C2 |
| ATOM | 3515 | O | ALA | 512 | 38.201 | 42.668 | 9.874 | 1.00 24.61 | C2 |
| ATOM | 3516 | N | ASP | 513 | 39.417 | 44.539 | 9.544 | 1.00 25.96 | C2 |
| ATOM | 3517 | H | ASP | 513 | 40.300 | 44.888 | 9.291 | 1.00 0.00 | C2 |
| ATOM | 3518 | CA | ASP | 513 | 38.374 | 45.471 | 9.947 | 1.00 25.37 | C2 |
| ATOM | 3519 | CB | ASP | 513 | 38.958 | 46.787 | 10.373 | 1.00 26.88 | C2 |
| ATOM | 3520 | CG | ASP | 513 | 39.682 | 46.679 | 11.712 | 1.00 32.35 | C2 |
| ATOM | 3521 | OD1 | ASP | 513 | 40.371 | 47.644 | 12.058 | 1.00 35.06 | C2 |
| ATOM | 3522 | OD2 | ASP | 513 | 39.580 | 45.646 | 12.390 | 1.00 34.10 | C2 |
| ATOM | 3523 | C | ASP | 513 | 37.392 | 45.730 | 8.846 | 1.00 24.95 | C2 |
| ATOM | 3524 | O | ASP | 513 | 36.185 | 45.868 | 9.090 | 1.00 26.92 | C2 |
| ATOM | 3525 | N | PHE | 514 | 37.867 | 45.739 | 7.634 | 1.00 22.88 | C2 |

FIG.5-42

| | | | | | | | | | |
|---|---|---|---|---|---|---|---|---|---|
| ATOM | 3526 | H | PHE | 514 | 38.829 | 45.614 | 7.475 | 1.00 0.00 | C2 |
| ATOM | 3527 | CA | PHE | 514 | 36.974 | 45.922 | 6.530 | 1.00 24.09 | C2 |
| ATOM | 3528 | CB | PHE | 514 | 37.812 | 46.061 | 5.266 | 1.00 18.11 | C2 |
| ATOM | 3529 | CG | PHE | 514 | 36.956 | 46.470 | 4.072 | 1.00 17.86 | C2 |
| ATOM | 3530 | CD1 | PHE | 514 | 35.715 | 47.089 | 4.245 | 1.00 15.18 | C2 |
| ATOM | 3531 | CD2 | PHE | 514 | 37.440 | 46.197 | 2.804 | 1.00 13.77 | C2 |
| ATOM | 3532 | CE1 | PHE | 514 | 34.983 | 47.419 | 3.130 | 1.00 14.53 | C2 |
| ATOM | 3533 | CE2 | PHE | 514 | 36.693 | 46.539 | 1.705 | 1.00 12.10 | C2 |
| ATOM | 3534 | CZ | PHE | 514 | 35.468 | 47.146 | 1.868 | 1.00 10.68 | C2 |
| ATOM | 3535 | C | PHE | 514 | 36.026 | 44.703 | 6.450 | 1.00 29.23 | C2 |
| ATOM | 3536 | O | PHE | 514 | 34.788 | 44.828 | 6.350 | 1.00 29.80 | C2 |
| ATOM | 3537 | N | ALA | 515 | 36.604 | 43.490 | 6.531 | 1.00 31.15 | C2 |
| ATOM | 3538 | H | ALA | 515 | 37.581 | 43.450 | 6.639 | 1.00 0.00 | C2 |
| ATOM | 3539 | CA | ALA | 515 | 35.839 | 42.260 | 6.416 | 1.00 32.36 | C2 |
| ATOM | 3540 | CB | ALA | 515 | 36.851 | 41.126 | 6.402 | 1.00 32.35 | C2 |
| ATOM | 3541 | C | ALA | 515 | 34.801 | 42.089 | 7.535 | 1.00 32.39 | C2 |
| ATOM | 3542 | O | ALA | 515 | 33.676 | 41.609 | 7.331 | 1.00 32.63 | C2 |
| ATOM | 3543 | N | THR | 516 | 35.164 | 42.457 | 8.735 | 1.00 33.01 | C2 |
| ATOM | 3544 | H | THR | 516 | 36.117 | 42.578 | 8.935 | 1.00 0.00 | C2 |
| ATOM | 3545 | CA | THR | 516 | 34.231 | 42.566 | 9.821 | 1.00 35.18 | C2 |
| ATOM | 3546 | CB | THR | 516 | 35.016 | 43.018 | 10.988 | 1.00 35.40 | C2 |
| ATOM | 3547 | OG1 | THR | 516 | 35.685 | 41.818 | 11.336 | 1.00 42.65 | C2 |
| ATOM | 3548 | HG1 | THR | 516 | 36.505 | 41.713 | 10.816 | 1.00 0.00 | C2 |
| ATOM | 3549 | CG2 | THR | 516 | 34.262 | 43.672 | 12.097 | 1.00 35.56 | C2 |
| ATOM | 3550 | C | THR | 516 | 33.140 | 43.554 | 9.482 | 1.00 37.62 | C2 |
| ATOM | 3551 | O | THR | 516 | 32.005 | 43.315 | 9.857 | 1.00 40.37 | C2 |
| ATOM | 3552 | N | THR | 517 | 33.387 | 44.666 | 8.802 | 1.00 38.61 | C2 |
| ATOM | 3553 | H | THR | 517 | 34.291 | 44.850 | 8.469 | 1.00 0.00 | C2 |
| ATOM | 3554 | CA | THR | 517 | 32.359 | 45.641 | 8.512 | 1.00 38.92 | C2 |
| ATOM | 3555 | CB | THR | 517 | 33.123 | 46.903 | 7.962 | 1.00 40.46 | C2 |
| ATOM | 3556 | OG1 | THR | 517 | 33.832 | 47.429 | 9.103 | 1.00 43.22 | C2 |
| ATOM | 3557 | HG1 | THR | 517 | 34.536 | 46.815 | 9.335 | 1.00 0.00 | C2 |
| ATOM | 3558 | CG2 | THR | 517 | 32.232 | 47.926 | 7.253 | 1.00 39.90 | C2 |
| ATOM | 3559 | C | THR | 517 | 31.343 | 45.012 | 7.551 | 1.00 38.30 | C2 |
| ATOM | 3560 | O | THR | 517 | 30.137 | 45.125 | 7.811 | 1.00 38.69 | C2 |
| ATOM | 3561 | N | ILE | 518 | 31.790 | 44.344 | 6.466 | 1.00 37.54 | C2 |
| ATOM | 3562 | H | ILE | 518 | 32.756 | 44.386 | 6.297 | 1.00 0.00 | C2 |
| ATOM | 3563 | CA | ILE | 518 | 30.923 | 43.646 | 5.510 | 1.00 36.10 | C2 |
| ATOM | 3564 | CB | ILE | 518 | 31.699 | 42.912 | 4.439 | 1.00 33.81 | C2 |
| ATOM | 3565 | CG2 | ILE | 518 | 30.703 | 42.202 | 3.555 | 1.00 33.46 | C2 |
| ATOM | 3566 | CG1 | ILE | 518 | 32.623 | 43.842 | 3.699 | 1.00 32.91 | C2 |
| ATOM | 3567 | CD | ILE | 518 | 32.019 | 44.700 | 2.596 | 1.00 34.89 | C2 |
| ATOM | 3568 | C | ILE | 518 | 30.172 | 42.591 | 6.317 | 1.00 38.63 | C2 |
| ATOM | 3569 | O | ILE | 518 | 28.938 | 42.545 | 6.205 | 1.00 39.93 | C2 |
| ATOM | 3570 | N | TRP | 519 | 30.842 | 41.785 | 7.179 | 1.00 38.64 | C2 |
| ATOM | 3571 | H | TRP | 519 | 31.785 | 41.959 | 7.361 | 1.00 0.00 | C2 |
| ATOM | 3572 | CA | TRP | 519 | 30.144 | 40.784 | 7.945 | 1.00 38.15 | C2 |
| ATOM | 3573 | CB | TRP | 519 | 31.124 | 40.083 | 8.780 | 1.00 38.52 | C2 |
| ATOM | 3574 | CG | TRP | 519 | 30.493 | 38.793 | 9.255 | 1.00 42.26 | C2 |
| ATOM | 3575 | CD2 | TRP | 519 | 29.880 | 38.578 | 10.473 | 1.00 41.70 | C2 |
| ATOM | 3576 | CE2 | TRP | 519 | 29.437 | 37.278 | 10.335 | 1.00 41.69 | C2 |
| ATOM | 3577 | CE3 | TRP | 519 | 29.648 | 39.282 | 11.629 | 1.00 42.26 | C2 |
| ATOM | 3578 | CD1 | TRP | 519 | 30.448 | 37.695 | 8.419 | 1.00 42.92 | C2 |
| ATOM | 3579 | NE1 | TRP | 519 | 29.788 | 36.793 | 9.115 | 1.00 44.19 | C2 |
| ATOM | 3580 | HE1 | TRP | 519 | 29.485 | 35.935 | 8.741 | 1.00 0.00 | C2 |
| ATOM | 3581 | CZ2 | TRP | 519 | 28.753 | 36.671 | 11.360 | 1.00 41.91 | C2 |
| ATOM | 3582 | CZ3 | TRP | 519 | 28.964 | 38.666 | 12.652 | 1.00 41.77 | C2 |
| ATOM | 3583 | CH2 | TRP | 519 | 28.522 | 37.375 | 12.515 | 1.00 41.05 | C2 |
| ATOM | 3584 | C | TRP | 519 | 29.027 | 41.368 | 8.815 | 1.00 39.33 | C2 |
| ATOM | 3585 | O | TRP | 519 | 27.888 | 40.919 | 8.726 | 1.00 38.28 | C2 |
| ATOM | 3586 | N | GLN | 520 | 29.264 | 42.375 | 9.650 | 1.00 41.86 | C2 |
| ATOM | 3587 | H | GLN | 520 | 30.180 | 42.717 | 9.700 | 1.00 0.00 | C2 |
| ATOM | 3588 | CA | GLN | 520 | 28.240 | 43.016 | 10.464 | 1.00 44.63 | C2 |
| ATOM | 3589 | CB | GLN | 520 | 28.691 | 44.198 | 11.239 | 1.00 47.03 | C2 |
| ATOM | 3590 | CG | GLN | 520 | 29.602 | 43.808 | 12.360 | 1.00 54.78 | C2 |
| ATOM | 3591 | CD | GLN | 520 | 29.910 | 45.009 | 13.243 | 1.00 60.14 | C2 |
| ATOM | 3592 | OE1 | GLN | 520 | 28.988 | 45.566 | 13.854 | 1.00 61.62 | C2 |
| ATOM | 3593 | NE2 | GLN | 520 | 31.172 | 45.456 | 13.371 | 1.00 60.46 | C2 |
| ATOM | 3594 | HE21 | GLN | 520 | 31.289 | 46.260 | 13.910 | 1.00 0.00 | C2 |
| ATOM | 3595 | HE22 | GLN | 520 | 31.895 | 44.966 | 12.932 | 1.00 0.00 | C2 |
| ATOM | 3596 | C | GLN | 520 | 27.141 | 43.577 | 9.621 | 1.00 46.28 | C2 |
| ATOM | 3597 | O | GLN | 520 | 26.001 | 43.474 | 10.059 | 1.00 48.62 | C2 |
| ATOM | 3598 | N | GLN | 521 | 27.362 | 44.145 | 8.442 | 1.00 46.99 | C2 |
| ATOM | 3599 | H | GLN | 521 | 28.272 | 44.257 | 8.092 | 1.00 0.00 | C2 |
| ATOM | 3600 | CA | GLN | 521 | 26.226 | 44.638 | 7.716 | 1.00 49.02 | C2 |
| ATOM | 3601 | CB | GLN | 521 | 26.632 | 45.553 | 6.566 | 1.00 50.06 | C2 |
| ATOM | 3602 | CG | GLN | 521 | 25.456 | 46.226 | 5.790 | 1.00 50.87 | C2 |
| ATOM | 3603 | CD | GLN | 521 | 24.616 | 47.278 | 6.534 | 1.00 51.82 | C2 |
| ATOM | 3604 | OE1 | GLN | 521 | 24.864 | 47.694 | 7.671 | 1.00 52.47 | C2 |
| ATOM | 3605 | NE2 | GLN | 521 | 23.577 | 47.776 | 5.888 | 1.00 50.36 | C2 |
| ATOM | 3606 | HE21 | GLN | 521 | 23.392 | 47.455 | 4.987 | 1.00 0.00 | C2 |
| ATOM | 3607 | HE22 | GLN | 521 | 23.044 | 48.424 | 6.390 | 1.00 0.00 | C2 |
| ATOM | 3608 | C | GLN | 521 | 25.454 | 43.446 | 7.155 | 1.00 50.15 | C2 |
| ATOM | 3609 | O | GLN | 521 | 24.214 | 43.514 | 7.177 | 1.00 51.82 | C2 |
| ATOM | 3610 | N | MET | 522 | 26.057 | 42.348 | 6.668 | 1.00 49.18 | C2 |
| ATOM | 3611 | H | MET | 522 | 27.038 | 42.291 | 6.688 | 1.00 0.00 | C2 |

FIG.5-43

| | | | | | | | | | |
|---|---|---|---|---|---|---|---|---|---|
| ATOM | 3612 | CA | MET | 522 | 25.280 | 41.227 | 6.171 | 1.00 48.22 | C2 |
| ATOM | 3613 | CB | MET | 522 | 26.185 | 40.167 | 5.607 | 1.00 46.36 | C2 |
| ATOM | 3614 | CG | MET | 522 | 26.942 | 40.661 | 4.412 | 1.00 44.32 | C2 |
| ATOM | 3615 | SD | MET | 522 | 27.855 | 39.435 | 3.426 | 1.00 48.35 | C2 |
| ATOM | 3616 | CE | MET | 522 | 28.795 | 38.447 | 4.565 | 1.00 42.80 | C2 |
| ATOM | 3617 | C | MET | 522 | 24.453 | 40.642 | 7.316 | 1.00 50.14 | C2 |
| ATOM | 3618 | O | MET | 522 | 23.380 | 40.124 | 7.038 | 1.00 50.60 | C2 |
| ATOM | 3619 | N | GLU | 523 | 24.848 | 40.722 | 8.596 | 1.00 51.91 | C2 |
| ATOM | 3620 | H | GLU | 523 | 25.766 | 41.031 | 8.769 | 1.00 0.00 | C2 |
| ATOM | 3621 | CA | GLU | 523 | 24.027 | 40.313 | 9.718 | 1.00 54.53 | C2 |
| ATOM | 3622 | CB | GLU | 523 | 24.654 | 40.486 | 11.081 | 1.00 54.60 | C2 |
| ATOM | 3623 | CG | GLU | 523 | 25.732 | 39.525 | 11.398 | 1.00 57.05 | C2 |
| ATOM | 3624 | CD | GLU | 523 | 25.386 | 38.150 | 10.888 | 1.00 61.72 | C2 |
| ATOM | 3625 | OE1 | GLU | 523 | 24.515 | 37.487 | 11.477 | 1.00 64.60 | C2 |
| ATOM | 3626 | OE2 | GLU | 523 | 25.979 | 37.773 | 9.872 | 1.00 63.19 | C2 |
| ATOM | 3627 | C | GLU | 523 | 22.773 | 41.116 | 9.836 | 1.00 58.29 | C2 |
| ATOM | 3628 | O | GLU | 523 | 21.688 | 40.538 | 9.850 | 1.00 59.32 | C2 |
| ATOM | 3629 | N | ALA | 524 | 22.920 | 42.432 | 9.992 | 1.00 61.41 | C2 |
| ATOM | 3630 | H | ALA | 524 | 23.834 | 42.798 | 10.024 | 1.00 0.00 | C2 |
| ATOM | 3631 | CA | ALA | 524 | 21.815 | 43.360 | 10.076 | 1.00 63.58 | C2 |
| ATOM | 3632 | CB | ALA | 524 | 22.382 | 44.768 | 9.992 | 1.00 64.11 | C2 |
| ATOM | 3633 | C | ALA | 524 | 20.818 | 43.109 | 8.946 | 1.00 64.79 | C2 |
| ATOM | 3634 | O | ALA | 524 | 19.655 | 42.824 | 9.206 | 1.00 65.69 | C2 |
| ATOM | 3635 | N | ALA | 525 | 21.251 | 43.083 | 7.693 | 1.00 66.44 | C2 |
| ATOM | 3636 | H | ALA | 525 | 22.196 | 43.283 | 7.516 | 1.00 0.00 | C2 |
| ATOM | 3637 | CA | ALA | 525 | 20.371 | 42.789 | 6.574 | 1.00 68.58 | C2 |
| ATOM | 3638 | CB | ALA | 525 | 21.117 | 43.044 | 5.288 | 1.00 67.42 | C2 |
| ATOM | 3639 | C | ALA | 525 | 19.841 | 41.356 | 6.558 | 1.00 71.11 | C2 |
| ATOM | 3640 | O | ALA | 525 | 19.116 | 40.946 | 5.651 | 1.00 71.65 | C2 |
| ATOM | 3641 | N | GLY | 526 | 20.257 | 40.510 | 7.498 | 1.00 74.20 | C2 |
| ATOM | 3642 | H | GLY | 526 | 21.019 | 40.780 | 8.043 | 1.00 0.00 | C2 |
| ATOM | 3643 | CA | GLY | 526 | 19.728 | 39.157 | 7.653 | 1.00 76.30 | C2 |
| ATOM | 3644 | C | GLY | 526 | 20.430 | 38.085 | 6.842 | 1.00 78.19 | C2 |
| ATOM | 3645 | O | GLY | 526 | 20.174 | 36.910 | 7.094 | 1.00 79.05 | C2 |
| ATOM | 3646 | N | MET | 527 | 21.388 | 38.433 | 5.970 | 1.00 80.23 | C2 |
| ATOM | 3647 | H | MET | 527 | 21.759 | 39.337 | 6.075 | 1.00 0.00 | C2 |
| ATOM | 3648 | CA | MET | 527 | 22.055 | 37.489 | 5.063 | 1.00 81.73 | C2 |
| ATOM | 3649 | CB | MET | 527 | 22.771 | 38.256 | 3.928 | 1.00 81.72 | C2 |
| ATOM | 3650 | CG | MET | 527 | 22.385 | 39.719 | 3.720 | 1.00 83.52 | C2 |
| ATOM | 3651 | SD | MET | 527 | 23.364 | 40.523 | 2.436 | 1.00 87.64 | C2 |
| ATOM | 3652 | CE | MET | 527 | 22.600 | 42.117 | 2.409 | 1.00 84.47 | C2 |
| ATOM | 3653 | C | MET | 527 | 23.078 | 36.584 | 5.780 | 1.00 82.64 | C2 |
| ATOM | 3654 | OT1 | MET | 527 | 22.974 | 35.357 | 5.624 | 1.00 83.38 | C2 |
| ATOM | 3655 | OT2 | MET | 527 | 23.949 | 37.104 | 6.500 | 1.00 82.90 | C2 |
| ATOM | 3656 | CB | MET | 538 | 47.224 | 28.531 | 2.401 | 1.00 77.43 | C3 |
| ATOM | 3657 | CG | MET | 538 | 47.397 | 30.041 | 2.427 | 1.00 77.15 | C3 |
| ATOM | 3658 | SD | MET | 538 | 46.205 | 30.708 | 3.604 | 1.00 79.03 | C3 |
| ATOM | 3659 | CE | MET | 538 | 44.850 | 31.067 | 2.515 | 1.00 77.20 | C3 |
| ATOM | 3660 | C | MET | 538 | 48.549 | 27.839 | 0.386 | 1.00 75.32 | C3 |
| ATOM | 3661 | O | MET | 538 | 49.130 | 26.745 | 0.405 | 1.00 77.11 | C3 |
| ATOM | 3662 | HT1 | MET | 538 | 47.563 | 26.068 | 1.449 | 1.00 0.00 | C3 |
| ATOM | 3663 | HT2 | MET | 538 | 46.638 | 26.204 | 0.075 | 1.00 0.00 | C3 |
| ATOM | 3664 | N | MET | 538 | 46.724 | 26.552 | 1.050 | 1.00 77.52 | C3 |
| ATOM | 3665 | HT3 | MET | 538 | 45.873 | 26.401 | 1.617 | 1.00 0.00 | C3 |
| ATOM | 3666 | CA | MET | 538 | 47.153 | 27.940 | 0.995 | 1.00 76.57 | C3 |
| ATOM | 3667 | N | PRO | 539 | 49.089 | 28.870 | -0.224 | 1.00 72.65 | C3 |
| ATOM | 3668 | CD | PRO | 539 | 48.346 | 29.821 | -1.046 | 1.00 72.26 | C3 |
| ATOM | 3669 | CA | PRO | 539 | 50.526 | 29.020 | -0.349 | 1.00 70.34 | C3 |
| ATOM | 3670 | CB | PRO | 539 | 50.677 | 30.365 | -1.006 | 1.00 71.39 | C3 |
| ATOM | 3671 | CG | PRO | 539 | 49.437 | 30.503 | -1.837 | 1.00 71.52 | C3 |
| ATOM | 3672 | C | PRO | 539 | 51.250 | 28.931 | 0.991 | 1.00 67.83 | C3 |
| ATOM | 3673 | O | PRO | 539 | 50.666 | 29.294 | 2.029 | 1.00 68.05 | C3 |
| ATOM | 3674 | N | ALA | 540 | 52.484 | 28.417 | 0.961 | 1.00 64.48 | C3 |
| ATOM | 3675 | H | ALA | 540 | 52.858 | 28.098 | 0.111 | 1.00 0.00 | C3 |
| ATOM | 3676 | CA | ALA | 540 | 53.389 | 28.498 | 2.112 | 1.00 61.83 | C3 |
| ATOM | 3677 | CB | ALA | 540 | 54.004 | 27.200 | 2.619 | 1.00 63.57 | C3 |
| ATOM | 3678 | C | ALA | 540 | 54.559 | 29.212 | 1.496 | 1.00 58.74 | C3 |
| ATOM | 3679 | O | ALA | 540 | 54.835 | 29.036 | 0.301 | 1.00 58.30 | C3 |
| ATOM | 3680 | N | PHE | 541 | 55.256 | 30.008 | 2.292 | 1.00 55.25 | C3 |
| ATOM | 3681 | H | PHE | 541 | 55.093 | 30.068 | 3.257 | 1.00 0.00 | C3 |
| ATOM | 3682 | CA | PHE | 541 | 56.299 | 30.814 | 1.702 | 1.00 51.38 | C3 |
| ATOM | 3683 | CB | PHE | 541 | 55.964 | 32.306 | 1.942 | 1.00 48.80 | C3 |
| ATOM | 3684 | CG | PHE | 541 | 54.789 | 32.703 | 1.058 | 1.00 45.77 | C3 |
| ATOM | 3685 | CD1 | PHE | 541 | 54.992 | 32.939 | -0.279 | 1.00 44.20 | C3 |
| ATOM | 3686 | CD2 | PHE | 541 | 53.507 | 32.747 | 1.582 | 1.00 44.76 | C3 |
| ATOM | 3687 | CE1 | PHE | 541 | 53.901 | 33.207 | -1.074 | 1.00 43.98 | C3 |
| ATOM | 3688 | CE2 | PHE | 541 | 52.428 | 33.018 | 0.769 | 1.00 42.86 | C3 |
| ATOM | 3689 | CZ | PHE | 541 | 52.625 | 33.247 | -0.563 | 1.00 42.52 | C3 |
| ATOM | 3690 | C | PHE | 541 | 57.586 | 30.364 | 2.333 | 1.00 49.80 | C3 |
| ATOM | 3691 | O | PHE | 541 | 58.002 | 30.807 | 3.395 | 1.00 49.55 | C3 |
| ATOM | 3692 | N | ALA | 542 | 58.172 | 29.442 | 1.562 | 1.00 48.21 | C3 |
| ATOM | 3693 | H | ALA | 542 | 57.825 | 29.298 | 0.656 | 1.00 0.00 | C3 |
| ATOM | 3694 | CA | ALA | 542 | 59.326 | 28.711 | 1.968 | 1.00 45.37 | C3 |
| ATOM | 3695 | CB | ALA | 542 | 59.700 | 27.749 | 0.898 | 1.00 45.21 | C3 |
| ATOM | 3696 | C | ALA | 542 | 60.510 | 29.567 | 2.266 | 1.00 44.87 | C3 |
| ATOM | 3697 | O | ALA | 542 | 61.001 | 29.504 | 3.374 | 1.00 46.49 | C3 |

FIG.5-44

| | | | | | | | | | |
|---|---|---|---|---|---|---|---|---|---|
| ATOM | 3698 | N | SER | 543 | 61.013 | 30.408 | 1.395 | 1.00 42.63 | C3 |
| ATOM | 3699 | H | SER | 543 | 60.477 | 30.685 | 0.630 | 1.00 0.00 | C3 |
| ATOM | 3700 | CA | SER | 543 | 62.253 | 31.108 | 1.708 | 1.00 40.31 | C3 |
| ATOM | 3701 | CB | SER | 543 | 63.170 | 30.861 | 0.587 | 1.00 37.74 | C3 |
| ATOM | 3702 | OG | SER | 543 | 62.391 | 31.181 | -0.554 | 1.00 35.74 | C3 |
| ATOM | 3703 | HG | SER | 543 | 61.824 | 30.423 | -0.751 | 1.00 0.00 | C3 |
| ATOM | 3704 | C | SER | 543 | 62.087 | 32.613 | 1.896 | 1.00 40.88 | C3 |
| ATOM | 3705 | O | SER | 543 | 61.016 | 33.115 | 1.536 | 1.00 42.63 | C3 |
| ATOM | 3706 | N | ALA | 544 | 63.120 | 33.383 | 2.310 | 1.00 38.84 | C3 |
| ATOM | 3707 | H | ALA | 544 | 63.929 | 32.951 | 2.650 | 1.00 0.00 | C3 |
| ATOM | 3708 | CA | ALA | 544 | 63.035 | 34.836 | 2.345 | 1.00 37.31 | C3 |
| ATOM | 3709 | CB | ALA | 544 | 64.340 | 35.450 | 2.808 | 1.00 35.74 | C3 |
| ATOM | 3710 | C | ALA | 544 | 62.723 | 35.372 | 0.947 | 1.00 37.06 | C3 |
| ATOM | 3711 | O | ALA | 544 | 61.829 | 36.220 | 0.820 | 1.00 38.23 | C3 |
| ATOM | 3712 | N | PHE | 545 | 63.357 | 34.881 | -0.130 | 1.00 35.72 | C3 |
| ATOM | 3713 | H | PHE | 545 | 64.131 | 34.298 | -0.010 | 1.00 0.00 | C3 |
| ATOM | 3714 | CA | PHE | 545 | 62.992 | 35.268 | -1.484 | 1.00 33.66 | C3 |
| ATOM | 3715 | CB | PHE | 545 | 63.738 | 34.534 | -2.593 | 1.00 29.71 | C3 |
| ATOM | 3716 | CG | PHE | 545 | 63.140 | 34.742 | -3.990 | 1.00 29.62 | C3 |
| ATOM | 3717 | CD1 | PHE | 545 | 62.317 | 35.788 | -4.557 | 1.00 29.80 | C3 |
| ATOM | 3718 | CD2 | PHE | 545 | 63.371 | 35.915 | -4.689 | 1.00 31.90 | C3 |
| ATOM | 3719 | CE1 | PHE | 545 | 61.723 | 33.984 | -5.795 | 1.00 28.61 | C3 |
| ATOM | 3720 | CE2 | PHE | 545 | 62.777 | 36.113 | -5.928 | 1.00 31.00 | C3 |
| ATOM | 3721 | CZ | PHE | 545 | 61.955 | 35.150 | -6.480 | 1.00 31.01 | C3 |
| ATOM | 3722 | C | PHE | 545 | 61.543 | 34.900 | -1.667 | 1.00 34.81 | C3 |
| ATOM | 3723 | O | PHE | 545 | 60.901 | 35.660 | -2.389 | 1.00 38.88 | C3 |
| ATOM | 3724 | N | GLN | 546 | 60.912 | 33.847 | -1.135 | 1.00 34.77 | C3 |
| ATOM | 3725 | H | GLN | 546 | 61.396 | 33.223 | -0.558 | 1.00 0.00 | C3 |
| ATOM | 3726 | CA | GLN | 546 | 59.490 | 33.637 | -1.433 | 1.00 33.72 | C3 |
| ATOM | 3727 | CB | GLN | 546 | 59.145 | 32.232 | -1.140 | 1.00 34.85 | C3 |
| ATOM | 3728 | CG | GLN | 546 | 59.582 | 31.585 | -2.444 | 1.00 42.45 | C3 |
| ATOM | 3729 | CD | GLN | 546 | 59.374 | 30.085 | -2.473 | 1.00 46.05 | C3 |
| ATOM | 3730 | OE1 | GLN | 546 | 59.287 | 29.472 | -1.399 | 1.00 48.90 | C3 |
| ATOM | 3731 | NE2 | GLN | 546 | 59.339 | 29.442 | -3.644 | 1.00 47.20 | C3 |
| ATOM | 3732 | HE21 | GLN | 546 | 59.476 | 29.948 | -4.472 | 1.00 0.00 | C3 |
| ATOM | 3733 | HE22 | GLN | 546 | 59.154 | 28.481 | -3.609 | 1.00 0.00 | C3 |
| ATOM | 3734 | C | GLN | 546 | 58.504 | 34.541 | -0.729 | 1.00 31.62 | C3 |
| ATOM | 3735 | O | GLN | 546 | 57.429 | 34.850 | -1.233 | 1.00 29.88 | C3 |
| ATOM | 3736 | N | ARG | 547 | 58.907 | 34.929 | 0.465 | 1.00 31.09 | C3 |
| ATOM | 3737 | H | ARG | 547 | 59.750 | 34.566 | 0.811 | 1.00 0.00 | C3 |
| ATOM | 3738 | CA | ARG | 547 | 58.160 | 35.830 | 1.282 | 1.00 31.43 | C3 |
| ATOM | 3739 | CB | ARG | 547 | 58.813 | 35.874 | 2.601 | 1.00 31.74 | C3 |
| ATOM | 3740 | CG | ARG | 547 | 57.906 | 35.224 | 3.623 | 1.00 37.02 | C3 |
| ATOM | 3741 | CD | ARG | 547 | 58.344 | 33.858 | 4.076 | 1.00 40.56 | C3 |
| ATOM | 3742 | NE | ARG | 547 | 59.743 | 34.058 | 4.345 | 1.00 47.90 | C3 |
| ATOM | 3743 | HE | ARG | 547 | 60.389 | 33.924 | 3.620 | 1.00 0.00 | C3 |
| ATOM | 3744 | CZ | ARG | 547 | 60.190 | 34.394 | 5.543 | 1.00 49.48 | C3 |
| ATOM | 3745 | NH1 | ARG | 547 | 59.361 | 34.522 | 6.593 | 1.00 51.97 | C3 |
| ATOM | 3746 | HH11 | ARG | 547 | 58.380 | 34.356 | 6.488 | 1.00 0.00 | C3 |
| ATOM | 3747 | HH12 | ARG | 547 | 59.731 | 34.763 | 7.491 | 1.00 0.00 | C3 |
| ATOM | 3748 | NH2 | ARG | 547 | 61.464 | 34.775 | 5.616 | 1.00 48.55 | C3 |
| ATOM | 3749 | HH21 | ARG | 547 | 62.025 | 34.803 | 4.788 | 1.00 0.00 | C3 |
| ATOM | 3750 | HH22 | ARG | 547 | 61.854 | 35.034 | 6.501 | 1.00 0.00 | C3 |
| ATOM | 3751 | C | ARG | 547 | 58.167 | 37.181 | 0.590 | 1.00 32.26 | C3 |
| ATOM | 3752 | O | ARG | 547 | 57.084 | 37.694 | 0.317 | 1.00 34.25 | C3 |
| ATOM | 3753 | N | ARG | 548 | 59.348 | 37.717 | 0.205 | 1.00 31.44 | C3 |
| ATOM | 3754 | H | ARG | 548 | 60.148 | 37.203 | 0.444 | 1.00 0.00 | C3 |
| ATOM | 3755 | CA | ARG | 548 | 59.529 | 38.980 | -0.555 | 1.00 30.01 | C3 |
| ATOM | 3756 | CB | ARG | 548 | 60.995 | 39.213 | -0.949 | 1.00 25.42 | C3 |
| ATOM | 3757 | CG | ARG | 548 | 61.820 | 39.361 | 0.294 | 1.00 26.11 | C3 |
| ATOM | 3758 | CD | ARG | 548 | 63.280 | 39.158 | -0.054 | 1.00 29.34 | C3 |
| ATOM | 3759 | NE | ARG | 548 | 64.044 | 39.162 | 1.189 | 1.00 32.30 | C3 |
| ATOM | 3760 | HE | ARG | 548 | 63.572 | 38.883 | 1.995 | 1.00 0.00 | C3 |
| ATOM | 3761 | CZ | ARG | 548 | 65.344 | 39.518 | 1.325 | 1.00 32.66 | C3 |
| ATOM | 3762 | NH1 | ARG | 548 | 66.159 | 39.923 | 0.335 | 1.00 34.98 | C3 |
| ATOM | 3763 | HH11 | ARG | 548 | 67.107 | 40.170 | 0.533 | 1.00 0.00 | C3 |
| ATOM | 3764 | HH12 | ARG | 548 | 65.812 | 39.981 | -0.600 | 1.00 0.00 | C3 |
| ATOM | 3765 | NH2 | ARG | 548 | 65.837 | 39.518 | 2.549 | 1.00 32.03 | C3 |
| ATOM | 3766 | HH21 | ARG | 548 | 66.788 | 39.783 | 2.708 | 1.00 0.00 | C3 |
| ATOM | 3767 | HH22 | ARG | 548 | 65.250 | 39.275 | 3.321 | 1.00 0.00 | C3 |
| ATOM | 3768 | C | ARG | 548 | 58.713 | 38.997 | -1.832 | 1.00 29.81 | C3 |
| ATOM | 3769 | O | ARG | 548 | 57.778 | 39.790 | -1.968 | 1.00 33.03 | C3 |
| ATOM | 3770 | N | ALA | 549 | 58.979 | 38.102 | -2.761 | 1.00 27.87 | C3 |
| ATOM | 3771 | H | ALA | 549 | 59.684 | 37.436 | -2.601 | 1.00 0.00 | C3 |
| ATOM | 3772 | CA | ALA | 549 | 58.227 | 38.045 | -3.984 | 1.00 27.18 | C3 |
| ATOM | 3773 | CB | ALA | 549 | 58.797 | 36.934 | -4.857 | 1.00 28.72 | C3 |
| ATOM | 3774 | C | ALA | 549 | 56.748 | 37.810 | -3.770 | 1.00 25.91 | C3 |
| ATOM | 3775 | O | ALA | 549 | 55.896 | 38.337 | -4.468 | 1.00 26.03 | C3 |
| ATOM | 3776 | N | GLY | 550 | 56.421 | 37.074 | -2.748 | 1.00 26.53 | C3 |
| ATOM | 3777 | H | GLY | 550 | 57.103 | 36.657 | -2.185 | 1.00 0.00 | C3 |
| ATOM | 3778 | CA | GLY | 550 | 55.055 | 36.805 | -2.457 | 1.00 26.08 | C3 |
| ATOM | 3779 | C | GLY | 550 | 54.410 | 38.098 | -2.075 | 1.00 26.94 | C3 |
| ATOM | 3780 | O | GLY | 550 | 53.339 | 38.380 | -2.608 | 1.00 26.59 | C3 |
| ATOM | 3781 | N | GLY | 551 | 55.073 | 38.917 | -1.234 | 1.00 27.78 | C3 |
| ATOM | 3782 | H | GLY | 551 | 55.958 | 38.642 | -0.925 | 1.00 0.00 | C3 |
| ATOM | 3783 | CA | GLY | 551 | 54.540 | 40.212 | -0.779 | 1.00 26.51 | C3 |

FIG.5-45

```
ATOM 3784 C   GLY 551  54.302 41.113 -1.994 1.00 26.82 C3
ATOM 3785 O   GLY 551  53.313 41.852 -2.065 1.00 27.82 C3
ATOM 3786 N   VAL 552  55.154 41.013 -3.012 1.00 25.81 C3
ATOM 3787 H   VAL 552  55.916 40.396 -2.954 1.00 0.00  C3
ATOM 3788 CA  VAL 552  54.952 41.843 -4.176 1.00 28.39 C3
ATOM 3789 CB  VAL 552  56.178 41.743 -5.190 1.00 26.20 C3
ATOM 3790 CG1 VAL 552  55.917 42.391 -6.541 1.00 26.53 C3
ATOM 3791 CG2 VAL 552  57.327 42.546 -4.594 1.00 26.44 C3
ATOM 3792 C   VAL 552  53.650 41.406 -4.820 1.00 29.05 C3
ATOM 3793 O   VAL 552  52.744 42.251 -4.888 1.00 31.68 C3
ATOM 3794 N   LEU 553  53.455 40.120 -5.176 1.00 27.20 C3
ATOM 3795 H   LEU 553  54.122 39.447 -4.908 1.00 0.00  C3
ATOM 3796 CA  LEU 553  52.266 39.705 -5.915 1.00 23.80 C3
ATOM 3797 CB  LEU 553  52.357 38.262 -6.363 1.00 24.86 C3
ATOM 3798 CG  LEU 553  53.432 37.955 -7.357 1.00 23.06 C3
ATOM 3799 CD1 LEU 553  54.073 36.623 -7.092 1.00 24.31 C3
ATOM 3800 CD2 LEU 553  52.794 38.061 -8.703 1.00 21.87 C3
ATOM 3801 C   LEU 553  51.012 39.825 -5.114 1.00 23.72 C3
ATOM 3802 O   LEU 553  49.982 40.138 -5.712 1.00 24.63 C3
ATOM 3803 N   VAL 554  50.962 39.580 -3.803 1.00 24.37 C3
ATOM 3804 H   VAL 554  51.774 39.350 -3.295 1.00 0.00  C3
ATOM 3805 CA  VAL 554  49.660 39.691 -3.180 1.00 26.36 C3
ATOM 3806 CB  VAL 554  49.472 38.751 -1.802 1.00 26.55 C3
ATOM 3807 CG1 VAL 554  50.696 37.933 -1.418 1.00 23.95 C3
ATOM 3808 CG2 VAL 554  48.953 39.614 -0.682 1.00 25.58 C3
ATOM 3809 C   VAL 554  49.322 41.175 -2.960 1.00 27.53 C3
ATOM 3810 O   VAL 554  48.142 41.502 -3.192 1.00 27.44 C3
ATOM 3811 N   ALA 555  50.277 42.106 -2.716 1.00 28.04 C3
ATOM 3812 H   ALA 555  51.221 41.831 -2.658 1.00 0.00  C3
ATOM 3813 CA  ALA 555  49.956 43.539 -2.509 1.00 28.57 C3
ATOM 3814 CB  ALA 555  51.161 44.427 -2.217 1.00 28.07 C3
ATOM 3815 C   ALA 555  49.402 44.055 -3.803 1.00 28.12 C3
ATOM 3816 O   ALA 555  48.425 44.803 -3.847 1.00 30.12 C3
ATOM 3817 N   SER 556  49.985 43.521 -4.839 1.00 26.44 C3
ATOM 3818 H   SER 556  50.781 42.956 -4.710 1.00 0.00  C3
ATOM 3819 CA  SER 556  49.548 43.810 -6.152 1.00 30.09 C3
ATOM 3820 CB  SER 556  50.684 43.277 -6.965 1.00 31.42 C3
ATOM 3821 OG  SER 556  50.442 43.338 -8.344 1.00 37.88 C3
ATOM 3822 HG  SER 556  49.966 44.144 -8.576 1.00 0.00  C3
ATOM 3823 C   SER 556  48.143 43.243 -6.454 1.00 32.78 C3
ATOM 3824 O   SER 556  47.287 43.961 -7.003 1.00 34.56 C3
ATOM 3825 N   HIS 557  47.750 42.019 -6.088 1.00 32.78 C3
ATOM 3826 H   HIS 557  48.350 41.453 -5.560 1.00 0.00  C3
ATOM 3827 CA  HIS 557  46.396 41.605 -6.401 1.00 33.64 C3
ATOM 3828 CB  HIS 557  46.203 40.142 -6.242 1.00 37.88 C3
ATOM 3829 CG  HIS 557  46.986 39.518 -7.348 1.00 42.44 C3
ATOM 3830 CD2 HIS 557  46.694 39.665 -8.675 1.00 43.63 C3
ATOM 3831 ND1 HIS 557  48.108 38.837 -7.209 1.00 45.23 C3
ATOM 3832 HD1 HIS 557  48.641 38.764 -6.385 1.00 0.00  C3
ATOM 3833 CE1 HIS 557  48.524 38.569 -8.414 1.00 46.56 C3
ATOM 3834 NE2 HIS 557  47.676 39.066 -9.283 1.00 45.62 C3
ATOM 3835 HE2 HIS 557  47.793 39.018 -10.257 1.00 0.00 C3
ATOM 3836 C   HIS 557  45.383 42.249 -5.520 1.00 32.94 C3
ATOM 3837 O   HIS 557  44.256 42.444 -5.934 1.00 33.08 C3
ATOM 3838 N   LEU 558  45.744 42.534 -4.280 1.00 33.05 C3
ATOM 3839 H   LEU 558  46.657 42.356 -3.986 1.00 0.00  C3
ATOM 3840 CA  LEU 558  44.817 43.125 -3.348 1.00 31.91 C3
ATOM 3841 CB  LEU 558  45.420 43.107 -1.965 1.00 29.25 C3
ATOM 3842 CG  LEU 558  44.605 43.615 -0.818 1.00 26.02 C3
ATOM 3843 CD1 LEU 558  43.279 42.883 -0.742 1.00 25.00 C3
ATOM 3844 CD2 LEU 558  45.496 43.571 0.408  1.00 22.86 C3
ATOM 3845 C   LEU 558  44.527 44.521 -3.783 1.00 22.47 C3
ATOM 3846 O   LEU 558  43.402 44.944 -3.596 1.00 33.97 C3
ATOM 3847 N   GLN 559  45.482 45.231 -4.370 1.00 34.36 C3
ATOM 3848 H   GLN 559  46.386 44.855 -4.406 1.00 0.00  C3
ATOM 3849 CA  GLN 559  45.255 46.569 -4.912 1.00 36.75 C3
ATOM 3850 CB  GLN 559  46.598 47.067 -5.470 1.00 39.63 C3
ATOM 3851 CG  GLN 559  46.707 48.543 -5.875 1.00 42.07 C3
ATOM 3852 CD  GLN 559  46.530 49.618 -4.793 1.00 41.53 C3
ATOM 3853 OE1 GLN 559  45.961 50.687 -5.057 1.00 41.25 C3
ATOM 3854 NE2 GLN 559  46.951 49.416 -3.561 1.00 37.96 C3
ATOM 3855 HE21 GLN 559 47.271 48.528 -3.311 1.00 0.00  C3
ATOM 3856 HE22 GLN 559 47.001 50.190 -2.967 1.00 0.00  C3
ATOM 3857 C   GLN 559  44.142 46.635 -5.976 1.00 35.22 C3
ATOM 3858 O   GLN 559  43.165 47.404 -5.839 1.00 34.99 C3
ATOM 3859 N   SER 560  44.260 45.817 -7.025 1.00 33.46 C3
ATOM 3860 H   SER 560  45.083 45.292 -7.154 1.00 0.00  C3
ATOM 3861 CA  SER 560  43.222 45.683 -8.049 1.00 32.88 C3
ATOM 3862 CB  SER 560  43.693 44.776 -9.088 1.00 34.05 C3
ATOM 3863 OG  SER 560  45.021 45.174 -9.281 1.00 42.40 C3
ATOM 3864 HG  SER 560  45.042 45.996 -9.783 1.00 0.00  C3
ATOM 3865 C   SER 560  41.885 45.133 -7.559 1.00 32.01 C3
ATOM 3866 O   SER 560  40.791 45.582 -7.920 1.00 32.23 C3
ATOM 3867 N   PHE 561  41.969 44.123 -6.710 1.00 29.50 C3
ATOM 3868 H   PHE 561  42.850 43.767 -6.464 1.00 0.00  C3
ATOM 3869 CA  PHE 561  40.803 43.529 -6.118 1.00 28.17 C3
```

FIG.5-46

| ATOM | 3870 | CB  | PHE | 561 | 41.237 | 42.541 | -5.040  | 1.00 | 26.27 | C3 |
| --- | --- | --- | --- | --- | --- | --- | --- | --- | --- | --- |
| ATOM | 3871 | CG  | PHE | 561 | 40.069 | 41.966 | -4.268  | 1.00 | 25.68 | C3 |
| ATOM | 3872 | CD1 | PHE | 561 | 39.282 | 40.999 | -4.846  | 1.00 | 25.44 | C3 |
| ATOM | 3873 | CD2 | PHE | 561 | 39.761 | 42.482 | -3.051  | 1.00 | 25.45 | C3 |
| ATOM | 3874 | CE1 | PHE | 561 | 38.166 | 40.551 | -4.215  | 1.00 | 21.49 | C3 |
| ATOM | 3875 | CE2 | PHE | 561 | 38.635 | 42.027 | -2.421  | 1.00 | 26.89 | C3 |
| ATOM | 3876 | CZ  | PHE | 561 | 37.853 | 41.074 | -3.008  | 1.00 | 24.29 | C3 |
| ATOM | 3877 | C   | PHE | 561 | 39.987 | 44.645 | -5.505  | 1.00 | 28.81 | C3 |
| ATOM | 3878 | O   | PHE | 561 | 38.789 | 44.697 | -5.731  | 1.00 | 29.31 | C3 |
| ATOM | 3879 | N   | LEU | 562 | 40.672 | 45.565 | -4.797  | 1.00 | 28.39 | C3 |
| ATOM | 3880 | H   | LEU | 562 | 41.643 | 45.462 | -4.707  | 1.00 | 0.00  | C3 |
| ATOM | 3881 | CA  | LEU | 562 | 40.033 | 46.617 | -4.057  | 1.00 | 26.51 | C3 |
| ATOM | 3882 | CB  | LEU | 562 | 40.964 | 47.203 | -3.074  | 1.00 | 23.80 | C3 |
| ATOM | 3883 | CG  | LEU | 562 | 41.047 | 46.411 | -1.816  | 1.00 | 24.85 | C3 |
| ATOM | 3884 | CD1 | LEU | 562 | 42.207 | 46.868 | -1.049  | 1.00 | 24.07 | C3 |
| ATOM | 3885 | CD2 | LEU | 562 | 39.794 | 46.551 | -1.008  | 1.00 | 25.13 | C3 |
| ATOM | 3886 | C   | LEU | 562 | 39.586 | 47.669 | -4.988  | 1.00 | 29.27 | C3 |
| ATOM | 3887 | O   | LEU | 562 | 38.580 | 48.304 | -4.681  | 1.00 | 29.83 | C3 |
| ATOM | 3888 | N   | GLU | 563 | 40.239 | 47.871 | -6.115  | 1.00 | 30.88 | C3 |
| ATOM | 3889 | H   | GLU | 563 | 41.052 | 47.368 | -6.325  | 1.00 | 0.00  | C3 |
| ATOM | 3890 | CA  | GLU | 563 | 39.738 | 48.908 | -6.966  | 1.00 | 36.88 | C3 |
| ATOM | 3891 | CB  | GLU | 563 | 40.660 | 49.142 | -8.137  | 1.00 | 40.80 | C3 |
| ATOM | 3892 | CG  | GLU | 563 | 41.999 | 49.628 | -7.682  | 1.00 | 48.55 | C3 |
| ATOM | 3893 | CD  | GLU | 563 | 43.148 | 49.277 | -8.619  | 1.00 | 55.42 | C3 |
| ATOM | 3894 | OE1 | GLU | 563 | 44.301 | 49.283 | -8.135  | 1.00 | 57.39 | C3 |
| ATOM | 3895 | OE2 | GLU | 563 | 42.886 | 48.986 | -9.808  | 1.00 | 56.44 | C3 |
| ATOM | 3896 | C   | GLU | 563 | 38.375 | 48.469 | -7.466  | 1.00 | 39.02 | C3 |
| ATOM | 3897 | O   | GLU | 563 | 37.388 | 49.170 | -7.270  | 1.00 | 39.09 | C3 |
| ATOM | 3898 | N   | VAL | 564 | 38.289 | 47.255 | -8.030  | 1.00 | 42.30 | C3 |
| ATOM | 3899 | H   | VAL | 564 | 39.107 | 46.714 | -8.074  | 1.00 | 0.00  | C3 |
| ATOM | 3900 | CA  | VAL | 564 | 37.052 | 46.683 | -8.558  | 1.00 | 41.84 | C3 |
| ATOM | 3901 | CB  | VAL | 564 | 37.333 | 45.255 | -9.041  | 1.00 | 42.27 | C3 |
| ATOM | 3902 | CG1 | VAL | 564 | 36.055 | 44.538 | -9.435  | 1.00 | 41.17 | C3 |
| ATOM | 3903 | CG2 | VAL | 564 | 38.283 | 45.348 | -10.241 | 1.00 | 42.11 | C3 |
| ATOM | 3904 | C   | VAL | 564 | 36.030 | 46.709 | -7.442  | 1.00 | 41.68 | C3 |
| ATOM | 3905 | O   | VAL | 564 | 34.892 | 47.015 | -7.697  | 1.00 | 42.34 | C3 |
| ATOM | 3906 | N   | SER | 565 | 36.419 | 46.173 | -6.206  | 1.00 | 42.75 | C3 |
| ATOM | 3907 | H   | SER | 565 | 37.333 | 46.173 | -6.063  | 1.00 | 0.00  | C3 |
| ATOM | 3908 | CA  | SER | 565 | 35.562 | 46.602 | -5.064  | 1.00 | 44.85 | C3 |
| ATOM | 3909 | CB  | SER | 565 | 36.344 | 46.013 | -3.894  | 1.00 | 46.54 | C3 |
| ATOM | 3910 | OG  | SER | 565 | 35.590 | 45.714 | -2.731  | 1.00 | 51.75 | C3 |
| ATOM | 3911 | HG  | SER | 565 | 35.060 | 46.481 | -2.491  | 1.00 | 0.00  | C3 |
| ATOM | 3912 | C   | SER | 565 | 35.167 | 48.063 | -4.871  | 1.00 | 45.70 | C3 |
| ATOM | 3913 | O   | SER | 565 | 34.038 | 48.287 | -4.446  | 1.00 | 46.87 | C3 |
| ATOM | 3914 | N   | TYR | 566 | 35.965 | 49.093 | -5.146  | 1.00 | 47.59 | C3 |
| ATOM | 3915 | H   | TYR | 566 | 36.893 | 48.908 | -5.386  | 1.00 | 0.00  | C3 |
| ATOM | 3916 | CA  | TYR | 566 | 35.518 | 50.474 | -5.086  | 1.00 | 49.68 | C3 |
| ATOM | 3917 | CB  | TYR | 566 | 36.765 | 51.362 | -5.164  | 1.00 | 56.17 | C3 |
| ATOM | 3918 | CG  | TYR | 566 | 36.715 | 52.622 | -6.007  | 1.00 | 64.64 | C3 |
| ATOM | 3919 | CD1 | TYR | 566 | 37.264 | 52.538 | -7.278  | 1.00 | 69.53 | C3 |
| ATOM | 3920 | CE1 | TYR | 566 | 37.212 | 53.613 | -8.151  | 1.00 | 73.71 | C3 |
| ATOM | 3921 | CD2 | TYR | 566 | 36.109 | 53.797 | -5.569  | 1.00 | 67.98 | C3 |
| ATOM | 3922 | CE2 | TYR | 566 | 36.048 | 54.888 | -6.441  | 1.00 | 72.92 | C3 |
| ATOM | 3923 | CZ  | TYR | 566 | 36.599 | 54.787 | -7.735  | 1.00 | 75.29 | C3 |
| ATOM | 3924 | OH  | TYR | 566 | 36.538 | 55.838 | -8.652  | 1.00 | 77.42 | C3 |
| ATOM | 3925 | HH  | TYR | 566 | 36.905 | 55.565 | -9.494  | 1.00 | 0.00  | C3 |
| ATOM | 3926 | C   | TYR | 566 | 34.524 | 50.696 | -6.217  | 1.00 | 48.48 | C3 |
| ATOM | 3927 | O   | TYR | 566 | 33.545 | 51.376 | -5.950  | 1.00 | 46.35 | C3 |
| ATOM | 3928 | N   | ALA | 567 | 34.679 | 50.115 | -7.417  | 1.00 | 49.14 | C3 |
| ATOM | 3929 | H   | ALA | 567 | 35.512 | 49.625 | -7.572  | 1.00 | 0.00  | C3 |
| ATOM | 3930 | CA  | ALA | 567 | 33.670 | 50.165 | -8.490  | 1.00 | 52.09 | C3 |
| ATOM | 3931 | CB  | ALA | 567 | 34.210 | 49.574 | -9.788  | 1.00 | 48.37 | C3 |
| ATOM | 3932 | C   | ALA | 567 | 32.315 | 49.449 | -8.238  | 1.00 | 55.31 | C3 |
| ATOM | 3933 | O   | ALA | 567 | 31.226 | 50.008 | -8.501  | 1.00 | 56.87 | C3 |
| ATOM | 3934 | N   | VAL | 568 | 32.247 | 48.211 | -7.736  | 1.00 | 57.66 | C3 |
| ATOM | 3935 | H   | VAL | 568 | 33.083 | 47.729 | -7.564  | 1.00 | 0.00  | C3 |
| ATOM | 3936 | CA  | VAL | 568 | 30.980 | 47.573 | -7.490  | 1.00 | 59.61 | C3 |
| ATOM | 3937 | CB  | VAL | 568 | 31.119 | 46.031 | -7.339  | 1.00 | 58.96 | C3 |
| ATOM | 3938 | CG1 | VAL | 568 | 31.239 | 45.508 | -5.911  | 1.00 | 60.27 | C3 |
| ATOM | 3939 | CG2 | VAL | 568 | 29.851 | 45.471 | -7.922  | 1.00 | 60.44 | C3 |
| ATOM | 3940 | C   | VAL | 568 | 30.393 | 48.177 | -6.245  | 1.00 | 62.66 | C3 |
| ATOM | 3941 | O   | VAL | 568 | 29.174 | 48.154 | -6.180  | 1.00 | 64.78 | C3 |
| ATOM | 3942 | N   | LEU | 569 | 31.075 | 48.737 | -5.248  | 1.00 | 66.15 | C3 |
| ATOM | 3943 | H   | LEU | 569 | 32.058 | 48.719 | -5.243  | 1.00 | 0.00  | C3 |
| ATOM | 3944 | CA  | LEU | 569 | 30.359 | 49.334 | -4.123  | 1.00 | 69.85 | C3 |
| ATOM | 3945 | CB  | LEU | 569 | 31.285 | 49.858 | -3.023  | 1.00 | 69.91 | C3 |
| ATOM | 3946 | CG  | LEU | 569 | 32.007 | 48.887 | -2.095  | 1.00 | 70.17 | C3 |
| ATOM | 3947 | CD1 | LEU | 569 | 32.847 | 49.687 | -1.140  | 1.00 | 70.19 | C3 |
| ATOM | 3948 | CD2 | LEU | 569 | 31.039 | 48.054 | -1.286  | 1.00 | 70.56 | C3 |
| ATOM | 3949 | C   | LEU | 569 | 29.567 | 50.509 | -4.667  | 1.00 | 72.69 | C3 |
| ATOM | 3950 | O   | LEU | 569 | 28.365 | 50.553 | -4.425  | 1.00 | 73.80 | C3 |
| ATOM | 3951 | N   | ARG | 570 | 30.180 | 51.391 | -5.479  | 1.00 | 75.95 | C3 |
| ATOM | 3952 | H   | ARG | 570 | 31.153 | 51.299 | -5.580  | 1.00 | 0.00  | C3 |
| ATOM | 3953 | CA  | ARG | 570 | 29.510 | 52.498 | -6.173  | 1.00 | 78.78 | C3 |
| ATOM | 3954 | CB  | ARG | 570 | 30.399 | 53.068 | -7.308  | 1.00 | 80.07 | C3 |
| ATOM | 3955 | CG  | ARG | 570 | 29.658 | 54.222 | -7.997  | 1.00 | 84.16 | C3 |

FIG. 5-47

| | | | | | | | | | |
|---|---|---|---|---|---|---|---|---|---|
| ATOM | 3956 | CD | ARG | 570 | 29.976 | 54.744 | -9.417 | 1.00 85.66 | C3 |
| ATOM | 3957 | NE | ARG | 570 | 28.892 | 55.690 | -9.737 | 1.00 85.67 | C3 |
| ATOM | 3958 | HE | ARG | 570 | 27.971 | 55.354 | -9.727 | 1.00 0.00 | C3 |
| ATOM | 3959 | CZ | ARG | 570 | 29.051 | 56.991 | -10.026 | 1.00 85.06 | C3 |
| ATOM | 3960 | NH1 | ARG | 570 | 30.240 | 57.590 | -10.082 | 1.00 84.43 | C3 |
| ATOM | 3961 | HH11 | ARG | 570 | 31.069 | 57.056 | -9.908 | 1.00 0.00 | C3 |
| ATOM | 3962 | HH12 | ARG | 570 | 30.295 | 58.561 | -10.314 | 1.00 0.00 | C3 |
| ATOM | 3963 | NH2 | ARG | 570 | 27.958 | 57.316 | -10.154 | 1.00 84.57 | C3 |
| ATOM | 3964 | HH21 | ARG | 570 | 27.059 | 57.316 | -10.030 | 1.00 0.00 | C3 |
| ATOM | 3965 | HH22 | ARG | 570 | 28.042 | 58.708 | -10.375 | 1.00 0.00 | C3 |
| ATOM | 3966 | C | ARG | 570 | 28.201 | 52.009 | -6.812 | 1.00 79.92 | C3 |
| ATOM | 3967 | O | ARG | 570 | 27.107 | 52.565 | -6.709 | 1.00 79.61 | C3 |
| ATOM | 3968 | N | HIS | 571 | 28.362 | 50.900 | -7.511 | 1.00 81.35 | C3 |
| ATOM | 3969 | H | HIS | 571 | 29.214 | 50.417 | -7.440 | 1.00 0.00 | C3 |
| ATOM | 3970 | CA | HIS | 571 | 27.247 | 50.306 | -8.197 | 1.00 82.75 | C3 |
| ATOM | 3971 | CB | HIS | 571 | 27.882 | 49.274 | -9.167 | 1.00 83.42 | C3 |
| ATOM | 3972 | CG | HIS | 571 | 28.633 | 50.029 | -10.280 | 1.00 85.08 | C3 |
| ATOM | 3973 | CD2 | HIS | 571 | 28.921 | 49.529 | -11.532 | 1.00 85.81 | C3 |
| ATOM | 3974 | ND1 | HIS | 571 | 29.074 | 51.303 | -10.268 | 1.00 86.25 | C3 |
| ATOM | 3975 | HD1 | HIS | 571 | 29.080 | 51.900 | -9.489 | 1.00 0.00 | C3 |
| ATOM | 3976 | CE1 | HIS | 571 | 29.595 | 51.595 | -11.439 | 1.00 86.01 | C3 |
| ATOM | 3977 | NE2 | HIS | 571 | 29.494 | 50.518 | -12.187 | 1.00 86.28 | C3 |
| ATOM | 3978 | HE2 | HIS | 571 | 29.801 | 50.468 | -13.119 | 1.00 0.00 | C3 |
| ATOM | 3979 | C | HIS | 571 | 26.225 | 49.759 | -7.195 | 1.00 83.31 | C3 |
| ATOM | 3980 | O | HIS | 571 | 25.075 | 50.194 | -7.301 | 1.00 84.06 | C3 |
| ATOM | 3981 | N | LEU | 572 | 26.540 | 48.963 | -6.158 | 1.00 83.11 | C3 |
| ATOM | 3982 | H | LEU | 572 | 27.474 | 48.824 | -5.915 | 1.00 0.00 | C3 |
| ATOM | 3983 | CA | LEU | 572 | 25.527 | 48.457 | -5.241 | 1.00 83.71 | C3 |
| ATOM | 3984 | CB | LEU | 572 | 26.085 | 47.267 | -4.454 | 1.00 83.57 | C3 |
| ATOM | 3985 | CG | LEU | 572 | 25.439 | 45.884 | -4.721 | 1.00 83.79 | C3 |
| ATOM | 3986 | CD1 | LEU | 572 | 25.783 | 45.386 | -6.127 | 1.00 84.16 | C3 |
| ATOM | 3987 | CD2 | LEU | 572 | 25.958 | 44.866 | -3.714 | 1.00 84.08 | C3 |
| ATOM | 3988 | C | LEU | 572 | 24.997 | 49.511 | -4.261 | 1.00 84.78 | C3 |
| ATOM | 3989 | O | LEU | 572 | 24.265 | 49.192 | -3.295 | 1.00 84.85 | C3 |
| ATOM | 3990 | N | ALA | 573 | 25.349 | 50.796 | -4.483 | 1.00 85.56 | C3 |
| ATOM | 3991 | H | ALA | 573 | 26.020 | 50.980 | -5.174 | 1.00 0.00 | C3 |
| ATOM | 3992 | CA | ALA | 573 | 24.822 | 51.925 | -3.721 | 1.00 85.90 | C3 |
| ATOM | 3993 | CB | ALA | 573 | 25.600 | 53.207 | -3.970 | 1.00 85.79 | C3 |
| ATOM | 3994 | C | ALA | 573 | 23.373 | 52.245 | -4.057 | 1.00 87.21 | C3 |
| ATOM | 3995 | OT1 | ALA | 573 | 22.610 | 52.413 | -3.099 | 1.00 88.33 | C3 |
| ATOM | 3996 | OT2 | ALA | 573 | 23.022 | 52.309 | -5.248 | 1.00 88.34 | C3 |
| ATOM | 3997 | OH2 | H2O | 603 | 26.735 | 24.280 | 5.161 | 1.00 27.42 | W |
| ATOM | 3998 | H1 | H2O | 603 | 27.332 | 24.335 | 4.407 | 1.00 0.00 | W |
| ATOM | 3999 | H2 | H2O | 603 | 26.288 | 23.435 | 4.992 | 1.00 0.00 | W |
| ATOM | 4000 | OH2 | H2O | 605 | 47.880 | 37.960 | 12.073 | 1.00 56.30 | W |
| ATOM | 4001 | H1 | H2O | 605 | 47.789 | 37.874 | 13.031 | 1.00 0.00 | W |
| ATOM | 4002 | H2 | H2O | 605 | 46.980 | 37.858 | 11.753 | 1.00 0.00 | W |
| ATOM | 4003 | OH2 | H2O | 607 | 40.001 | 49.224 | 7.214 | 1.00 40.04 | W |
| ATOM | 4004 | H1 | H2O | 607 | 40.471 | 48.761 | 7.909 | 1.00 0.00 | W |
| ATOM | 4005 | H2 | H2O | 607 | 40.123 | 48.642 | 6.457 | 1.00 0.00 | W |
| ATOM | 4006 | OH2 | H2O | 610 | 59.883 | 42.530 | -9.698 | 1.00 38.90 | W |
| ATOM | 4007 | H1 | H2O | 610 | 60.512 | 41.833 | -9.477 | 1.00 0.00 | W |
| ATOM | 4008 | H2 | H2O | 610 | 59.189 | 42.046 | -10.160 | 1.00 0.00 | W |
| ATOM | 4009 | OH2 | H2O | 611 | 57.178 | 35.940 | -14.220 | 1.00 34.63 | W |
| ATOM | 4010 | H1 | H2O | 611 | 57.174 | 36.545 | -14.974 | 1.00 0.00 | W |
| ATOM | 4011 | H2 | H2O | 611 | 57.989 | 36.211 | -13.757 | 1.00 0.00 | W |
| ATOM | 4012 | OH2 | H2O | 612 | 25.793 | 27.337 | 19.130 | 1.00 29.21 | W |
| ATOM | 4013 | H1 | H2O | 612 | 26.709 | 27.661 | 19.145 | 1.00 0.00 | W |
| ATOM | 4014 | H2 | H2O | 612 | 25.762 | 26.792 | 19.929 | 1.00 0.00 | W |
| ATOM | 4015 | OH2 | H2O | 615 | 29.766 | 34.284 | 9.444 | 1.00 45.03 | W |
| ATOM | 4016 | H1 | H2O | 615 | 30.017 | 34.618 | 10.308 | 1.00 0.00 | W |
| ATOM | 4017 | H2 | H2O | 615 | 29.113 | 33.592 | 9.660 | 1.00 0.00 | W |
| ATOM | 4018 | OH2 | H2O | 617 | 37.316 | 40.012 | 10.872 | 1.00 35.21 | W |
| ATOM | 4019 | H1 | H2O | 617 | 36.600 | 40.017 | 11.519 | 1.00 0.00 | W |
| ATOM | 4020 | H2 | H2O | 617 | 37.944 | 39.376 | 11.259 | 1.00 0.00 | W |
| ATOM | 4021 | OH2 | H2O | 619 | 40.370 | 52.041 | -7.387 | 1.00 29.62 | W |
| ATOM | 4022 | H1 | H2O | 619 | 40.672 | 52.724 | -6.779 | 1.00 0.00 | W |
| ATOM | 4023 | H2 | H2O | 619 | 39.505 | 51.810 | -7.052 | 1.00 0.00 | W |
| ATOM | 4024 | OH2 | H2O | 621 | 27.903 | 32.440 | 10.664 | 1.00 39.99 | W |
| ATOM | 4025 | H1 | H2O | 621 | 27.553 | 33.207 | 11.141 | 1.00 0.00 | W |
| ATOM | 4026 | H2 | H2O | 621 | 27.929 | 31.808 | 11.398 | 1.00 0.00 | W |
| ATOM | 4027 | OH2 | H2O | 622 | 25.057 | 31.972 | 13.675 | 1.00 32.70 | W |
| ATOM | 4028 | H1 | H2O | 622 | 24.393 | 32.417 | 14.215 | 1.00 0.00 | W |
| ATOM | 4029 | H2 | H2O | 622 | 24.469 | 31.428 | 13.112 | 1.00 0.00 | W |
| ATOM | 4030 | OH2 | H2O | 623 | 20.791 | 28.583 | 14.218 | 1.00 50.17 | W |
| ATOM | 4031 | H1 | H2O | 623 | 20.499 | 28.803 | 13.325 | 1.00 0.00 | W |
| ATOM | 4032 | H2 | H2O | 623 | 19.939 | 28.549 | 14.688 | 1.00 0.00 | W |
| ATOM | 4033 | OH2 | H2O | 625 | 22.680 | 78.881 | 2.761 | 1.00 40.48 | W |
| ATOM | 4034 | H1 | H2O | 625 | 21.938 | 78.856 | 3.375 | 1.00 0.00 | W |
| ATOM | 4035 | H2 | H2O | 625 | 22.266 | 79.246 | 1.970 | 1.00 0.00 | W |
| ATOM | 4036 | OH2 | H2O | 626 | 39.689 | 36.486 | 9.730 | 1.00 23.36 | W |
| ATOM | 4037 | H1 | H2O | 626 | 39.090 | 35.724 | 9.672 | 1.00 0.00 | W |
| ATOM | 4038 | H2 | H2O | 626 | 39.627 | 36.872 | 8.853 | 1.00 0.00 | W |
| ATOM | 4039 | OH2 | H2O | 627 | 42.035 | 78.320 | 5.697 | 1.00 46.19 | W |
| ATOM | 4040 | H1 | H2O | 627 | 42.416 | 77.450 | 5.832 | 1.00 0.00 | W |
| ATOM | 4041 | H2 | H2O | 627 | 41.243 | 78.146 | 5.181 | 1.00 0.00 | W |

FIG.5-48

| | | | | | | | | |
|---|---|---|---|---|---|---|---|---|
| ATOM | 4042 | OH2 H2O | 631 | 47.227 31.440 6.299 | 1.00 34.17 | W |
| ATOM | 4043 | H1 H2O | 631 | 47.533 32.209 5.809 | 1.00 0.00 | W |
| ATOM | 4044 | H2 H2O | 631 | 47.442 30.713 5.714 | 1.00 0.00 | W |
| ATOM | 4045 | OH2 H2O | 636 | 24.043 65.423 -0.336 | 1.00 73.38 | W |
| ATOM | 4046 | H1 H2O | 636 | 24.179 65.781 -1.228 | 1.00 0.00 | W |
| ATOM | 4047 | H2 H2O | 636 | 23.469 66.096 0.054 | 1.00 0.00 | W |
| ATOM | 4048 | OH2 H2O | 638 | 38.984 67.955 -11.226 | 1.00 29.97 | W |
| ATOM | 4049 | H1 H2O | 638 | 38.283 67.402 -11.580 | 1.00 0.00 | W |
| ATOM | 4050 | H2 H2O | 638 | 39.568 68.046 -11.998 | 1.00 0.00 | W |
| ATOM | 4051 | OH2 H2O | 639 | 27.930 66.675 -7.733 | 1.00 43.40 | W |
| ATOM | 4052 | H1 H2O | 639 | 28.192 67.028 -6.876 | 1.00 0.00 | W |
| ATOM | 4053 | H2 H2O | 639 | 26.975 66.791 -7.705 | 1.00 0.00 | W |
| ATOM | 4054 | OH2 H2O | 643 | 50.619 62.802 0.813 | 1.00 36.55 | W |
| ATOM | 4055 | H1 H2O | 643 | 51.575 62.904 0.824 | 1.00 0.00 | W |
| ATOM | 4056 | H2 H2O | 643 | 50.301 63.665 0.525 | 1.00 0.00 | W |
| ATOM | 4057 | OH2 H2O | 646 | 62.897 38.367 3.759 | 1.00 73.55 | W |
| ATOM | 4058 | H1 H2O | 646 | 62.414 38.098 2.978 | 1.00 0.00 | W |
| ATOM | 4059 | H2 H2O | 646 | 62.244 38.247 4.461 | 1.00 0.00 | W |
| ATOM | 4060 | OH2 H2O | 650 | 29.587 68.480 -9.555 | 1.00 65.67 | W |
| ATOM | 4061 | H1 H2O | 650 | 28.846 68.630 -10.148 | 1.00 0.00 | W |
| ATOM | 4062 | H2 H2O | 650 | 29.180 67.844 -8.936 | 1.00 0.00 | W |
| ATOM | 4063 | OH2 H2O | 652 | 51.408 56.331 4.056 | 1.00 62.90 | W |
| ATOM | 4064 | H1 H2O | 652 | 50.718 56.353 3.365 | 1.00 0.00 | W |
| ATOM | 4065 | H2 H2O | 652 | 51.052 55.671 4.648 | 1.00 0.00 | W |
| ATOM | 4066 | OH2 H2O | 653 | 49.404 56.022 2.161 | 1.00 51.28 | W |
| ATOM | 4067 | H1 H2O | 653 | 49.442 55.351 1.474 | 1.00 0.00 | W |
| ATOM | 4068 | H2 H2O | 653 | 49.323 56.829 1.630 | 1.00 0.00 | W |
| ATOM | 4069 | OH2 H2O | 654 | 68.215 42.294 -2.563 | 1.00 40.77 | W |
| ATOM | 4070 | H1 H2O | 654 | 68.347 41.428 -5.011 | 1.00 44.08 | W |
| ATOM | 4071 | H2 H2O | 654 | 68.189 43.181 -2.190 | 1.00 0.00 | W |
| ATOM | 4072 | OH2 H2O | 655 | 66.374 40.425 -2.489 | 1.00 42.31 | W |
| ATOM | 4073 | H1 H2O | 655 | 66.936 41.162 -2.766 | 1.00 0.00 | W |
| ATOM | 4074 | H2 H2O | 655 | 66.452 39.841 -3.252 | 1.00 0.00 | W |
| ATOM | 4075 | OH2 H2O | 656 | 66.927 41.428 -5.011 | 1.00 44.08 | W |
| ATOM | 4076 | H1 H2O | 656 | 66.207 42.071 -4.989 | 1.00 0.00 | W |
| ATOM | 4077 | H2 H2O | 656 | 67.542 41.824 -4.374 | 1.00 0.00 | W |
| ATOM | 4078 | OH2 H2O | 657 | 40.371 57.111 5.730 | 1.00 66.56 | W |
| ATOM | 4079 | H1 H2O | 657 | 39.958 56.259 5.613 | 1.00 0.00 | W |
| ATOM | 4080 | H2 H2O | 657 | 40.021 57.651 5.014 | 1.00 0.00 | W |
| ATOM | 4081 | OH2 H2O | 658 | 48.780 47.580 -3.122 | 1.00 52.09 | W |
| ATOM | 4082 | H1 H2O | 658 | 48.811 46.671 -3.438 | 1.00 0.00 | W |
| ATOM | 4083 | H2 H2O | 658 | 49.568 47.955 -3.542 | 1.00 0.00 | W |
| ATOM | 4084 | OH2 H2O | 663 | 29.095 62.889 1.825 | 1.00 39.23 | W |
| ATOM | 4085 | H1 H2O | 663 | 29.380 62.827 2.739 | 1.00 0.00 | W |
| ATOM | 4086 | H2 H2O | 663 | 28.377 63.526 1.887 | 1.00 0.00 | W |
| ATOM | 4087 | OH2 H2O | 664 | 27.132 25.640 7.430 | 1.00 50.65 | W |
| ATOM | 4088 | H1 H2O | 664 | 26.870 24.838 7.876 | 1.00 0.00 | W |
| ATOM | 4089 | H2 H2O | 664 | 27.001 25.362 6.496 | 1.00 0.00 | W |
| ATOM | 4090 | OH2 H2O | 665 | 23.367 30.554 12.167 | 1.00 49.69 | W |
| ATOM | 4091 | H1 H2O | 665 | 24.026 30.006 11.707 | 1.00 0.00 | W |
| ATOM | 4092 | H2 H2O | 665 | 22.941 31.016 11.438 | 1.00 0.00 | W |
| ATOM | 4093 | OH2 H2O | 666 | 46.015 32.192 10.179 | 1.00 66.86 | W |
| ATOM | 4094 | H1 H2O | 666 | 46.060 31.519 9.497 | 1.00 0.00 | W |
| ATOM | 4095 | H2 H2O | 666 | 45.411 31.827 10.833 | 1.00 0.00 | W |
| ATOM | 4096 | OH2 H2O | 667 | 38.943 37.883 11.978 | 1.00 47.87 | W |
| ATOM | 4097 | H1 H2O | 667 | 39.367 37.487 11.188 | 1.00 0.00 | W |
| ATOM | 4098 | H2 H2O | 667 | 38.521 37.114 12.362 | 1.00 0.00 | W |
| ATOM | 4099 | OH2 H2O | 671 | 33.437 58.101 2.269 | 1.00 46.65 | W |
| ATOM | 4100 | H1 H2O | 671 | 33.555 57.162 2.433 | 1.00 0.00 | W |
| ATOM | 4101 | H2 H2O | 671 | 33.962 58.514 2.961 | 1.00 0.00 | W |
| ATOM | 4102 | OH2 H2O | 672 | 27.551 31.314 20.022 | 1.00 30.15 | W |
| ATOM | 4103 | H1 H2O | 672 | 27.929 32.042 20.533 | 1.00 0.00 | W |
| ATOM | 4104 | H2 H2O | 672 | 26.845 31.764 19.552 | 1.00 0.00 | W |
| ATOM | 4105 | OH2 H2O | 673 | 25.714 36.908 21.385 | 1.00 36.95 | W |
| ATOM | 4106 | H1 H2O | 673 | 24.806 37.123 21.637 | 1.00 0.00 | W |
| ATOM | 4107 | H2 H2O | 673 | 25.599 36.284 20.654 | 1.00 0.00 | W |
| ATOM | 4108 | OH2 H2O | 674 | 38.244 66.897 12.076 | 1.00 57.36 | W |
| ATOM | 4109 | H1 H2O | 674 | 37.773 67.536 12.626 | 1.00 0.00 | W |
| ATOM | 4110 | H2 H2O | 674 | 38.153 66.104 12.618 | 1.00 0.00 | W |
| ATOM | 4111 | OH2 H2O | 675 | 35.762 36.553 -3.986 | 1.00 58.40 | W |
| ATOM | 4112 | H1 H2O | 675 | 35.600 37.449 -3.677 | 1.00 0.00 | W |
| ATOM | 4113 | H2 H2O | 675 | 35.549 36.642 -4.923 | 1.00 0.00 | W |
| ATOM | 4114 | OH2 H2O | 676 | 30.689 32.814 25.675 | 1.00 59.30 | W |
| ATOM | 4115 | H1 H2O | 676 | 30.093 33.571 25.680 | 1.00 0.00 | W |
| ATOM | 4116 | H2 H2O | 676 | 31.550 33.214 25.540 | 1.00 0.00 | W |
| END | | | | | | |

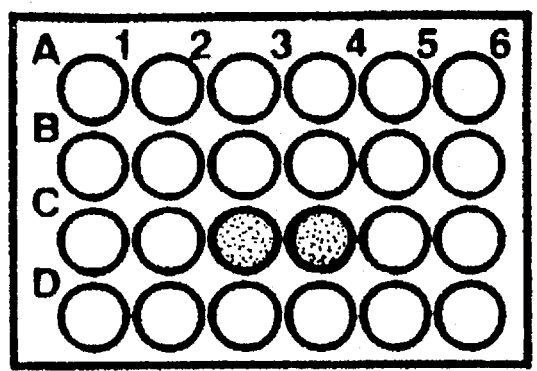
FIG. 6A
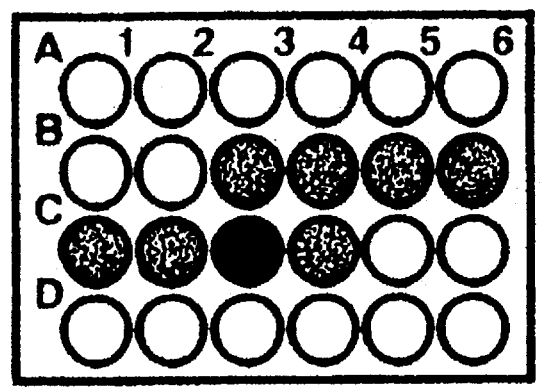
FIG. 6B
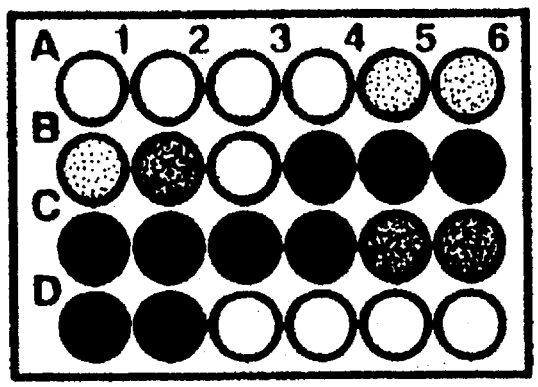
FIG. 6C

COMPUTER-BASED METHODS AND ARTICLES OF MANUFACTURE FOR PREPARING G-CSF ANALOGS

FIELD OF THE INVENTION

This invention relates to granulocyte colony stimulating factor ("G-SF") analogs, compositions containing such analogs, and related compositions. In another aspect, the present invention relates to nucleic acids encoding the present analogs or related nucleic acids, related host cells and vectors. In another aspect, the invention relates to computer programs and apparatuses for expressing the three dimensional structure of G-CSF and analogs thereof. In another aspect, the invention relates to methods for rationally designing G-CSF analogs and related compositions. In yet another aspect, the present invention relates to methods for treatment using the present G-CSF analogs.

BACKGROUND

Hematopoiesis is controlled by two systems: the cells within the bone marrow microenvironment and growth factors. The growth factors, also called colony stimulating factors, stimulate committed progenitor cells to proliferate and to form colonies of differentiating blood cells. One of these factors is granulocyte colony stimulating factor, herein called G-CSF, which preferentially stimulates the growth and development of neutrophils, indicating a potential use in neutropenic states. Welte et al., PNAS-U.S.A. 82: 1526–1530 (1985); Souza et al., Science 232: 61–65 (1986) and Gabrilove, J. Seminars in Hematology 26: (2) 1–14 (1989).

In humans, endogenous G-CSF is detectable in blood plasma. Jones et al., Bailliere's Clinical Hematology 2 (1): 83–111 (1989). G-CSF is produced by fibroblasts, macrophages, T cells trophoblasts, endothelial cells and epithelial cells and is the expression product of a single copy gene comprised of four exons and five introns located on chromosome seventeen. Transcription of this locus produces a mRNA species which is differentially processed, resulting in two forms of G-CSF mRNA, one version coding for a protein of 177 amino acids, the other coding for a protein of 174 amino acids, Nagata et al., EMBO J 5: 575–581 acids has been found to have the greatest specific in vivo biological activity. G-CSF is species cross-reactive, such that when human G-CSF is administered to another mammal such as a mouse, canine or monkey, sustained neutrophil leukocytosis is elicited. Moore et al., PNAS-U.S.A. 84: 7134–7138 (1987).

Human G-CSF can be obtained and purified from a number of sources. Natural human G-CSF (nhG-CSF) can be isolated from the supernatants of cultured human tumor cell lines. The development of recombinant DNA technology, see, for instance, U.S. Pat. No. 4,810,643 (Souza) incorporated herein by reference, has enabled the production of commercial scale quantities of G-CSF in glycosylated form as a product of eukaryotic host cell expression, and of G-CSF in non-glycosylated form as a product of prokaryotic host cell expression.

G-CSF has been found to be useful in the treatment of indications where an increase in neutrophils will provide benefits. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture, for example, for bone marrow transplants.

Signal transduction, the way in which G-CSF effects cellular metabolism, is not currently thoroughly understood. G-CSF binds to a cell-surface receptor which apparently initiates the changes within particular progenitor cells, leading to cell differentiation.

Various altered G-CSF's have been reported. Generally, for design of drugs, certain changes are known to have certain structural effects. For example, deleting one cysteine could result in the unfolding of a molecule which is, in its unaltered state, normally folded via a disulfide bridge. There are other known methods for adding, deleting or substituting amino acids in order to change the function of a protein.

Recombinant human G-CSF mutants have been prepared, but the method of preparation does not include overall structure/function relationship information. For example, the mutation and biochemical modification of Cys 18 has been reported. Kuga et al., Biochem. Biophy. Res. Comm 159: 103–111 (1989); Lu et al., Arch. Biochem. Biophys. 268: 81–92 (1989).

In U.S. Pat. No. 4,810,643, entitled, "Production of Pluripotent Granulocyte Colony-Stimulating Factor" (as cited above), polypeptide analogs and peptide fragments of G-CSF are disclosed generally. Specific G-CSF analogs disclosed include those with the cysteins at positions 17, 36, 42, 64, and 74 (of the 174 amino acid species or of those having 175 amino acids, the additional amino acid being an N-terminal methionine) substituted with another amino acid, (such as serine), and G-CSF with an alanine in the first (N-terminal) position.

EP 0 335 423 entitled "Modified human G-CSF" reportedly discloses the modification of at least one amino group in a polypeptide having hG-CSF activity.

EP 0 272 703 entitled "Novel Polypeptide" reportedly discloses G-CSF derivatives having an amino acid substituted or deleted at or "in the neighborhood" of the N terminus.

EP 0 459 630, entitled "Polypeptides" reportedly discloses derivatives of naturally occurring G-CSF having at least one of the biological properties of naturally occurring G-CSF and a solution stability of at least 35% at 5 mg/ml in which the derivative has at least $Cys^{17}$ of the native sequence replaced by a $Ser^{17}$ residue and $Asp^{27}$ of the native sequence replaced by a $Ser^{27}$ residue.

EP 0 256 843 entitled "Expression of G-CSF and Muteins Thereof and Their Uses" reportedly discloses a modified DNA sequence encoding G-CSF wherein the N-terminus is modified for enhanced expression of protein in recombinant host cells, without changing the amino acid sequence of the protein.

EP 0 243 153 entitled "Human G-CSF Protein Expression" reportedly discloses G-CSF to be modified by inactivating at least one yeast KEX2 protease processing site for increased yield in recombinant production using yeast.

Shaw, U.S. Pat. No. 4,904,584, entitled "Site-Specific Homogeneous Modification of Polypeptides," reportedly discloses lysine altered proteins.

WO/9012874 reportedly discloses cysteine altered variants of proteins.

Australian patent application Document No. AU-A-10948/92, entitled, "Improved Activation of Recombinant Proteins" reportedly discloses the addition of amino acids to either terminus of a G-CSF molecule for the purpose of aiding in the folding of the molecule after prokaryotic expression.

Australian patent application Document No. AU-A-76380/91, entitled, "Muteins of the Granulocyte Colony Stimulating Factor (G-CSF)" reportedly discloses muteins of the granulocyte stimulating factor G-CSF in the sequence Leu-Gly-His-Ser-Leu-Gly-Ile at position 50–56 of G-CSF with 174 amino acids, and position 53 to 59 of the G-CSF with 177 amino acids, or/and at least one of the four histadine residues at positions 43, 79, 156 and 170 of the mature G-CSF with 174 amino acids or at positions 46, 82, 159, or 173 of the mature G-CSF with 177 amino acids.

GB 2 213 821, entitled "Synthetic Human Granulocyte Colony Stimulating Factor Gene" reportedly discloses a synthetic G-CSF-encoding nucleic acid sequence incorporating restriction sites to facilitate the cassette mutagenesis of selected regions, and flanking restriction sites to facilitate the incorporation of the gene into a desired expression system.

G-CSF has reportedly been crystallized to some extent, e.g., EP 344 796, and the overall structure of G-CSF has been surmised, but only on a gross level. Bazan, Immunology Today 11: 350–354 (1990); Parry et al., J. Molecular Recognition 8: 107–110 (1988). To date, there have been no reports of the overall structure of G-CSF, and no systematic studies of the relationship of the overall structure and function of the molecule, studies which are essential to the systematic design of G-CSF analogs. Accordingly, there exists a need for a method of this systematic design of G-CSF analogs, and the resultant compositions.

SUMMARY OF THE INVENTION

The three dimensional structure of G-CSF has now been determined to the atomic level. From this three-dimensional structure, one can now forecast with substantial certainty how changes in the composition of a G-CSF molecule may result in structural changes. These structural characteristics may be correlated with biological activity to design and produce G-CSF analogs.

Although others had speculated regarding the three dimensional structure of G-CSF, Bazan, Immunology Today 11: 350–354 (1990); Parry et al., J. Molecular Recognition 8: 107–110 (1988), these speculations were of no help to those wishing to prepare G-CSF analogs either because the surmised structure was incorrect (Parry et al., supra) and/or because the surmised structure provided no detail correlating the constituent moieties with structure. The present determination of the three-dimensional structure to the atomic level is by far the most complete analysis to date, and provides important information to those wishing to design and prepare G-CSF analogs. For example, from the present three dimensional structural analysis, precise areas of hydrophobicity and hydrophilicity have been determined.

Relative hydrophobicity is important because it directly relates to the stability of the molecule. Generally, biological molecules, found in aqueous environments, are externally hydrophilic and internally hydrophobic; in accordance with the second law of thermodynamics provides, this is the lowest energy state and provides for stability. Although one could have speculated that G-CSF's internal core would be hydrophobic, and the outer areas would be hydrophilic, one would have had no way of knowing specific hydrophobic or hydrophilic areas. With the presently provided knowledge of areas of hydrophobicity/philicity, one may forecast with substantial certainty which changes to the G-CSF molecule will affect the overall structure of the molecule.

As a general rule, one may use knowledge of the geography of the hydrophobic and hydrophilic regions to design analogs in which the overall G-CSF structure is not changed, but change does affect biological activity ("biological activity" being used here in its broadest sense to denote function). One may correlate biological activity to structure. If the structure is not changed, and the mutation has no effect on biological activity, then the mutation has no biological function. If, however, the structure is not changed and the mutation does affect biological activity, then the residue (or atom) is essential to at least one biological function. Some of the present working examples were designed to provide no change in overall structure, yet have a change in biological function.

Based on the correlation of structure to biological activity, one aspect of the present invention relates to G-CSF analogs. These analogs are molecules which have more, fewer, different or modified amino acid residues from the G-CSF amino acid sequence. The modifications may be by addition, substitution, or deletion of one or more amino acid residues. The modification may include the addition or substitution of analogs of the amino acids themselves, such as peptidomimetics or amino acids with altered moieties such as altered side groups. The G-CSF used as a basis for comparison may be of human, animal or recombinant nucleic acid-technology origin (although the working examples disclosed herein are based on the recombinant production of the 174 amino acid species of human G-CSF, having an extra N-terminus methionyl residue). The analogs may possess functions different from natural human G-CSF molecule, or may exhibit the same functions, or varying degrees of the same functions. For example, the analogs may be designed to have a higher or lower biological activity, have a longer shelf-life or a decrease in stability, be easier to formulate, or more difficult to combine with other ingredients. The analogs may have no hematopoietic activity, and may therefore be useful as an antagonist against G-CSF effect (as, for example, in the overproduction of G-CSF). From time to time herein the present analogs are referred to as proteins or peptides for convenience, but contemplated herein are other types of molecules, such as peptidomimetics or chemically modified peptides.

In another aspect, the present invention relates to related compositions containing a G-CSF analog as an active ingredient. The term, "related composition", as used herein, is meant to denote a composition which may be obtained once the identity of the G-CSF analog is ascertained (such as a G-CSF analog labeled with a detectable label, related receptor or pharmaceutical composition). Also considered a related composition are chemically modified versions of the G-CSF analog, such as those having attached at least one polyethylene glycol molecule.

For example, one may prepare a G-CSF analog to which a detectable label is attached, such as a fluorescent, chemiluminescent or radioactive molecule.

Another example is a pharmaceutical composition which may be formulated by known techniques using known materials, see, e.g., Remington's Pharmaceutical Sciences, 18th Ed. (1990, Mack Publishing Co., Easton, Pa. 18042) pages 1435–1712, which are herein incorporated by reference. Generally, the formulation will depend on a variety of factors such as administration, stability, production concerns and other factors. The G-CSF analog may be administered by injection or by pulmonary administration via inhalation. Enteric dosage forms may also be available for the present G-CSF analog compositions, and therefore oral administration may be effective. G-CSF analogs may be inserted into liposomes or other microcarriers for delivery, and may be formulated in gels or other compositions for sustained release. Although preferred compositions will vary depending on the use to which the composition will be put, generally, for G-CSF analogs having at least one of the biological activities of natural G-CSF, preferred pharmaceutical compositions are those prepared for subcutaneous injection or for pulmonary administration via inhalation, although the particular formulations for each type of administration will depend on the characteristics of the analog.

Another example of related composition is a receptor for the present analog. As used herein, the term "receptor" indicates a moiety which selectively binds to the present analog molecule. For example, antibodies, or fragments thereof, or "recombinant antibodies" (see Huse et al., Science 246:1275 (1989)) may be used as receptors. Selective binding does not mean only specific binding (although binding-specific receptors are encompassed herein), but rather that the binding is not a random event. Receptors may be on the cell surface or intra- or extra-cellular, and may act to effectuate, inhibit or localize the biological activity of the present analogs. Receptor binding may also be a triggering mechanism for a cascade of activity indirectly related to the analog itself. Also contemplated herein are nucleic acids, vectors containing such nucleic acids and host cells containing such nucleic acids which encode such receptors.

Another example of a related composition is a G-CSF analog with a chemical moiety attached. Generally, chemical modification may alter biological activity or antigenicity of a protein, or may alter other characteristics, and these factors will be taken into account by a skilled practitioner. As noted above, one example of such chemical moiety is polyethylene glycol. Modification may include the addition of one or more hydrophilic or hydrophobic polymer molecules, fatty acid molecules, or polysaccharide molecules. Examples of chemical modifiers include polyethylene glycol, alklpolyethylene glycols, DI-poly(amino acids), polyvinylpyrrolidone, polyvinyl alcohol, pyran copolymer, acetic acid/acylation, proprionic acid, palmitic acid, stearic acid, dextran, carboxymethyl cellulose, pullulan, or agarose. See, Francis, *Focus on Growth Factors* 3: 4–10 (May 1992)(published by Mediscript, Mountview Court, Friern Barnet Lane, London N20 OLD, UK). Also, chemical modification may include an additional protein or portion thereof, use of a cytotoxic agent, or an antibody. The chemical modification may also include lecithin.

In another aspect, the present invention relates to nucleic acids encoding such analogs. The nucleic acids may be DNAs or RNAs or derivatives thereof, and will typically be cloned and expressed on a vector, such as a phage or plasmid containing appropriate regulatory sequences. The nucleic acids may be labeled (such as using a radioactive, chemiluminescent, or fluorescent label) for diagnostic or prognostic purposes, for example. The nucleic acid sequence may be optimized for expression, such as including codons preferred for bacterial expression. The nucleic acid and its complementary strand, and modifications thereof which do not prevent encooooding of the desired analog are here contemplated.

In another aspect, the present invention relates to host cells containing the above nucleic acids encoding the present analogs. Host cells may be eukaryotic or prokaryotic, and expression systems may include extra steps relating to the attachment (or prevention) of sugar groups (glycosylation), proper folding of the molecule, the addition or deletion of leader sequences or other factors incident to recombinant expression.

In another aspect the present invention relates to antisense nucleic acids which act to prevent or modify the type or amount of expression of such nucleic acid sequences. These may be prepared by known methods.

In another aspect of the present invention, the nucleic acids encoding a present analog may be used for gene therapy purposes, for example, by placing a vector containing the analog-encoding sequence into a recipient so the nucleic acid itself is expressed inside the recipient who is in need of the analog composition. The vector may first be placed in a carrier, such as a cell, and then the carrier placed into the recipient. Such expression may be localized or systemic. Other carriers include non-naturally occurring carriers, such as liposomes or other microcarriers or particles, which may act to mediate gene transfer into a recipient.

The present invention also provides for computer programs for the expression (such as visual display) of the G-CSF or analog three dimensional structure, and further, a computer program which expresses the identity of each constituent of a G-CSF molecule and the precise location within the overall structure of that constituent, down to the atomic level. Set forth below is one example of such program. There are many currently available computer programs for the expression of the three dimensional structure of a molecule. Generally, these programs provide for inputting of the coordinates for the three dimensional structure of a molecule (i.e., for example, a numerical assignment for each atom of a G-CSF molecule along an x, y, and z axis), means to express (such as visually display) such coordinates, means to alter such coordinates and means to express an image of a molecule having such altered coordinates. One may program crystallographic information, i.e., the coordinates of the location of the atoms of a G-CSF molecule in three dimension space, wherein such coordinates have been obtained from crystallographic analysis of said G-CSF molecule, into such programs to generate a computer program for the expression (such as visual display) of the G-CSF three dimensional structure. Also provided, therefore, is a computer program for the expression of G-CSF analog three dimensional structure. Preferred is the computer program Insight II, version 4, available from Biosym, San Diego, Calif., with the coordinates as set forth in FIG. 5 input. Preferred expression means is on a Silicon Graphics 320 VGX computer, with Crystal Eyes glasses (also available from Silicon Graphics), which allows one to view the G-CSF molecule or its analog stereoscopically. Alternatively, the present G-CSF crystallographic coordinates and diffraction data are also deposited in the Protein Data Bank, Chemistry Department, Brookhaven National Laboratory, Upton, N.Y. 119723, U.S.A.. One may use these data in preparing a different computer program for expression of the three dimensional structure of a G-CSF molecule or analog thereof. Therefore, another aspect of the present invention is a computer program for the expression of the three dimensional structure of a G-CSF molecule. Also provided is said computer program for visual display of the three dimensional structure of a G-CSF molecule; and further, said program having means for altering such visual display. Apparatus useful for expression of such computer program, particularly for the visual display of the computer image of said three dimensional structure of a G-CSF molecule or analog thereof is also therefore here provided, as well as means for preparing said computer program and apparatus.

The computer program is useful for preparation of G-CSF analogs because one may select specific sites on the G-CSF molecule for alteration and readily ascertain the effect the alteration will have on the overall structure of the G-CSF molecule. Selection of said site for alteration will depend on the desired biological characteristic of the G-CSF analog. If one were to randomly change said G-CSF molecule (r-met-hu-G-CSF) there would be $175^{20}$ possible substitutions, and even more analogs having multiple changes, additions or deletions. By viewing the three dimensional structure wherein said structure is correlated with the composition of the molecule, the selection for sites of alteration is no longer a random event, but sites for alteration may be determined rationally.

As set forth above, identity of the three dimensional structure of G-CSF, including the placement of each constituent down to the atomic level has now yielded information regarding which moieties are necessary to maintain the overall structure of the G-CSF molecule. One may therefore select whether to maintain the overall structure of the G-CSF molecule when preparing a G-CSF analog of the present invention, or whether (and how) to change the overall structure of the G-CSF molecule when preparing a G-CSF analog of the present invention. Optionally, once one has prepared such analog, one may test such analog for a desired characteristic.

One may, for example, seek to maintain the overall structure possessed by a non-altered natural or recombinant G-CSF molecule. The overall structure is presented in FIGS. 2, 3, and 4, and is described in more detail below. Maintenance of the overall structure may ensure receptor binding, a necessary characteristic for an analog possessing the hematopoietic capabilities of natural G-CSF (if no receptor binding, signal transduction does not result from the presence of the analog). It is contemplated that one class of G-CSF analogs will possess the three dimensional core structure of a natural or recombinant (non-altered) G-CSF molecule, yet possess different characteristics, such as an increased ability to selectively stimulate neutrophils. Another class of G-CSF analogs are those with a different overall structure which diminishes the ability of a G-CSF analog molecule to bind to a G-CSF receptor, and possesses a diminished ability to selectively stimulate neutrophils as compared to non-altered natural or recombinant G-CSF.

For example, it is now known which moieties within the internal regions of the G-CSF molecule are hydrophobic, and, correspondingly, which moieties on the external portion of the G-CSF molecule are hydrophilic. Without knowledge of the overall three dimensional structure, preferably to the atomic level as provided herein, one could not forecast which alterations within this hydrophobic internal area would result in a change in the overall structural conformation of the molecule. An overall structural change could result in a functional change, such as lack of receptor binding, for example, and therefore, diminishment of biological activity as found in non-altered G-CSF. Another class of G-CSF analogs is therefore G-CSF analogs which possess the same hydrophobicity as (non-altered) natural or recombinant G-CSF. More particularly, another class of G-CSF analogs possesses the same hydrophobic moieties within the four helical bundle of its internal core as those hydrophobic moieties possessed by (non-altered) natural or recombinant G-CSF yet have a composition different from said non-altered natural or recombinant G-CSF.

Another example relates to external loops which are structures which connect the internal core (helices) of the G-CSF molecule. From the three dimensional structure—including information regarding the spatial location of the amino acid residues—one may forecast that certain changes in certain loops will not result in overall conformational changes. Therefore, another class of G-CSF analogs provided herein is that having an altered external loop but possessing the same overall structure as (non-altered) natural or recombinant G-CSF. More particularly, another class of G-CSF analogs provided herein are those having an altered external loop, said loop being selected from the loop present between helices A and B; between helices B and C; between helices C and D; between helices D and A, as those loops and helices are identified herein. More particularly, said loops, preferably the AB loop and/or the CD loop are altered to increase the half life of the molecule by stabilizing said loops. Such stabilization may be by connecting all or a portion of said loop(s) to a portion of an alpha helical bundle found in the core of a G-CSF (or analog) molecule. Such connection may be via beta sheet, salt bridge, disulfide bonds, hydrophobic interaction or other connecting means available to those skilled in the art, wherein such connecting means serves to stabilize said external loop or loops. For example, one may stabilize the AB or CD loops by connecting the AB loop to one of the helices within the internal region of the molecule.

The N-terminus also may be altered without change in the overall structure of a G-CSF molecule, because the N-terminus does not effect structural stability of the internal helices, and, although the external loops are preferred for modification, the same general statements apply to the N-terminus.

Additionally, such external loops may be the site(s) for chemical modification because in (non-altered) natural or recombinant G-CSF such loops are relatively flexible and tend not to interfere with receptor binding. Thus, there would be additional room for a chemical moiety to be directly attached (or indirectly attached via another chemical moiety which serves as a chemical connecting means). The chemical moiety may be selected from a variety of moieties available for modification of one or more function of a G-CSF molecule. For example, an external loop may provide sites for the addition of one or more polymer which serves to increase serum half-life, such as a polyethylene glycol molecule. Such polyethylene glycol molecule(s) may be added wherein said loop is altered to include additional lysines which have reactive side groups to which polyethylene glycol moieties are capable of attaching. Other classes of chemical moieties may also be attached to one or more external loops, including but not limited to other biologically active molecules, such as receptors, other therapeutic proteins (such as other hematopoietic factors which would engender a hybrid molecule), or cytotoxic agents (such as diphtheria toxin). This list is of course not complete; one skilled in the art possessed of the desired chemical moiety will have the means to effect attachment of said desired moiety to the desired external loop. Therefore, another class of the present G-CSF analogs includes those with at least one alteration in an external loop wherein said alteration provides for the addition of a chemical moiety such as at least one polyethylene glycol molecule.

Deletions, such as deletions of sites recognized by proteins for degradation of the molecule, may also be effectual in the external loops. This provides alternative means for increasing half-life of a molecule otherwise having the G-CSF receptor binding and signal transduction capabilities (i.e., the ability to selectively stimulate the maturation of neutrophils). Therefore, another class of the present G-CSF analogs includes those with at least one alteration in an external loop wherein said alteration decreases the turnover of said analog by proteases. Preferred loops for such alterations are the AB loop and the CD loop. One may prepare an abbreviated G-CSF molecule by deleting a portion of the amino acid residues found in the external loops (identified in more detail below), said abbreviated G-CSF molecule may have additional advantages in preparation or in biological function.

Another example relates to the relative charges between amino acid residues which are in proximity to each other. As noted above, the G-CSF molecule contains a relatively tightly packed four helical bundle. Some of the faces on the helices face other helices. At the point (such as a residue) where a helix faces another helix, the two amino acid moieties which face each other may have the same charge, and thus tend to repel each other, which lends instability to the overall molecule. This may be eliminated by changing the charge (to an opposite charge or a neutral charge) of one or both of the amino acid moieties so that there is no repelling. Therefore, another class of G-CSF analogs includes those G-CSF analogs having been altered to modify instability due to surface interactions, such as electron charge location.

In another aspect, the present invention relates to methods for designing G-CSF analogs and related compositions and the products of those methods. The end products of the methods may be the G-CSF analogs as defined above or related compositions. For instance, the examples disclosed herein demonstrate (a) the effects of changes in the constituents (i.e., chemical moieties) of the G-CSF molecule on the G-CSF structure and (b) the effects of changes in structure on biological function. Essentially, therefore, another aspect of the present invention is a method for preparing a G-CSF analog comprising the steps of:

(a) viewing information conveying the three dimensional structure of a G-CSF molecule wherein the chemical moieties, such as each amino acid residue or each atom of each amino acid residue, of the G-CSF molecule are correlated with said structure;

(b) selecting from said information a site on a G-CSF molecule for alteration;

(c) preparing a G-CSF analog molecule having such alteration; and (d) optionally, testing such G-CSF analog molecule for a desired characteristic.

One may use the here provided computer programs for a computer-based method for preparing a G-CSF analog. Another aspect of the present invention is therefore a computer based method for preparing a G-CSF analog comprising the steps of:

(a) providing computer expression of the three dimensional structure of a G-CSF molecule wherein the chemical moieties, such as each amino acid residue or each atom of each amino acid residue, of the G-CSF molecule are correlated with said structure;

(b) selecting from said computer expression a site on a G-CSF molecule for alteration;

(c) preparing a G-CSF molecule having such alteration; and (d) optionally, testing such G-CSF molecule for a desired characteristic.

More specifically, the present invention provides a method for preparing a G-CSF analog comprising the steps of:

(a) viewing the three dimensional structure of a G-CSF molecule via a computer, said computer programmed (i) to express the coordinates of a G-CSF molecule in three dimensional space, and (ii) to allow for entry of information for alteration of said G-CSF expression and viewing thereof;

(b) selecting a site on said visual image of said G-CSF molecule for alteration;

(c) entering information for said alteration on said computer;

(d) viewing a three dimensional structure of said altered G-CSF molecule via said computer;

(e) optionally repeating steps (a)–(e);

(f) preparing a G-CSF analog with said alteration; and (g) optionally testing said G-CSF analog for a desired characteristic.

In another aspect, the present invention relates to methods of using the present G-CSF analogs and related compositions and methods for the treatment or protection of mammals, either alone or in combination with other hematopoietic factors or drugs in the treatment of hematopoietic disorders. It is contemplated that one aspect of designing G-CSF analogs will be the goal of enhancing or modifying the characteristics non-modified G-CSF is known to have.

For example, the present analogs may possess enhanced or modified activities, so, where G-CSF is useful in the treatment of (for example) neutropenia, the present compositions and methods may also be of such use.

Another example is the modification of G-CSF for the purpose of interacting more effectively when used in combination with other factors particularly in the treatment of hematopoietic disorders. One example of such combination use is to use an early-acting hematopoietic factor (i.e., a factor which acts earlier in the hematopoiesis cascade on relatively undifferentiated cells) and either simultaneously or in seriatim use of a later-acting hematopoietic factor, such as G-CSF or analog thereof (as G-CSF acts on the CFU-GM lineage in the selective stimulation of neutrophils). The present methods and compositions may be useful in therapy involving such combinations or "cocktails" of hematopoietic factors.

The present compositions and methods may also be useful in the treatment of leukopenia, mylogenous leukemia, severe chronic neutropenia, aplastic anemia, glycogen storage disease, mucosistitis, and other bone marrow failure states. The present compositions and methods may also be useful in the treatment of hematopoietic deficits arising from chemotherapy or from radiation therapy. The success of bone marrow transplantation, or the use of peripheral blood progenitor cells for transplantation, for example, may be enhanced by application of the present compositions (proteins or nucleic acids for gene therapy) and methods. The present compositions and methods may also be useful in the treatment of infectious diseases, such in the context of wound healing, burn treatment, bacteremia, septicemia, fungal infections, endocarditis, osteopyelitis, infection related to abdominal trauma, infections not responding to antibiotics, pneumonia and the treatment of bacterial inflammation may also benefit from the application of the present compositions and methods. In addition, the present compositions and methods may be useful in the treatment of leukemia based upon a reported ability to differentiate leukemic cells. Welte et al., PNAS-U.S.A. 82: 1526–1530 (1985). Other applications include the treatment of individuals with tumors, using the present compositions and methods, optionally in the presence of receptors (such as antibodies)

which bind to the tumor cells. For review articles on therapeutic applications, see Lieshhke and Burgess, N. Engl. J. Med. 327: 28–34 and 99–106 (1992) both of which are herein incorporated by reference.

The present compositions and methods may also be useful to act as intermediaries in the production of other moieties; for example, G-CSF has been reported to influence the production of other hematopoietic factors and this function (if ascertained) may be enhanced or modified via the present compositions and/or methods.

The compositions related to the present G-CSF analogs, such as receptors, may be useful to act as an antagonist which prevents the activity of G-CSF or an analog. One may obtain a composition with some or all of the activity of non-altered G-CSF or a G-CSF analog, and add one or more chemical moieties to alter one or more properties of such G-CSF or analog. With knowledge of the three dimensional conformation, one may forecast the best geographic location for such chemical modification to achieve the desired effect.

General objectives in chemical modification may include improved half-life (such as reduced renal, immunological or cellular clearance), altered bioactivity (such as altered enzymatic properties, dissociated bioactivities or activity in organic solvents), reduced toxicity (such as concealing toxic epitopes, compartmentalization, and selective biodistribution), altered immunoreactivity (reduced immunogenicity, reduced antigenicity or adjuvant action), or altered physical properties (such as increased solubility, improved thermal stability, improved mechanical stability, or conformational stabilization). See Francis, *Focus on Growth Factors* 3: 4–10 (May 1992)(published by Mediscript, Mountview Court, Friern Barnet Lane, London N20 OLD, UK).

The examples below are illustrative of the present invention and are not intended as a limitation. It is understood that variations and modifications will occur to those skilled in the art, and it is intended that the appended claims cover all such equivalent variations which come within the scope of the invention as claimed.

DETAILED DESCRIPTION OF THE DRAWINGS

FIG. 1 is an illustration of the amino acid sequence of the 174 amino acid species of G-CSF with an additional N-terminal methionine (Seq. ID No.: 1) (Seq. ID No.: 2).

FIG. 2 is an topology diagram of the crystalline structure of G-CSF, as well as hGH, pGH, GM-CSF, INF-B, IL-2, and IL-4. These illustrations are based on inspection of cited references. The length of secondary structural elements are drawn in proportion to the number of residues. A, B, C, and D helices are labeled according to the scheme used herein for G-CSF. For INF-β, the original labeling of helices is indicated in parentheses.

FIG. 3 is an "ribbon diagram" of the three dimensional structure of G-CSF. Helix A is amino acid residues 11–39 (numbered according to FIG. 1, above), helix B is amino acid residues 72–91, helix C is amino acid residues 100–123, and helix D is amino acid residues 143–173. The relatively short $3^{10}$ helix is at amino acid residues 45–48, and the alpha helix is at amino acid residues 48–53. Residues 93–95 form almost one turn of a left handed helix.

FIG. 4 is a "barrel diagram" of the three dimensional structure of G-CSF. Shown in various shades of gray are the overall cylinders and their orientations for the three dimensional structure of G-CSF. The numbers indicate amino acid residue position according to FIG. 1 above.

FIG. 5 is a list of the coordinates used to generate a computer-aided visual image of the three-dimensional structure of G-CSF. The coordinates are set forth below. The columns correspond to separate field:

(i) Field 1 (from the left hand side) is the atom, (ii) Field 2 is the assigned atom number, (iii) Field 3 is the atom name (according to the periodic table standard nomenclature, with CB being carbon atom Beta, CG is Carbon atom Gamma, etc.);

(iv) Field 4 is the residue type (according to three letter nomenclature for amino acids as found in, e.g., Stryer, Biochemistry, 3d Ed., W. H. Freeman and Company, New York 1988, inside back cover);

(v) Fields 5–7 are the x-axis, y-axis and z-axis positions of the atom;

(vi) Field 8 (often a "1.00") designates occupancy at that position;

(vii) Field 9 designates the B-factor;

(viii) Field 10 designates the molecule designation. Three molecules (designated a, b, and c) of G-CSF crystallized together as a unit. The designation a, b, or c indicates which coordinates are from which molecule. The number after the letter (1, 2, or 3) indicates the assigned amino acid residue position, with molecule A having assigned positions 10–175, molecule B having assigned positions 210–375, and molecule C having assigned positions 410–575. These positions were so designated so that there would be no overlap among the three molecules which crystallized together. (The "W" designation indicates water).

FIG. 6A–C is a schematic representation of the strategy involved in refining the crystallization matrix for parameters involved in crystallization. The crystallization matrix corresponds to the final concentration of the components (salts, buffers and precipitants) of the crystallization solutions in the wells of a 24 well tissue culture plate. These concentrations are produced by pipetting the appropriate volume of stock solutions into the wells of the microtiter plate. To design the matrix, the crystallographer decides on an upper and lower concentration of the component. These upper and lower concentrations can be pipetted along either the rows (e.g., A1-A6, B1-B6, C1-C6 or D1-D6) or along the entire tray (A1-D6). The former method is useful for checking reproducibility of crystal growth of a single component along a limited number of wells, whereas the later method is more useful in initial screening. The results of several stages of refinement of the crystallization matrix are illustrated by a representation of three plates. The increase in shading in the wells indicates a positive crystallization result which, in the final stages, would be X-ray quality crystals but in the initial stages could be oil droplets, granular precipitates or small crystals approximately less than 0.05 mm in size. Part A represents an initial screen of one parameter in which the range of concentration between the first well (A1) and last well (D6) is large and the concentration increase between wells is calculated as (((concentration A1)-(concentration D6))/23). Part B represents that in later stages of the crystallization matrix refinement of the concentration spread between A1 and D6 would be reduced which would result in more crystals formed per plate. Part C indicates a final stage of matrix refinement in which quality crystals are found in most wells of the plate.

DETAILED DESCRIPTION OF THE INVENTION

The present invention grows out of the discovery of the three dimensional structure of G-CSF. This three dimensional structure has been expressed via computer program for stereoscopic viewing. By viewing this stereoscopically, structure-function relationships identified and G-CSF analogs have been designed and made.

The Overall Three Dimensional Structure of G-CSF

The G-CSF used to ascertain the structure was a non-glycosylated 174 amino acid species having an extra N-terminal methionine residue incident to bacterial expression. The DNA and amino acid sequence of this G-CSF are illustrated in FIG. 1.

Overall, the three dimensional structure of G-CSF is predominantly helical, with 103 of the 175 residues forming a 4-alpha-helical bundle. The only other secondary structure is found in the loop between the first two long helices where a 4 residue $3^{10}$ helix is immediately followed by a 6 residue alpha helix. As shown in FIG. 2, the overall structure has been compared with the structure reported for other proteins: growth hormone (Abdel-Meguid et al., PNAS-U.S.A. 84: 6434 (1987) and Vos et al., Science 255: 305–312 (1992)), granulocyte macrophage colony stimulating factor (Diederichs et al., Science 254: 1779–1782 (1991), interferon-β (Senda et al., EMBO J. 11: 3193–3201 (1992)), interleukin-2 (McKay Science 257: 1673–1677 (1992)) and interleukin-4 (Powers et al., Science 256: 1673–677 (1992), and Smith et al., J. Mol. Biol. 224: 899–904 (1992)). Structural similarity among these growth factors occurs despite the absence of similarity in their amino acid sequences.

Presently, the structural information was correlation of G-CSF biochemistry, and this can be summarized as follows (with sequence position 1 being at the N-terminus):

TABLE 1

| Sequence Position | Description of Structure | Analysis |
|---|---|---|
| 1–10 | Extended chain | Deletion causes no loss of biological activity |
| Cys 18 | Partially buried | Reactive with DTNB and Thimersososl but not with iodo-acetate |
| 34 | Alternative splice site | Insertion reduces biological activity |
| 20–47 (inclusive) | Helix A, first disulfide and portion of AB helix | Predicted receptor binding region based on neutralizing antibody data |
| 20, 23, 24 | Helix A | Single alanine mutation of residue(s) reduces biological activity. Predicted receptor binding (Site B). |
| 165–175 (inclusive) | Carboxy terminus | Deletion reduces biological activity |

This biochemical information, having been gleaned from antibody binding studies, see Layton et al., Biochemistry 266: 23815–23823 (1991), was superimposed on the three-dimensional structure in order to design G-CSF analogs. The design, preparation, and testing of these G-CSF analogs is described in Example 1 below.

EXAMPLE 1

This Example describes the preparation of crystalline G-CSF, the visualization of the three dimensional structure of recombinant human G-CSF via computer-generated image, the preparation of analogs, using site-directed mutagenesis or nucleic acid amplification methods, the biological assays and HPLC analysis used to analyze the G-CSF analogs, and the resulting determination of overall structure/function relationships. All cited publications are herein incorporated by reference.

A. Use of Automated Crystallization

The need for a three-dimensional structure of recombinant human granulocyte colony stimulating factor (r-hu-G-CSF), and the availability of large quantities of the purified protein, led to methods of crystal growth by incomplete factorial sampling and seeding. Starting with the implementation of incomplete factorial crystallization described by Jancarik and Kim, J. Appl. Crystallogr. 24: 409 (1991) solution conditions that yielded oil droplets and birefringence aggregates were ascertained. Also, software and hardware of an automated pipetting system were modified to produce some 400 different crystallization conditions per day. Weber, J. Appl. Crystallogr. 20: 366–373 (1987). This procedure led to a crystallization solution which produced r-hu-G-CSF crystals.

The size, reproducibility and quality of the crystals was improved by a seeding method in which the number of "nucleation initiating units" was estimated by serial dilution of a seeding solution. These methods yielded reproducible growth of 2.0 mm r-hu-G-CSF crystals. The space group of these crystals is $P2_12_12_1$ with cell dimensions of a=90 Å, b=110 Å and c=49 Å, and they diffract to a resolution of 2.0 Å.

1. Overall Methodology

To search for the crystallizing conditions of a new protein, Carter and Carter, J. Biol. Chem. 254:122219–12223 (1979) proposed the incomplete factorial method. They suggested that a sampling of a large number of randomly selected, but generally probable, crystallizing conditions may lead to a successful combination of reagents that produce protein crystallization. This idea was implemented by Jancarik and Kim, J. Appl. Crystallogr. 24: 409(1991), who described 32 solutions for the initial crystallization trials which cover a range of pH, salts and precipitants. Here we describe an extension of their implementation to an expanded set of 70 solutions. To minimize the human effort and error of solution preparation, the method has been programmed for an automatic pipetting machine.

Following Weber's method of successive automated grid searching (SAGS), J. Cryst. Growth 90: 318–324(1988), the robotic system was used to generate a series of solutions which continually refined the crystallization conditions of temperature, pH, salts and precipitant. Once a solution that could reproducibly grow crystals was determined, a seeding technique which greatly improved the quality of the crystals was developed. When these methods were combined, hundreds of diffraction quality crystals (crystals diffracting to at least about 2.5 Angstroms, preferably having at least portions diffracting to below 2 Angstroms, and more preferably, approximately 1 Angstrom) were produced in a few days.

Generally, the method for crystallization, which may be used with any protein one desires to crystallize, comprises the steps of:

(a) combining aqueous aliquots of the desired protein with either (i) aliquots of a salt solution, each aliquot having a different concentration of salt; or (ii) aliquots of a precipitant solution, each aliquot having a different concentration of precipitant, optionally wherein each combined aliquot is combined in the presence of a range of pH;

(b) observing said combined aliquots for precrystalline formations, and selecting said salt or precipitant combination and said pH which is efficacious in producing precrystalline forms, or, if no precrystalline forms are so produced, increasing the protein starting concentration of said aqueous aliquots of protein;

(c) after said salt or said precipitant concentration is selected, repeating step (a) with said previously unselected solution in the presence of said selected concentration; and (d) repeating step (b) and step (a) until a crystal of desired quality is obtained.

The above method may optionally be automated, which provides vast savings in time and labor. Preferred protein starting concentrations are between 10 mg/ml and 20 mg/ml, however this starting concentration will vary with the protein (the G-CSF below was analyzed using 33 mg/ml). A preferred range of salt solution to begin analysis with is (NaCl) of 0–2.5M. A preferred precipitant is polyethylene glycol 8000, however, other precipitants include organic solvents (such as ethanol), polyethylene glycol molecules having a molecular weight in the range of 500–20,000, and other precipitants known to those skilled in the art. The preferred pH range is pH 4.5, 5.0, 5.5, 6.0, 6.5, 7.0, 7.5, 8.0, 8.5, and 9.0. Precrystallization forms include oils, birefringement precipitants, small crystals (<approximately 0.05 mm), medium crystals (approximately 0.5 to 0.5 mm) and large crystals (>approximately 0.5 mm). The preferred time for waiting to see a crystalline structure is 48 hours, although weekly observation is also preferred, and generally, after about one month, a different protein concentration is utilized (generally the protein concentration is increased). Automation is preferred, using the Accuflex system as modified. The preferred automation parameters are described below.

Generally, protein with a concentration between 10 mg/ml and 20 mg/ml was combined with a range of NaCl solutions from 0–2.5M, and each such combination was performed (separately) in the presence of the above range of concentrations. Once a precrystallization structure is observed, that salt concentration and pH range are optimized in a separate experiment, until the desired crystal quality is achieved. Next, the precipitant concentration, in the presence of varying levels of pH is also optimized. When both are optimized, the optimal conditions are performed at once to achieve the desired result (this is diagrammed in FIG. 6).

a. Implementation of an automated pipetting system

Drops and reservoir solutions were prepared by an Accuflex pipetting system (ICN Pharmaceuticals, Costa Mesa, Calif.) which is controlled by a personal computer that sends ASCII codes through a standard serial interface. The pipetter samples six different solutions by means of a rotating valve and pipettes these solutions onto a plate whose translation in a x-y coordinate system can be controlled. The vertical component of the system manipulates a syringe that is capable both of dispensing and retrieving liquid.

The software provided with the Accuflex was based on the SAGS method as proposed by Cox and Weber, J. Appl. Crystallogr. 20: 366–373 (1987). This method involves the systematic variation of two major crystallization parameters, pH and precipitant concentration, with provision to vary two others. While building on these concepts, the software used here provided greater flexibility in the design and implementation of the crystallization solutions used in the automated grid searching strategy. As a result of this flexibility the present software also created a larger number of different solutions. This is essential for the implementation of the incomplete factorial method as described in that section below.

To improve the speed and design of the automated grid searching strategy, the Accuflex pipetting system required software and hardware modifications. The hardware changes allowed the use of two different micro-titer trays, one used for handing drop and one used for sitting drop experiments, and a Plexiglas tray which held 24 additional buffer, salt and precipitant solutions. These additional solutions expanded the grid of crystallizing conditions that could be surveyed.

To utilize the hardware modifications, the pipetting software was written in two subroutines; one subroutine allows the crystallographer to design a matrix of crystallization solutions based on the concentrations of their components and the second subroutine to translate these concentrations into the computer code which pipettes the proper volumes of the solutions into the crystallization trays. The concentration matrices can be generated by either of two programs. The first program (MRF, available from Amgen, Inc., Thousand Oaks, Calif.) refers to a list of stock solution concentrations supplied by the crystallographer and calculates the required volume to be pipette to achieve the designated concentration. The second method, which is preferred, incorporates a spread sheet program (Lotus) which can be used to make more sophisticated gradients of precipitants or pH. The concentration matrix created by either program is interpreted by the control program (SUX, a modification of the program found in the Accuflex pipetter originally and available from Amgen, Inc., Thousand Oaks, Calif.) and the wells are filled accordingly.

b. Implementation of the Incomplete Factorial Method

The convenience of the modified pipetting system for preparing diverse solutions improved the implementation of an expanded incomplete factorial method. The development of a new set of crystallization solutions having "random" components was generated using the program INFAC, Carter et al., J. Cryst. Growth 90: 60–73(1988) which produced a list containing 96 random combinations of one factor from three variables. Combinations of calcium and phosphate which immediately precipitated were eliminated, leaving 70 distinct combinations of precipitants, salts and buffers. These combinations were prepared using the automated pipetter and incubated for 1 week. The mixtures were inspected and solutions which formed precipitants were prepared again with lower concentrations of their components. This was repeated until all wells were clear of precipitant.

c. Crystallization of r-hu-G-CSF

Several different crystallization strategies were used to find a solution which produced x-ray quality crystals. These strategies included the use of the incomplete factorial method, refinement of the crystallization conditions using successive automated grid searches (SAGS), implementation of a seeding technique and development of a crystal production procedure which yielded hundreds of quality crystals overnight. Unless otherwise noted the screening and production of r-hu-G-CSF crystals utilized the hanging drop vapor diffusion method. Afinsen et al., Physical principles of protein crystallization. In: Eisenberg (ed.), Advances in Protein Chemistry 41: 1–33 (1991).

The initial screening for crystallization conditions of r-hu-G-CSF used the Jancarik and Kim, J. Appl. Crystallogr. 24: 409(1991) incomplete factorial method which resulted in several solutions that produced "precrystallization" results. These results included birefringent precipitants, oils and very small crystals (<0.05 mm). These precrystallizations solutions then served as the starting points for systematic screening.

The screening process required the development of crystallization matrices. These matrices corresponded to the concentration of the components in the crystallization solutions and were created using the IBM-PC based spread sheet Lotus™ and implemented with the modified Accuflex pipetting system. The strategy in designing the matrices was to vary one crystallization condition (such as salt concentration) while holding the other conditions such as pH, and precipitant concentration constant. At the start of screening, the concentration range of the varied condition was large but the concentration was successively refined until all wells in the micro-titer tray produced the same crystallization result. These results were scored as follows: crystals, birefringement precipitate, granular precipitate, oil droplets and amorphous mass. If the concentration of a crystallization parameter did not produce at least a precipitant, the concentration of that parameter was increased until a precipitant formed. After each tray was produced, it was left undisturbed for at least two days and then inspected for crystal growth. After this initial screening, the trays were then inspected on a weekly basis.

From this screening process, two independent solutions with the same pH and precipitant but differing in salts (MgCl, LiSO$_4$) were identified which produced small (0.1× 0.05×0.05 mm) crystals. Based on these results, a new series of concentration matrices were produced which varied MgCl with respect to LiSO$_4$ while keeping the other crystallization parameters constant. This series of experiments resulted in identification of a solution which produced diffraction quality crystals (>approximately 0.5 mm) in about three weeks. To find this crystallization growth solution (100 mM Mes pH 5.8, 380 mM MgCl$_2$, 220 mM LiSO$_4$ and 8% PEG 8k) approximately 8,000 conditions had been screened which consumed about 300 mg of protein.

The size of the crystals depended on the number of crystals forming per drop. Typically 3 to 5 crystals would be formed with average size of (1.0×0.7×0.7 mm). Two morphologies which had an identical space group (P2$_1$2$_1$2$_1$) and unit cell dimensions a=90.2, b=110.2, c=49.5 were obtained depending on whether or not seeding (see below) was implemented. Without seeding, the r-hu-G-CSF crystals had one long flat surface and rounded edges.

When seeding was employed, crystals with sharp faces were observed in the drop within 4 to 6 hours (0.05 by 0.05 by 0.05 mm). Within 24 hours, crystals had grown to (0.7 by 0.7 by 0.7 mm) and continued to grow beyond 2 mm depending on the number of crystals forming in the drop.

d. Seeding and determination of nucleation initiation sites.

The presently provided method for seeding crystals establishes the number of nucleation initiation units in each individual well used (here, after the optimum conditions for growing crystals had been determined). The method here is advantageous in that the number of "seeds" affects the quality of the crystals, and this in turn affects the degree of resolution. The present seeding here also provides advantages in that with seeding, G-CSF crystal grows in a period of about 3 days, whereas without seeding, the growth takes approximately three weeks.

In one series of production growth (see methods), showers of small but well defined crystals were produced overnight (<0.01×0.01×0.01 mm). Crystallization conditions were followed as described above except that a pipette tip employed in previously had been reused. Presumably, the crystal showering effect was caused by small nucleation units which had formed in the used tip and which provided sites of nucleation for the crystals. Addition of a small amount (0.5 ul) of the drops containing the crystal showers to a new drop under standard production growth conditions resulted in a shower of crystals overnight. This method was used to produce several trays of drops containing crystal showers which we termed "seed stock".

The number of nucleation initiation units (NIU) contained within the "seed stock" drops was estimated to attempt to improve the reproducibility and quality of the r-hu-GCSF crystals. To determine the number of NIU in the "seed stock", an aliquot of the drop was serially diluted along a 96 well microtiter plate. The microtiter plate was prepared by adding 50 ul of a solution containing equal volumes of r-hu-G-CSF (33 mg/ml) and the crystal growth solution (described above) in each well. An aliquot (3 ul) of one of the "seed stock" drops was transferred to the first well of the microtiter plate. The solution in the well was mixed and 3 ul was then transferred to the next well along the row of the microtiter plate. Each row of the microtiter plate was similarly prepared and the tray was sealed with plastic tape. Overnight, small crystals formed in the bottom of the wells of the microtiter plate and the number of crystals in the wells were correlated to the dilution of the original "seed stock". To produce large single crystals, the "seed stock" drop was appropriately diluted into fresh CGS and then an aliquot of this solution containing the NIU was transferred to a drop.

Once crystallization conditions had been optimized, crystals were grown in a production method in which 3 ml each of CGS and r-hu-G-CSF (33 mg/ml) were mixed to create 5 trays (each having 24 wells). This method included the production of the refined crystallization solution in liter quantities, mixing this solution with protein and placing the protein/crystallization solution in either hanging drop or sitting drop trays. This process typically yielded 100 to 300 quality crystals (>0.5 mm) in about 5 days.

e. Experimental Methods Materials

Crystallographic information was obtained starting with r-hu-met-G-CSF with the amino acid sequence as provided in FIG. 1 with a specific activity of 1.0±0.6×10$^8$U/mg (as measured by cell mitogenesis assay in a 10 mM acetate buffer at pH 4.0 (in Water for Injection) at a concentration of approximately 3 mg/ml solution was concentrated with an Amicon concentrator at 75 psi using a YM10 filter. The solution was typically concentrated 10 fold at 4° C. and stored for several months.

Initial Screening

Crystals suitable for X-ray analysis were obtained by vapor-diffusion equilibrium using hanging drops. For preliminary screening, 7 ul of the protein solution at 33 mg/ml (as prepared above) was mixed with an equal volume of the well solution, placed on siliconized glass plates and suspended over the well solution utilizing Linbro tissue culture plates (Flow Laboratories, McLean, Va). All of the pipetting was performed with the Accuflex pipetter, however, trays were removed from the automated pipetter after the well solutions had been created and thoroughly mixed for at least 10 minutes with a table top shaker. The Linbro trays were then returned to the pipetter which added the well and protein solutions to the siliconized cover slips. The cover slips were then inverted and sealed over 1 ml of the well solutions with silicon grease.

The components of the automated crystallization system are as follows. A PC-DOS computer system was used to design a matrix of crystallization solutions based on the concentration of their components. These matrices were produced with either MRF of the Lotus spread sheet (described above). The final product of these programs is a data file. This file contains the information required by the SUX program to pipette the appropriate volume of the stock solutions to obtain the concentrations described in the matrices. The SUX program information was passed through a serial I/O port and used to dictate to the Accuflex pipetting system the position of the valve relative to the stock solutions, the amount of solution to be retrieved, and then pipetted into the wells of the microtiter plates and the X-Y position of each well (the column/row of each well). Addition information was transmitted to the pipetter which included the Z position (height) of the syringe during filling as well as the position of a drain where the system pauses to purge the syringe between fillings of different solutions. The 24 well microtiter plate (either Linbro or Cryschem) and cover slip holder was placed on a plate which was moved in the X-Y plane. Movement of the plate allowed the pipetter to position the syringe to pipette into the wells. It also positioned the coverslips and vials and extract solutions from these sources. Prior the pipetting, the Linbro microtiter plates had a thin film of grease applied around the edges of the wells. After the crystallization solutions were prepared in the wells and before they were transferred to the cover slips, the microtiter plate was removed from the pipetting system, and solutions were allowed to mix on a table top shaker for ten minutes. After mixing, the well solution was either transferred to the cover slips (in the case of the hanging drop protocol) or transferred to the middle post in the well (in the case of the sitting drop protocol). Protein was extracted from a vial and added to the coverslip drop containing the well solution (or to the post). Plastic tape was applied to the top of the Cryschem plate to seal the wells.

Production Growth

Once conditions for crystallization had been optimized, crystal growth was performed utilizing a "production" method. The crystallization solution which contained 100 mM Mes pH 5.8, 380 mM MgCl2, 220 mM $LiSO_4$, and 8% PEG 8K was made in 1 liter quantities. Utilizing an Eppindorf syringe pipetter, 1 ml aliquots of this solution were pipetted into each of the wells of the Linbro plate. A solution containing 50% of this solution and 50% G-CSF (33 mg/ml) was mixed and pipetted onto the siliconized cover slips. Typical volumes of these drops were between 50 and 100 ul and because of the large size of these drops, great care was taken in flipping the coverslips and suspending the drops over the wells.

Data Collection

The structure has been refined with X-PLOR (Bruniger, X-PLOR version 3.0, A system for crystallography and NMR, Yale University, New Haven Conn.) against 2.2 Å data collected on an R-AXIS (Molecular Structure, Corp. Houston, Tex.) imaging plate detector.

f. Observations

As an effective recombinant human therapeutic, r-hu-G-CSF has been produced in large quantities and gram levels have been made available for structural analysis. The crystallization methods provided herein are likely to find other applications as other proteins of interest become available. This method can be applied to any crystallographic project which has large quantities of protein (approximately >200 mg). As one skilled in the art will recognize, the present materials and methods may be modified and equivalent materials and methods may be available for crystallization of other proteins.

B. Computer Program For Visualizing The Three Dimensional Structure of G-CSF

Although diagrams, such as those in the Figures herein, are useful for visualizing the three dimensional structure of G-CSF, a computer program which allows for stereoscopic viewing of the molecule is contemplated as preferred. This stereoscopic viewing, or "virtual reality" as those in the art sometimes refer to it, allows one to visualize the structure in its three dimensional form from every angle in a wide range of resolution, from macromolecular structure down to the atomic level. The computer programs contemplated herein also allow one to change perspective of the viewing angle of the molecule, for example by rotating the molecule. The contemplated programs also respond to changes so that one may, for example, delete, add, or substitute one or more images of atoms, including entire amino acid residues, or add chemical moieties to existing or substituted groups, and visualize the change in structure.

Other computer based systems may be used; the elements being: (a) a means for entering information, such as orthogonal coordinates or other numerically assigned coordinates of the three dimensional structure of G-CSF; (b) a means for expressing such coordinates, such as visual means so that one may view the three dimensional structure and correlate such three dimensional structure with the composition of the G-CSF molecule, such as the amino acid composition; (c) optionally, means for entering information which alters the composition of the G-CSF molecule expressed, so that the image of such three dimensional structure displays the altered composition.

The coordinates for the preferred computer program used are presented in FIG. 5. The preferred computer program is Insight II, version 4, available from Biosym in San Diego, Calif. For the raw crystallographic structure, the observed intensities of the diffraction data ("F-obs") and the orthogonal coordinates are also deposited in the Protein Data Bank, Chemistry Department, Brookhaven National Laboratory, Upton, N.Y. 119723, U.S.A. and these are herein incorporated by reference.

Once the coordinates are entered into the Insight II program, one can easily display the three dimensional G-CSF molecule representation on a computer screen. The preferred computer system for display is Silicon Graphics 320 VGX (San Diego, Calif.). For stereoscopic viewing, one may wear eyewear (Crystal Eyes, Silicon Graphics) which allows one to visualize the G-CSF molecule in three dimensions stereoscopically, so one may turn the molecule and envision molecular design.

Thus, the present invention provides a method of designing or preparing a G-CSF analog with the aid of a computer comprising:

(a) providing said computer with the means for displaying the three dimensional structure of a G-CSF molecule including displaying the composition of moieties of said G-CSF molecule, preferably displaying the three dimensional location of each amino acid, and more preferably displaying the three dimensional location of each atom of a G-CSF molecule;

(b) viewing said display;

(c) selecting a site on said display for alteration in the composition of said molecule or the location of a moiety; and (d) preparing a G-CSF analog with such alteration.

The alteration may be selected based on the desired structural characteristics of the end-product G-CSF analog, and considerations for such design are described in more detail below. Such considerations include the location and compositions of hydrophobic amino acid residues, particularly residues internal to the helical structures of a G-CSF molecule which residues, when altered, alter the overall structure of the internal core of the molecule and may prevent receptor binding; the location and compositions of external loop structures, alteration of which may not affect the overall structure of the G-CSF molecule.

FIGS. 2–4 illustrate the overall three dimensional conformation in different ways. The topological diagram, the ribbon diagram, and the barrel diagram all illustrate aspects of the conformation of G-CSF.

FIG. 2 illustrates a comparison between G-CSF and other molecules. There is a similarity of architecture, although these growth factors differ in the local conformations of their loops and bundle geometries. The up-up-down-down topology with two long crossover connections is conserved, however, among all six of these molecules, despite the dissimilarity in amino acid sequence.

FIG. 3 illustrates in more detail the secondary structure of recombinant human G-CSF. This ribbon diagram illustrates the handedness of the helices and their positions relative to each other.

FIG. 4 illustrates in a different way the conformation of recombinant human G-CSF. This "barrel" diagram illustrates the overall architecture of recombinant human G-CSF.

Figure 2A:
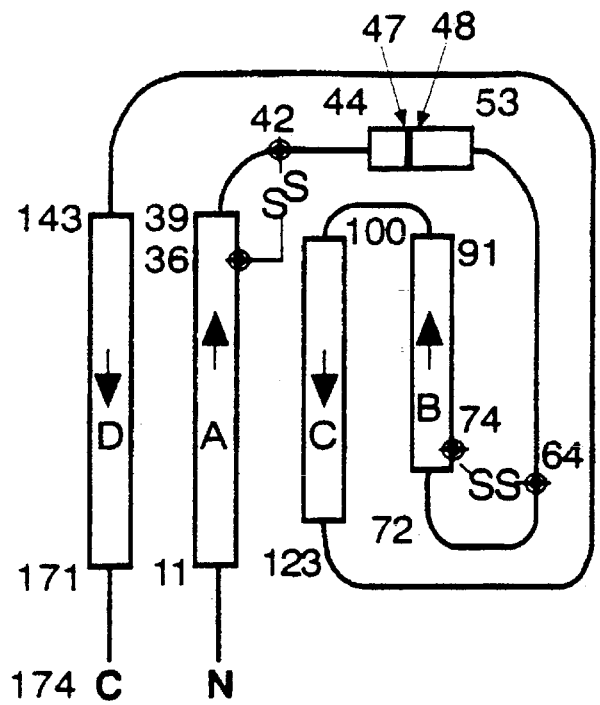
Figure 2B:
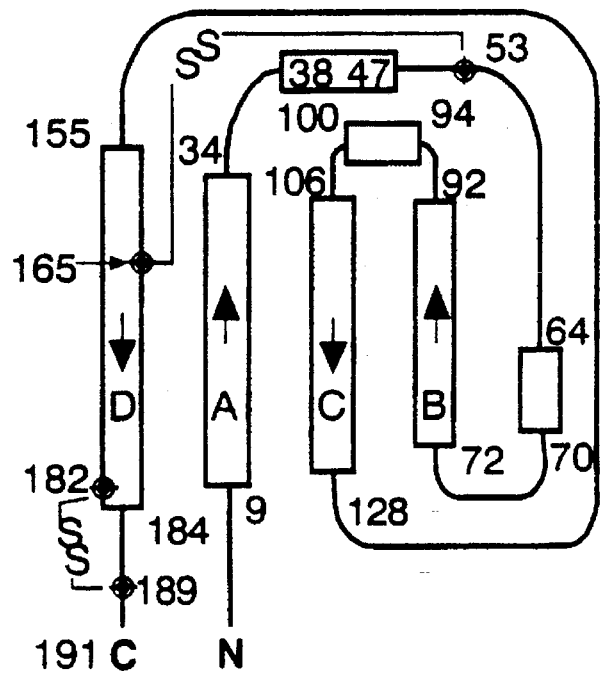
Figure 2C:
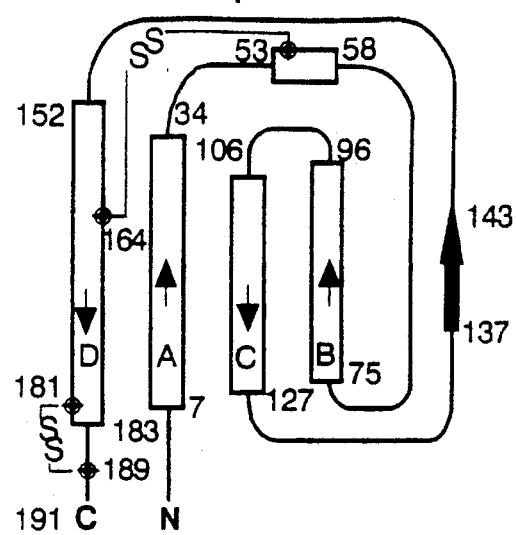
Figure 2D:
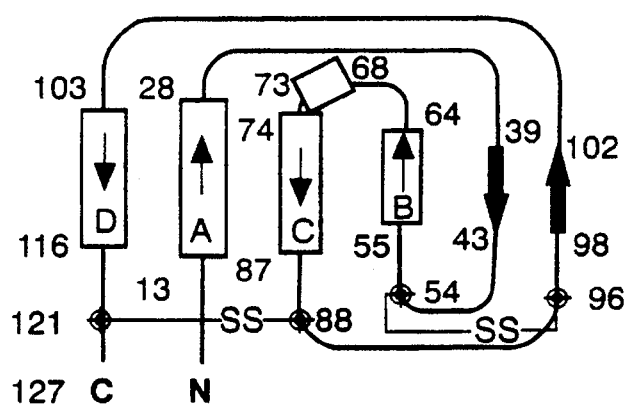
Figure 2E:
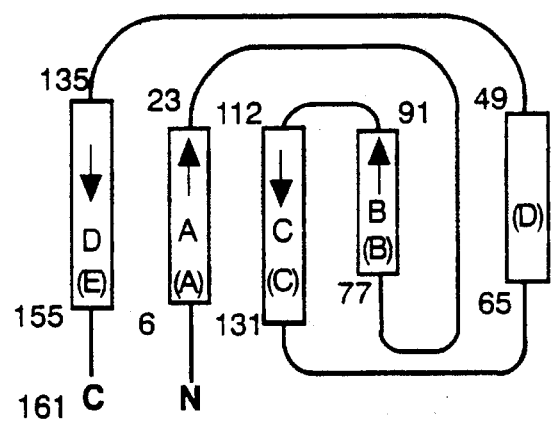
Figure 2F:
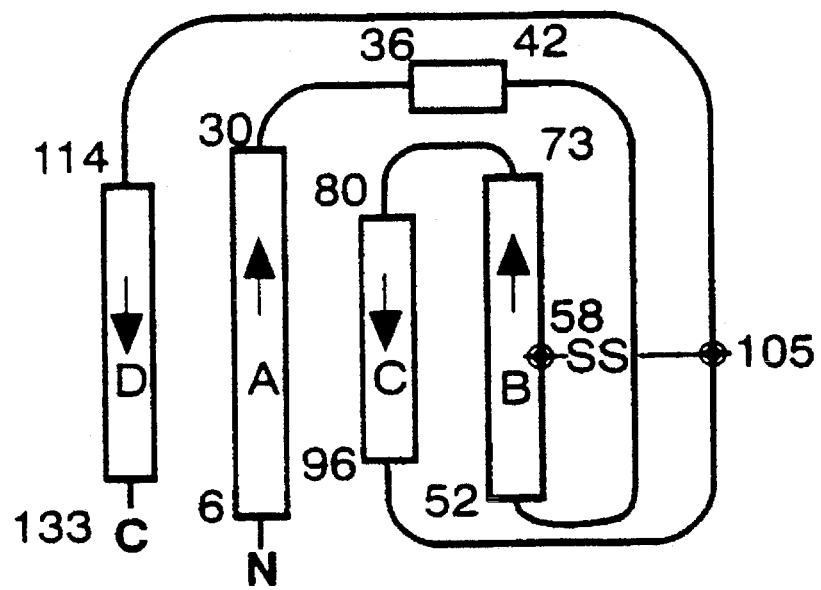
Figure 2G:
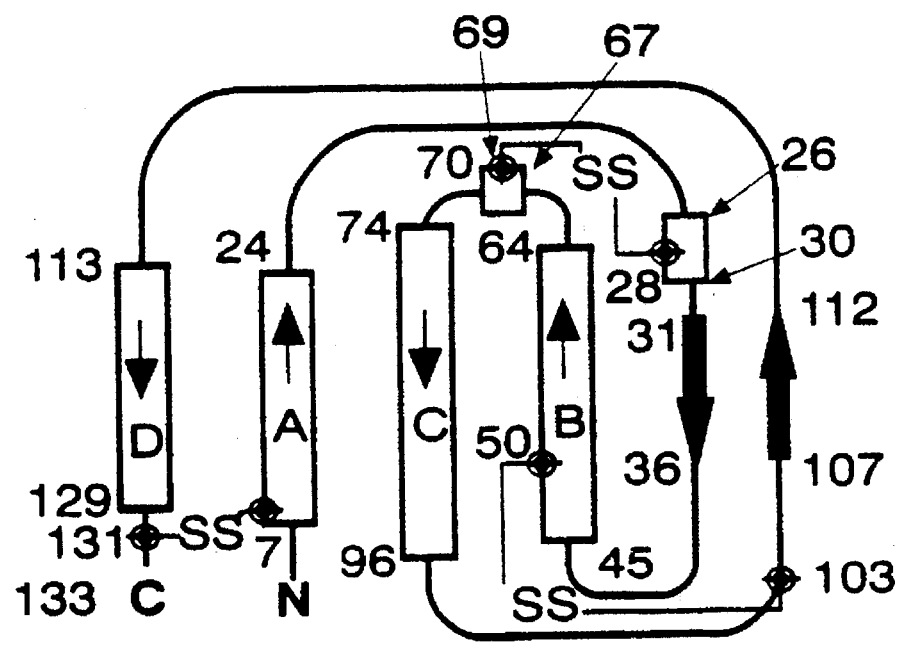

C. Preparation of Analogs using M13 Mutagenesis

This example relates to the preparation of G-CSF analogs using site directed mutagenesis techniques involving the single stranded bacteriophage M13, according to methods published in PCT Application No. WO 85/00817 (Souza et al., published Feb. 28, 1985, herein incorporated by reference). This method essentially involves using a single-stranded nucleic acid template of the non-mutagenized sequence, and binding to it a smaller oligonucleotide containing the desired change in the sequence. Hybridization conditions allow for non-identical sequences to hybridize and the remaining sequence is filled in to be identical to the original template. What results is a double stranded molecule, with one of the two strands containing the desired change. This mutagenized single strand is separated, and used itself as a template for its complementary strand. This creates a double stranded molecule with the desired change.

The original G-CSF nucleic acid sequence used is presented in FIG. 1, and the oligonucleotides containing the mutagenized nucleic acid(s) are presented in Table 2. Abbreviations used herein for amino acid residues and nucleotides are conventional, see Stryer, Biochemistry, 3d Ed., W. H. Freeman and Company, N.Y., N.Y. 1988, inside back cover.

The original G-CSF nucleic acid sequence was first placed into vector M13mp21. The DNA from single stranded phage M13mp21 containing the original G-CSF sequence was then isolated, and resuspended in water. For each reaction, 200 ng of this DNA was mixed with a 1.5 pmole of phosphorylated oligonucleotide (Table 2) and suspended in 0.1M Tris, 0.01M $MgCl_2$, 0.005M DTT, 0.1 k mM ATP, pH 8.0. The DNAs were annealed by heating to 65° C. and slowly cooling to room temperature.

Once cooled, 0.5 mM of each ATP, dATP, dCTP, dGTP, TTP, 1 unit of T4 DNA ligase and 1 unit of Klenow fragment of E. coli polymerase 1 were added to the 1 unit of annealed DNA in 0.1M Tris, 0.025M NaCl, 0.01M $MgCl_2$, 0.01M DTT, pH 7.5.

The now double stranded, closed circular DNA was used to transfect E. coli without further purification. Plaques were screened by lifting the plaques with nitrocellulose filters, and then hybridizing the filters with single stranded DNA end-labeled with p32 for 1 hour at 55°–60° C. After hybridization, the filters were washed at 0°–3° C. below the melt temperature of the oligo (2° C. for A-T, 4° C. for G-C) which selectively left autoradiography signals corresponding to plaques with phage containing the mutated sequence. Positive clones were confirmed by sequencing.

Set forth below are the oligonucleotides used for each G-CSF analog prepared via the M13 mutagenesis method. The nomenclature indicates the residue and the position of the original amino acid (e.g., Lysine at position 17), and the residue and position of the substituted amino acid (e.g., arginine 17). A substitution involving more than one residue is indicated via superscript notation, with commas between the noted positions or a semicolon indicating different residues. Deletions with no substitutions are so noted. The oligonucleotide sequences used for M13-based mutagenesis are next indicated; these oligonucleotides were manufactured synthetically, although the method of preparation is not critical, any nucleic acid synthesis method and/or equipment may be used. The length of the oligo is also indicated. As indicated above, these oligos were allowed to contact the single stranded phage vector, and then single nucleotides were added to complete the G-CSF analog nucleic acid sequence.

TABLE 2

| G-CSF ANALOGS | SEQUENCES (5'→3') | Length (nucleotide) | Seq. ID |
|---|---|---|---|
| $Lys^{17} \to Arg^{17}$ | CTT TCT GCT GCG TTG TCT GGA ACA | 24 | 3 |
| $Lys^{24} \to Arg^{24}$ | ACA GGT TCG TCG TAT CCA GGG TG | 23 | 4 |
| $Lys^{35} \to Arg^{35}$ | CAC TGC AAG AAC GTC TGT GCG CT | 23 | 5 |
| $Lys^{41} \to Arg^{41}$ | CGC TAC TTA CCG TCT GTG CCA TC | 23 | 6 |
| $Lys^{17,24,35} \to Arg^{17,24,35}$ | CTT TCT GCT GCG TTG TCT GGA ACA | 24 | 7 |
|  | ACA GGT TCG TCG TAT CCA GGG TG | 23 | 8 |
|  | CAC TGC AAG AAC GTC TGT GCG CT | 23 | 9 |
| $Lys^{17,24,41} \to Arg^{17,24,41}$ | CTT TCT GCT GCG TTG TCT GGA ACA | 24 | 10 |
|  | ACA GGT TCG TCG TAT CCA GGG TG | 23 | 11 |
|  | CGC TAC TTA CCG TCT GTC CCA TC | 23 | 12 |
| $Lys^{17,35,41} \to Arg^{17,35,41}$ | CTT TCT GCT GCG TTG TCT GGA ACA | 24 | 13 |
|  | CAC TGC AAG AAC GTC TGT GCG CT | 23 | 14 |
|  | CGC TAC TTA CCG TCT GTG CCA TC | 23 | 15 |
| $Lys^{24,35,41} \to Arg^{24,35,41}$ | ACA GGT TCG TCG TAT CCA GGG TG | 23 | 16 |
|  | CAC TGC AAG AAC GTC TGT GCG CT | 23 | 17 |
|  | CGC TAC TTA CCG TCT GTG CCA TC | 23 | 18 |
| $Lys^{17,24,35,41} \to Arg^{17,24,35,41}$ | CTT TCT GCT GCG TTG TCT GGA ACA | 24 | 19 |
|  | ACA GGT TCG TCG TAT CCA GGG TG | 23 | 20 |
|  | CAC TGC AAG AAC GTC TGT GCG CT | 23 | 21 |
|  | CGC TAC TTA CCG TCT GTG CCA TC | 23 | 22 |
| $Cys^{18} \to Ala^{18}$ | TCT GCT GAA AGC TCT GGA ACA GG | 23 | 23 |
| $Gln^{68} \to Glu^{68}$ | CTT GTC CAT CTG AAG CTC TTC AG | 23 | 24 |
| $Cys^{37,43} \to Ser^{37,43}$ | GAA AAA CTG TCC GCT ACT TAC AAA CTG TCC CAT CCG G | 37 | 25 |

TABLE 2-continued

| G-CSF ANALOGS | SEQUENCES (5'→3') | Length (nucleotide) | Seq. ID |
|---|---|---|---|
| Gln$^{26}$→Ala$^{26}$ | TTC GTA AAA TCG CGG GTG ACG G | 22 | 26 |
| Gln$^{174}$→Ala$^{174}$ | TCA TCT GGC TGC GCC GTA ATA G | 22 | 27 |
| Arg$^{170}$→Ala$^{170}$ | CCG TGT TCT GGC TCA TCT GGC T | 22 | 28 |
| Arg$^{167}$→Ala$^{167}$ | GAA GTA TCT TAC GCT GTT CTG CGT | 24 | 29 |
| Deletion 167 | GAA GTA TCT TAC TAA GTT CTG CGT C | 25 | 30 |
| Lys$^{41}$→Ala$^{41}$ | CGC TAC TTA CGC ACT GTG CCA T | 22 | 31 |
| His$^{44}$→Lys$^{44}$ | CAA ACT GTG CAA GCC GGA AGA G | 22 | 32 |
| Glu$^{47}$→Ala$^{47}$ | CAT CCG GAA GCA CTG GTA CTG C | 22 | 33 |
| Arg$^{23}$→Ala$^{23}$ | GGA ACA GGT TGC TAA AAT CCA GG | 23 | 34 |
| Lys$^{24}$→Ala$^{24}$ | GAA CAG GTT CGT GCG ATC CAG GGT G | 25 | 35 |
| Glu$^{20}$→Ala$^{20}$ | GAA ATG TCT GGC ACA GGT TCG T | 22 | 36 |
| Asp$^{28}$→Ala$^{28}$ | TCC AGG GTG CCG GTG CTG C | 19 | 37 |
| Met$^{127}$→Glu$^{127}$ | AAG AGC TCG GTG AGG CAC CAG CT | 23 | 38 |
| Met$^{138}$→Glu$^{138}$ | CTC AAG GTG CTG AGC CGG CAT TC | 23 | 39 |
| Met$^{127}$→Leu$^{127}$ | GAG CTC GGT CTG GCA CCA GC | 20 | 40 |
| Met$^{138}$→Leu$^{138}$ | TCA AGG TGC TCT GCC GGC ATT | 21 | 41 |
| Ser$^{13}$→Ala$^{13}$ | TCT GCC GCA AGC CTT TCT GCT GA | 23 | 42 |
| Lys$^{17}$→Ala$^{17}$ | CTT TCT GCT GGC ATG TCT GGA ACA | 24 | 43 |
| Gln$^{121}$→Ala$^{121}$ | CTA TTT GGC AAG CGA TGG AAG AGC | 24 | 44 |
| Glu$^{124}$→Ala$^{124}$ | CAG ATG GAA GCG CTC GGT ATG | 21 | 45 |
| Met$^{127,138}$→Leu$^{127,138}$ | GAG CTC GGT CTG GCA CCA GC | 20 | 46 |
|  | TCA AGG TGC TCT GCC GGC ATT | 21 | 47 |
| **Glu$^{20}$→Ala$^{20}$; Ser$^{13}$→Gly$^{13}$ | GAA ATG TCT GGC ACA GGT TCG T | 22 | 48 |

**This analog came about during the preparation of G-CSF analog Glu$^{20}$→Ala$^{20}$. As several clones were being sequenced to identify the Glu$^{20}$→Ala$^{20}$ analog, the Glu$^{20}$→Ala$^{20}$; Ser$^{13}$→Gly$^{13}$ analog was identified. This double mutant was the result of an in vitro Klenow DNA polymerase reaction mistake.

D. Preparation of G-CSF Analogs Using DNA Amplification

This example relates to methods for producing G-CSF analogs using a DNA amplification technique. Essentially, DNA encoding each analog was amplified in two separate pieces, combined, and then the total sequence itself amplified. Depending upon where the desired change in the original G-CSF DNA was to be made, internal primers were used to incorporate the change, and generate the two separate amplified pieces. For example, for amplification of the 5' end of the desired analog DNA, a 5' flanking primer (complementary to a sequence of the plasmid upstream from the G-CSF original DNA) was used at one end of the region to be amplified, and an internal primer, capable of hybridizing to the original DNA but incorporating the desired change, was used for priming the other end. The resulting amplified region stretched from the 5' flanking primer through the internal primer. The same was done for the 3' terminus, using a 3' flanking primer (complementary to a sequence of the plasmid downstream from the G-CSF original DNA) and an internal primer complementary to the region of the intended mutation. Once the two "halves" (which may or may not be equal in size, depending on the location of the internal primer) were amplified, the two "halves" were allowed to connect. Once connected, the 5' flanking primer and the 3' flanking primer were used to amplify the entire sequence containing the desired change.

If more than one change is desired, the above process may be modified to incorporate the change into the internal primer, or the process may be repeated using a different internal primer. Alternatively, the gene amplification process may be used with other methods for creating changes in nucleic acid sequence, such as the phage based mutagenesis technique as described above. Examples of process for preparing analogs with more than one change are described below.

To create the G-CSF analogs described below, the template DNA used was the sequence as in FIG. 1 plus certain flanking regions (from a plasmid containing the G-CSF coding region). These flanking regions were used as the 5' and 3' flanking primers and are set forth below. The amplification reactions were performed in 40 ul volumes containing 10 mM Tris-HCl, 1.5 mM $MgCl_2$, 50 mM KCl, 0.1 mg/ml gelatin, pH 8.3 at 20° C. The 40 ul reactions also contained 0.1 mM of each dNTP, 10 pmoles of each primer, and 1 ng of template DNA. Each amplification was repeated for 15 cycles. Each cycle consisted of 0.5 minutes at 94° C. 0.5 minutes at 50° C., and 0.75 minutes at 72° C. Flanking primers were 20 nucleotides in length and internal primers were 20 to 25 nucleotides in length. This resulted in multiple copies of double stranded DNA encoding either the front portion or the back portion of the desired G-CSF analog.

For combining the two "halves", one fortieth of each of the two reactions was combined in a third DNA amplification reaction. The two portions were allowed to anneal at the internal primer location, as their ends bearing the mutation were complementary, and following a cycle of polymerization, give rise to a full length DNA sequence. Once so annealed, the whole analog was amplified using the 5' and 3' flanking primers. This amplification process was repeated for 15 cycles as described above.

The completed, amplified analog DNA sequence was cleaved with XbaI and XhoI restriction endonuclease to produce cohesive ends for insertion into a vector. The cleaved DNA was placed into a plasmid vector, and that vector was used to transform *E. coli*. Transformants were challenged with kanamycin at 50 ug/ml and incubated at 30° C. Production of G-CSF analog protein was confirmed by polyacrylamide gel electrophoresis of a whole cell lysate. The presence of the desired mutation was confirmed by DNA sequence analysis of plasmid purified from the production isolate. Cultures were then grown, and cells were harvested, and the G-CSF analogs were purified as set forth below.

Set forth below in Table 3 are the specific primers used for eachanalog made using gene amplification.

TABLE 3

| Analog | Internal Primer (5'→3') | Seq. ID |
|---|---|---|
| His⁴⁴→Ala⁴⁴ | 5'primer-TTCCGGAGCGCACAGTTTG | 49 |
| | 3'primer-CAAACTGTGGGCTCCGGAAGAGC | 50 |
| Thr¹¹⁷→Ala¹¹⁷ | 5'primer-ATGCCAAATTGCAGTAGCAAAG | 51 |
| | 3'primer-CTTTGCTACTGCAATTTGGCAACA | 52 |
| Asp¹¹⁰→Ala¹¹⁰ | 5'primer-ATCAGCTACTGCTAGCTGCAGA | 53 |
| | 3'primer-TCTGCAGCTAGCAGTAGCTGACT | 54 |
| Gln²¹→Ala²¹ | 5'primer-TTACGAACCGCTTCCAGACATT | 55 |
| | 3'primer-AATGTCTGGAAGCGGTTCGTAAAAT | 56 |
| Asp¹¹³→Ala¹¹³ | 5'primer-GTAGCAAATGCAGCTACATCTA | 57 |
| | 3'primer-TAGATGTAGCTGCATTTGCTACTAC | 58 |
| His⁵³→Ala⁵³ | 5'primer-CCAAGAGAAGCACCCAGCAG | 59 |
| | 3'primer-CTGCTGGGTGCTTCTCTTGGGA | 60 |

For each analog, the following 5' flanking primer was used:

5'-CACTGGCGGTGATAATGAGC    61

For each analog, the following 3' flanking primer was used:

3'-GGTCATTACGGACCGGATC    62

1. Construction of Double Mutation

To make G-CSF analog Gln$^{12,21}$→Glu$^{12,21}$ two separate DNA amplifications were conducted to create the two DNA mutations. The template DNA used was the sequence as in FIG. 1 plus certain flanking regions (from a plasmid containing the G-CSF coding region). The precise sequences are listed below. Each of the two DNA amplification reactions were carried out using a Perkin Elmer/Cetus DNA Thermal Cycler. The 40 ul reaction mix consisted of 1× PCR Buffer (Cetus), 0.2 mM each of the 4 dXTPs (Cetus), 50 pmoles of each primer oligonucleotide, 2 ng of G-CSF template DNA (on a plasmid vector), and 1 unit of Taq polymerase (Cetus). The amplification process was carried out for 30 cycles. Each cycle consisted of 1 minute at 94° C. 2 minutes at 50° C. and 3 minutes at 72° C.

DNA amplification "A" used the oligonucleotides:

5' CCACTGGCGGTGATACTGAGC 3' (Seq. ID 63) and

5' AGCAGAAAGCTTTCCGGCAGAGAAGAAG-CAGGA 3' (Seq. ID 64)

DNA amplification "B" used the oligonucleotides:

5' GCCGCAAAGCTTTCTGCTGAAATGTCTG-GAAGAGGTTCGTAAAATCCAGGGTGA 3' (Seq. ID 65) and

5' CTGGAATGCAGAAGCAAATGCCGGCAT-AGCACCTTCAGTCGGTTGCAGAGCTGGTGCCA 3' (Seq. ID 66)

From the 109 base pair double stranded DNA product obtained after DNA amplification "A", a 64 base pair XbaI to HindIII DNA fragment was cut and isolated that contained the DNA mutation Gln$^{12}$→Glu$^{12}$. From the 509 base pair double stranded DNA product obtained after DNA amplification "B", a 197 base pair HindIII to BsmI DNA fragment was cut and isolated that contained the DNA mutation Gln$^{21}$→Glu$^{21}$.

The "A" and "B" fragments were ligated together with a 4.8 kilo-base pair XbaI to BsmI DNA plasmid vector fragment. The ligation mix consisted of equal molar DNA restriction fragments, ligation buffer (25 mM Tris-HCl pH 7.8, 10 mM MgCl$_2$, 2 mM DTT, 0.5 mM rATP, and 100 ug/ml BSA) and T4 DNA ligase and was incubated overnight at 14° C. The ligated DNA was then transformed into E. coli FM5 cells by electroporation using a Bio Rad Gene Pulsar apparatus (BioRad, Richmond, Calif.). A clone was isolated and the plasmid construct verified to contain the two mutations by DNA sequencing. This 'intermediate' vector also contained a deletion of a 193 base pair BsmI to BsmI DNA fragment. The final plasmid vector was constructed by ligation and transformation (as described above) of DNA fragments obtained by cutting and isolating a 2 kilo-base pair SstI to BamHI DNA fragment from the intermediate vector, a 2.8 kbp SstI to EcoRI DNA fragment from the plasmid vector, and a 360 bp BamHI to EcoRI DNA fragment from the plasmid vector. The final construct was verified by DNA sequencing the G-CSF gene. Cultures were grown, and the cells were harvested, and the G-CSF analogs were purified as set forth below.

As indicated above, any combination of mutagenesis techniques may be used to generate a G-CSF analog nucleic acid (and expression product) having one or more than one alteration. The two examples above, using M13-based mutagenesis and gene amplification-based mutagenesis, are illustrative.

E. Expression of G-CSF Analog DNA

The G-CSF analog DNAs were then placed into a plasmid vector and used to transform E. coli strain FM5 (ATCC#53911). The present G-CSF analog DNAs contained on plasmids and in bacterial host cells are available from the American Type Culture Collection, Rockville, Md., and the accession designations are indicated below.

One liter cultures were grown in broth containing 10 g tryptone, 5 g yeast extract and 5 g NaCl) at 30° C. until reaching a density at $A^{600}$ of 0.5, at which point they were rapidly heated to 42° C. The flasks were allowed to continue shaking at for three hours.

Other prokaryotic or eukaryotic host cells may also be used, such as other bacterial cells, strains or species, mammalian cells in culture (COS, CHO or other types) insect cells or multicellular organs or organisms, or plant cells or multicellular organs or organisms, and a skilled practitioner will recognize the appropriate host. The present G-CSF analogs and related compositions may also be prepared synthetically, as, for example, by solid phase peptide synthesis methods, or other chemical manufacturing techniques. Other cloning and expression systems will be apparent to those skilled in the art.

F. Purification of G-CSF Analog Protein

Cells were harvested by centrifugation (10,000×G, 20 minutes, 4° C.). The pellet (usually 5 grams) was resuspended in 30 ml of 1 mM DTT and passed three times through a French press cell at 10,000 psi. The broken cell suspension was centrifuged at 10,000 g for 30 minutes, the supernatant removed, and the pellet resuspended in 30–40 ml water. This was recentrifuged at 10,000×G for 30 minutes, and this pellet was dissolved in 25 ml of 2% Sarkosyl and 50 mM Tris at pH 8. Copper sulfate was added to a concentration of 40 uM, and the mixture was allowed to stir for at least 15 hours at 15°–25° C. The mixture was then centrifuged at 20,000×G for 30 minutes. The resultant solubilized protein mixture was diluted four-fold with 13.3 mM Tris, pH 7.7, after which was added approximately 20 g Dowex™ (BioRad, Richmond, Calif.) equilibrated in 20 mM Tris, pH 7.7. The mixture was stirred 90 minutes at room temperature and then the Dowex™ was filtered out. The supernatant was then applied to a DEAE-cellulose (Whatman DE-52) column equilibrated in 20 mM Tris, pH 7.7. After loading and washing the column with the same buffer, the analogs were eluted with 20 mM Tris/NaCl (between 35 mM to 100 mM depending on the analog, as indicated below), pH 7.7. For most of the analogs, the eluent from the DEAE column was adjusted to a pH of 5.4, with 50% acetic acid and diluted as necessary (to obtain the proper conductivity) with 5 mM sodium acetate pH 5.4. The solution was then loaded onto a CM-sepharose column equilibrated in 20 mM sodium acetate, pH 5.4. The column was then washed with 20 mM NaAc, pH 5.4 until the absorbance at 280 nm was approximately zero. The G-CSF analog was then eluted with sodium acetate/NaCl in concentrations as described below in Table 4. The DEAE column eluents for those analogs not applied to the CM-sepharose column were dialyzed directly into 10 mM NaAc, ph 4.0 buffer. The purified G-CSF analogs were then suitably isolated for in vitro analysis. The salt concentrations used for eluting the analogs varied, as noted above. Below, the salt concentrations for the DEAE cellulose column and for the CM-sepharose column are listed:

TABLE 4

| Analog | Salt Concentrations | |
|---|---|---|
| | DEAE Cellulose | CM-Sepharose |
| $Lys^{17} \rightarrow Arg^{17}$ | 35 mM | 37.5 mM |
| $Lys^{24} \rightarrow Arg^{24}$ | 35 mM | 37.5 mM |
| $Lys^{35} \rightarrow Arg^{35}$ | 35 mM | 37.5 mM |
| $Lys^{41} \rightarrow Arg^{41}$ | 35 mM | 37.5 mM |
| $Lys^{17,24,35} \rightarrow Arg^{17,24,35}$ | 35 mM | 37.5 mM |
| $Lys^{17,35,41} \rightarrow Arg^{17,35,41}$ | 35 mM | 37.5 mM |
| $Lys^{24,35,41} \rightarrow Arg^{24,35,41}$ | 35 mM | 37.5 mM |
| $Lys^{17,24,35,41} \rightarrow Arg^{17,24,35,41}$ | 35 mM | 37.5 mM |
| $Lys^{17,24,41} \rightarrow Arg^{17,24,41}$ | 35 mM | 37.5 mM |
| $Gln^{68} \rightarrow Glu^{68}$ | 60 mM | 37.5 mM |
| $Cys^{37,43} \rightarrow Ser^{37,43}$ | 40 mM | 37.5 mM |
| $Gln^{26} \rightarrow Ala^{26}$ | 40 mM | 40 mM |
| $Gln^{174} \rightarrow Ala^{174}$ | 40 mM | 40 mM |
| $Arg^{170} \rightarrow Ala^{170}$ | 40 mM | 40 mM |
| $Arg^{167} \rightarrow Ala^{167}$ | 40 mM | 40 mM |
| Deletion 167* | N/A | N/A |
| $Lys^{41} \rightarrow Ala^{41}$ | 160 mM | 40 mM |
| $His^{44} \rightarrow Lys^{44}$ | 40 mM | 60 mM |
| $Glu^{47} \rightarrow Ala^{47}$ | 40 mM | 40 mM |
| $Arg^{23} \rightarrow Ala^{23}$ | 40 mM | 40 mM |
| $Lys^{24} \rightarrow Ala^{24}$ | 120 mM | 40 mM |
| $Glu^{20} \rightarrow Ala^{20}$ | 40 mM | 60 mM |
| $Asp^{28} \rightarrow Ala^{28}$ | 40 mM | 80 mM |
| $Met^{127} \rightarrow Glu^{127}$ | 80 mM | 40 mM |
| $Met^{138} \rightarrow Glu^{138}$ | 80 mM | 40 mM |
| $Met^{127} \rightarrow Leu^{127}$ | 40 mM | 40 mM |
| $Met^{138} \rightarrow Leu^{138}$ | 40 mM | 40 mM |
| $Cys^{18} \rightarrow Ala^{18}$ | 40 mM | 37.5 mM |
| $Gln^{12,21} \rightarrow Glu^{12,21}$ | 60 mM | 37.5 mM |
| $Gln^{12,21,68} \rightarrow Glu^{12,21,68}$ | 60 mM | 37.5 mM |
| $Glu^{20} \rightarrow Ala^{20}; Ser^{13} \rightarrow Gly^{13}$ | 40 mM | 80 mM |
| $Met^{127,138} \rightarrow Leu^{127,138}$ | 40 mM | 40 mM |
| $Ser^{13} \rightarrow Ala^{13}$ | 40 mM | 40 mM |
| $Lys^{17} \rightarrow Ala^{17}$ | 80 mM | 40 mM |
| $Gln^{121} \rightarrow Ala^{121}$ | 40 mM | 60 mM |
| $Gln^{21} \rightarrow Ala^{21}$ | 50 mM | Gradient 0–150 mM |
| $His^{44} \rightarrow Ala^{44}$** | 40 mM | N/A |
| $His^{53} \rightarrow Ala^{53}$** | 50 mM | N/A |
| $Asp^{110} \rightarrow Ala^{110}$** | 40 mM | N/A |
| $Asp^{113} \rightarrow Ala^{113}$** | 40 mM | N/A |
| $Thr^{117} \rightarrow Ala^{117}$** | 50 mM | N/A |
| $Asp^{28} \rightarrow Ala^{28}; Asp^{110} \rightarrow Ala^{110}$** | 50 mM | N/A |
| $Glu^{124} \rightarrow Ala^{124}$** | 40 mM | 40 mM |

*For Deletion 167, the data are unavailable.
**For these analogs, the DEAE cellulose column alone was use for purification.

The above purification methods are illustrative, and a skilled practitioner will recognize that other means are available for obtaining the present G-CSF analogs.

G. Biological Assays

Regardless of which methods were used to create the present G-CSF analogs, the analogs were subject to assays for biological activity. Tritiated thymidine assays were conducted to ascertain the degree of cell division. Other biological assays, however, may be used to ascertain the desired activity. Biological assays such as assaying for the ability to induce terminal differentiation in mouse WEHI-3B (D+) leukemic cell line, also provides indication of G-CSF activity. See Nicola, et al., Blood 54: 614–27 (1979). Other in vitro assays may be used to ascertain biological activity. See Nicola, Annu. Rev. Biochem. 58: 45–77 (1989). In general, the test for biological activity should provide analysis for the desired result, such as increase or decrease in biological activity (as compared to non-altered G-CSF), different biological activity (as compared to non-altered G-CSF), receptor affinity analysis, or serum half-life analysis. The list is incomplete, and those skilled in the art will recognize other assays useful for testing for the desired end result.

The $^3$H-thymidine assay was performed using standard methods. Bone marrow was obtained from sacrificed female Balb C mice. Bone marrow cells were briefly suspended, centrifuged, and resuspended in a growth medium. A 160 ul aliquot containing approximately 10,000 cells was placed into each well of a 96 well micro-titer plate. Samples of the purified G-CSF analog (as prepared above) were added to each well, and incubated for 68 hours. Tritiated thymidine was added to the wells and allowed to incubate for 5 additional hours. After the 5 hour incubation time, the cells were harvested, filtered, and thoroughly rinsed. The filters were added to a vial containing scintillation fluid. The beta emissions were counted (LKB Betaplate scintillation counter). Standards and analogs were analyzed in triplicate, and samples which fell substantially above or below the standard curve were reassayed with the proper dilution. The results reported here are the average of the triplicate analog data relative to the unaltered recombinant human G-CSF standard results.

H. HPLC Analysis

High pressure liquid chromatography was performed on purified samples of analog. Although peak position on a reverse phase HPLC column is not a definitive indication of structural similarity between two proteins, analogs which have similar retention times may have the same type of hydrophobic interactions with the HPLC column as the non-altered molecule. This is one indication of an overall similar structure.

Samples of the analog and the non-altered recombinant human G-CSF were analyzed on a reverse phase (0.46×25 cm) Vydac 214TP54 column (Separations Group, Inc. Hesperia, Calif.). The purified analog G-CSF samples were prepared in 20 mM acetate and 40 mM NaCl solution buffered at pH 5.2 to a final concentration of 0.1 mg/ml to 5 mg/ml, depending on how the analog performed in the column. Varying amounts (depending on the concentration) were loaded onto the HPLC column, which had been equilibrated with an aqueous solution containing 1% isopropanol, 52.8% acetonitrile, and 0.38% trifluoro acetate (TFA). The samples were subjected to a gradient of 0.86% minute acetonitrile, and 0.002% TFA.

I. Results

Presented below are the results of the above biological assays and HPLC analysis. Biological activity is the average of triplicate data and reported as a percentage of the control standard (non-altered G-CSF). Relative HPLC peak position is the position of the analog G-CSF relative to the control standard (non-altered G-CSF) peak. The "+" or "−" symbols indicate whether the analog HPLC peak was in advance of or followed the control standard peak (in minutes). Not all of the variants had been analyzed for relative HPLC peak, and only those so analyzed are included below. Also presented are the American Type Culture Collection designations for *E. coli* host cells containing the nucleic acids coding for the present analogs, as prepared above.

TABLE 5

| Seg. ID | Variant | Analog | Relative HPLC Peak | ATCC No. | % Normal G-CSF Activity |
|---|---|---|---|---|---|
| 67 | 1 | $Lys^{17} \rightarrow Arg^{17}$ | N/A | 69184 | N/A |
| 68 | 2 | $Lys^{24} \rightarrow Arg^{24}$ | N/A | 69185 | N/A |
| 69 | 3 | $Lys^{35} \rightarrow Arg^{35}$ | N/A | 69186 | N/A |
| 70 | 4 | $Lys^{41} \rightarrow Arg^{41}$ | N/A | 69187 | N/A |
| 71 | 5 | $Lys^{17,24,35} \rightarrow Arg^{17,24,35}$ | N/A | 69189 | N/A |
| 72 | 6 | $Lys^{17,35,41} \rightarrow Arg^{17,35,41}$ | N/A | 69192 | N/A |
| 73 | 7 | $Lys^{24,35,41} \rightarrow Arg^{24,35,41}$ | N/A | 69191 | N/A |
| 74 | 8 | $Lys^{17,24,35,41} \rightarrow Arg^{17,24,35,41}$ | N/A | 69193 | N/A |
| 75 | 9 | $Lys^{17,24,41} \rightarrow Arg^{17,24,41}$ | N/A | 69190 | N/A |
| 76 | 10 | $Gln^{68} \rightarrow Glu^{68}$ | N/A | 69196 | N/A |
| 77 | 11 | $Cys^{37,43} \rightarrow Ser^{37,43}$ | N/A | 69197 | N/A |
| 78 | 12 | $Gln^{26} \rightarrow Ala^{26}$ | +.96 | 69201 | 51% |
| 79 | 13 | $Gln^{174} \rightarrow Ala^{174}$ | +.14 | 69202 | 100% |
| 80 | 14 | $Arg^{170} \rightarrow Ala^{170}$ | +.78 | 69203 | 100% |
| 81 | 15 | $Arg^{167} \rightarrow Ala^{167}$ | +.54 | 69204 | 110% |
| 82 | 16 | Deletion 167 | −.99 | 69207 | N/A |
| 83 | 17 | $Lys^{41} \rightarrow Ala^{41}$ | +.25 | 69208 | 81% |
| 84 | 18 | $His^{44} \rightarrow Lys^{44}$ | −1.53 | 69212 | 70% |
| 85 | 19 | $Glu^{47} \rightarrow Ala^{47}$ | +.14 | 69205 | 0% |
| 86 | 20 | $Arg^{23} \rightarrow Ala^{23}$ | −.03 | 69206 | 31% |
| 87 | 21 | $Lys^{24} \rightarrow Ala^{24}$ | +1.95 | 69213 | 0% |
| 88 | 22 | $Glu^{20} \rightarrow Ala^{20}$ | −0.07 | 69211 | 0% |
| 89 | 23 | $Asp^{28} \rightarrow Ala^{28}$ | −.30 | 69210 | 147% |
| 90 | 24 | $Met^{127} \rightarrow Glu^{127}$ | N/A | 69223 | N/A |
| 91 | 25 | $Met^{138} \rightarrow Glu^{138}$ | N/A | 69222 | N/A |
| 92 | 26 | $Met^{127} \rightarrow Leu^{127}$ | N/A | 69198 | N/A |
| 93 | 27 | $Met^{138} \rightarrow Leu^{138}$ | N/A | 69199 | N/A |
| 94 | 28 | $Cys^{18} \rightarrow Ala^{18}$ | N/A | 69188 | N/A |
| 95 | 29 | $Gln^{12,21} \rightarrow Glu^{12,21}$ | N/A | 69194 | N/A |
| 96 | 30 | $Gln^{12,21,68} \rightarrow Glu^{12,21,68}$ | N/A | 69195 | N/A |
| 97 | 31 | $Glu^{20} \rightarrow Ala^{20}$; $Ser^{13} \rightarrow Gly^{13}$ | +1.74 | 69209 | 0% |
| 98 | 32 | $Met^{127,138} \rightarrow Leu^{127,138}$ | +1.43 | 69200 | 98% |
| 99 | 33 | $Ser^{13} \rightarrow Ala^{13}$ | 0 | 69221 | 110% |
| 100 | 34 | $Lys^{17} \rightarrow Ala^{17}$ | +.50 | 69226 | 70% |
| 101 | 35 | $Gln^{121} \rightarrow Ala^{121}$ | +2.7 | 69225 | 100% |
| 102 | 36 | $Gln^{21} \rightarrow Ala^{21}$ | +0.63 | 69217 | 9.6% |
| 103 | 37 | $His^{44} \rightarrow Ala^{44}$ | +1.52 | 69215 | 10.8% |
| 104 | 38 | $His^{53} \rightarrow Ala^{53}$ | +0.99 | 69219 | 8.3% |
| 105 | 39 | $Asp^{110} \rightarrow Ala^{110}$ | +1.97 | 69216 | 29% |
| 106 | 40 | $Asp^{113} \rightarrow Ala^{113}$ | −0.34 | 69218 | 0% |
| 107 | 41 | $Thr^{117} \rightarrow Ala^{117}$ | +0.4 | 69214 | 9.7% |
| 108 | 42 | $Asp^{28} \rightarrow Ala^{28}$; $Asp^{110}$ $Ala^{110}$ | +3.2 | 69220 | 20.6% |
| 109 | 43 | $Glu^{124} \rightarrow Ala^{124}$ | +0.16 | 69224 | 75% |
| 110 | 44 | $Phe^{114} \rightarrow Val^{114}$, $T^{117} \rightarrow A^{117}$** | +0.53 | | 0% |

**This analog was apparently a result of an inadvertent error in the oligo which was used to prepare number 41, above ($Thr^{117} \rightarrow Ala^{117}$), and thus was prepared identically to the process used for that analog.
"N/A" indicates data which are not available.

1. Identification of Structure-Function Relationships

The first step used to design the present analogs was to determine what moieties are necessary for structural integrity of the G-CSF molecule. This was done at the amino acid residue level, although the atomic level is also available for analysis. Modification of the residues necessary for structural integrity results in change in the overall structure of the G-CSF molecule. This may or may not be desirable, depending on the analog one wishes to produce. The working examples here were designed to maintain the overall structural integrity of the G-CSF molecule, for the purpose of maintain G-CSF receptor binding of the analog to the G-CSF receptor (as used in this section below, the "G-CSF receptor" refers to the natural G-CSF receptor, found on hematopoietic cells). It was assumed, and confirmed by the studies presented here, that G-CSF receptor binding is a necessary step for at least one biological activity, as determined by the above biological assays.

As can be seen from the figures, G-CSF (here, recombinant human met-G-CSF) is an antiparallel 4-alpha helical bundle with a left-handed twist, and with overall dimensions of 45 Å×30 Å×24 Å. The four helices within the bundle are referred to as helices A, B, C and D, and their connecting loops are known as the AB, BC and CD loops. The helix crossing angles range from −167.5° to −159.4°. Helices A, B, and C are straight, whereas helix D contains two kinds of structural characteristics, at Gly 150 and Ser 160 (of the recombinant human met-G-CSF). Overall, the G-CSF molecules is a bundle of four helices, connected in series by external loops. This structural information was then correlated with known functional information. It was known that residues (including methionine at position 1) 47, 23, 24, 20, 21, 44, 53, 113, 110, 28 and 114 may be modified, and the effect on biological activity would be substantial.

The majority of single mutations which lowered biological activity were centered around two regions of G-CSF that are separated by 30 Å, and are located on different faces of the four helix bundle. One region involves interactions between the A helix and the D helix. This is further confirmed by the presence of salt bridges in the non-altered molecule as follows:

| Atom | Helix | Atom | Helix | Distance |
|---|---|---|---|---|
| Arg 170 N1 | D | Tyr 166 OH | A | 3.3 |
| Tyr 166 OH | D | Arg 23 N2 | A | 3.3 |
| Glu 163 OE1 | D | Arg 23 N1 | A | 2.8 |
| Arg 23 N1 | A | Gln 26 OE1 | A | 3.1 |
| Gln 159 NE2 | D | Gln 26 O | A | 3.3 |

Distances reported here were for molecule A, as indicated in FIG. 5 (wherein three G-CSF molecules crystallized together and were designated as A, B, and C). As can be seen, there is a web of salt bridges between helix A and helix D, which act to stabilize the helix A structure, and therefore affect the overall structure of the G-CSF molecule.

The area centering around residues Glu 20, Arg 23 and Lys 24 are found on the hydrophilic face of the A helix (residues 20–37). Substitution of the residues with the non-charged alanine residue at positions 20 and 23 resulted in similar HPLC retention times, indicating similarity in structure. Alteration of these sites altered the biological activity (as indicated by the present assays). Substitution at Lys 24 altered biological activity, but did not result in a similar HPLC retention time as the other two alterations.

The second site at which alteration lowered biological activity involves the AB helix. Changing glutamine at position 47 to alanine (analog no. 19, above) reduced biological activity (in the thymidine uptake assay) to zero. The AB helix is predominantly hydrophobic, except at the amino and carboxy termini; it contains one turn of a $3^{10}$ helix. There are two histadines at each termini (His 44 and His 56) and an additional glutamate at residue 46 which has the potential to form a salt bridge to His 44. The fourier transformed infra red spectrographic analysis (FTIR) of the analog suggests this analog is structurally similar to the non-altered recombinant G-CSF molecule. Further testing showed that this analog would not crystallize under the same conditions as the non-altered recombinant molecule.

Alterations at the carboxy terminus (Gln 174, Arg 167 and Arg 170) had little effect on biological activity. In contrast, deletion of the last eight residues (167–175) lowered biological activity. These results may indicate that the deletion destabilizes the overall structure which prevents the mutant from proper binding to the G-CSF receptor (and thus initiating signal transduction).

Generally, for the G-CSF internal core—the internal four helix bundle lacking the external loops—the hydrophobic internal residues are essential for structural integrity. For example, in helix A, the internal hydrophobic residues are (with methionine being position 1) Phe 14, Cys 18, Val 22, Ile 25, Ile 32 and Leu 36. Generally, for the G-CSF internal core—the internal four helix bundle lacking the external loops—the hydrophobic internal residues are essential for structural integrity. For example, in helix A, the internal hydrophobic residues are (with methionine being position 1 as in FIG. 1) Phe 14, Cys 18, Val 22, Ile 25, lie 32 and Leu 36. The other hydrophobic residues (again with the met at position 1) are: helix B, Ala 72, Leu 76, Leu 79, Leu 83, Tyr 86, Leu 90 Leu 93; helix C, Leu 104, Leu 107, Val 111, Ala 114, Ile118, Met 122; and helix D, Val 154, Val 158, Phe 161, Val 164, Val 168, Leu 172.

The above biological activity data, from the presently prepared G-CSF analogs, demonstrate that modification of the external loops interfere least with G-CSF overall structure. Preferred loops for analog preparation are the AB loop and the CD loop. The loops are relatively flexible structures as compared to the helices. The loops may contribute to the proteolysis of the molecule. G-CSF is relatively fast acting in vivo as the purpose the molecule serves is to generate a response to a biological challenge, i.e., selectively stimulate neutrophils. The G-CSF turnover rate is also relatively fast. The flexibility of the loops may provide a "handle" for proteases to attach to the molecule to inactivate the molecule. Modification of the loops to prevent protease degradation, yet have (via retention of the overall structure of non-modified G-CSF) no loss in biological activity may be accomplished.

This phenomenon is probably not limited to the G-CSF molecule but may also be common to the other molecules with known similar overall structures, as presented in FIG. 2. Alteration of the external loop of, for example hGH, Interferon B, IL-2, GM-CSF and IL-4 may provide the least change to the overall structure. The external loops on the GM-CSF molecule are not as flexible as those found on the G-CSF molecule, and this may indicate a longer serum life, consistent with the broader biological activity of GM-CSF. Thus, the external loops of GM-CSF may be modified by releasing the external loops from the beta-sheet structure, which may make the loops more flexible (similar to those G-CSF) and therefore make the molecule more susceptible to protease degradation (and thus increase the turnover rate).

Alteration of these external loops may be effected by stabilizing the loops by connection to one or more of the internal helices. Connecting means are known to those in the art, such as the formation of a beta sheet, salt bridge, disulfide bonding or hydrophobic interactions, and other means are available. Also, deletion of one or more moieties, such as one or more amino acid residues or portions thereof, to prepare an abbreviated molecule and thus eliminate certain portions of the external loops may be effected.

Thus, by alteration of the external loops, preferably the AB loop (amino acids 58–72 of r-hu-met G-CSF) or the CD loop (amino acids 119 to 145 of r-hu-met-G-CSF), and less preferably the amino terminus (amino acids 1–10), one may therefore modify the biological function without elimination of G-CSF G-CSF receptor binding. For example, one may: (1) increase half-life (or prepare an oral dosage form, for example) of the G-CSF molecule by, for example, decreasing the ability of proteases to act on the G-CSF molecule or adding chemical modifications to the G-CSF molecule, such as one or more polyethylene glycol molecules or enteric coatings for oral formulation which would act to change some characteristic of the G-CSF molecule as described above, such as increasing serum or other half-life or decreasing antigenicity; (2) prepare a hybrid molecule, such as combining G-CSF with part or all of another protein such as another cytokine or another protein which effects signal transduction via entry through the cell through a G-CSF G-CSF receptor transport mechanism; or (3) increase the biological activity as in, for example, the ability to selectively stimulate neutrophils (as compared to a non-modified G-CSF molecule). This list is not limited to the above exemplars.

Another aspect observed from the above data is that stabilizing surface interactions may affect biological activity. This is apparent from comparing analogs 23 and 40. Analog 23 contains a substitution of the charged asparagine residue at position 28 for the neutrally-charged alanine residue in that position, and such substitution resulted in a 50% increase in the biological activity (as measured by the disclosed thymidine uptake assays). The asparagine residue at position 28 has a surface interaction with the asparagine residue at position 113; both residues being negatively charged, there is a certain amount of instability (due to the repelling of like charged moieties). When, however the asparagine at position 113 is replaced with the neutrally-charged alanine, the biological activity drops to zero (in the present assay system). This indicates that the asparagine at position 113 is critical to biological activity, and elimination of the asparagine at position 28 serves to increase the effect that asparagine at position 113 possesses.

The domains required for G-CSF receptor binding were also determined based on the above analogs prepared and the G-CSF structure. The G-CSF receptor binding domain is located at residues (with methionine being position 1) 11–57 (between the A and AB helix) and 100–118 (between the B and C helices). One may also prepare abbreviated molecules capable of binding to a G-CSF receptor and initiate signal transduction for selectively stimulating neutrophils by changing the external loop structure and having the receptor binding domains remain intact.

Residues essential for biological activity and presumably G-CSF receptor binding or signal transduction have been identified. Two distinct sites are located on two different regions of the secondary structure. What is here called "Site A" is located on a helix which is constrained by salt bridge contacts between two other members of the helical bundle. The second site, "Site B" is located on a relatively more flexible helix, AB. The AB helix is potentially more sensitive to local pH changes because of the type and position of the residues at the carboxy and amino termini. The functional importance of this flexible helix may be important in a conformationally induced fit when binding to the G-CSF receptor. Additionally, the extended portion of the D helix is also indicated to be a G-CSF receptor binding domain, as ascertained by direct mutational and indirect comparative protein structure analysis. Deletion of the carboxy terminal end of r-hu-met-G-CSF reduces activity as it does for hGH, see, Cunningham and Wells, Science 244: 1081–1084 (1989). Cytokines which have similar structures, such as IL-6 and GM-CSF with predicted similar topology also center their biological activity along the carboxy end of the D helix, see Bazan, Immunology Today 11: 350–354 (1990).

A comparison of the structures and the positions of G-CSF receptor binding determinants between G-CSF and hGH suggests both molecules have similar means of signal transduction. Two separate G-CSF receptor binding sites have been identified for hGH De Vos et al., Science 255: 306–32 (1991). One of these binding sites (called "Site I") is formed by residues on the exposed faces of hGH's helix 1, the connection region between helix 1 and 2, and helix 4. The second binding site (called "Site II") is formed by surface residues of helix 1 and helix 3.

The G-CSF receptor binding determinates identified for G-CSF are located in the same relative positions as those identified for hGH. The G-CSF receptor binding site located in the connecting region between helix A and B on the AB helix (Site A) is similar in position to that reported for a small piece of helix (residues 38–47) of hGH. A single point mutation in the AB helix of G-CSF significantly reduces biological activity (as ascertained in the present assays), indicating the role in a G-CSF receptor-ligand interface. Binding of the G-CSF receptor may destabilize the $3^{10}$ helical nature of this region and induce a conformation change improving the binding energy of the ligand/G-CSF receptor complex.

In the hGH receptor complex, the first helix of the bundle donates residues to both of the binding sites required to dimerize the hGH receptor Mutational analysis of the corresponding helix of G-CSF (helix A) has identified three residues which are required for biological activity. Of these three residues, Glu 20 and Arg 24 lie on one face of the helical bundle towards helix C, whereas the side chain of Arg 23 (in two of the three molecules in the asymmetric unit) points to the face of the bundle towards helix D. The position of side chains of these biologically important residues indicates that similar to hGH, G-CSF may have a second G-CSF receptor binding site along the interface between helix A and helix C. In contrast with the hGH molecule, the amino terminus of G-CSF has a limited biological role as deletion of the first 11 residues has little effect on the biological activity.

As indicated above (see FIG. 2, for example), G-CSF has a topological similarity with other cytokines. A correlation of the structure with previous biochemical studies, mutational analysis and direct comparison of specific residues of the hGH receptor complex indicates that G-CSF has two receptor binding sites. Site A lies along the interface of the A and D helices and includes residues in the small AB helix. Site B also includes residues in the A helix but lies along the interface between helices A and C. The conservation of structure and relative positions of biologically important residues between G-CSF and hGH is one indication of a common method of signal transduction in that the receptor is bound in two places. It is therefore found that G-CSF analogs possessing altered G-CSF receptor binding domains may be prepared by alteration at either of the G-CSF receptor binding sites (residues 20–57 and 145–175).

Knowledge of the three dimensional structure and correlation of the composition of G-CSF protein makes possible a systematic, rational method for preparing G-CSF analogs. The above working examples have demonstrated that the limitations of the size and polarity of the side chains within the core of the structure dictate how much change the molecule can tolerate before the overall structure is changed.

SEQUENCE LISTING ( 1 ) GENERAL INFORMATION:

( i i i ) NUMBER OF SEQUENCES: 110

( 2 ) INFORMATION FOR SEQ ID NO:1:

( i ) SEQUENCE CHARACTERISTICS:
        ( A ) LENGTH: 565 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 30..554

( x i ) SEQUENCE DESCRIPTION: SEQ ID NO:1:

```
TCTAGAAAAA ACCAAGGAGG TAATAAATA ATG ACT CCA TTA GGT CCT GCT TCT        53
                                Met Thr Pro Leu Gly Pro Ala Ser
                                 1               5

TCT CTG CCG CAA AGC TTT CTG CTG AAA TGT CTG GAA CAG GTT CGT AAA       101
Ser Leu Pro Gln Ser Phe Leu Leu Lys Cys Leu Glu Gln Val Arg Lys
        10              15                  20

ATC CAG GGT GAC GGT GCT GCA CTG CAA GAA AAA CTG TGC GCT ACT TAC       149
Ile Gln Gly Asp Gly Ala Ala Leu Gln Glu Lys Leu Cys Ala Thr Tyr
 25              30                  35                      40

AAA CTG TGC CAT CCG GAA GAA CTG GTA CTG CTG GGT CAT TCT CTT GGG       197
Lys Leu Cys His Pro Glu Glu Leu Val Leu Leu Gly His Ser Leu Gly
                 45                  50                  55

ATC CCG TGG GCT CCG CTG TCT TCT TGC CCA TCT CAA GCT CTT CAG CTG       245
Ile Pro Trp Ala Pro Leu Ser Ser Cys Pro Ser Gln Ala Leu Gln Leu
             60                  65                  70

GCT GGT TGT CTG TCT CAA CTG CAT TCT GGT CTG TTC CTG TAT CAG GGT       293
Ala Gly Cys Leu Ser Gln Leu His Ser Gly Leu Phe Leu Tyr Gln Gly
         75                  80                  85

CTT CTG CAA GCT CTG GAA GGT ATC TCT CCG GAA CTG GGT CCG ACT CTG       341
Leu Leu Gln Ala Leu Glu Gly Ile Ser Pro Glu Leu Gly Pro Thr Leu
         90                  95                 100

GAC ACT CTG CAG CTA GAT GTA GCT GAC TTT GCT ACT ACT ATT TGG CAA       389
Asp Thr Leu Gln Leu Asp Val Ala Asp Phe Ala Thr Thr Ile Trp Gln
105                 110                 115                 120

CAG ATG GAA GAG CTC GGT ATG GCA CCA GCT CTG CAA CCG ACT CAA GGT       437
Gln Met Glu Glu Leu Gly Met Ala Pro Ala Leu Gln Pro Thr Gln Gly
                125                 130                 135

GCT ATG CCG GCA TTC GCT TCT GCA TTC CAG CGT CGT GCA GGA GGT GTA       485
Ala Met Pro Ala Phe Ala Ser Ala Phe Gln Arg Arg Ala Gly Gly Val
            140                 145                 150

CTG GTT GCT TCT CAT CTG CAA TCT TTC CTG GAA GTA TCT TAC CGT GTT       533
Leu Val Ala Ser His Leu Gln Ser Phe Leu Glu Val Ser Tyr Arg Val
            155                 160                 165

CTG CGT CAT CTG GCT CAG CCG TAATAGAATT C                              565
Leu Arg His Leu Ala Gln Pro
        170                 175
```

( 2 ) INFORMATION FOR SEQ ID NO:2:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Lys | Ile | Gln | Gly | Asp | Gly | Ala | Ala | Leu |
| | | | 20 | | | | 25 | | | | | 30 | | | |
| Gln | Glu | Lys | Leu | Cys | Ala | Thr | Tyr | Lys | Leu | Cys | His | Pro | Glu | Glu | Leu |
| | | 35 | | | | 40 | | | | | 45 | | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |
| Asp | Phe | Ala | Thr | Thr | Ile | Trp | Gln | Gln | Met | Glu | Glu | Leu | Gly | Met | Ala |
| | | | 115 | | | | | 120 | | | | | 125 | | |
| Pro | Ala | Leu | Gln | Pro | Thr | Gln | Gly | Ala | Met | Pro | Ala | Phe | Ala | Ser | Ala |
| | 130 | | | | | 135 | | | | | 140 | | | | |
| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |
| Phe | Leu | Glu | Val | Ser | Tyr | Arg | Val | Leu | Arg | His | Leu | Ala | Gln | Pro | |
| | | | | 165 | | | | | 170 | | | | | 175 | |

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CTTTCTGCTG CGTTGTCTGG AACA 24

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

ACAGGTTCGT CGTATCCAGG GTG 23

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

CACTGCAAGA ACGTCTGTGC GTC 23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CGCTACTTAC CGTCTGTGCC ATC 23

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CTTTCTGCTG CGTTGTCTGG AACA 24

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

ACAGGTTCGT CGTATCCAGG GTG 23

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CACTGCAAGA ACGTCTGTGC GCT 23

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

CTTTCTGCTG CGTTGTCTGG AACA 24

( 2 ) INFORMATION FOR SEQ ID NO:11:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:11:

ACAGGTTCGT CGTATCCAGG GTG                23

( 2 ) INFORMATION FOR SEQ ID NO:12:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:12:

CGCTACTTAC CGTCTGTCCC ATC                23

( 2 ) INFORMATION FOR SEQ ID NO:13:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:13:

CTTTCTGCTG CGTTGTCTGG AACA               24

( 2 ) INFORMATION FOR SEQ ID NO:14:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:14:

CACTGCAAGA ACGTCTGTGC GCT                23

( 2 ) INFORMATION FOR SEQ ID NO:15:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:15:

CGCTACTTAC CGTCTGTGCC ATC                23

( 2 ) INFORMATION FOR SEQ ID NO:16:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:16:

ACAGGTTCGT CGTATCCAGG GTG                                                                               2 3

( 2 ) INFORMATION FOR SEQ ID NO:17:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

CACTGCAAGA ACGTCTGTGC GCT                                                                               2 3

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

CGCTACTTAC CGTCTGTGCC ATC                                                                               2 3

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

CTTTCTGCTG CGTTGTCTGG AACA                                                                              2 4

( 2 ) INFORMATION FOR SEQ ID NO:20:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

ACAGGTTCGT CGTATCCAGG GTG                                                                               2 3

( 2 ) INFORMATION FOR SEQ ID NO:21:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

CACTGCAAGA ACGTCTGTGC GCT 23

( 2 ) INFORMATION FOR SEQ ID NO:22:

( i ) SEQUENCE CHARACTERISTICS:
          ( A ) LENGTH: 23 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:22:

CGCTACTTAC CGTCTGTGCC ATC 23

( 2 ) INFORMATION FOR SEQ ID NO:23:

( i ) SEQUENCE CHARACTERISTICS:
          ( A ) LENGTH: 23 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:23:

TCTGCTGAAA GCTCTGGAAC AGG 23

( 2 ) INFORMATION FOR SEQ ID NO:24:

( i ) SEQUENCE CHARACTERISTICS:
          ( A ) LENGTH: 23 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:24:

CTTGTCCATC TGAAGCTCTT CAG 23

( 2 ) INFORMATION FOR SEQ ID NO:25:

( i ) SEQUENCE CHARACTERISTICS:
          ( A ) LENGTH: 37 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:25:

GAAAAACTGT CCGCTACTTA CAAACTGTCC CATCCGG 37

( 2 ) INFORMATION FOR SEQ ID NO:26:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA ( x i ) SEQUENCE DESCRIPTION: SEQ ID NO:26:

TTCGTAAAAT CGCGGGTGAC GG 22

( 2 ) INFORMATION FOR SEQ ID NO:27:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:27:

TCATCTGGCT GCGCCGTAAT AG                                      22

( 2 ) INFORMATION FOR SEQ ID NO:28:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

CCGTGTTCTG GCTCATCTGG CT                                      22

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

GAAGTATCTT ACGCTGTTCT GCGT                                  24

( 2 ) INFORMATION FOR SEQ ID NO:30:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

GAAGTATCTT ACTAAGTTCT GCGTC                               25

( 2 ) INFORMATION FOR SEQ ID NO:31:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

CGCTACTTAC GCACTGTGCC AT                                      22

( 2 ) INFORMATION FOR SEQ ID NO:32:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

CAAACTGTGC AAGCCGGAAG AG 22

( 2 ) INFORMATION FOR SEQ ID NO:33:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

CATCCGGAAG CACTGGTACT GC 22

( 2 ) INFORMATION FOR SEQ ID NO:34:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

GGAACAGGTT GCTAAAATCC AGG 23

( 2 ) INFORMATION FOR SEQ ID NO:35:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

GAACAGGTTC GTGCGATCCA GGGTG 25

( 2 ) INFORMATION FOR SEQ ID NO:36:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

GAAATGTCTG GCACAGGTTC GT 22

( 2 ) INFORMATION FOR SEQ ID NO:37:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:37:

TCCAGGGTGC CGGTGCTGC 19

( 2 ) INFORMATION FOR SEQ ID NO:38:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

AAGAGCTCGG TGAGGCACCA GCT 23

( 2 ) INFORMATION FOR SEQ ID NO:39:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

CTCAAGGTGC TGAGCCGGCA TTC 23

( 2 ) INFORMATION FOR SEQ ID NO:40:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

GAGCTCGGTC TGGCACCAGC 20

( 2 ) INFORMATION FOR SEQ ID NO:41:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

TCAAGGTGCT CTGCCGGCAT T 21

( 2 ) INFORMATION FOR SEQ ID NO:42:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

TCTGCCGCAA GCCTTTCTGC TGA 23

( 2 ) INFORMATION FOR SEQ ID NO:43:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:43:

CTTTCTGCTG GCATGTCTGG AACA 24

(2) INFORMATION FOR SEQ ID NO:44:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:44:

CTATTTGGCA AGCGATGGAA GAGC 24

(2) INFORMATION FOR SEQ ID NO:45:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:45:

CAGATGGAAG CGCTCGGTAT G 21

(2) INFORMATION FOR SEQ ID NO:46:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:46:

GAGCTCGGTC TGGCACCAGC 20

(2) INFORMATION FOR SEQ ID NO:47:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:47:

TCAAGGTGCT CTGCCGGCAT T 21

(2) INFORMATION FOR SEQ ID NO:48:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:48:

GAAATGTCTG GCACAGGTTC GT 22

(2) INFORMATION FOR SEQ ID NO:49:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:49:

TTCCGGAGCG CACAGTTTG 19

(2) INFORMATION FOR SEQ ID NO:50:

(i) SEQUENCE CHARACTERISTICS:
  (A) LENGTH: 23 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:50:

CGAGAAGGCC TCGGGTGTCA AAC 23

(2) INFORMATION FOR SEQ ID NO:51:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:51:

ATGCCAAATT GCAGTAGCAA AG 22

(2) INFORMATION FOR SEQ ID NO:52:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:52:

ACAACGGTTT AACGTCATCG TTTC 24

(2) INFORMATION FOR SEQ ID NO:53:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:53:

ATCAGCTACT GCTAGCTGCA GA                                                                    22

( 2 ) INFORMATION FOR SEQ ID NO:54:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:54:

TCAGTCGATG ACGATCGACG TCT                                                                   23

( 2 ) INFORMATION FOR SEQ ID NO:55:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:55:

TTACGAACCG CTTCCAGACA TT                                                                    22

( 2 ) INFORMATION FOR SEQ ID NO:56:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

TAAAATGCTT GGCGAAGGTC TGTAA                                                                 25

( 2 ) INFORMATION FOR SEQ ID NO:57:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

GTAGCAAATG CAGCTACATC TA                                                                    22

( 2 ) INFORMATION FOR SEQ ID NO:58:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

CATCATCGTT TACGTCGATG TAGAT                                                                 25

( 2 ) INFORMATION FOR SEQ ID NO:59:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:59:

CCAAGAGAAG CACCCAGCAG 20

(2) INFORMATION FOR SEQ ID NO:60:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:60:

AGGGTTCTCT TCGTGGGTCG TC 22

(2) INFORMATION FOR SEQ ID NO:61:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:61:

CACTGGCGGT GATAATGAGC 20

(2) INFORMATION FOR SEQ ID NO:62:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:62:

CTAGGCCAGG CATTACTGG 19

(2) INFORMATION FOR SEQ ID NO:63:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:63:

CCACTGGCGG TGATACTGAG C 21

(2) INFORMATION FOR SEQ ID NO:64:

(i) SEQUENCE CHARACTERISTICS:
(A) LENGTH: 33 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:64:

AGCAGAAAGC TTTCCGGCAG AGAAGAAGCA GGA   33

( 2 ) INFORMATION FOR SEQ ID NO:65:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:65:

GCCGCAAAGC TTTCTGCTGA AATGTCTGGA AGAGGTTCGT AAAATCCAGG GTGA   54

( 2 ) INFORMATION FOR SEQ ID NO:66:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:66:

CTGGAATGCA GAAGCAAATG CCGGCATAGC ACCTTCAGTC GGTTGCAGAG CTGGTGCCA   59

( 2 ) INFORMATION FOR SEQ ID NO:67:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:67:

```
Met Thr Pro Leu Gly Pro Ala Ser Ser Leu Pro Gln Ser Phe Leu Leu
 1               5                  10                  15

Arg Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Gly Ile Pro Trp Ala Pro Leu Ser Ser
    50                  55                  60

Cys Pro Ser Gln Ala Leu Gln Leu Ala Gly Cys Leu Ser Gln Leu His
65                      70                  75                  80

Ser Gly Leu Phe Leu Tyr Gln Gly Leu Leu Gln Ala Leu Glu Gly Ile
                    85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
```

(2) INFORMATION FOR SEQ ID NO:68:

(i) SEQUENCE CHARACTERISTICS:
(A) LENGTH: 175 amino acids
(B) TYPE: amino acid
(D) TOPOLOGY: linear (ii) MOLECULE TYPE: protein (xi) SEQUENCE DESCRIPTION: SEQ ID NO:68:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Arg | Ile | Gln | Gly | Asp | Gly | Ala | Ala | Leu |
| | | | 20 | | | | | 25 | | | | | 30 | | |
| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |
| Asp | Phe | Ala | Thr | Thr | Ile | Trp | Gln | Gln | Met | Glu | Glu | Leu | Gly | Met | Ala |
| | | | 115 | | | | | 120 | | | | | 125 | | |
| Pro | Ala | Leu | Gln | Pro | Thr | Gln | Gly | Ala | Met | Pro | Ala | Phe | Ala | Ser | Ala |
| | 130 | | | | | 135 | | | | | 140 | | | | |
| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |
| Phe | Leu | Glu | Val | Ser | Tyr | Arg | Val | Leu | Arg | His | Leu | Ala | Gln | Pro | |
| | | | | 165 | | | | | 170 | | | | | 175 | |

(2) INFORMATION FOR SEQ ID NO:69:

(i) SEQUENCE CHARACTERISTICS:
(A) LENGTH: 175 amino acids
(B) TYPE: amino acid
(D) TOPOLOGY: linear (ii) MOLECULE TYPE: protein (xi) SEQUENCE DESCRIPTION: SEQ ID NO:69:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |
| Gln | Glu | Arg | Leu | Cys | Ala | Thr | Tyr | Lys | Leu | Cys | His | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |

-continued

```
Asp  Phe  Ala  Thr  Thr  Ile  Trp  Gln  Gln  Met  Glu  Glu  Leu  Gly  Met  Ala
          115                 120                      125

Pro  Ala  Leu  Gln  Pro  Thr  Gln  Gly  Ala  Met  Pro  Ala  Phe  Ala  Ser  Ala
     130                      135                 140

Phe  Gln  Arg  Arg  Ala  Gly  Gly  Val  Leu  Val  Ala  Ser  His  Leu  Gln  Ser
145                           150                 155                      160

Phe  Leu  Glu  Val  Ser  Tyr  Arg  Val  Leu  Arg  His  Leu  Ala  Gln  Pro
                    165                 170                      175
```

(2) INFORMATION FOR SEQ ID NO:70:

(i) SEQUENCE CHARACTERISTICS:
      (A) LENGTH: 175 amino acids
      (B) TYPE: amino acid
      (D) TOPOLOGY: linear (ii) MOLECULE TYPE: protein (xi) SEQUENCE DESCRIPTION: SEQ ID NO:70:

```
Met  Thr  Pro  Leu  Gly  Pro  Ala  Ser  Ser  Leu  Pro  Gln  Ser  Phe  Leu  Leu
1                    5                      10                      15

Lys  Cys  Leu  Glu  Gln  Val  Arg  Lys  Ile  Gln  Gly  Asp  Gly  Ala  Ala  Leu
               20                      25                      30

Gln  Glu  Lys  Leu  Cys  Ala  Thr  Tyr  Arg  Leu  Cys  His  Pro  Glu  Glu  Leu
          35                      40                      45

Val  Leu  Leu  Gly  His  Ser  Leu  Gly  Ile  Pro  Trp  Ala  Pro  Leu  Ser  Ser
     50                      55                      60

Cys  Pro  Ser  Gln  Ala  Leu  Gln  Leu  Ala  Gly  Cys  Leu  Ser  Gln  Leu  His
65                            70                 75                      80

Ser  Gly  Leu  Phe  Leu  Tyr  Gln  Gly  Leu  Leu  Gln  Ala  Leu  Glu  Gly  Ile
                    85                      90                      95

Ser  Pro  Glu  Leu  Gly  Pro  Thr  Leu  Asp  Thr  Leu  Gln  Leu  Asp  Val  Ala
               100                     105                     110

Asp  Phe  Ala  Thr  Thr  Ile  Trp  Gln  Gln  Met  Glu  Glu  Leu  Gly  Met  Ala
          115                 120                      125

Pro  Ala  Leu  Gln  Pro  Thr  Gln  Gly  Ala  Met  Pro  Ala  Phe  Ala  Ser  Ala
     130                      135                 140

Phe  Gln  Arg  Arg  Ala  Gly  Gly  Val  Leu  Val  Ala  Ser  His  Leu  Gln  Ser
145                           150                 155                      160

Phe  Leu  Glu  Val  Ser  Tyr  Arg  Val  Leu  Arg  His  Leu  Ala  Gln  Pro
                    165                 170                      175
```

(2) INFORMATION FOR SEQ ID NO:71:

(i) SEQUENCE CHARACTERISTICS:
      (A) LENGTH: 175 amino acids
      (B) TYPE: amino acid
      (D) TOPOLOGY: linear (ii) MOLECULE TYPE: protein (xi) SEQUENCE DESCRIPTION: SEQ ID NO:71:

```
Met  Thr  Pro  Leu  Gly  Pro  Ala  Ser  Ser  Leu  Pro  Gln  Ser  Phe  Leu  Leu
1                    5                      10                      15

Arg  Cys  Leu  Glu  Gln  Val  Arg  Arg  Ile  Gln  Gly  Asp  Gly  Ala  Ala  Leu
               20                      25                      30

Gln  Glu  Arg  Leu  Cys  Ala  Thr  Tyr  Lys  Leu  Cys  His  Pro  Glu  Glu  Leu
          35                      40                      45

Val  Leu  Leu  Gly  His  Ser  Leu  Gly  Ile  Pro  Trp  Ala  Pro  Leu  Ser  Ser
     50                      55                      60
```

```
Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

( 2 ) INFORMATION FOR SEQ ID NO:72:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:72:

```
Met Thr Pro Leu Gly Pro Ala Ser Ser Leu Pro Gln Ser Phe Leu Leu
  1               5                  10                  15

Arg Cys Leu Glu Gln Val Arg Lys Ile Gln Gly Asp Gly Ala Ala Leu
                 20                  25                  30

Gln Glu Arg Leu Cys Ala Thr Tyr Arg Leu Cys His Pro Glu Glu Leu
             35                  40                  45

Val Leu Leu Gly His Ser Leu Gly Ile Pro Trp Ala Pro Leu Ser Ser
     50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

( 2 ) INFORMATION FOR SEQ ID NO:73:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:73:

```
Met Thr Pro Leu Gly Pro Ala Ser Ser Leu Pro Gln Ser Phe Leu Leu
```

|   1   |       |       |   5   |       |       |       |       |  10   |       |       |       |       |  15   |       |
|-------|-------|-------|-------|-------|-------|-------|-------|-------|-------|-------|-------|-------|-------|-------|
| Lys   | Cys   | Leu   | Glu   | Val   | Arg   | Arg   | Ile   | Gln   | Gly   | Asp   | Gly   | Ala   | Ala   | Leu   |
|       |       |       | 20    |       |       |       |       | 25    |       |       |       | 30    |       |       |
| Gln   | Glu   | Arg   | Leu   | Cys   | Ala   | Thr   | Tyr   | Arg   | Leu   | Cys   | His   | Pro   | Glu   | Glu   | Leu
|       |       | 35    |       |       |       |       | 40    |       |       |       |       | 45    |       |       |
| Val   | Leu   | Leu   | Gly   | His   | Ser   | Leu   | Gly   | Ile   | Pro   | Trp   | Ala   | Pro   | Leu   | Ser   | Ser
|       | 50    |       |       |       |       | 55    |       |       |       |       | 60    |       |       |       |
| Cys   | Pro   | Ser   | Gln   | Ala   | Leu   | Gln   | Leu   | Ala   | Gly   | Cys   | Leu   | Ser   | Gln   | Leu   | His
| 65    |       |       |       |       | 70    |       |       |       |       | 75    |       |       |       |       | 80
| Ser   | Gly   | Leu   | Phe   | Leu   | Tyr   | Gln   | Gly   | Leu   | Leu   | Gln   | Ala   | Leu   | Glu   | Gly   | Ile
|       |       |       |       | 85    |       |       |       |       | 90    |       |       |       |       | 95    |
| Ser   | Pro   | Glu   | Leu   | Gly   | Pro   | Thr   | Leu   | Asp   | Thr   | Leu   | Gln   | Leu   | Asp   | Val   | Ala
|       |       |       | 100   |       |       |       |       | 105   |       |       |       | 110   |       |       |
| Asp   | Phe   | Ala   | Thr   | Thr   | Ile   | Trp   | Gln   | Gln   | Met   | Glu   | Glu   | Leu   | Gly   | Met   | Ala
|       |       | 115   |       |       |       |       | 120   |       |       |       |       | 125   |       |       |
| Pro   | Ala   | Leu   | Gln   | Pro   | Thr   | Gln   | Gly   | Ala   | Met   | Pro   | Ala   | Phe   | Ala   | Ser   | Ala
|       | 130   |       |       |       |       | 135   |       |       |       |       | 140   |       |       |       |
| Phe   | Gln   | Arg   | Arg   | Ala   | Gly   | Gly   | Val   | Leu   | Val   | Ala   | Ser   | His   | Leu   | Gln   | Ser
| 145   |       |       |       |       | 150   |       |       |       |       | 155   |       |       |       |       | 160
| Phe   | Leu   | Glu   | Val   | Ser   | Tyr   | Arg   | Val   | Leu   | Arg   | His   | Leu   | Ala   | Gln   | Pro   |
|       |       |       |       | 165   |       |       |       |       | 170   |       |       |       |       | 175   |

(2) INFORMATION FOR SEQ ID NO:74:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO:74:

| Met   | Thr   | Pro   | Leu   | Gly   | Pro   | Ala   | Ser   | Ser   | Leu   | Pro   | Gln   | Ser   | Phe   | Leu   | Leu
| 1     |       |       |       | 5     |       |       |       |       | 10    |       |       |       |       | 15    |
| Arg   | Cys   | Leu   | Glu   | Gln   | Val   | Arg   | Arg   | Ile   | Gln   | Gly   | Asp   | Gly   | Ala   | Ala   | Leu
|       |       |       | 20    |       |       |       |       | 25    |       |       |       | 30    |       |       |
| Gln   | Glu   | Arg   | Leu   | Cys   | Ala   | Thr   | Tyr   | Arg   | Leu   | Cys   | His   | Pro   | Glu   | Glu   | Leu
|       |       | 35    |       |       |       |       | 40    |       |       |       |       | 45    |       |       |
| Val   | Leu   | Leu   | Gly   | His   | Ser   | Leu   | Gly   | Ile   | Pro   | Trp   | Ala   | Pro   | Leu   | Ser   | Ser
|       | 50    |       |       |       |       | 55    |       |       |       |       | 60    |       |       |       |
| Cys   | Pro   | Ser   | Gln   | Ala   | Leu   | Gln   | Leu   | Ala   | Gly   | Cys   | Leu   | Ser   | Gln   | Leu   | His
| 65    |       |       |       |       | 70    |       |       |       |       | 75    |       |       |       |       | 80
| Ser   | Gly   | Leu   | Phe   | Leu   | Tyr   | Gln   | Gly   | Leu   | Leu   | Gln   | Ala   | Leu   | Glu   | Gly   | Ile
|       |       |       |       | 85    |       |       |       |       | 90    |       |       |       |       | 95    |
| Ser   | Pro   | Glu   | Leu   | Gly   | Pro   | Thr   | Leu   | Asp   | Thr   | Leu   | Gln   | Leu   | Asp   | Val   | Ala
|       |       |       | 100   |       |       |       |       | 105   |       |       |       | 110   |       |       |
| Asp   | Phe   | Ala   | Thr   | Thr   | Ile   | Trp   | Gln   | Gln   | Met   | Glu   | Glu   | Leu   | Gly   | Met   | Ala
|       |       | 115   |       |       |       |       | 120   |       |       |       |       | 125   |       |       |
| Pro   | Ala   | Leu   | Gln   | Pro   | Thr   | Gln   | Gly   | Ala   | Met   | Pro   | Ala   | Phe   | Ala   | Ser   | Ala
|       | 130   |       |       |       |       | 135   |       |       |       |       | 140   |       |       |       |
| Phe   | Gln   | Arg   | Arg   | Ala   | Gly   | Gly   | Val   | Leu   | Val   | Ala   | Ser   | His   | Leu   | Gln   | Ser
| 145   |       |       |       |       | 150   |       |       |       |       | 155   |       |       |       |       | 160
| Phe   | Leu   | Glu   | Val   | Ser   | Tyr   | Arg   | Val   | Leu   | Arg   | His   | Leu   | Ala   | Gln   | Pro   |
|       |       |       |       | 165   |       |       |       |       | 170   |       |       |       |       | 175   |

(2) INFORMATION FOR SEQ ID NO:75:

( i ) SEQUENCE CHARACTERISTICS:
    ( A ) LENGTH: 175 amino acids
    ( B ) TYPE: amino acid
    ( D ) TOPOLOGY: linear ( i i ) MOLECULE TYPE: protein ( x i ) SEQUENCE DESCRIPTION: SEQ ID NO:75:

| Met | Thr | Pro | Leu | Gly | Pro | Ala | Ser | Ser | Leu | Pro | Gln | Ser | Phe | Leu | Leu |
| 1 | | | | 5 | | | | | 10 | | | | | 15 | |
| Arg | Cys | Leu | Glu | Gln | Val | Arg | Arg | Ile | Gln | Gly | Asp | Gly | Ala | Ala | Leu |
| | | | 20 | | | | 25 | | | | | 30 | | | |
| Gln | Glu | Lys | Leu | Cys | Ala | Thr | Tyr | Arg | Leu | Cys | His | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | 105 | | | | | 110 | | | |
| Asp | Phe | Ala | Thr | Thr | Ile | Trp | Gln | Gln | Met | Glu | Glu | Leu | Gly | Met | Ala |
| | | 115 | | | | | 120 | | | | | 125 | | | |
| Pro | Ala | Leu | Gln | Pro | Thr | Gln | Gly | Ala | Met | Pro | Ala | Phe | Ala | Ser | Ala |
| | 130 | | | | | 135 | | | | | 140 | | | | |
| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |
| Phe | Leu | Glu | Val | Ser | Tyr | Arg | Val | Leu | Arg | His | Leu | Ala | Gln | Pro | |
| | | | | 165 | | | | | 170 | | | | | 175 | |

( 2 ) INFORMATION FOR SEQ ID NO:76:

( i ) SEQUENCE CHARACTERISTICS:
    ( A ) LENGTH: 175 amino acids
    ( B ) TYPE: amino acid
    ( D ) TOPOLOGY: linear ( i i ) MOLECULE TYPE: protein ( x i ) SEQUENCE DESCRIPTION: SEQ ID NO:76:

| Met | Thr | Pro | Leu | Gly | Pro | Ala | Ser | Ser | Leu | Pro | Gln | Ser | Phe | Leu | Leu |
| 1 | | | | 5 | | | | | 10 | | | | | 15 | |
| Lys | Cys | Leu | Glu | Gln | Val | Arg | Lys | Ile | Gln | Gly | Asp | Gly | Ala | Ala | Leu |
| | | | 20 | | | | 25 | | | | | 30 | | | |
| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Glu | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | 105 | | | | | 110 | | | |
| Asp | Phe | Ala | Thr | Thr | Ile | Trp | Gln | Gln | Met | Glu | Glu | Leu | Gly | Met | Ala |
| | | 115 | | | | | 120 | | | | | 125 | | | |
| Pro | Ala | Leu | Gln | Pro | Thr | Gln | Gly | Ala | Met | Pro | Ala | Phe | Ala | Ser | Ala |
| | 130 | | | | | 135 | | | | | 140 | | | | |

```
Phe  Gln  Arg  Arg  Ala  Gly  Gly  Val  Leu  Val  Ala  Ser  His  Leu  Gln  Ser
145                      150                 155                           160

Phe  Leu  Glu  Val  Ser  Tyr  Arg  Val  Leu  Arg  His  Leu  Ala  Gln  Pro
                    165                      170                      175
```

( 2 ) INFORMATION FOR SEQ ID NO:77:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:77:

```
Met  Thr  Pro  Leu  Gly  Pro  Ala  Ser  Ser  Leu  Pro  Gln  Ser  Phe  Leu  Leu
1                        5                        10                      15

Lys  Cys  Leu  Glu  Gln  Val  Arg  Lys  Ile  Gln  Gly  Asp  Gly  Ala  Ala  Leu
                    20                       25                      30

Gln  Glu  Lys  Leu  Ser  Ala  Thr  Tyr  Lys  Leu  Ser  His  Pro  Glu  Glu  Leu
               35                      40                 45

Val  Leu  Leu  Gly  His  Ser  Leu  Gly  Ile  Pro  Trp  Ala  Pro  Leu  Ser  Ser
          50                      55                      60

Cys  Pro  Ser  Gln  Ala  Leu  Gln  Leu  Ala  Gly  Cys  Leu  Ser  Gln  Leu  His
65                       70                      75                           80

Ser  Gly  Leu  Phe  Leu  Tyr  Gln  Gly  Leu  Leu  Gln  Ala  Leu  Glu  Gly  Ile
               85                      90                      95

Ser  Pro  Glu  Leu  Gly  Pro  Thr  Leu  Asp  Thr  Leu  Gln  Leu  Asp  Val  Ala
               100                     105                     110

Asp  Phe  Ala  Thr  Thr  Ile  Trp  Gln  Gln  Met  Glu  Glu  Leu  Gly  Met  Ala
          115                     120                     125

Pro  Ala  Leu  Gln  Pro  Thr  Gln  Gly  Ala  Met  Pro  Ala  Phe  Ala  Ser  Ala
     130                     135                     140

Phe  Gln  Arg  Arg  Ala  Gly  Gly  Val  Leu  Val  Ala  Ser  His  Leu  Gln  Ser
145                      150                 155                           160

Phe  Leu  Glu  Val  Ser  Tyr  Arg  Val  Leu  Arg  His  Leu  Ala  Gln  Pro
                    165                      170                      175
```

( 2 ) INFORMATION FOR SEQ ID NO:78:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:78:

```
Met  Thr  Pro  Leu  Gly  Pro  Ala  Ser  Ser  Leu  Pro  Gln  Ser  Phe  Leu  Leu
1                        5                        10                      15

Lys  Cys  Leu  Glu  Gln  Val  Arg  Lys  Ile  Ala  Gly  Asp  Gly  Ala  Ala  Leu
                    20                       25                      30

Gln  Glu  Lys  Leu  Cys  Ala  Thr  Tyr  Lys  Leu  Cys  His  Pro  Glu  Glu  Leu
               35                      40                 45

Val  Leu  Leu  Gly  His  Ser  Leu  Gly  Ile  Pro  Trp  Ala  Pro  Leu  Ser  Ser
          50                      55                      60

Cys  Pro  Ser  Gln  Ala  Leu  Gln  Leu  Ala  Gly  Cys  Leu  Ser  Gln  Leu  His
65                       70                      75                           80

Ser  Gly  Leu  Phe  Leu  Tyr  Gln  Gly  Leu  Leu  Gln  Ala  Leu  Glu  Gly  Ile
```

|     |     |     |     | 85  |     |     |     |     | 90  |     |     |     |     | 95  |
|-----|-----|-----|-----|-----|-----|-----|-----|-----|-----|-----|-----|-----|-----|-----|

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

( 2 ) INFORMATION FOR SEQ ID NO:79:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:79:

Met Thr Pro Leu Gly Pro Ala Ser Ser Leu Pro Gln Ser Phe Leu Leu
1                   5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Ala Pro
                165                 170                 175

( 2 ) INFORMATION FOR SEQ ID NO:80:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:80:

Met Thr Pro Leu Gly Pro Ala Ser Ser Leu Pro Gln Ser Phe Leu Leu
1                   5                   10                  15

Lys Cys Leu Glu Gln Val Arg Lys Ile Gln Gly Asp Gly Ala Ala Leu
            20                  25                  30

| Gln | Glu | Lys | Leu | Cys | Ala | Thr | Tyr | Lys | Leu | Cys | His | Pro | Glu | Glu | Leu |
|---|---|---|---|---|---|---|---|---|---|---|---|---|---|---|---|
| | | 35 | | | | | 40 | | | | | 45 | | | |

| Val | Leu | Leu | Gly | His | Ser | Leu | Gly | Ile | Pro | Trp | Ala | Pro | Leu | Ser | Ser |
|---|---|---|---|---|---|---|---|---|---|---|---|---|---|---|---|
| | 50 | | | | | 55 | | | | | 60 | | | | |

| Cys | Pro | Ser | Gln | Ala | Leu | Gln | Leu | Ala | Gly | Cys | Leu | Ser | Gln | Leu | His |
|---|---|---|---|---|---|---|---|---|---|---|---|---|---|---|---|
| 65 | | | | | 70 | | | | | 75 | | | | | 80 |

| Ser | Gly | Leu | Phe | Leu | Tyr | Gln | Gly | Leu | Leu | Gln | Ala | Leu | Glu | Gly | Ile |
|---|---|---|---|---|---|---|---|---|---|---|---|---|---|---|---|
| | | | | 85 | | | | | 90 | | | | | 95 | |

| Ser | Pro | Glu | Leu | Gly | Pro | Thr | Leu | Asp | Thr | Leu | Gln | Leu | Asp | Val | Ala |
|---|---|---|---|---|---|---|---|---|---|---|---|---|---|---|---|
| | | | 100 | | | | | 105 | | | | 110 | | | |

| Asp | Phe | Ala | Thr | Thr | Ile | Trp | Gln | Gln | Met | Glu | Glu | Leu | Gly | Met | Ala |
|---|---|---|---|---|---|---|---|---|---|---|---|---|---|---|---|
| | | 115 | | | | | 120 | | | | | 125 | | | |

| Pro | Ala | Leu | Gln | Pro | Thr | Gln | Gly | Ala | Met | Pro | Ala | Phe | Ala | Ser | Ala |
|---|---|---|---|---|---|---|---|---|---|---|---|---|---|---|---|
| | 130 | | | | | 135 | | | | | 140 | | | | |

| Phe | Gln | Arg | Arg | Ala | Gly | Gly | Val | Leu | Val | Ala | Ser | His | Leu | Gln | Ser |
|---|---|---|---|---|---|---|---|---|---|---|---|---|---|---|---|
| 145 | | | | | 150 | | | | | 155 | | | | | 160 |

| Phe | Leu | Glu | Val | Ser | Tyr | Arg | Val | Leu | Ala | His | Leu | Ala | Gln | Pro |
|---|---|---|---|---|---|---|---|---|---|---|---|---|---|---|
| | | | | 165 | | | | | 170 | | | | | 175 |

( 2 ) INFORMATION FOR SEQ ID NO:81:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:81:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |

| Lys | Cys | Leu | Glu | Gln | Val | Arg | Lys | Ile | Gln | Gly | Asp | Gly | Ala | Ala | Leu |
|---|---|---|---|---|---|---|---|---|---|---|---|---|---|---|---|
| | | | | 20 | | | | | 25 | | | | | 30 | |

| Gln | Glu | Lys | Leu | Cys | Ala | Thr | Tyr | Lys | Leu | Cys | His | Pro | Glu | Glu | Leu |
|---|---|---|---|---|---|---|---|---|---|---|---|---|---|---|---|
| | | 35 | | | | | 40 | | | | | 45 | | | |

| Val | Leu | Leu | Gly | His | Ser | Leu | Gly | Ile | Pro | Trp | Ala | Pro | Leu | Ser | Ser |
|---|---|---|---|---|---|---|---|---|---|---|---|---|---|---|---|
| | 50 | | | | | 55 | | | | | 60 | | | | |

| Cys | Pro | Ser | Gln | Ala | Leu | Gln | Leu | Ala | Gly | Cys | Leu | Ser | Gln | Leu | His |
|---|---|---|---|---|---|---|---|---|---|---|---|---|---|---|---|
| 65 | | | | | 70 | | | | | 75 | | | | | 80 |

| Ser | Gly | Leu | Phe | Leu | Tyr | Gln | Gly | Leu | Leu | Gln | Ala | Leu | Glu | Gly | Ile |
|---|---|---|---|---|---|---|---|---|---|---|---|---|---|---|---|
| | | | | 85 | | | | | 90 | | | | | 95 | |

| Ser | Pro | Glu | Leu | Gly | Pro | Thr | Leu | Asp | Thr | Leu | Gln | Leu | Asp | Val | Ala |
|---|---|---|---|---|---|---|---|---|---|---|---|---|---|---|---|
| | | | 100 | | | | | 105 | | | | 110 | | | |

| Asp | Phe | Ala | Thr | Thr | Ile | Trp | Gln | Gln | Met | Glu | Glu | Leu | Gly | Met | Ala |
|---|---|---|---|---|---|---|---|---|---|---|---|---|---|---|---|
| | | 115 | | | | | 120 | | | | | 125 | | | |

| Pro | Ala | Leu | Gln | Pro | Thr | Gln | Gly | Ala | Met | Pro | Ala | Phe | Ala | Ser | Ala |
|---|---|---|---|---|---|---|---|---|---|---|---|---|---|---|---|
| | 130 | | | | | 135 | | | | | 140 | | | | |

| Phe | Gln | Arg | Arg | Ala | Gly | Gly | Val | Leu | Val | Ala | Ser | His | Leu | Gln | Ser |
|---|---|---|---|---|---|---|---|---|---|---|---|---|---|---|---|
| 145 | | | | | 150 | | | | | 155 | | | | | 160 |

| Phe | Leu | Glu | Val | Ser | Tyr | Ala | Val | Leu | Arg | His | Leu | Ala | Gln | Pro |
|---|---|---|---|---|---|---|---|---|---|---|---|---|---|---|
| | | | | 165 | | | | | 170 | | | | | 175 |

( 2 ) INFORMATION FOR SEQ ID NO:82:

( i ) SEQUENCE CHARACTERISTICS:
        ( A ) LENGTH: 174 amino acids
        ( B ) TYPE: amino acid
        ( D ) TOPOLOGY: linear ( i i ) MOLECULE TYPE: protein ( x i ) SEQUENCE DESCRIPTION: SEQ ID NO:82:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |
| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |
| Asp | Phe | Ala | Thr | Thr | Ile | Trp | Gln | Gln | Met | Glu | Glu | Leu | Gly | Met | Ala |
| | | 115 | | | | | 120 | | | | | 125 | | | |
| Pro | Ala | Leu | Gln | Pro | Thr | Gln | Gly | Ala | Met | Pro | Ala | Phe | Ala | Ser | Ala |
| | 130 | | | | | 135 | | | | | 140 | | | | |
| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |
| Phe | Leu | Glu | Val | Ser | Tyr | Val | Leu | Arg | His | Leu | Ala | Gln | Pro | | |
| | | | | 165 | | | | | 170 | | | | 174 | | |

( 2 ) INFORMATION FOR SEQ ID NO:83:

( i ) SEQUENCE CHARACTERISTICS:
( A ) LENGTH: 175 amino acids
( B ) TYPE: amino acid
( D ) TOPOLOGY: linear ( i i ) MOLECULE TYPE: protein ( x i ) SEQUENCE DESCRIPTION: SEQ ID NO:83:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |
| Gln | Glu | Lys | Leu | Cys | Ala | Thr | Tyr | Ala | Leu | Cys | His | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |
| Asp | Phe | Ala | Thr | Thr | Ile | Trp | Gln | Gln | Met | Glu | Glu | Leu | Gly | Met | Ala |
| | | 115 | | | | | 120 | | | | | 125 | | | |
| Pro | Ala | Leu | Gln | Pro | Thr | Gln | Gly | Ala | Met | Pro | Ala | Phe | Ala | Ser | Ala |
| | 130 | | | | | 135 | | | | | 140 | | | | |
| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |
| Phe | Leu | Glu | Val | Ser | Tyr | Arg | Val | Leu | Arg | His | Leu | Ala | Gln | Pro | |

165 170 175

(2) INFORMATION FOR SEQ ID NO:84:

(i) SEQUENCE CHARACTERISTICS:
(A) LENGTH: 175 amino acids
(B) TYPE: amino acid
(D) TOPOLOGY: linear (ii) MOLECULE TYPE: protein (xi) SEQUENCE DESCRIPTION: SEQ ID NO:84:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |
| Gln | Glu | Lys | Leu | Cys | Ala | Thr | Tyr | Lys | Leu | Cys | Lys | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |
| Asp | Phe | Ala | Thr | Thr | Ile | Trp | Gln | Gln | Met | Glu | Glu | Leu | Gly | Met | Ala |
| | | | 115 | | | | | 120 | | | | | 125 | | |
| Pro | Ala | Leu | Gln | Pro | Thr | Gln | Gly | Ala | Met | Pro | Ala | Phe | Ala | Ser | Ala |
| | 130 | | | | | 135 | | | | | 140 | | | | |
| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |
| Phe | Leu | Glu | Val | Ser | Tyr | Arg | Val | Leu | Arg | His | Leu | Ala | Gln | Pro | |
| | | | | 165 | | | | | 170 | | | | | 175 | |

(2) INFORMATION FOR SEQ ID NO:85:

(i) SEQUENCE CHARACTERISTICS:
(A) LENGTH: 175 amino acids
(B) TYPE: amino acid
(D) TOPOLOGY: linear (ii) MOLECULE TYPE: protein (xi) SEQUENCE DESCRIPTION: SEQ ID NO:85:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |
| Gln | Glu | Lys | Leu | Cys | Ala | Thr | Tyr | Lys | Leu | Cys | His | Pro | Glu | Ala | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |

| Asp | Phe | Ala | Thr | Thr | Ile | Trp | Gln | Gln | Met | Glu | Glu | Leu | Gly | Met | Ala |
|-----|-----|-----|-----|-----|-----|-----|-----|-----|-----|-----|-----|-----|-----|-----|-----|
|  |  | 115 |  |  |  |  | 120 |  |  |  |  | 125 |  |  |  |

| Pro | Ala | Leu | Gln | Pro | Thr | Gln | Gly | Ala | Met | Pro | Ala | Phe | Ala | Ser | Ala |
|-----|-----|-----|-----|-----|-----|-----|-----|-----|-----|-----|-----|-----|-----|-----|-----|
|  | 130 |  |  |  |  | 135 |  |  |  |  | 140 |  |  |  |  |

| Phe | Gln | Arg | Arg | Ala | Gly | Gly | Val | Leu | Val | Ala | Ser | His | Leu | Gln | Ser |
|-----|-----|-----|-----|-----|-----|-----|-----|-----|-----|-----|-----|-----|-----|-----|-----|
| 145 |  |  |  |  | 150 |  |  |  |  | 155 |  |  |  |  | 160 |

| Phe | Leu | Glu | Val | Ser | Tyr | Arg | Val | Leu | Arg | His | Leu | Ala | Gln | Pro |
|-----|-----|-----|-----|-----|-----|-----|-----|-----|-----|-----|-----|-----|-----|-----|
|  |  |  |  | 165 |  |  |  |  | 170 |  |  |  |  | 175 |

( 2 ) INFORMATION FOR SEQ ID NO:86:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:86:

| Met | Thr | Pro | Leu | Gly | Pro | Ala | Ser | Ser | Leu | Pro | Gln | Ser | Phe | Leu | Leu |
|-----|-----|-----|-----|-----|-----|-----|-----|-----|-----|-----|-----|-----|-----|-----|-----|
| 1 |  |  |  | 5 |  |  |  |  | 10 |  |  |  |  | 15 |  |

| Lys | Cys | Leu | Glu | Gln | Val | Ala | Lys | Ile | Gln | Gly | Asp | Gly | Ala | Ala | Leu |
|-----|-----|-----|-----|-----|-----|-----|-----|-----|-----|-----|-----|-----|-----|-----|-----|
|  |  |  | 20 |  |  |  |  | 25 |  |  |  |  | 30 |  |  |

| Gln | Glu | Lys | Leu | Cys | Ala | Thr | Tyr | Lys | Leu | Cys | His | Pro | Glu | Glu | Leu |
|-----|-----|-----|-----|-----|-----|-----|-----|-----|-----|-----|-----|-----|-----|-----|-----|
|  |  | 35 |  |  |  |  | 40 |  |  |  |  | 45 |  |  |  |

| Val | Leu | Leu | Gly | His | Ser | Leu | Gly | Ile | Pro | Trp | Ala | Pro | Leu | Ser | Ser |
|-----|-----|-----|-----|-----|-----|-----|-----|-----|-----|-----|-----|-----|-----|-----|-----|
|  | 50 |  |  |  |  | 55 |  |  |  |  | 60 |  |  |  |  |

| Cys | Pro | Ser | Gln | Ala | Leu | Gln | Leu | Ala | Gly | Cys | Leu | Ser | Gln | Leu | His |
|-----|-----|-----|-----|-----|-----|-----|-----|-----|-----|-----|-----|-----|-----|-----|-----|
| 65 |  |  |  |  | 70 |  |  |  |  | 75 |  |  |  |  | 80 |

| Ser | Gly | Leu | Phe | Leu | Tyr | Gln | Gly | Leu | Leu | Gln | Ala | Leu | Glu | Gly | Ile |
|-----|-----|-----|-----|-----|-----|-----|-----|-----|-----|-----|-----|-----|-----|-----|-----|
|  |  |  |  | 85 |  |  |  |  | 90 |  |  |  |  | 95 |  |

| Ser | Pro | Glu | Leu | Gly | Pro | Thr | Leu | Asp | Thr | Leu | Gln | Leu | Asp | Val | Ala |
|-----|-----|-----|-----|-----|-----|-----|-----|-----|-----|-----|-----|-----|-----|-----|-----|
|  |  |  |  | 100 |  |  |  |  | 105 |  |  |  |  | 110 |  |

| Asp | Phe | Ala | Thr | Thr | Ile | Trp | Gln | Gln | Met | Glu | Glu | Leu | Gly | Met | Ala |
|-----|-----|-----|-----|-----|-----|-----|-----|-----|-----|-----|-----|-----|-----|-----|-----|
|  |  | 115 |  |  |  |  | 120 |  |  |  |  | 125 |  |  |  |

| Pro | Ala | Leu | Gln | Pro | Thr | Gln | Gly | Ala | Met | Pro | Ala | Phe | Ala | Ser | Ala |
|-----|-----|-----|-----|-----|-----|-----|-----|-----|-----|-----|-----|-----|-----|-----|-----|
|  | 130 |  |  |  |  | 135 |  |  |  |  | 140 |  |  |  |  |

| Phe | Gln | Arg | Arg | Ala | Gly | Gly | Val | Leu | Val | Ala | Ser | His | Leu | Gln | Ser |
|-----|-----|-----|-----|-----|-----|-----|-----|-----|-----|-----|-----|-----|-----|-----|-----|
| 145 |  |  |  |  | 150 |  |  |  |  | 155 |  |  |  |  | 160 |

| Phe | Leu | Glu | Val | Ser | Tyr | Arg | Val | Leu | Arg | His | Leu | Ala | Gln | Pro |
|-----|-----|-----|-----|-----|-----|-----|-----|-----|-----|-----|-----|-----|-----|-----|
|  |  |  |  | 165 |  |  |  |  | 170 |  |  |  |  | 175 |

( 2 ) INFORMATION FOR SEQ ID NO:87:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:87:

| Met | Thr | Pro | Leu | Gly | Pro | Ala | Ser | Ser | Leu | Pro | Gln | Ser | Phe | Leu | Leu |
|-----|-----|-----|-----|-----|-----|-----|-----|-----|-----|-----|-----|-----|-----|-----|-----|
| 1 |  |  |  | 5 |  |  |  |  | 10 |  |  |  |  | 15 |  |

| Lys | Cys | Leu | Glu | Gln | Val | Arg | Ala | Ile | Gln | Gly | Asp | Gly | Ala | Ala | Leu |
|-----|-----|-----|-----|-----|-----|-----|-----|-----|-----|-----|-----|-----|-----|-----|-----|
|  |  |  | 20 |  |  |  |  | 25 |  |  |  |  | 30 |  |  |

| Gln | Glu | Lys | Leu | Cys | Ala | Thr | Tyr | Lys | Leu | Cys | His | Pro | Glu | Glu | Leu |
|-----|-----|-----|-----|-----|-----|-----|-----|-----|-----|-----|-----|-----|-----|-----|-----|
|  |  | 35 |  |  |  |  | 40 |  |  |  |  | 45 |  |  |  |

| Val | Leu | Leu | Gly | His | Ser | Leu | Gly | Ile | Pro | Trp | Ala | Pro | Leu | Ser | Ser |
|-----|-----|-----|-----|-----|-----|-----|-----|-----|-----|-----|-----|-----|-----|-----|-----|
|  | 50 |  |  |  |  | 55 |  |  |  |  | 60 |  |  |  |  |

| Cys | Pro | Ser | Gln | Ala | Leu | Gln | Leu | Ala | Gly | Cys | Leu | Ser | Gln | Leu | His |
| 65 | | | | 70 | | | | | 75 | | | | | | 80 |

| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |

| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |

| Asp | Phe | Ala | Thr | Thr | Ile | Trp | Gln | Gln | Met | Glu | Glu | Leu | Gly | Met | Ala |
| | | 115 | | | | | 120 | | | | | 125 | | | |

| Pro | Ala | Leu | Gln | Pro | Thr | Gln | Gly | Ala | Met | Pro | Ala | Phe | Ala | Ser | Ala |
| | 130 | | | | | 135 | | | | 140 | | | | | |

| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |

| Phe | Leu | Glu | Val | Ser | Tyr | Arg | Val | Leu | Arg | His | Leu | Ala | Gln | Pro | |
| | | | | 165 | | | | | 170 | | | | | 175 | |

( 2 ) INFORMATION FOR SEQ ID NO:88:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:88:

| Met | Thr | Pro | Leu | Gly | Pro | Ala | Ser | Ser | Leu | Pro | Gln | Ser | Phe | Leu | Leu |
| 1 | | | | 5 | | | | | 10 | | | | | 15 | |

| Lys | Cys | Leu | Ala | Gln | Val | Arg | Lys | Ile | Gln | Gly | Asp | Gly | Ala | Ala | Leu |
| | | | 20 | | | | | 25 | | | | | 30 | | |

| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |

| Val | Leu | Leu | Gly | His | Ser | Leu | Gly | Ile | Pro | Trp | Ala | Pro | Leu | Ser | Ser |
| | 50 | | | | | 55 | | | | | 60 | | | | |

| Cys | Pro | Ser | Gln | Ala | Leu | Gln | Leu | Ala | Gly | Cys | Leu | Ser | Gln | Leu | His |
| 65 | | | | 70 | | | | | 75 | | | | | | 80 |

| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |

| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |

| Asp | Phe | Ala | Thr | Thr | Ile | Trp | Gln | Gln | Met | Glu | Glu | Leu | Gly | Met | Ala |
| | | 115 | | | | | 120 | | | | | 125 | | | |

| Pro | Ala | Leu | Gln | Pro | Thr | Gln | Gly | Ala | Met | Pro | Ala | Phe | Ala | Ser | Ala |
| | 130 | | | | | 135 | | | | 140 | | | | | |

| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |

| Phe | Leu | Glu | Val | Ser | Tyr | Arg | Val | Leu | Arg | His | Leu | Ala | Gln | Pro | |
| | | | | 165 | | | | | 170 | | | | | 175 | |

( 2 ) INFORMATION FOR SEQ ID NO:89:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:89:

| Met | Thr | Pro | Leu | Gly | Pro | Ala | Ser | Ser | Leu | Pro | Gln | Ser | Phe | Leu | Leu |

|   | 1 |   |   |   | 5 |   |   |   |   | 10 |   |   |   |   | 15 |
|---|---|---|---|---|---|---|---|---|---|---|---|---|---|---|---|

Lys Cys Leu Glu Gln Val Arg Lys Ile Gln Gly Ala Gly Ala Ala Leu
        20                      25                  30

Gln Glu Lys Leu Cys Ala Thr Tyr Lys Leu Cys His Pro Glu Glu Leu
        35                      40                  45

Val Leu Leu Gly His Ser Leu Gly Ile Pro Trp Ala Pro Leu Ser Ser
    50                      55                  60

Cys Pro Ser Gln Ala Leu Gln Leu Ala Gly Cys Leu Ser Gln Leu His
65                      70                  75                  80

Ser Gly Leu Phe Leu Tyr Gln Gly Leu Leu Gln Ala Leu Glu Gly Ile
            85                      90                  95

Ser Pro Glu Leu Gly Pro Thr Leu Asp Thr Leu Gln Leu Asp Val Ala
            100                     105                 110

Asp Phe Ala Thr Thr Ile Trp Gln Gln Met Glu Glu Leu Gly Met Ala
            115                     120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                     150                 155                 160

Phe Leu Glu Val Ser Tyr Arg Val Leu Arg His Leu Ala Gln Pro
                165                     170                 175

(2) INFORMATION FOR SEQ ID NO:90:

(i) SEQUENCE CHARACTERISTICS:
    (A) LENGTH: 175 amino acids
    (B) TYPE: amino acid
    (D) TOPOLOGY: linear (ii) MOLECULE TYPE: protein (xi) SEQUENCE DESCRIPTION: SEQ ID NO:90:

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
        20                      25                  30

Gln Glu Lys Leu Cys Ala Thr Tyr Lys Leu Cys His Pro Glu Glu Leu
        35                      40                  45

Val Leu Leu Gly His Ser Leu Gly Ile Pro Trp Ala Pro Leu Ser Ser
    50                      55                  60

Cys Pro Ser Gln Ala Leu Gln Leu Ala Gly Cys Leu Ser Gln Leu His
65                      70                  75                  80

Ser Gly Leu Phe Leu Tyr Gln Gly Leu Leu Gln Ala Leu Glu Gly Ile
            85                      90                  95

Ser Pro Glu Leu Gly Pro Thr Leu Asp Thr Leu Gln Leu Asp Val Ala
            100                     105                 110

Asp Phe Ala Thr Thr Ile Trp Gln Gln Met Glu Glu Leu Gly Glu Ala
            115                     120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                     150                 155                 160

Phe Leu Glu Val Ser Tyr Arg Val Leu Arg His Leu Ala Gln Pro
                165                     170                 175

(2) INFORMATION FOR SEQ ID NO:91:

( i ) SEQUENCE CHARACTERISTICS:
    ( A ) LENGTH: 175 amino acids
    ( B ) TYPE: amino acid
    ( D ) TOPOLOGY: linear ( i i ) MOLECULE TYPE: protein ( x i ) SEQUENCE DESCRIPTION: SEQ ID NO:91:

```
Met Thr Pro Leu Gly Pro Ala Ser Ser Leu Pro Gln Ser Phe Leu Leu
 1               5                  10                  15
Lys Cys Leu Glu Gln Val Arg Lys Ile Gln Gly Asp Gly Ala Ala Leu
            20                  25                  30
Gln Glu Lys Leu Cys Ala Thr Tyr Lys Leu Cys His Pro Glu Glu Leu
        35                  40                  45
Val Leu Leu Gly His Ser Leu Gly Ile Pro Trp Ala Pro Leu Ser Ser
    50                  55                  60
Cys Pro Ser Gln Ala Leu Gln Leu Ala Gly Cys Leu Ser Gln Leu His
 65                  70                  75                  80
Ser Gly Leu Phe Leu Tyr Gln Gly Leu Leu Gln Ala Leu Glu Gly Ile
                    85                  90                  95
Ser Pro Glu Leu Gly Pro Thr Leu Asp Thr Leu Gln Leu Asp Val Ala
            100                 105                 110
Asp Phe Ala Thr Thr Ile Trp Gln Gln Met Glu Glu Leu Gly Met Ala
            115                 120                 125
Pro Ala Leu Gln Pro Thr Gln Gly Ala Glu Pro Ala Phe Ala Ser Ala
130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175
```

( 2 ) INFORMATION FOR SEQ ID NO:92:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:92:

```
Met Thr Pro Leu Gly Pro Ala Ser Ser Leu Pro Gln Ser Phe Leu Leu
 1               5                  10                  15
Lys Cys Leu Glu Gln Val Arg Lys Ile Gln Gly Asp Gly Ala Ala Leu
            20                  25                  30
Gln Glu Lys Leu Cys Ala Thr Tyr Lys Leu Cys His Pro Glu Glu Leu
        35                  40                  45
Val Leu Leu Gly His Ser Leu Gly Ile Pro Trp Ala Pro Leu Ser Ser
    50                  55                  60
Cys Pro Ser Gln Ala Leu Gln Leu Ala Gly Cys Leu Ser Gln Leu His
 65                  70                  75                  80
Ser Gly Leu Phe Leu Tyr Gln Gly Leu Leu Gln Ala Leu Glu Gly Ile
                    85                  90                  95
Ser Pro Glu Leu Gly Pro Thr Leu Asp Thr Leu Gln Leu Asp Val Ala
            100                 105                 110
Asp Phe Ala Thr Thr Ile Trp Gln Gln Met Glu Glu Leu Gly Leu Ala
            115                 120                 125
Pro Ala Leu Gln Pro Thr Gln Gly Ala Met Pro Ala Phe Ala Ser Ala
130                 135                 140
```

| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |

| Phe | Leu | Glu | Val | Ser | Tyr | Arg | Val | Leu | Arg | His | Leu | Ala | Gln | Pro |
| | | | | 165 | | | | | 170 | | | | | 175 |

(2) INFORMATION FOR SEQ ID NO:93:

(i) SEQUENCE CHARACTERISTICS:
  (A) LENGTH: 175 amino acids
  (B) TYPE: amino acid
  (D) TOPOLOGY: linear (ii) MOLECULE TYPE: protein (xi) SEQUENCE DESCRIPTION: SEQ ID NO:93:

| Met | Thr | Pro | Leu | Gly | Pro | Ala | Ser | Ser | Leu | Pro | Gln | Ser | Phe | Leu | Leu |
| 1 | | | | 5 | | | | | 10 | | | | | 15 | |

| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |

| Gln | Glu | Lys | Leu | Cys | Ala | Thr | Tyr | Lys | Leu | Cys | His | Pro | Glu | Glu | Leu |
| | | | 35 | | | | | 40 | | | | | 45 | | |

| Val | Leu | Leu | Gly | His | Ser | Leu | Gly | Ile | Pro | Trp | Ala | Pro | Leu | Ser | Ser |
| | | | 50 | | | | | 55 | | | | | 60 | | |

| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |

| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |

| Ser | Pro | Glu | Leu | Gly | Pro | Thr | Leu | Asp | Thr | Leu | Gln | Leu | Asp | Val | Ala |
| | | | | 100 | | | | | 105 | | | | | 110 | |

| Asp | Phe | Ala | Thr | Thr | Ile | Trp | Gln | Gln | Met | Glu | Glu | Leu | Gly | Met | Ala |
| | | | 115 | | | | | 120 | | | | | 125 | | |

| Pro | Ala | Leu | Gln | Pro | Thr | Gln | Gly | Ala | Leu | Pro | Ala | Phe | Ala | Ser | Ala |
| | | 130 | | | | | 135 | | | | | 140 | | | |

| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |

| Phe | Leu | Glu | Val | Ser | Tyr | Arg | Val | Leu | Arg | His | Leu | Ala | Gln | Pro |
| | | | | 165 | | | | | 170 | | | | | 175 |

(2) INFORMATION FOR SEQ ID NO:94:

(i) SEQUENCE CHARACTERISTICS:
  (A) LENGTH: 175 amino acids
  (B) TYPE: amino acid
  (D) TOPOLOGY: linear (ii) MOLECULE TYPE: protein (xi) SEQUENCE DESCRIPTION: SEQ ID NO:94:

| Met | Thr | Pro | Leu | Gly | Pro | Ala | Ser | Ser | Leu | Pro | Gln | Ser | Phe | Leu | Leu |
| 1 | | | | 5 | | | | | 10 | | | | | 15 | |

| Lys | Ala | Leu | Glu | Gln | Val | Arg | Lys | Ile | Gln | Gly | Asp | Gly | Ala | Ala | Leu |
| | | | 20 | | | | | 25 | | | | | 30 | | |

| Gln | Glu | Lys | Leu | Cys | Ala | Thr | Tyr | Lys | Leu | Cys | His | Pro | Glu | Glu | Leu |
| | | | 35 | | | | | 40 | | | | | 45 | | |

| Val | Leu | Leu | Gly | His | Ser | Leu | Gly | Ile | Pro | Trp | Ala | Pro | Leu | Ser | Ser |
| | | | 50 | | | | | 55 | | | | | 60 | | |

| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |

| Ser | Gly | Leu | Phe | Leu | Tyr | Gln | Gly | Leu | Leu | Gln | Ala | Leu | Glu | Gly | Ile |

|   |   |   | 85 |   |   |   |   | 90 |   |   |   |   | 95 |   |
|---|---|---|---|---|---|---|---|---|---|---|---|---|---|---|

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
        130             135                 140

Phe Gln Arg Arg Ala Gly Gly Val Leu Val Ala Ser His Leu Gln Ser
145                 150                 155                     160

Phe Leu Glu Val Ser Tyr Arg Val Leu Arg His Leu Ala Gln Pro
                165                 170                 175

(2) INFORMATION FOR SEQ ID NO:95:

(i) SEQUENCE CHARACTERISTICS:
      (A) LENGTH: 175 amino acids
      (B) TYPE: amino acid
      (D) TOPOLOGY: linear (ii) MOLECULE TYPE: protein (xi) SEQUENCE DESCRIPTION: SEQ ID NO:95:

Met Thr Pro Leu Gly Pro Ala Ser Ser Leu Pro Glu Ser Phe Leu Leu
1               5                   10                  15

Lys Cys Leu Glu Glu Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
        130             135                 140

Phe Gln Arg Arg Ala Gly Gly Val Leu Val Ala Ser His Leu Gln Ser
145                 150                 155                     160

Phe Leu Glu Val Ser Tyr Arg Val Leu Arg His Leu Ala Gln Pro
                165                 170                 175

(2) INFORMATION FOR SEQ ID NO:96:

(i) SEQUENCE CHARACTERISTICS:
      (A) LENGTH: 175 amino acids
      (B) TYPE: amino acid
      (D) TOPOLOGY: linear (ii) MOLECULE TYPE: protein (xi) SEQUENCE DESCRIPTION: SEQ ID NO:96:

Met Thr Pro Leu Gly Pro Ala Ser Ser Leu Pro Glu Ser Phe Leu Leu
1               5                   10                  15

Lys Cys Leu Glu Glu Val Arg Lys Ile Gln Gly Asp Gly Ala Ala Leu
            20                  25                  30

```
Gln  Glu  Lys  Leu  Cys  Ala  Thr  Tyr  Lys  Leu  Cys  His  Pro  Glu  Glu  Leu
          35                       40                      45

Val  Leu  Leu  Gly  His  Ser  Leu  Gly  Ile  Pro  Trp  Ala  Pro  Leu  Ser  Ser
     50                       55                      60

Cys  Pro  Ser  Glu  Ala  Leu  Gln  Leu  Ala  Gly  Cys  Leu  Ser  Gln  Leu  His
65                       70                      75                            80

Ser  Gly  Leu  Phe  Leu  Tyr  Gln  Gly  Leu  Leu  Gln  Ala  Leu  Glu  Gly  Ile
                    85                       90                           95

Ser  Pro  Glu  Leu  Gly  Pro  Thr  Leu  Asp  Thr  Leu  Gln  Leu  Asp  Val  Ala
               100                      105                     110

Asp  Phe  Ala  Thr  Thr  Ile  Trp  Gln  Gln  Met  Glu  Glu  Leu  Gly  Met  Ala
               115                      120                     125

Pro  Ala  Leu  Gln  Pro  Thr  Gln  Gly  Ala  Met  Pro  Ala  Phe  Ala  Ser  Ala
     130                      135                     140

Phe  Gln  Arg  Arg  Ala  Gly  Gly  Val  Leu  Val  Ala  Ser  His  Leu  Gln  Ser
145                      150                     155                           160

Phe  Leu  Glu  Val  Ser  Tyr  Arg  Val  Leu  Arg  His  Leu  Ala  Gln  Pro
                    165                      170                     175
```

(2) INFORMATION FOR SEQ ID NO:97:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO:97:

```
Met  Thr  Pro  Leu  Gly  Pro  Ala  Ser  Ser  Leu  Pro  Gln  Gly  Phe  Leu  Leu
1                    5                       10                          15

Lys  Cys  Leu  Ala  Gln  Val  Arg  Lys  Ile  Gln  Gly  Asp  Gly  Ala  Ala  Leu
               20                       25                      30

Gln  Glu  Lys  Leu  Cys  Ala  Thr  Tyr  Lys  Leu  Cys  His  Pro  Glu  Glu  Leu
          35                       40                      45

Val  Leu  Leu  Gly  His  Ser  Leu  Gly  Ile  Pro  Trp  Ala  Pro  Leu  Ser  Ser
     50                       55                      60

Cys  Pro  Ser  Gln  Ala  Leu  Gln  Leu  Ala  Gly  Cys  Leu  Ser  Gln  Leu  His
65                       70                      75                            80

Ser  Gly  Leu  Phe  Leu  Tyr  Gln  Gly  Leu  Leu  Gln  Ala  Leu  Glu  Gly  Ile
                    85                       90                           95

Ser  Pro  Glu  Leu  Gly  Pro  Thr  Leu  Asp  Thr  Leu  Gln  Leu  Asp  Val  Ala
               100                      105                     110

Asp  Phe  Ala  Thr  Thr  Ile  Trp  Gln  Gln  Met  Glu  Glu  Leu  Gly  Met  Ala
               115                      120                     125

Pro  Ala  Leu  Gln  Pro  Thr  Gln  Gly  Ala  Met  Pro  Ala  Phe  Ala  Ser  Ala
     130                      135                     140

Phe  Gln  Arg  Arg  Ala  Gly  Gly  Val  Leu  Val  Ala  Ser  His  Leu  Gln  Ser
145                      150                     155                           160

Phe  Leu  Glu  Val  Ser  Tyr  Arg  Val  Leu  Arg  His  Leu  Ala  Gln  Pro
                    165                      170                     175
```

(2) INFORMATION FOR SEQ ID NO:98:

(i) SEQUENCE CHARACTERISTICS:
        (A) LENGTH: 175 amino acids
        (B) TYPE: amino acid
        (D) TOPOLOGY: linear ( i i ) MOLECULE TYPE: protein ( x i ) SEQUENCE DESCRIPTION: SEQ ID NO:98:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |
| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |
| Asp | Phe | Ala | Thr | Thr | Ile | Trp | Gln | Gln | Met | Glu | Glu | Leu | Gly | Leu | Ala |
| | | | 115 | | | | | 120 | | | | | 125 | | |
| Pro | Ala | Leu | Gln | Pro | Thr | Gln | Gly | Ala | Leu | Pro | Ala | Phe | Ala | Ser | Ala |
| | | 130 | | | | | 135 | | | | | 140 | | | |
| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |
| Phe | Leu | Glu | Val | Ser | Tyr | Arg | Val | Leu | Arg | His | Leu | Ala | Gln | Pro | |
| | | | | 165 | | | | | 170 | | | | | 175 | |

( 2 ) INFORMATION FOR SEQ ID NO:99:

( i ) SEQUENCE CHARACTERISTICS:
( A ) LENGTH: 175 amino acids
( B ) TYPE: amino acid
( D ) TOPOLOGY: linear ( i i ) MOLECULE TYPE: protein ( x i ) SEQUENCE DESCRIPTION: SEQ ID NO:99:

| Met | Thr | Pro | Leu | Gly | Pro | Ala | Ser | Ser | Leu | Pro | Gln | Ala | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |
| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |
| Asp | Phe | Ala | Thr | Thr | Ile | Trp | Gln | Gln | Met | Glu | Glu | Leu | Gly | Met | Ala |
| | | | 115 | | | | | 120 | | | | | 125 | | |
| Pro | Ala | Leu | Gln | Pro | Thr | Gln | Gly | Ala | Met | Pro | Ala | Phe | Ala | Ser | Ala |
| | | 130 | | | | | 135 | | | | | 140 | | | |
| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |
| Phe | Leu | Glu | Val | Ser | Tyr | Arg | Val | Leu | Arg | His | Leu | Ala | Gln | Pro | |

165 170 175

(2) INFORMATION FOR SEQ ID NO:100:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO:100:

```
Met Thr Pro Leu Gly Pro Ala Ser Ser Leu Pro Gln Ser Phe Leu Leu
 1               5                  10                  15
Ala Cys Leu Glu Gln Val Arg Lys Ile Gln Gly Asp Gly Ala Ala Leu
            20                  25                  30
Gln Glu Lys Leu Cys Ala Thr Tyr Lys Leu Cys His Pro Glu Glu Leu
        35                  40                  45
Val Leu Leu Gly His Ser Leu Gly Ile Pro Trp Ala Pro Leu Ser Ser
    50                  55                  60
Cys Pro Ser Gln Ala Leu Gln Leu Ala Gly Cys Leu Ser Gln Leu His
 65                 70                  75                  80
Ser Gly Leu Phe Leu Tyr Gln Gly Leu Leu Gln Ala Leu Glu Gly Ile
                85                  90                  95
Ser Pro Glu Leu Gly Pro Thr Leu Asp Thr Leu Gln Leu Asp Val Ala
            100                 105                 110
Asp Phe Ala Thr Thr Ile Trp Gln Gln Met Glu Glu Leu Gly Met Ala
            115                 120                 125
Pro Ala Leu Gln Pro Thr Gln Gly Ala Met Pro Ala Phe Ala Ser Ala
    130                 135                 140
Phe Gln Arg Arg Ala Gly Gly Val Leu Val Ala Ser His Leu Gln Ser
145                 150                 155                 160
Phe Leu Glu Val Ser Tyr Arg Val Leu Arg His Leu Ala Gln Pro
                165                 170                 175
```

(2) INFORMATION FOR SEQ ID NO:101:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO:101:

```
Met Thr Pro Leu Gly Pro Ala Ser Ser Leu Pro Gln Ser Phe Leu Leu
 1               5                  10                  15
Lys Cys Leu Glu Gln Val Arg Lys Ile Gln Gly Asp Gly Ala Ala Leu
            20                  25                  30
Gln Glu Lys Leu Cys Ala Thr Tyr Lys Leu Cys His Pro Glu Glu Leu
        35                  40                  45
Val Leu Leu Gly His Ser Leu Gly Ile Pro Trp Ala Pro Leu Ser Ser
    50                  55                  60
Cys Pro Ser Gln Ala Leu Gln Leu Ala Gly Cys Leu Ser Gln Leu His
 65                 70                  75                  80
Ser Gly Leu Phe Leu Tyr Gln Gly Leu Leu Gln Ala Leu Glu Gly Ile
                85                  90                  95
Ser Pro Glu Leu Gly Pro Thr Leu Asp Thr Leu Gln Leu Asp Val Ala
            100                 105                 110
```

5,581,476

-continued

| Asp | Phe | Ala | Thr | Thr | Ile | Trp | Gln | Ala | Met | Glu | Glu | Leu | Gly | Met | Ala |
| | | 115 | | | | | 120 | | | | | 125 | | | |

| Pro | Ala | Leu | Gln | Pro | Thr | Gln | Gly | Ala | Met | Pro | Ala | Phe | Ala | Ser | Ala |
| | | 130 | | | | 135 | | | | | 140 | | | | |

| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |

| Phe | Leu | Glu | Val | Ser | Tyr | Arg | Val | Leu | Arg | His | Leu | Ala | Gln | Pro |
| | | | | 165 | | | | | 170 | | | | | 175 |

( 2 ) INFORMATION FOR SEQ ID NO:102:

( i ) SEQUENCE CHARACTERISTICS:
    ( A ) LENGTH: 175 amino acids
    ( B ) TYPE: amino acid
    ( D ) TOPOLOGY: linear ( i i ) MOLECULE TYPE: protein ( x i ) SEQUENCE DESCRIPTION: SEQ ID NO:102:

| Met | Thr | Pro | Leu | Gly | Pro | Ala | Ser | Ser | Leu | Pro | Gln | Ser | Phe | Leu | Leu |
| 1 | | | | 5 | | | | | 10 | | | | | 15 | |

| Lys | Cys | Leu | Glu | Ala | Val | Arg | Lys | Ile | Gln | Gly | Asp | Gly | Ala | Ala | Leu |
| | | | 20 | | | | | 25 | | | | | 30 | | |

| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |

| Val | Leu | Leu | Gly | His | Ser | Leu | Gly | Ile | Pro | Trp | Ala | Pro | Leu | Ser | Ser |
| | 50 | | | | | 55 | | | | | 60 | | | | |

| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |

| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |

| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |

| Asp | Phe | Ala | Thr | Thr | Ile | Trp | Gln | Gln | Met | Glu | Glu | Leu | Gly | Met | Ala |
| | | 115 | | | | | 120 | | | | | 125 | | | |

| Pro | Ala | Leu | Gln | Pro | Thr | Gln | Gly | Ala | Met | Pro | Ala | Phe | Ala | Ser | Ala |
| | | 130 | | | | 135 | | | | | 140 | | | | |

| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |

| Phe | Leu | Glu | Val | Ser | Tyr | Arg | Val | Leu | Arg | His | Leu | Ala | Gln | Pro |
| | | | | 165 | | | | | 170 | | | | | 175 |

( 2 ) INFORMATION FOR SEQ ID NO:103:

( i ) SEQUENCE CHARACTERISTICS:
    ( A ) LENGTH: 175 amino acids
    ( B ) TYPE: amino acid
    ( D ) TOPOLOGY: linear ( i i ) MOLECULE TYPE: protein ( x i ) SEQUENCE DESCRIPTION: SEQ ID NO:103:

| Met | Thr | Pro | Leu | Gly | Pro | Ala | Ser | Ser | Leu | Pro | Gln | Ser | Phe | Leu | Leu |
| 1 | | | | 5 | | | | | 10 | | | | | 15 | |

| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |

| Gln | Glu | Lys | Leu | Cys | Ala | Thr | Tyr | Lys | Leu | Cys | Ala | Pro | Glu | Glu | Leu |
| | | 35 | | | | | 40 | | | | | 45 | | | |

| Val | Leu | Leu | Gly | His | Ser | Leu | Gly | Ile | Pro | Trp | Ala | Pro | Leu | Ser | Ser |
| | 50 | | | | | 55 | | | | | 60 | | | | |

| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |

| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |

| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |

| Asp | Phe | Ala | Thr | Thr | Ile | Trp | Gln | Gln | Met | Glu | Glu | Leu | Gly | Met | Ala |
| | | | 115 | | | | | 120 | | | | | 125 | | |

| Pro | Ala | Leu | Gln | Pro | Thr | Gln | Gly | Ala | Met | Pro | Ala | Phe | Ala | Ser | Ala |
| | | 130 | | | | | 135 | | | | | 140 | | | |

| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |

| Phe | Leu | Glu | Val | Ser | Tyr | Arg | Val | Leu | Arg | His | Leu | Ala | Gln | Pro | |
| | | | | 165 | | | | | 170 | | | | | 175 | |

( 2 ) INFORMATION FOR SEQ ID NO:104:

( i ) SEQUENCE CHARACTERISTICS:
    ( A ) LENGTH: 175 amino acids
    ( B ) TYPE: amino acid
    ( D ) TOPOLOGY: linear ( i i ) MOLECULE TYPE: protein ( x i ) SEQUENCE DESCRIPTION: SEQ ID NO:104:

| Met | Thr | Pro | Leu | Gly | Pro | Ala | Ser | Ser | Leu | Pro | Gln | Ser | Phe | Leu | Leu |
| 1 | | | | 5 | | | | | 10 | | | | | 15 | |

| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |

| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |

| Val | Leu | Leu | Gly | Ala | Ser | Leu | Gly | Ile | Pro | Trp | Ala | Pro | Leu | Ser | Ser |
| | 50 | | | | | 55 | | | | | 60 | | | | |

| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |

| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |

| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |

| Asp | Phe | Ala | Thr | Thr | Ile | Trp | Gln | Gln | Met | Glu | Glu | Leu | Gly | Met | Ala |
| | | | 115 | | | | | 120 | | | | | 125 | | |

| Pro | Ala | Leu | Gln | Pro | Thr | Gln | Gly | Ala | Met | Pro | Ala | Phe | Ala | Ser | Ala |
| | | 130 | | | | | 135 | | | | | 140 | | | |

| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |

| Phe | Leu | Glu | Val | Ser | Tyr | Arg | Val | Leu | Arg | His | Leu | Ala | Gln | Pro | |
| | | | | 165 | | | | | 170 | | | | | 175 | |

( 2 ) INFORMATION FOR SEQ ID NO:105:

( i ) SEQUENCE CHARACTERISTICS:
    ( A ) LENGTH: 175 amino acids
    ( B ) TYPE: amino acid
    ( D ) TOPOLOGY: linear ( i i ) MOLECULE TYPE: protein ( x i ) SEQUENCE DESCRIPTION: SEQ ID NO:105:

| Met | Thr | Pro | Leu | Gly | Pro | Ala | Ser | Ser | Leu | Pro | Gln | Ser | Phe | Leu | Leu |

|  | 1 |  |  |  | 5 |  |  |  |  | 10 |  |  |  |  | 15 |  |
|---|---|---|---|---|---|---|---|---|---|---|---|---|---|---|---|---|
| Lys | Cys | Leu | Glu 20 | Gln | Val | Arg | Lys | Ile | Gln 25 | Gly | Asp | Gly | Ala 30 | Ala | Leu |
| Gln | Glu | Lys 35 | Leu | Cys | Ala | Thr | Tyr 40 | Lys | Leu | Cys | His | Pro 45 | Glu | Glu | Leu |
| Val | Leu 50 | Leu | Gly | His | Ser | Leu 55 | Gly | Ile | Pro | Trp | Ala 60 | Pro | Leu | Ser | Ser |
| Cys 65 | Pro | Ser | Gln | Ala | Leu 70 | Gln | Leu | Ala | Gly | Cys 75 | Leu | Ser | Gln | Leu | His 80 |
| Ser | Gly | Leu | Phe | Leu 85 | Tyr | Gln | Gly | Leu | Leu 90 | Gln | Ala | Leu | Glu | Gly 95 | Ile |
| Ser | Pro | Glu | Leu 100 | Gly | Pro | Thr | Leu | Asp 105 | Thr | Leu | Gln | Leu | Ala 110 | Val | Ala |
| Asp | Phe | Ala 115 | Thr | Thr | Ile | Trp | Gln 120 | Gln | Met | Glu | Glu | Leu 125 | Gly | Met | Ala |
| Pro | Ala 130 | Leu | Gln | Pro | Thr | Gln 135 | Gly | Ala | Met | Pro | Ala 140 | Phe | Ala | Ser | Ala |
| Phe 145 | Gln | Arg | Arg | Ala | Gly 150 | Gly | Val | Leu | Val | Ala 155 | Ser | His | Leu | Gln | Ser 160 |
| Phe | Leu | Glu | Val | Ser 165 | Tyr | Arg | Val | Leu | Arg 170 | His | Leu | Ala | Gln | Pro 175 |  |

( 2 ) INFORMATION FOR SEQ ID NO:106:

( i ) SEQUENCE CHARACTERISTICS:
( A ) LENGTH: 175 amino acids
( B ) TYPE: amino acid
( D ) TOPOLOGY: linear ( i i ) MOLECULE TYPE: protein ( x i ) SEQUENCE DESCRIPTION: SEQ ID NO:106:

| Met 1 | Thr | Pro | Leu | Gly 5 | Pro | Ala | Ser | Ser | Leu 10 | Pro | Gln | Ser | Phe | Leu 15 | Leu |
|---|---|---|---|---|---|---|---|---|---|---|---|---|---|---|---|
| Lys | Cys | Leu | Glu 20 | Gln | Val | Arg | Lys | Ile | Gln 25 | Gly | Asp | Gly | Ala 30 | Ala | Leu |
| Gln | Glu | Lys 35 | Leu | Cys | Ala | Thr | Tyr 40 | Lys | Leu | Cys | His | Pro 45 | Glu | Glu | Leu |
| Val | Leu 50 | Leu | Gly | His | Ser | Leu 55 | Gly | Ile | Pro | Trp | Ala 60 | Pro | Leu | Ser | Ser |
| Cys 65 | Pro | Ser | Gln | Ala | Leu 70 | Gln | Leu | Ala | Gly | Cys 75 | Leu | Ser | Gln | Leu | His 80 |
| Ser | Gly | Leu | Phe | Leu 85 | Tyr | Gln | Gly | Leu | Leu 90 | Gln | Ala | Leu | Glu | Gly 95 | Ile |
| Ser | Pro | Glu | Leu 100 | Gly | Pro | Thr | Leu | Asp 105 | Thr | Leu | Gln | Leu | Asp 110 | Val | Ala |
| Ala | Phe | Ala 115 | Thr | Thr | Ile | Trp | Gln 120 | Gln | Met | Glu | Glu | Leu 125 | Gly | Met | Ala |
| Pro | Ala 130 | Leu | Gln | Pro | Thr | Gln 135 | Gly | Ala | Met | Pro | Ala 140 | Phe | Ala | Ser | Ala |
| Phe 145 | Gln | Arg | Arg | Ala | Gly 150 | Gly | Val | Leu | Val | Ala 155 | Ser | His | Leu | Gln | Ser 160 |
| Phe | Leu | Glu | Val | Ser 165 | Tyr | Arg | Val | Leu | Arg 170 | His | Leu | Ala | Gln | Pro 175 |  |

( 2 ) INFORMATION FOR SEQ ID NO:107:

( i ) SEQUENCE CHARACTERISTICS:
    ( A ) LENGTH: 175 amino acids
    ( B ) TYPE: amino acid
    ( D ) TOPOLOGY: linear ( i i ) MOLECULE TYPE: protein ( x i ) SEQUENCE DESCRIPTION: SEQ ID NO:107:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |
| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |
| Asp | Phe | Ala | Thr | Ala | Ile | Trp | Gln | Gln | Met | Glu | Glu | Leu | Gly | Met | Ala |
| | | 115 | | | | | 120 | | | | | 125 | | | |
| Pro | Ala | Leu | Gln | Pro | Thr | Gln | Gly | Ala | Met | Pro | Ala | Phe | Ala | Ser | Ala |
| | 130 | | | | | 135 | | | | | 140 | | | | |
| Phe | Gln | Arg | Arg | Ala | Gly | Gly | Val | Leu | Val | Ala | Ser | His | Leu | Gln | Ser |
| 145 | | | | | 150 | | | | | 155 | | | | | 160 |
| Phe | Leu | Glu | Val | Ser | Tyr | Arg | Val | Leu | Arg | His | Leu | Ala | Gln | Pro | |
| | | | | 165 | | | | | 170 | | | | | 175 | |

( 2 ) INFORMATION FOR SEQ ID NO:108:

( i ) SEQUENCE CHARACTERISTICS:
    ( A ) LENGTH: 175 amino acids
    ( B ) TYPE: amino acid
    ( D ) TOPOLOGY: linear ( i i ) MOLECULE TYPE: protein ( x i ) SEQUENCE DESCRIPTION: SEQ ID NO:108:

| Met | Thr | Pro | Leu | Gly | Pro | Ala | Ser | Ser | Leu | Pro | Gln | Ser | Phe | Leu | Leu |
|---|---|---|---|---|---|---|---|---|---|---|---|---|---|---|---|
| 1 | | | | 5 | | | | | 10 | | | | | 15 | |
| Lys | Cys | Leu | Glu | Gln | Val | Arg | Lys | Ile | Gln | Gly | Ala | Gly | Ala | Ala | Leu |
| | | | 20 | | | | | 25 | | | | | 30 | | |
| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |
| Val | Leu | Leu | Gly | His | Ser | Leu | Gly | Ile | Pro | Trp | Ala | Pro | Leu | Ser | Ser |
| | 50 | | | | | 55 | | | | | 60 | | | | |
| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |
| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |
| Ser | Pro | Glu | Leu | Gly | Pro | Thr | Leu | Asp | Thr | Leu | Gln | Leu | Ala | Val | Ala |
| | | | 100 | | | | | 105 | | | | | 110 | | |
| Asp | Phe | Ala | Thr | Thr | Ile | Trp | Gln | Gln | Met | Glu | Glu | Leu | Gly | Met | Ala |
| | | 115 | | | | | 120 | | | | | 125 | | | |
| Pro | Ala | Leu | Gln | Pro | Thr | Gln | Gly | Ala | Met | Pro | Ala | Phe | Ala | Ser | Ala |
| | 130 | | | | | 135 | | | | | 140 | | | | |

| Phe | Gln | Arg | Arg | Ala | Gly | Gly | Val | Leu | Val | Ala | Ser | His | Leu | Gln | Ser |
| 145 | | | | | 150 | | | | 155 | | | | | | 160 |

| Phe | Leu | Glu | Val | Ser | Tyr | Arg | Val | Leu | Arg | His | Leu | Ala | Gln | Pro |
| | | | | 165 | | | | | 170 | | | | | 175 |

( 2 ) INFORMATION FOR SEQ ID NO:109:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:109:

| Met | Thr | Pro | Leu | Gly | Pro | Ala | Ser | Ser | Leu | Pro | Gln | Ser | Phe | Leu | Leu |
| 1 | | | | 5 | | | | | 10 | | | | | 15 | |

| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |

| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |

| Val | Leu | Leu | Gly | His | Ser | Leu | Gly | Ile | Pro | Trp | Ala | Pro | Leu | Ser | Ser |
| | 50 | | | | | 55 | | | | | 60 | | | | |

| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |

| Ser | Gly | Leu | Phe | Leu | Tyr | Gln | Gly | Leu | Leu | Gln | Ala | Leu | Glu | Gly | Ile |
| | | | | 85 | | | | | 90 | | | | | 95 | |

| Ser | Pro | Glu | Leu | Gly | Pro | Thr | Leu | Asp | Thr | Leu | Gln | Leu | Asp | Val | Ala |
| | | | 100 | | | | | 105 | | | | | 110 | | |

| Asp | Phe | Ala | Thr | Thr | Ile | Trp | Gln | Gln | Met | Glu | Ala | Leu | Gly | Met | Ala |
| | | | 115 | | | | | 120 | | | | | 125 | | |

| Pro | Ala | Leu | Gln | Pro | Thr | Gln | Gly | Ala | Met | Pro | Ala | Phe | Ala | Ser | Ala |
| | | 130 | | | | | 135 | | | | | 140 | | | |

| Phe | Gln | Arg | Arg | Ala | Gly | Gly | Val | Leu | Val | Ala | Ser | His | Leu | Gln | Ser |
| 145 | | | | | 150 | | | | 155 | | | | | | 160 |

| Phe | Leu | Glu | Val | Ser | Tyr | Arg | Val | Leu | Arg | His | Leu | Ala | Gln | Pro |
| | | | | 165 | | | | | 170 | | | | | 175 |

( 2 ) INFORMATION FOR SEQ ID NO:110:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:110:

| Met | Thr | Pro | Leu | Gly | Pro | Ala | Ser | Ser | Leu | Pro | Gln | Ser | Phe | Leu | Leu |
| 1 | | | | 5 | | | | | 10 | | | | | 15 | |

| Lys | Cys | Leu | Glu | Gln | Val | Arg | Lys | Ile | Gln | Gly | Asp | Gly | Ala | Ala | Leu |
| | | | 20 | | | | | 25 | | | | | 30 | | |

| Gln | Glu | Lys | Leu | Cys | Ala | Thr | Tyr | Lys | Leu | Cys | His | Pro | Glu | Glu | Leu |
| | | 35 | | | | | 40 | | | | | 45 | | | |

| Val | Leu | Leu | Gly | His | Ser | Leu | Gly | Ile | Pro | Trp | Ala | Pro | Leu | Ser | Ser |
| | 50 | | | | | 55 | | | | | 60 | | | | |

| Cys | Pro | Ser | Gln | Ala | Leu | Gln | Leu | Ala | Gly | Cys | Leu | Ser | Gln | Leu | His |
| 65 | | | | | 70 | | | | | 75 | | | | | 80 |

| Ser | Gly | Leu | Phe | Leu | Tyr | Gln | Gly | Leu | Leu | Gln | Ala | Leu | Glu | Gly | Ile |

|  |  |  |  |  | 85 |  |  |  |  | 90 |  |  |  |  | 95 |  |
|---|---|---|---|---|---|---|---|---|---|---|---|---|---|---|---|---|
| Ser | Pro | Glu | Leu<br>100 | Gly | Pro | Thr | Leu | Asp<br>105 | Thr | Leu | Gln | Leu | Asp<br>110 | Val | Ala |
| Asp | Val | Ala<br>115 | Thr | Ala | Ile | Trp | Gln<br>120 | Gln | Met | Glu | Glu | Leu<br>125 | Gly | Met | Ala |
| Pro | Ala<br>130 | Leu | Gln | Pro | Thr | Gln<br>135 | Gly | Ala | Met | Pro | Ala<br>140 | Phe | Ala | Ser | Ala |
| Phe<br>145 | Gln | Arg | Arg | Ala | Gly<br>150 | Gly | Val | Leu | Val | Ala<br>155 | Ser | His | Leu | Gln | Ser<br>160 |
| Phe | Leu | Glu | Val | Ser<br>165 | Tyr | Arg | Val | Leu | Arg<br>170 | His | Leu | Ala | Gln | Pro<br>175 |  |

What is claimed is:

1. A computer based method for preparing a G-CSF analog comprising the steps of:
   (a) providing computer expression of the three dimensional structure of an unglycosylatd r-hu-met G-CSF (SEQ ID NO:2) molecule using its X-ray crystallographic coordinates;
   (b) selecting from said computer expression at least one site on said G-CSF molecule for alteration;
   (c) preparing a G-CSF molecule having an alteration at said at least one site selected; and,
   (d) optionally, testing such G-CSF molecule for a desired characteristic.

2. A method of claim 1 wherein said computer expression allows for display of the amino acids of said G-CSF molecule.

3. A method of claim 1 wherein said computer expression allows for display of each atom of said G-CSF molecule.

* * * * *

UNITED STATES PATENT AND TRADEMARK OFFICE
CERTIFICATE OF CORRECTION

PATENT NO.  : 5,581,476
DATED       : 12/3/96
INVENTOR(S) : Osslund

It is certified that error appears in the above-identified patent and that said Letters Patent is hereby corrected as shown below:

Column 1, Line 44, after "575-581" insert --(1986)--.
Column 13, Line 26, delete "1673-677" and insert --1673-1677--.
Column 14, Line 33, delete "254:122219" and insert --254:12219--
Column 20, Line 28, delete "119723" and insert --19723--
Column 22, Line 4, after "0.1", delete "k"
Column 24, Line 65, delete "eachanalog" and replace with --each analog--
Column 27, Table 4, Line 13, delete "37,5" and replace with --37.5--.
Column 32, Line 18, delete "lie 32" and replace with --Ile 32--
Column 33, Line 1, delete "G-CSF G-CSF" and replace with --G-CSF--
Column 33, Line 14, delete "G-CSF G-CSF" and replace with --G-CSF--

Signed and Sealed this

Eighth Day of May, 2001

*Attest:*

NICHOLAS P. GODICI

*Attesting Officer*   Acting Director of the United States Patent and Trademark Office